(12) United States Patent
Dalton et al.

(10) Patent No.: US 9,078,888 B2
(45) Date of Patent: Jul. 14, 2015

(54) NUCLEAR RECEPTOR BINDING AGENTS

(75) Inventors: James T. Dalton, Upper Arlington, OH (US); Duane D. Miller, Germantown, TN (US); Michael L. Mohler, Memphis, TN (US); Seoung-Soo Hong, Collierville, TN (US); Zhongzhi Wu, Memphis, TN (US); Devesh Srivastava, Collierville, TN (US)

(73) Assignee: GTX, INC., Memphis, TN (US)

( * ) Notice: Subject to any disclaimer, the term of this patent is extended or adjusted under 35 U.S.C. 154(b) by 371 days.

(21) Appl. No.: 12/010,225

(22) Filed: Jan. 22, 2008

(65) Prior Publication Data

US 2009/0030036 A1    Jan. 29, 2009

Related U.S. Application Data

(60) Provisional application No. 60/881,476, filed on Jan. 22, 2007, provisional application No. 60/907,754, filed on Apr. 16, 2007.

(51) Int. Cl.
*A61K 31/47* (2006.01)
*A61K 31/472* (2006.01)
*C07D 217/22* (2006.01)
*C07D 217/24* (2006.01)

(52) U.S. Cl.
CPC ............ *A61K 31/472* (2013.01); *C07D 217/22* (2013.01); *C07D 217/24* (2013.01)

(58) Field of Classification Search
None
See application file for complete search history.

(56) References Cited

U.S. PATENT DOCUMENTS

| | | | |
|---|---|---|---|
| 2,848,356 A | 8/1958 | Pritchard et al. |
| 4,910,208 A | 3/1990 | Misra |
| 4,942,163 A | 7/1990 | Behrems |
| 5,004,747 A | 4/1991 | Ashton et al. |
| 5,112,869 A | 5/1992 | Watanabe et al. |
| 5,177,075 A | 1/1993 | Suto et al. |
| 5,416,094 A | 5/1995 | Lal et al. |
| 5,612,359 A | 3/1997 | Murugesan |
| 5,719,144 A | 2/1998 | Hartman et al. |
| 5,968,949 A | 10/1999 | Dondio et al. |
| 6,034,097 A | 3/2000 | DiMaio et al. |
| 6,043,265 A | 3/2000 | Murugesan |
| 6,486,155 B1 | 11/2002 | Pamukcu et al. |
| 6,630,508 B1 | 10/2003 | Dodge et al. |
| 6,664,269 B2 | 12/2003 | Martin et al. |
| 6,686,351 B2 | 2/2004 | Bhagwat et al. |
| 6,723,747 B2 | 4/2004 | Mewshew et al. |
| 6,756,375 B2 | 6/2004 | Veeneman et al. |
| 6,774,248 B2 | 8/2004 | Miller et al. |
| 6,794,403 B2 | 9/2004 | Malamas et al. |
| 6,835,745 B2 | 12/2004 | Coghlan et al. |
| 6,852,727 B2 | 2/2005 | Goulet et al. |
| 6,870,055 B2 | 3/2005 | Claremon et al. |
| 6,903,238 B2 | 6/2005 | McDevitt et al. |
| 6,914,074 B2 | 7/2005 | Mewshaw et al. |
| 6,943,162 B2 | 9/2005 | Hale et al. |
| 6,960,607 B2 | 11/2005 | Malamas et al. |
| 7,015,219 B2 | 3/2006 | Dickson et al. |
| 7,034,039 B2 | 4/2006 | Oi et al. |
| 7,084,276 B2 | 8/2006 | Vu et al. |
| 7,087,599 B2 | 8/2006 | Parker, Jr. et al. |
| 7,138,426 B2 | 11/2006 | Dininno et al. |
| 7,151,196 B2 | 12/2006 | Wilkening et al. |
| 7,157,491 B2 | 1/2007 | Mewshaw et al. |
| 7,157,492 B2 | 1/2007 | Mewshaw et al. |
| 7,256,201 B2 | 8/2007 | Barlaam et al. |
| 7,265,131 B2 | 9/2007 | Johnson et al. |
| 7,279,499 B2 | 10/2007 | Durst et al. |
| 7,294,635 B2 | 11/2007 | Scarborough et al. |
| 7,354,951 B2 | 4/2008 | Norman et al. |
| 8,188,117 B2 | 5/2012 | Plettenburg et al. |
| 2002/0077486 A1 | 6/2002 | Scarborough et al. |
| 2003/0008896 A1 | 1/2003 | Martin et al. |
| 2003/0013699 A1 | 1/2003 | Davis et al. |
| 2003/0069303 A1 | 4/2003 | Veeneman et al. |
| 2003/0119800 A1 | 6/2003 | Manolagas et al. |
| 2003/0220227 A1 | 11/2003 | Gungor et al. |
| 2003/0220377 A1 | 11/2003 | Chesworth |
| 2004/0038959 A1 | 2/2004 | Bunker et al. |
| 2004/0044030 A1 | 3/2004 | Claremon et al. |
| 2004/0082575 A1 | 4/2004 | Bhagwat et al. |

(Continued)

FOREIGN PATENT DOCUMENTS

AU    2003264386 A1    4/2004
CN    101072564    11/2007

(Continued)

OTHER PUBLICATIONS

Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Pinto de Sueza et al (Ind J Chem B Org, 29B(10):961-965, 1990).*
STN Search Report (Accession No. 1991:101677).*
STN Search Report (Accession No. 1995:866647—Hellwinkel et al (Synthesis 9:1135-1141, 1995)).*
Anderson (Chem and Biol 10:787-797, 2003).*
Thiel (Nature Biotechnol 2:513-519, 2004).*
Kirkwood and Agarwala, "Systemic Cytotoxic and Biologic Therapy of Melanoma" (1993) *Principles and Practice of Oncology* 7:1-16.
U.S. Appl. No. 09/519,079, filed Mar. 6, 2000, Vu.

(Continued)

*Primary Examiner* — Craig Ricci

(74) *Attorney, Agent, or Firm* — Mark S. Cohen; Pearl Cohen Zedek Latzer Baratz LLP

(57) ABSTRACT

The present invention relates to a novel class of nuclear receptor binding agents (NRBAs). The NRBAs are applicable for use in the prevention and/or treatment of a variety of diseases and conditions including prevention and treatment of cancers such as prostate and breast cancer, osteoporosis, hormone-related diseases, inflammatory diseases, oxidative stress related disorders such as Parkinson's and stroke, neurological disorders, ophthalamic disorders, cardiovascular disease, and obesity.

13 Claims, 11 Drawing Sheets

(56) References Cited

U.S. PATENT DOCUMENTS

| | | |
|---|---|---|
| 2004/0082607 A1 | 4/2004 | Oi et al. |
| 2004/0092506 A1 | 5/2004 | Thompson et al. |
| 2004/0138244 A1 | 7/2004 | Dalton et al. |
| 2004/0171006 A1 | 9/2004 | Xiao |
| 2004/0176361 A1 | 9/2004 | Fujio et al. |
| 2004/0204447 A1 | 10/2004 | Johnson et al. |
| 2004/0214790 A1 | 10/2004 | Borgens |
| 2005/0009784 A1 | 1/2005 | Vu |
| 2005/0059723 A1 | 3/2005 | Mewshaw et al. |
| 2005/0101584 A1 | 5/2005 | Barlaam et al. |
| 2005/0113399 A1 | 5/2005 | Scarborough et al. |
| 2005/0148560 A1 | 7/2005 | Fritzemeier et al. |
| 2005/0148624 A1 | 7/2005 | Itoh et al. |
| 2005/0182045 A1 | 8/2005 | Nagase |
| 2005/0256210 A1 | 11/2005 | Olsson et al. |
| 2006/0004087 A1 | 1/2006 | Miller et al. |
| 2006/0052410 A1 | 3/2006 | Vu |
| 2006/0111318 A1 | 5/2006 | Okamoto |
| 2006/0173039 A1 | 8/2006 | Shiga et al. |
| 2006/0183744 A1 | 8/2006 | Rohrer et al. |
| 2006/0199858 A1 | 9/2006 | Durst et al. |
| 2006/0211602 A1 | 9/2006 | Ansorge et al. |
| 2006/0211672 A1 | 9/2006 | Jacobson et al. |
| 2006/0222721 A1 | 10/2006 | Cohen |
| 2006/0241094 A1 | 10/2006 | Chen |
| 2006/0270591 A1 | 11/2006 | Chang |
| 2006/0270704 A1 | 11/2006 | Isaacs et al. |
| 2006/0281743 A1 | 12/2006 | Dinsmore |
| 2007/0010526 A1 | 1/2007 | Haeberlein et al. |
| 2007/0021495 A1 | 1/2007 | Katzenellenbogen et al. |
| 2007/0027177 A1 | 2/2007 | Trotter et al. |
| 2007/0043077 A1 | 2/2007 | Mewshaw et al. |
| 2007/0049605 A1 | 3/2007 | Mewshaw et al. |
| 2007/0072810 A1 | 3/2007 | Asakawa |
| 2007/0099880 A1 | 5/2007 | Blizzard et al. |
| 2007/0099912 A1 | 5/2007 | Zhou et al. |
| 2007/0105827 A1 | 5/2007 | Blizzard et al. |
| 2007/0197488 A1 | 8/2007 | Peters et al. |
| 2007/0203102 A1 | 8/2007 | Blizzard et al. |
| 2007/0225330 A1 | 9/2007 | Merril et al. |
| 2009/0030036 A1 | 1/2009 | Dalton et al. |
| 2009/0076019 A1 | 3/2009 | Tyers et al. |
| 2010/0009960 A1 | 1/2010 | Robl et al. |
| 2010/0029734 A1 | 2/2010 | White et al. |
| 2010/0256698 A1 | 10/2010 | Trotter et al. |
| 2010/0267767 A1 | 10/2010 | Naranayan et al. |
| 2010/0286204 A1 | 11/2010 | Vicker et al. |
| 2011/0071146 A1 | 3/2011 | Niimi et al. |
| 2012/0009204 A1 | 1/2012 | Reinhardt et al. |

FOREIGN PATENT DOCUMENTS

| | | |
|---|---|---|
| EP | 00326386 A2 | 8/1989 |
| EP | 01414443 B1 | 8/1989 |
| EP | 0482939 A1 | 4/1992 |
| EP | 0502575 A1 | 9/1992 |
| EP | 1454898 | 9/2004 |
| EP | 01484320 A1 | 12/2004 |
| EP | 1537880 A1 | 6/2005 |
| EP | 1604983 A1 | 12/2005 |
| JP | H10-259176 | 9/1998 |
| JP | 2000-072675 | 3/2000 |
| JP | 2005513027 | 11/2001 |
| JP | 05513027 | 5/2005 |
| WO | WO 89/00165 | 1/1989 |
| WO | WO9509842 A1 | 4/1995 |
| WO | WO9730047 | 8/1997 |
| WO | WO9731940 | 9/1997 |
| WO | WO9838168 A1 | 2/1998 |
| WO | WO9829407 | 7/1998 |
| WO | WO9838168 A1 | 9/1998 |
| WO | WO9851307 A1 | 11/1998 |
| WO | WO 99/11624 | 3/1999 |
| WO | WO 00/01389 | 1/2000 |
| WO | WO00/01389 | 1/2000 |
| WO | WO00/19994 | 4/2000 |
| WO | WO 00/19994 | 4/2000 |
| WO | WO 02032373 | 10/2000 |
| WO | WO 02/41835 | 11/2000 |
| WO | WO0246164 | 12/2000 |
| WO | WO 02046168 | 12/2000 |
| WO | WO02051821 | 12/2000 |
| WO | WO 0258639 | 1/2001 |
| WO | WO0109096 A2 | 2/2001 |
| WO | WO0122960 A1 | 4/2001 |
| WO | WO 02/91993 | 5/2001 |
| WO | WO 03015761 | 8/2001 |
| WO | WO 0168603 | 9/2001 |
| WO | WO0168603 | 9/2001 |
| WO | WO 03045930 | 11/2001 |
| WO | WO03053994 | 12/2001 |
| WO | WO0224655 A1 | 3/2002 |
| WO | WO 02/26325 | 4/2002 |
| WO | WO 02032373 | 4/2002 |
| WO | WO 02/41835 | 5/2002 |
| WO | WO0246164 | 6/2002 |
| WO | WO0246168 | 6/2002 |
| WO | WO02051821 | 7/2002 |
| WO | WO 02058639 | 8/2002 |
| WO | WO02062764 A1 | 8/2002 |
| WO | WO 02/091993 | 11/2002 |
| WO | WO02090334 A1 | 11/2002 |
| WO | WO02090334 A1 | 11/2002 |
| WO | WO 03015761 | 2/2003 |
| WO | WO 2004094400 | 4/2003 |
| WO | WO03037887 | 5/2003 |
| WO | WO03045930 | 6/2003 |
| WO | WO03053994 A1 | 7/2003 |
| WO | WO 2006/007503 | 8/2003 |
| WO | WO 2003074044 | 9/2003 |
| WO | WO 2004/004750 | 1/2004 |
| WO | WO 2004/026823 | 1/2004 |
| WO | WO 2004006906 A2 | 1/2004 |
| WO | WO 2005/082880 | 2/2004 |
| WO | WO2004014378 A1 | 2/2004 |
| WO | WO 2004/009912 | 4/2004 |
| WO | WO 2004/09912 | 4/2004 |
| WO | WO 2004/026823 | 4/2004 |
| WO | WO 2005/099700 | 4/2004 |
| WO | WO 2004094400 | 4/2004 |
| WO | WO2004048339 A1 | 6/2004 |
| WO | WO 2005123757 | 6/2004 |
| WO | WO 2006009912 | 6/2004 |
| WO | WO2004058717 A1 | 7/2004 |
| WO | WO 2004/073612 | 9/2004 |
| WO | WO 2006062876 | 12/2004 |
| WO | WO2005035520 A1 | 4/2005 |
| WO | WO 2005/082880 | 9/2005 |
| WO | WO 2005/099700 | 10/2005 |
| WO | WO 2006/007503 | 1/2006 |
| WO | WO 2006/026395 | 3/2006 |
| WO | WO 2006044176 A1 | 4/2006 |
| WO | WO 2006062876 | 6/2006 |
| WO | WO 2006/081152 | 8/2006 |
| WO | WO2006088716 | 8/2006 |
| WO | WO2006018107 | 10/2006 |
| WO | WO 2006/116401 | 11/2006 |
| WO | WO2006108107 | 12/2006 |
| WO | WO 2007093364 A1 | 2/2007 |
| WO | WO 2007093366 | 2/2007 |
| WO | WO2007053353 A2 | 5/2007 |
| WO | WO2007149031 | 6/2007 |
| WO | WO 2007-089291 | 8/2007 |
| WO | WO 2007089291 | 8/2007 |
| WO | WO 2007093364 A1 | 8/2007 |
| WO | WO 2007093366 | 8/2007 |
| WO | WO2007137000 A2 | 11/2007 |
| WO | WO2007149031 | 12/2007 |
| WO | WO 2008/016768 | 2/2008 |
| WO | WO 03074044 | 3/2008 |

OTHER PUBLICATIONS

Kalin MF, et al (1990). Sex hormones and coronary disease: a review of the clinical studies. Steroids; 55:330-352.

(56) References Cited

OTHER PUBLICATIONS

Wenger NK, et al (1993). Cardiovascular health and disease in women. N. Engl J Med; 329:247-256.

Mendelsohn ME et al. (1999). Mechanism of disease: the protective effects of estrogen on the cardiovascular system. N Engl J Med;340:1801-1811.

Karas RH, el al (1994). Human Vascular smooth muscle cells contain functional estrogen receptor. Circulation; 89:1943-1950.

Lindner V. et al (1998). Increased expression of ER b mRNA in male blood vessels following vascular injury. Circ Res; 83:224-229.

Wada-Hirake O, et al. (2006). Role of estrogen receptor beta in uterine stroma and epithelium: insights from estrogen receptor beta −/− mice. PNAS; 103(48)18350-5.

Dubey RK, et al (1999). Phytoestrogens inhibit growth and Map kinase activity in human aortic smooth muscle cells. Hypertension; 33:177-182.

Siow RCM, et al (2007). Cardiovascular targets for estrogens and phytoestrogens; Transcriptional regulation of nitric oxide synthase and antioxidant defense genes. Free Radical biology and Medicine; 42:909-925.

Langer, "New methods of Drug Delivery", Science 249:1627-1633 (1990).

Treat et at Liposomes in the Therapy of Infectious Disease and Cancer Liss, New York pp. 353-365.

Buchwald et al. (1980) "Long-term, continuous intravenous heparin administration by an implantable infusion pump in ambulatory patients with recurrent venous thrombosis.", Surgery 88:507.

Saudek et al. (1989) "A preliminary trial of the programmable implantable medication system for insulin delivery.", N. Engl. J. Med. 321:574.

Goodson, in Medical Applications of Controlled Release, supra, vol. 2, pp. 116-138 (1984).

Gungor T. et al.,"Synthesis and characterization of 3-arylquinazolinone and 3-arylquinazolinethione derivatives as selective estrogen receptor beta modulators" J. Med. Chem. 2006, 49, 2440-2455.

Crabtree JS et al. "Activity of three selective estrogen receptor modulators on hormone-dependant responses in the mouse uterus and mammary gland." Molecular and Cellular Endocrinology, Feb. 12, 2008. Online.

Leventhal et al., European Journal of Pharmacology, 553: 146-148, 2006. "An estrogen receptor-β agonist is active in models of inflammatory and chemical-induced pain".

Harris HA, Nuclear Receptor Signaling, 2006, pp. 1-4. "The unexpected science of estrogen receptor-β selective agonists: a new class of anti-inflammatory agents?".

Kajta, M,; et al, "Genistein inhibits glutamate-induced apoptosis in primary neuronal cell cultures of mouse brain cortex and cerebellum". Behav Pharmacol (2006): 549 (EBPS Workshop, Abstract P27).

Katzenellenbogen J. A. et al, Workshop 1.4: Nature of the ligand-binding pocket of estrogen receptor alpha and beta: The search for subtype-selective ligands and implications for the prediction of estrogenic activity. Pure Appl. Chem, (2003) 75(11-12), 2397-2403.

Krishnan, G.; et al. Pharmacological actions of a selective estrogen receptor beta (ER beta) agonist in ovarlectomlzed rats. J Bone Miner Res 2005, 20(Suppl. 1): Abst SA427. 27th Annu Meet Am Sot Bone Miner Res (ASBHR) (Sep. 23-27r Nashville, United States) 2005.

Sun, W. et al., "6H-Benzo[c]chromen-6-one derivatives as selective ERbeta agonists" 230th ACS Natl Meet (Aug. 28-Sep. 1, Washington DC) 2005, Abst MEDI 25.

Ullrich, J.W., Singhaws R.; Unwalla, R., Harris, H.A. 4-Hydroxy-N-phenyl substituted phthalimides as selective estrogen receptor beta (ER.b) ligands, 230th ACS Nat! Meet (Aug. 28-Sep. 1, Washington DC) 2005, Abst MEDI 27 (Wyeth).

Akiyama, T. et al. (1987). Genistein, a specific inhibitor of tyrosine-specific protein kinases. JBiol Chem 262(12), 5592-5.

Arias-Loza, P. A., et al (2007), Both estrogen receptor subtypes, alpha and beta, attenuate cardiovascular remodeling in aldosterone salt-treated rats. Hypertension 5(1(2). 432-8.

Arias-Loza, P. A., et al (2007), Both estrogen receptor subtypes, alpha and beta, attenuate cardiovascular remodeling in aldosterone salt-treated rats. Hypertension 5(1(2), 432-8.

Ascenzi P., et al. (2006). Structure-function relationship of estrogen receptor alpha and beta: Impact on human health. Mol Aspects Med 27 (4) 299-402.

Barkhem, T., et al. (1998). Differential response of estrogen receptor alpha and estrogen receptor beta to partial estrogen agonists/antagonists, Mol Pharmacol 54(1), 105-12.

Blizzard, T. A., et al (2007a). Bridged androstenediol analogs as ER-beta selective SERMs. Bioorg Med Chem Lett 17(10), 2944-8.

Blizzard, T. A., (2007b). Androstene-3,5-dienes as ER-beta selective SERMs. Bioorg Med Chem Lett 17(22), 6295-8.

Bodo, C. and Rissman, E. F. (2006). New roles for estrogen receptor beta in behavior and neuroendocrinology. Front Neuroendocrinol 27(2), 217-32.

Booth, E. A., et al. (2007). The pathway-selective estrogen receptor ligand WAY-169916 reduces infarct size after myocardial ischemia and reperfusion by an estrogen receptor dependent mechanism. J Cardiovasc Pharmacol 49(6), 401-7.

Chadwick, C, et al (2005). Identification of pathway-selective estrogen receptor ligands that inhibit NF-kappaB kappaB transcriptionsal activity. Proc NatlAcadSci USA 102(7), 2543-8.

Remmers et al. (1997) "Testosterone receptor blockade after trauma-hemorrhage improves cardiac and hepatic functions in males" Am J. Physiol—Heart Circ Physiol., 287: 2919-2925, esp abstract, p. H2924, col. 1.

Mckinnon et al. (2003) "Glaucoma: ocular Alzhelmer's disease? Frontiers in Bioscience" 8:s 1140-1156, esp, abstract; p. 1141, col. 2, para 2; p. 1150, col. 1, para 2.

Chan, K. K., et al (2008). Estrogen receptor subtypes in ovarian, cancer: a clinical correlation. Obstet Gynecol 111(1) 144-51.

Chan, Y. C. et al.; "Raloxifene Relaxes Rat Pulmonary Arteries and Veins: Roles of Gender, Endothelium, and Antagonism of Ca2+ Influx."; The Journal of Pharmacology and Experimental Therapeutics; 312(3), pp. 1266-1271; (2005).

Chang, E. C, et al (2006), Impact of estrogen receptor beta on gene networks regulated by estrogen receptor alpha in breast cancer cells. Endocrinology 147(10), 4831-42.

Chen, W., et al. (2007), Aza analogues of equol: novel ligands for estrogen receptor beta, Bioorg Med Chem 15(17), 5828-36.

Chesworth R, et al. (2005). Estrogen receptor beta selective ligands: discovery and SAR of novel heterocyclic ligands, Bioorg Med Ckem Lett 15(24), 5562-6.

Chesworth, R., et al. (2004). Tetrahydroisoquinolines as subtype selective estrogen agonists/antagonists. Bioorg Med Chem Lett 14(11), 2729-33.

Christian, R. C, et al (2006). Initial estrogen receptor (ER)beta, but not ERalpha expression. Is correlated with coronary calcification and atherosclerosis in pre- and postmenopausal women. JClin Endocrinol Metab 91(7)j 2713-20.

Collini M.D. et al. (2004). 7-Substituted 2-phenyl-benzofurans as ER beta selective ligands. *Bioorg Med Chem Lett* 14(19), 4925-9.

Compton, D. R., et al (2004). Pyrazolo[1,5-a] pyrimidines as estrogen receptor ligands: defining the orientation of a novel heterocyclic core. *Bioorg Med Chem Lett* 14(22), 5681-4.

Compton, D. R. et al. (2004). Pyrazolo[1,5-a]pyrimidines: estrogen receptor ligands possessing estrogen receptor beta antagonist activity. *J Med Chem* 47(24), 5872-93.

Cvoro, A., et al. (2008), Selective estrogen receptor-beta agonists repress transcription of proinflammatory genes, J Immunol 180(1), 630-6.

De Angelis, et al (2005a), Indazole estrogens: highly selective ligands for the estrogen receptor beta. *JMed Chem* 4S(4)s 1132-44.

De Angelis, et al (2005b). Isocoumarins as estrogen receptor beta selective ligands: Isomers of Isoflavone phytoestrogens and their metabolites. *Bioorg Med Chem* 13(23), 6529-42.

Dick, G. M. et al. "(Xeno)Estrogen Sensitivity of Smooth Muscle BK Channels Conferred by the Regulatory β1 Subunit, a Study of β1Knockout Mice"; The Journal of Biological Chemistry; 276(48); pp. 44835-44840; (2001).

(56) References Cited

OTHER PUBLICATIONS

Pinthus et al. (2007) "Androgen Induces Adaptation to Oxidative Stress in Prostate Cancer: Implications for Treatment with Radiation Theraphy, Neoplasia" vol. 9:68-80, esp. Abstract; p. 70, col. 2, para 6; p. 71, col. 1, para 2.
Edsall, R. J., et al. (2003). ERbeta ligands. Part 1: the discovery of ERbeta selective ligands which embrace the 4-hydroxy-biphenyl template. *Bioorg Med Chem* 11(16), 3457-74.
Fotsis, T. et al, (1993). Genistein, a dietary-derived Inhibitor of in vitro angiogenesis. *Proc Natl Acad Sci USA* 90(7), 2690-4.
Fritzemeier, K. H., et al. (2004). Biological effects of ERalpha- and ERbeta-selective estrogens. *Ernst Schering Res Found Workshop*(46), 127-50.
Fu X. H., et al (2008). Synthesis of genistein derivatives and determination of their protective effects against vascular endothelial cell damages caused by hydrogen peroxide. *Bioorg Med Chem Lett* 18(2), 513-7.
Green, KLA., and Carroll, J. S (2007). Oestrogen-receptor-mediated transcription and the influence of co-factors and chromatin state. *Nat Rev Cancer* 7(9), 713-22.
Greene, G. L., Shiau A. K., and Nettles, K. W. (2004). A structural explanation for ERalpha/ERbeta SERM discrimination. *Ernst Schering Res Found Workshop* (46), 33-45.
Gungor, T. et al. (2006) M. Synthesis and Characterization of 3-Arylquinazolinone and 3-Arylquinazolinethione Derivatives as Selective Estrogen Receptor Beta Modulators. J. Med. Chem. 2006, 49, 2440-2455.
Gupta, A. K., et al (2007). QSAR analysis of indazole estrogens as selective beta- estrogen receptor ligands: rationalization of physicochemical properties, *Med Chem* 3(4), 347-53.
Fotsis, T., et al, (1993). Genistein, a dietary-derived Inhibitor of in vitro angiogenesis. *Proc Natl Acad Sci USA* 90(7), 2690-4.
Fritzemeier, K. H., et al (2004). Biological effects of ERalpha- and ERbeta-selective estrogens. *Ernst Schering Res Found Workshop*(46), 127-50.
Günör, T. et al. (2006) M. Synthesis and Characterization of 3-Arylquinazolinone and 3-Arylquinazolinethione Derivatives as Selective Estrogen Receptor Beta Modulators. J. Med. Chem. 2006, 49, 2440-2455.
Gustafsson, J. A. (2006). ERbeta scientific visions translate to clinical uses, *Climacteric* 9(3)156-60.
Haas, E. et al.; "Differential Effects of 17β-Estradiol on Function and Expression of Estrogen Receptor α, Estrogen Receptor β, and GPR30 in Arteries and Veins of Patients with Atherosclerosis"; *Hypertension* 49(6); pp. 1358-1363; (2007).
Harrington, W, et al. (2003), Activities of estrogen receptor alpha- and beta-selective ligands at diverse estrogen responsive gene sites mediating transactivation or transrepression. *Mol Cell Endocrinol* 206(1-2), 13-22.
Harris, H. A. (2006). The unexpected science of estrogen receptor-beta selective agonists; a new class of anti-inflammatory agents? *Nucl Recept Signal* 4, e012.
Harris, H. A. (2007). Estrogen receptor-beta: recent lessons from, in vivo studies, *Mol Endocrinol* 21(1), 1-13.
Harris, H. A., et al (2003), Evaluation of an estrogen receptor-beta agonist in animal models of human disease. *Endocrinology* 144(10), 4241-9.
Hayashi, A., et al (1997). Genistein, a protein tyrosine kinase inhibitor, ameliorates retinal degeneration after ischemia-reperfusion injury in rat. *Invest Opthalmol Vis Sci* 38(6), 1193-202.
Henke, B. R., et al (2002). A new series of estrogen receptor modulators that display selectivity for estrogen receptor beta. *J Med Chem* 45(25), 5492-505.
Heynekamp, J. J., et al (2006). Substituted trans-stilbenes, including analogues of the natural product resveratrol, inhibit the human tumor necrosis factor alpha-induced activation of transcription factor nuclear factor kappaB. *J Med Chem* 49(24), 7182-9.
Hillisch, A., et al. (2004b). Dissecting physiological roles of estrogen receptor alpha and beta with potent selective ligands from structure-based design, *Mol Endocrinol* 18(7), 1599-609.

Ho, S. M. (2004). Estrogens and anti-estrogens: key mediators of prostate carcinogenesis and new therapeutic candidates. *J Cell Biochem* 91(3), 491-503.
Hoekstra, W.J., et al. (2005) Discovery of novel quinoline-based estrogen receptor ligands using peptide interaction profiling, *J Med Chem* 48(6), 2243-7.
Imamov, O., et al. (2004). Estrogen receptor beta in prostate cancer. *N Engl J Med* 351(26), 2773-4.
Imamov, O., et al (2005). Estrogen receptor beta in health and disease. *Biol Reprod* 73(5)866-71.
Jazbutyte, V. et al. (2008). ligand-dependent activation of ER{beta} lowers blood pressure and attenuates cardiac hypertrophy in ovariectomized spontaneously hypertensive rats. *Cardiovasc Res* 77(4), 774-81.
Kai M., et at (2004). Soybean isoflavones eliminate nifedipine-induced flushing of tail skin in ovariectomized mice. *J Pharmacol Set* 95(4), 476-8.
Kajta, M., et al. (2007). Genistein inhibits glutamate-induced apoptotic processes in primary cell cultures: an involvement of aryl hydrocarbon receptor and estrogen receptor/glycogen synthase kinase-3beta intracellular signaling pathway, *Neuroscience* 145(2), 592-604.
Karas, R. H., et al. (1998), Growth factor activation of the estrogen receptor in vascular cells occurs via a mitogen-activated protein kinase-independent pathway. *J Clin Invest* 101(12), 2851-61.
Kim, S et al (2004), Estrogen receptor ligands. Part 4: The SAR of the syn-dihydrobenzoxathi in SERAMs. *Bioorg Med Chem Lett* 14(11), 2741-5.
Koehler K., et al., (2005). Reflections on the discovery and significance of estrogen receptor beta *Endocr Rev* 26(3), 465-78.
Kuiper, G.G. et al. (1997). Comparison of the ligand binding specificity and transcript tissue distribution of estrogen receptors alpha and beta. *Endocrinology* 138(3), 863-70.
Lai S., et al (2004). Metastases of prostate cancer express estrogen receptor-beta. *Urology* 64(4), S14-20.
Leung, Y.K., et al (2006). Estrogen receptor (ER)-beta isoforms: a key to understanding ER-Beta signaling. *Proc NatlAcadSci USA* 103(35), 13162-7.
Luan F., et al., (2008) Classification of estrogen receptor-beta ligands on the basis of their binding affinities using support vector machine and linear discriminant analysis. *Eur J Med Chem* 43(1), 43-52.
Lund, T. D., et al (2004a), Androgen receptor expression in the rat prostate is down-regulated by dietary phytoestrogens. *Reprod Biol Endocrinol* 2, 5.
Lund, T.D et al (2004b). Equal is a novel anti-androgen that inhibits prostate growth and hormone feedback. *Biol Reprod* 70(4), 1188-95.
Lutty, G. et al (1999). Changes in choriocapiliaris and retinal pigment epithelium in age-related macular degeneration. *Mol Vis* 5, 35.
Malamas, M.S., et al. (2004). Design and synthesis of aryl diphenolic azoles as potent and selective estrogen receptor-beta ligands. *J Med Chem* 47(21), 5021-40.
Manas, E.S.,et al (2004), Structure-based design of estrogen receptor-beta selective ligands. *JArn Chem Soc* 126(46), 1510649.
McDevitt, R. E., et al. (2005). Estrogen receptor ligands: design and synthesis of new 2-arylidene-1-ones. *Bioorg Med Chem Lett* 15(12), 3137-42.
McPherson, S. J., et al. (2006). The role of ERalpha and ERheta in the prostate: insights from genetic models and isoform-selective ligands. *Ernst Schering Found Symp Proc* 1, 131-47.
Mewshaw, R, E. et al. (2007). ERbeta ligands. Part 5: synthesis and structure-activity relationships of a series of 4'-hydroxyphenyl-aryl-carbaldehyde oxime derivatives. *Bioorg Med Chem. Lett* 17(4), 902-6.
Mewshaw, R. E., et al. (2005). ERbeta ligands. 3. Exploiting two binding orientations of the 2-phenylnaphthalene scaffold to achieve ERbeta selectivity. *JMed Chem* 48(12), 3953-79.
Miller, C. P., et al. (2003). Constrained phytoestrogens and analogues as ERbeta selective ligands, *Bioorg Med Chem Lett* 13(14), 2399-403.
Minutolo, F., et al. (2008). Monoaryl-substituted salicylaldoximines as ligands for estrogen receptor Beta. *J Med Chem* 51(5), 1344-51.

(56) References Cited

OTHER PUBLICATIONS

Morani, A. et al (2006). Lung dysfunction causes systemic hypoxia in estrogen receptor beta knockout (ERbeta−/−) mice. *Proc Natl Acad Set USA* 103(18), 7165-9.

Morissette, M et al., (2008), Contribution of estrogen receptors alpha and beta to the effects of estradiol in the brain. *J Steroid Biochem MolBiol* 108(3-5), 327-38.

Muthyala, R, et al (2003). Exploration of the bicyclo[3.3.1]nonane system as a template for the development of new ligands for the estrogen receptor. *Bioorg Med Chem Lett* 13(24). 4485-8.

Muthyala, R. et al. (2003), Bridged bicyclic-cores containing a 1,1-diarylethylene motif are high-affinity subtype-selective ligands for the estrogen receptor, *J Med Chem* 46(9), 1589-602.

Nakajima, M, et al. (2001). Normalization of retinal, vascular permeability in experimental diabetes with genistein. *Invest Ophthalmol Vis Sci* 42(9),2U0-4.

Norman, B. H., et al. (2006). Benzopyrans are selective estrogen receptor beta agonists with novel activity in models of benign prostatic hyperplasia, *J Med Chem* 49(21) 6155-7.

Norman, B. H., et al. (2007). Benzopyrans as selective estrogen receptor beta agonists (SERBAs). Part 4: functionalization of the benzopyran A-ring. Bioorg Med Chem Left 17(18), 5082-5.

Ohshiro, K. et al. (2006). Biological role of estrogen receptor beta in salivary gland adenocarcinoma cells. Clin Cancer Res 12(20 Pt I\ 5994-9.

Parker, D.L., et al. (2006), Triazoio-tetrahydrofluorenones as selective estrogen receptor beta agonists. Bioorg Med Chem Lett 16(17), 4652-6.

Pike, A, et al. (1999). Structure of the ligand-binding domain of oestrogen receptor beta in, the presence of a partial agonist and a MI antagonist Embo J 18(17) 4608-18.

Pravettoni, A., et al. (2007). Estrogen receptor beta (ERbeta) and inhibition of prostate cancer cell proliferation: studies on the possible mechanism of action in DU145 cells. Mol Cell Endocrinol 263(1-2), 46-54.

Prossnitz, E R., et al. (2008). GPR30; a novel therapeutic target in estrogen-related disease, Trends Pharmacol Sci 29(3% 116-23.

Qin C, et al., (2008) Understanding the Cardioprotective Effects of Flavonols: Discovery of Relaxant Flavonols without Antioxidant Activity. JMed Chem 51(6) 1874-84.

Rhodes, M. E. et al. (2006), ERbeta-selective SERMs produce mnemonic-enhancing effects in the inhibitory avoidance and water maze tasks. Neurobiol Learn Mem 85(2), 183-91.

Richardson. T. L., et al. (2007a), Benzopyrans as selective estrogen receptor beta agonists (SERBAs). Part 3: synthesis of cyclopentanone and cyclohexanone intermediates for C-ring; modification. *Bioorg Med Chem Lett* 17(17), 4824-8.

Richardson, T.L., et al. (2007b). Benzopyrans as selective estrogen receptor beta agonists (SERBA5). Part 5: Combined A- and C-ring structure-activity relationship studies. *Bioorg Med Chem Lett* 17(20), 5563-6.

Richardson, TL., et al. (2007c). Benzopyrans as selective estrogen receptor beta agonists (SERBAs). Part 2: structure-activity relationship studies on the benzopyran scaffold. *Bioorg Med Chem Lett* 17(13), 3570-4.

Roelens, F., et al. (2006). Subtle side-chain modifications of the hop phytoestrogen 8-prenylnaringenin result in distinct agonist/antagonist activity profiles for estrogen receptors alpha and beta. *JMed Chem* 49(25)? 7357-65.

Safe, S., et al. (2006). The role of xenoestrogenic compounds in the development of breast cancer. *Trends Pharmacol Sci* 27(8), 447-54.

Seo J. et al. (2006). Fluorine-substituted cyclofenil derivatives as estrogen receptor ligands: synthesis and structure-affinity relationship study of potential positron emission tomography agents for imaging estrogen receptors in breast cancer. *JMed Chem* 49(8)7 2496-511.

Setchell K. D. (2006), Assessing risks and benefits of genistein and soy. *Environ Health Perspect* 114(6), A332-3.

Setchell, K. D., et al. (2005). S-equol, a potent ligand for estrogen receptor beta, is the exclusive enantiomeric form of the soy isoflavone metabolite produced by human intestinal bacterial flora, *Am J Gin Nutr* 81(5), 1072-9.

Shen, S. S, et al. (2006). Expression of estrogen receptors-alpha and -beta in bladder cancer cell lines and human bladder tumor tissue. Cancer 106(12), 2610-6.

Shiau, A. K, et al. (2002). Structural characterization of a subtype-selective ligand reveals a novel mode of estrogen receptor antagonism. *Nat Struct Biol* 9(5), 359-64.

Skliris G.P. et al., (2008) Estrogen receptor alpha negative breast cancer patients: Estrogen receptor beta as a therapeutic target *JSteroid Biochem Mol Biol* 109(1-2), 140.

Somjen, D., et al (2002), 6-Carboxymethyl genistein: a novel selective oestrogen receptor modulator (SERM) with unique, differential, effects on the vasculature, bone -and uterus. *J Endocrinol* 173(3), 415-27.

Strom, A., et al. (2004). Estrogen receptor beta inhibits 17beta-estradiol-stimulated proliferation of the breast cancer cell line T47D. *Proc Nat Acad Sci USA* 101(6) 1566-71.

Sun, J., et al (2003). Molecular basis for the subtype discrimination of the estrogen receptor-beta-selective ligand, diarylpropionitrile. *Mol Endocrinol* 17(2), 247-58.

Sun, Wet al. (2006). 6H-Benzo[c]chromen-6-one derivatives as selective ERbeta agonists. *BioorgMed Chem Lett* 16(6), 1468-72.

Szkudelska, K., and Nogowski, L. (2007). Genistein-a dietary compound inducing hormonal and metabolic changes. *J Steroid Biochem Mol Biol* 105(1-5), 37-45.

Takahashi, W., et al. (1997). Effect of estrogen on nitric oxide-induced relaxation of the rabbit urethra. *Eur J Pharmacol* 339(2-3), 165-71.

Tan, Q et al. (2004a). Estrogen receptor ligands. Part 5: Tue SAR of dihydrobenzoxathiins containing modified basic side chains. *BioorgMed Chem Lett* 14(14), 3747-51.

Tan, Q. et al. (2004b). Estrogen receptor ligands. Part 6: Synthesis and binding affinity of dihydrobenzodithiins. *Bioorg Med Chem Lett* 14(14), 3753-5.

Tiwari-Woodruff, S., e tal (2007). Differential neuroprotective and antiinflammatory effects of estrogen receptor (ERalpha and ERbeta ligand treatment. *Proc NatlAcadSci USA* 104(37), 14813-8.

Traupe, T. et al. (2007). Distinct roles of estrogen receptors alpha and beta mediating acute vasodilation of epicardial coronary arteries. *Hypertension* 49(6)1364-70.

Treeck, O., et al. (2007). Novel estrogen receptor beta transcript variants identified in human breast cancer cells affect cell growth and apoptosis of COS-1 cells. *Mol Cell Endocrinol* 264(1-2) 50-60.

Tremblay, A., et al. (1999). Ligand-independent recruitment of SRC-1 to estrogen receptor beta through phosphorylation of activation function AF-1. *Mol Cell* 3(4), 513-9.

Trotter, B. W., et al. (2006). Design and synthesis of novel isoquinoline-3-nitriles as orally bioavailabe Kv1.5 antagonists for the treatment of atrial fibrillation. *J Med Chem* 49(24), 6954-7.

Ullrich, J. W. et al. (2007). Estrogen receptor beta ligands: design and synthesis of new 2-phenyl-isoindole-1,3-diones, *Bioorg Med Chem Lett* 17(1), 118-22.

Vivacqua, A. et al. (2006); The G protein-coupled receptor GPR30 mediates the proliferative effects induced by 17beta-estradiol and hydroxytamoxifen in endometrial cancer cells, *Mol Endocrinol* 20(3), 631-46.

Vu, A. T, et al. (2007). ERbeta ligands. Part 6; 6H-Chromeno[4,3-b]quinolines as a new series of estrogen receptor beta-selective ligands. *Bioorg Med Chem Lett* 17(14), 4053-6.

Vu, A. T., et al. (2005). ERbeta ligands. Part 4: Synthesis and structure-activity relationships of a series of 2-phenyiquinoline derivatives. *Bioorg Med Chem Lett* 15(20), 4520-5.

Walker, H. A, et al. (2001). The phytoestrogen genistein produces acute nitric oxide-dependent dilation of human forearm vasculature with similar potency to 17beta-estradiol. *Circulation* 103(2), 258-62.

Wang. S. F.. et al, (2005). Genistein derivatives as selective estrogen receptor modulators: sonochemical synthesis and in vivo anti-osteoporotic action. *Bioorg Med Chem* 13(16)>> 4§80-90.

(56) References Cited

OTHER PUBLICATIONS

Wang, Y., et al. (2006), A second binding site for hydroxytamoxifen within the coactivator-binding groove of estrogen receptor beta. *Proc NatlAcctdSci USA* 103(26), 9908-fl.

Waring, R. H., et al. (2008). Phytoestrogens and xenoestrogens: the cotribution of diet and environment to endocrine disruption. *J Steroid Biochem Mol BM* 108(3-5), 213-20.

Weihua, Z., et al. (2002). An endocrine pathway in the prostate, ERbeta, AR, 5alpha-androstane-3beta,17beta-diol, and CYP7B1, regulates prostate growth. *Proc Nati Acad Sci USA* 99(21), 13589-94.

Wildonger, K. L., et al (2006). Tetrahydrofluorenones with conformationally restricted side chains as selective estrogen receptor beta ligands. *Bioorg Med Chem Lett* 16(17), 4462-6.

Wilkening, R. R., et al. (2006a). Estrogen receptor beta-subtype selective tetrahydrofluorenones: use of a fused pyrazole as a phenol bioisostere, *Bioorg Med Chem Lett* 16(15), 3896-901.

Wilkening, R. R. (2006) The discovery of tetrahydrofluorenones as a new class of estrogen receptor beta-subtype selective ligands. *Bioorg Med Chem Lett* 16(13) 3489-94.

Yang, C. et al. (2004a). ERbeta ligands. Part 2: Synthesis and structure-activity relationships of a series of 4-hydroxy-biphenyl-carbaldehyde oxime derivatives, *Bioorg Med Chem* 12(10), 2553-70.

Yang, W., et al. (2004b). Synthesis and structure-activity relationship of 3-arylbenzoxazines as selective estrogen receptor beta agonists, *Bioorg Med Chem Lett* 14(9), 2327-30.

Yoo, J. et al. (2005). Synthesis of an estrogen receptor beta-selective radioligand: 5-[18F]fl-uoro-(2R,3S)-2,3-bis(4-hydroxyphenyl)pentanenitrile and comparison of in vivo distribution with 16alpha-[18F]fluoro-17beta-estradiol. *JMedChem* 48(20), 6366-78.

Yu, H. P., et al. (2006). Salutary effects of estrogen receptor-beta agonist on lung injury after trauma-hemorrhage, *Am J Physiol Lung Cell Mol Physiol* 290(5), L1004-9.

Zhou, H. B, et al. (2005). Synthesis and evaluation of estrogen receptor ligands with bridged oxabicyclic cores containing a diarylethylene motif: estrogen antagonists of unusual structure. *J Med Chem* 48(23), 7261-74.

Munaut "Presence of Estroegen receptor type beta in human retina" Br. J. Opthalmol. 2001; 85: 877-882.

Kaja, "Estrogen protects the inner retina from apoptosis and ischemia-induced loss of Vs1-1L/Homer 1C immunoreactive synoptic connections" Inv. Opthalmol and Vis. Sci, Jul. 2005, vol. 44, No. 7, pp. 3155-3162.

Nakajima "Normalization of retinal vascular permeability in experimental diabetes with genistein" Inv. Opthalmol and Vis. Sci, Aug. 2001, vol. 42, No. 9, pp. 2110-2114.

Ogueta "Estrogen receptor in the human eye: influence of gender and age on gene expression" Inv. Opthalmol and Vis. Sci, Aug. 1999, vol. 40, No. 9, pp. 1906-1911.

Yager, "Mitochondrial estrogen receptors—new insights into specific functions", Trends in Endocr. And Metabol., vol. 18, No. 3, pp. 89-91.

Elloso et al, "Suppression of experimental autoimmune encephalomyelitis using estrogen receptor-selective ligands" Journal of Endocrinology (20050 185, 243-252.

Follettie et al "Organ messenger Ribonucleic Acid and plasma proteome Changes in the Adjuvant-Induced Arthritis model: Responses to Diseas Induction and Therapy with the Estogen Receptor-β Selective Agonist ERB-041" Endocrinology 1472):714-723 (2006).

Harris et al "Characterization of the Biological Roles of the Estrogen Receptors, ERα-Selective Ligand" Endocrinology 143 (11):4172-4177 (2002).

Blizzard, T. A. et al (2004). Estrogen receptor ligands. Part 7: Dihydrobenzoxathiin SERAMs with bicyclic amine side chains. Bioorg Med Chem Lett 14(15), 3861-4.

Diamanti-Kandarakis et al. (1998) "The Effect of a Pure Anti-androgen Receptor Blocker, Flutamide, on the Lipid Profile in the Polycystic Ovary Syndrome". Journal of Clinical Endocrinology and Metabolism, 1998, 83:2699-2705; esp. abstract; p. col. 1, para 3.

Price et al. (2006) "Toremifene for the Prevention of Prostate Cancer in Men with High grade prostatic Intraephlthelial neoplasia; Results of a Double-Blind, Placebo Controlled, Phase iiB Clinical Trial" The Journal of Urology, 176:965-971, abstract only.

Palanki M. et al. (2007) "Development of Prodrug 4-Chloro-3-(5-methyl-3{[4-(2-pyrrolidin-1-yletpyoxy)phenyl]amino)-1,2,4-benzotriazin-7-yl)phenyl Benzoate (TG100801): A Topically Administered Therapeutic Candidate in Clinical Trials for the Treatment of Age-Related Macular Degeneration" J.Med.Chem.

Meyers et al. (2001) "Estrogen Receptor βPotency-Selective Ligands: Structure-Activity Relationship Studies fo Diarylpropionitriles and Their Acetylene and Polar Analogues" J.Med Chem 44, 4230-4251.

Schopfer U. et al (2002) "Toward Selective Erβ Agonists for Central Nervous System Disorders: Synthesis and Characterization of Aryl Benzthiophenes" J.Med.Chem 45, 1399-1401.

Chaum E (2002) "Retinal Neuroprotection by Growth Factors: A Mechanistic Perspecitve" JCB-02s-204.

Pinto de Souza et al., "Synthesis of 3-methyl-1-(2H)-isoquinolinone derivates and their biological activities", Ind. J. Chem. B. Org. 29B(10): 961-965, 1990.

Hellwinkel et al, "Synthesis of heterocycles with MF/A1203 base-systems: 2-arylbenzofurans and 2,3-diarylisoquinolin-1(2H)-ones", Synthesis 9: 1135-1141, 1995, STN Search Report Accession No. 1995:866647.

Veeneman, "Non-steroidal subtype selective endrogens", Current Medicinal Chemistry, vol. 12, No. 9, 2005, pp. 1077-1136.

Lopez-Berestein, "Treatment of systemic fungal infections with liposomal-amphotericin B" Liposomes in the Therapy of Infectious Disease and Cancer, Lopez- Berestein and Fidler (eds.), pp. 317-327, 1989.

Sefton, "Implantable pumps", CRC Crit. Ref. Biomed. Eng. 14:201 (1987).

Abuchowski et al., "Immunosuppressive properties and circulating life of achromobacter glutaminase-asparaginase covalently attached to polyethylene glycol in man", Cancer Treat. Rep. 65: 1077-1081, 1981.

Katre et al., "Chemical modification of recombinant interleukin 2 by polyethylene glycol increases its potency in the murine Meth A sarcoma model" Proc. Natl. Acad. Sci., vol. 84, pp. 1487-1491, 1987.

Cellular and Molecular Immunology (1991) (eds) Abbas, A. K., Lechtiman, A. H., Pober, J. S.; W. B. Saunders Company Philadelphia pp. 340-342.

Schoell, "Epidemiology and Biology of Cervical Cancer". Seminars in Surgical Oncology 1999 16:203-211.

Mahajan et. al.; "T-1032, a cyclic GMP phosphodiesterase-5 inhibitor, acutely blocks physiologic insulin-mediated muscle haemodynamic effects and glucose uptake in vivo", British J Pharmaco, vol. 140(7), 1283-1291, (2003).

Inoue et. al., "Acute and chronic effects of T-1032, a novel selective phosphodiesterase type 5 inhibitor, on monocrotaline-induced pulmonary hypertenstion in rats", Biol. Pharm. Bull., 1422-1426, (2002).

European Search Report of Application No. 11778267.2-1464/2566330 PCT/US2011035206 mailed on Oct. 7, 2013.

European Search Report of Application No. 13174659.6-1460 mailed on Aug. 2, 2013.

STN Search Report, Accession No. 2004:41298.

Roman et al.; "Association of Carotid Atherosclerosis and Left Ventricular Hypertrophy", JACC, vol. 25 No. 1, pp. 83-90, Jan. 1995.

Rose et al.; "The effects of a low-fat dietary intervention and tamoxifen adjuvant therapy on the serum estrogen and sex hormone-binding globulin concentrations of postmenopausal breast cancer patients", Breast Cancer Research and Treatment, 1993, vol. 27:253-262.

Wu et al.; "Meta-Analysis: Dietary Fat Intake, Serum Estrogen Levels, and the irsk of Breast Cancer", Journal of the National Cancer Institute, Mar. 17, 1999, vol. 91, No. 6.

Stanbrough et al.; "Increased expression of genes converting adrenal androgens to testosterone in androgen-independent prostate cancer", Cancer Res, 66: 2815-2825, 2006.

(56) References Cited

OTHER PUBLICATIONS

Qiu et al.; "Crystal structures of the multispecific 17beta-hydroxysteroid dehydrogenase type 5: critical androgen regulation in human peripheral tissues", Mol Endocrinol, 18: 1798-1807, 2004.

Soderberg et al.; "Direct observation of individual endogenous protein complexes in situ by proximity ligation", Nat Methods, 3: 995-1000, 2006.

Penning et al.; "Structure-function of human 3 alpha-hydroxysteroid dehydrogenases: genes and proteins", Mol Cell Endocrinol, 215: 63-72, 2004.

Narayanan et al.; "Cyclin-dependent kinase activity is required for progesterone receptor function: novel role for cyclin A/Cdk2 as a progesterone receptor coactivator", Mol Cell Biol 25(1):264-277, 2005.

Narayanan et al.; "Human progesterone receptor displays cell cycle-dependent changes in transcriptional activity", Mol Cell Biol 25(8):2885-2898, 2005.

Office Action issued on Nov. 11, 2014 for Japanese Application No. 2013-271202.

U.S. Appl. No. 09/519,079, filed Mar. 6, 2000, Robl.

* cited by examiner

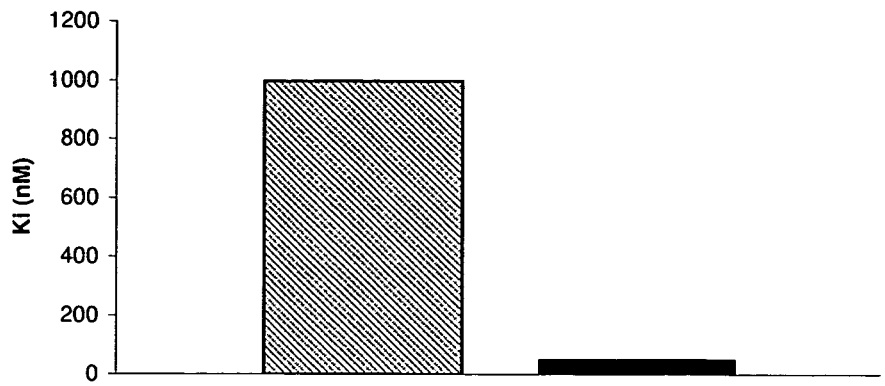
FIGURE 5 A (12b)
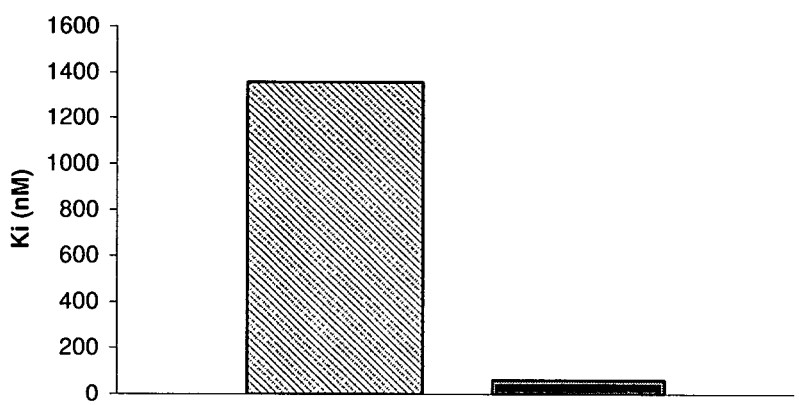
FIGURE 5 B (12f)
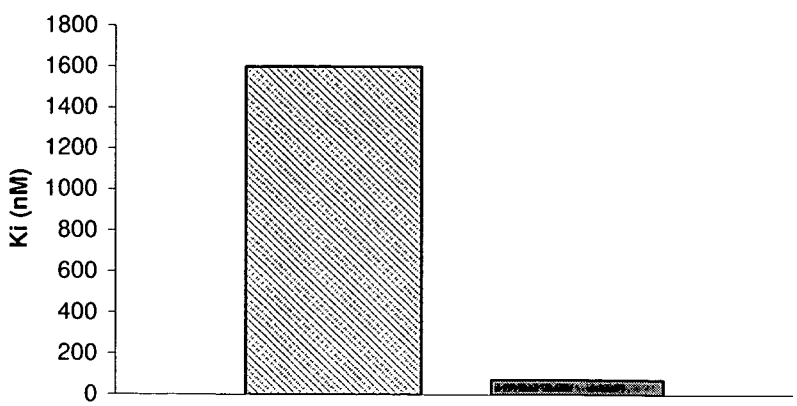
FIGURE 5 C (12h)

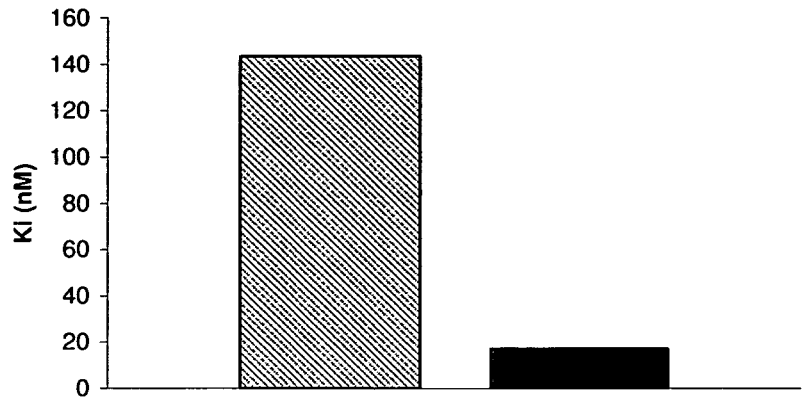
FIGURE 5 D (12p)
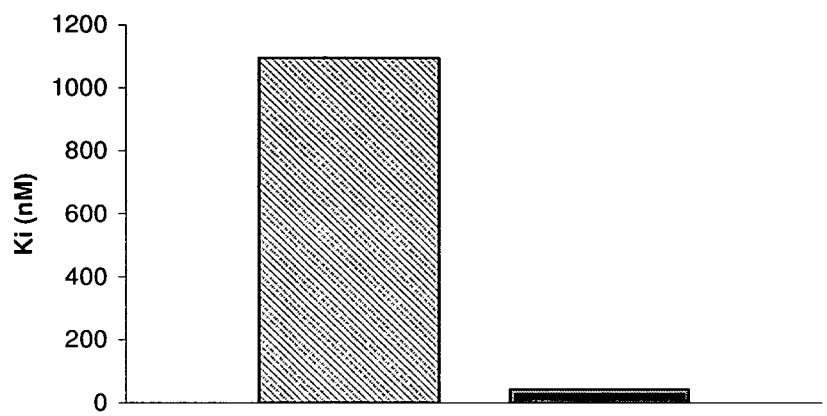
FIGURE 5E (12S)
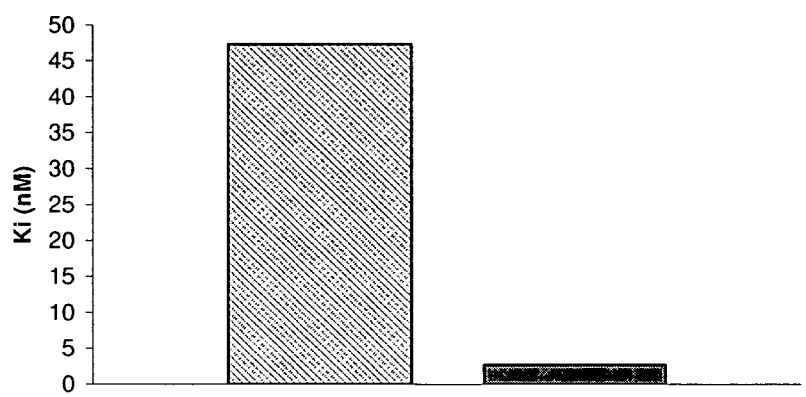
FIGURE 5 F (12u)

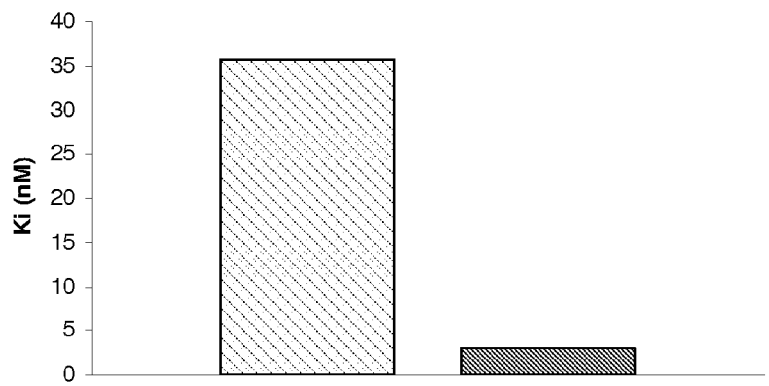
FIGURE 5 G (12y)
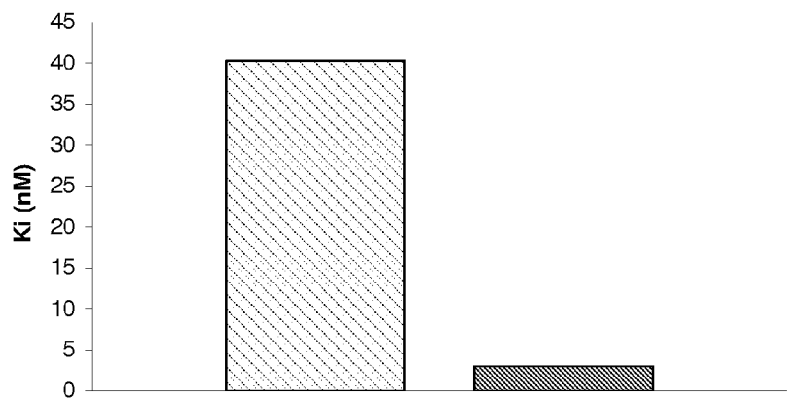
FIGURE 5 H (12z)
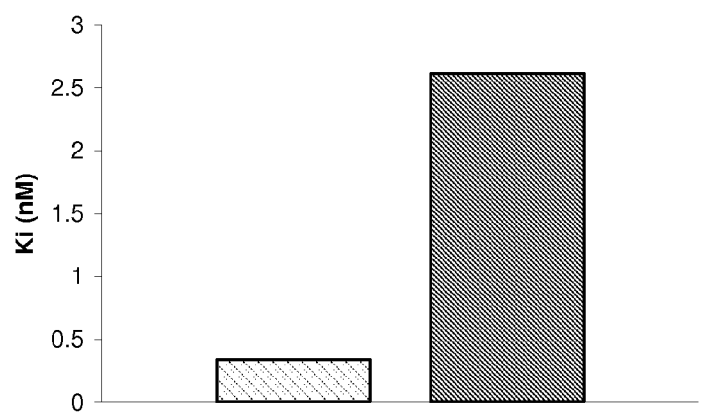
FIGURE 5 I (Estradiol)

NUCLEAR RECEPTOR BINDING AGENTS

CROSS REFERENCE TO RELATED APPLICATIONS

This application is claims priority of U.S. Provisional Application Ser. No. 60/881,476, filed Jan. 22, 2007 and U.S. Provisional Application Ser. No. 60/907,754, filed Apr. 16, 2007.

FIELD OF THE INVENTION

The present invention relates to a novel class of nuclear receptor binding agents (NRBAs). The NRBA are applicable for use in the prevention and/or treatment of a variety of diseases and conditions including, inter alia, prevention and treatment of hormone-related diseases including prostatic diseases, cancers, urogenital, gastrointestinal, inflammation, osteoporosis, peripheral vascular disease, neurological and mood disorders, oxidative damage related diseases such as Parkinson's and stroke, ocular disorders, neuroprotection, arthritis, prostate cancer, benign prostate hyperplasia (BPH), hot flashes, breast cancer, anti-angiogenic diseases, bladder cancer, cardiovascular disease and obesity.

BACKGROUND OF THE INVENTION

The nuclear hormone receptor superfamily of ligand activated transcription factors is present in various tissues, and responsible for a multitude of effects in these tissues.

The nuclear receptor (NR) superfamily presently comprises approximately 48 different proteins, most of which are believed to function as ligand activated transcription factors, exerting widely different biological responses by regulating gene expression. Members of this family include receptors for endogenous small, lipophilic molecules, such as steroid hormones, retinoids, vitamin D and thyroid hormone.

The nuclear receptor (NR) superfamily includes the steroid nuclear receptor subfamily, including the mineralocorticoid receptor (MR) (or aldosterone receptor), the estrogen receptors (ER), ER alpha (ER-α) and ER beta (ER-β), the androgen receptor (AR), the progesterone receptors (PR), glucocorticoid receptors (GR) and others. Also closely related in structure are the estrogen related receptors (ERRs) ERR-alpha, ERR-beta and ERR-gamma. The steroid nuclear receptors perform important functions in the body, some of which are related to the transcriptional homeostasis of electrolyte and water balance, growth, development and wound healing, fertility, stress responses, immunological function, and cognitive functioning. The effects may be mediated by cytosolic, mitochondrial or nuclear events. Accordingly, compounds that modulate (i.e. antagonize, agonize, partially antagonize, partially agonize) the activity of steroid nuclear receptors are important pharmaceutical agents that have specific utility in a number of methods, as well as for the treatment and prevention of a wide range of diseases and disorders modulated by the activity of steroid nuclear receptors. For instance, ER-β is present in, among other tissues, brain, bone, immune system, gastrointestinal tract, lung, ovary, endometrium, prostate, vasculature, urogenital tract, salivary gland, etc. The role of ER beta in these tissues was confirmed by observed phenotypes in ER beta knockout mice. Pathologies in these tissues may be treated by administration of ER-β selective ligands. ER-β in some cases functions as an antagonist of ER-α through heterodimerization with ER-α. For instance, agonists of ER-β may block the proliferative influence of ER-α in tissues such as prostate and breast where ER-α is known to promote neoplasia. In addition to its anti-ER-α mediated growth inhibition, ER-β autonomously inhibits proliferation and promotes differentiation of prostate and other cancers. ER-β is also believed to antagonize the proliferative effects AR in prostatic tissues. Prostatic hypertrophy and hyperplasia/dysplasia may result from a combination of androgenic stimulation of proliferation and/or failed activation of ER-β by locally synthesized estrogens. This hypertrophy or hyperplasia/dysplasia often leads to a variety of prostatic maladies such as BPH, prostatic inflammatory atropy (a precursor to neoplasia), PIN, and CaP. Administration of exogenous ER-β agonists can be expected to provide prostatic anti-proliferation thereby being beneficial in the prevention or treatment of these prostatic diseases. Additionally, decreased side effects can be expected for ER-β selective agents compared to isoform nonselective ligands for treating many of these diseases.

Non-lipid level dependent effects of estrogens on the vasculature are well known as evidenced by the cardioprotection conferred to pre-menopausal women by endogenous estrogen. Estrogens produce a direct vasodilatation (i.e. decreased vascular contractility or vascular tone) on a wide variety of vascular tissues which reduces systemic vascular resistance and improves microvascular circulation. Estrogens also reduce vascular cell proliferation and migration, vasoreactivity and hypertrophic remodeling, and vascular fibrosis. Although ER-α and ER-β are both thought to function in the vasculature, the deletion of ER-β as in knockout mice produces an elevation of blood pressure and moderate cardiac hypertrophy suggesting ER-β has a role in maintenance of vascular tone and proliferation. This cumulatively suggests that ER-β agonists may have therapeutic utility in hypertension, and a variety of other cardiovascular diseases such atherosclerosis and congestive heart failure. Some of the rapid effects of estrogens, particularly in the vasculature are believed to be independent of protein expression (i.e. nongenomic).

Members of the steroid nuclear receptor sub-family exhibit significant homology to each other and possess closely related DNA and ligand binding domains. Given the close similarity in ligand binding domains of the steroid nuclear receptors, it is not surprising that many naturally occurring and synthetic molecules possess the ability to modulate the activity of more than one steroid nuclear receptor.

In some embodiments of this invention, the NRBAs may also have anti-oxidant activity. Many of the processes that occur in vivo such as oxidative phosphorylation result in the production of a variety of reactive oxygen species (ROS) which are free radical and/or unstable molecules such as superoxide ($O_2^-$) and hydrogen peroxide ($H_2O_2$). These ROS react with a variety of endogenous macromolecules such as DNA, lipids, and proteins, oxidizing them and compromising their function. Over time this oxidative damage accumulates, producing or exacerbating various age-related pathologies. Nonlimiting examples include neurodegenerative diseases including Alzheimer's disease, Parkinson's disease, Huntington's disease, multiple sclerosis, amytrophic lateral sclerosis, many types of cancer to include prostate and colon, vascular diseases such as stroke and various age-related dementias, and atherosclerosis, to name just a few oxidative stress related pathologies. Molecules such as ascorbic acid (Vitamin C), polyphenols such as derived from wine, and phytoestrogens such as genistein and coumestrol derived from soybean products have functional groups which can be oxidized by ROS. This chemical reaction returns the ROS to innocuous species such as oxygen ($O_2$) and water, limiting the pathological damage inflicted to the cellular mileau. Additionally, ER-mediated anti-oxidant effects has been observed via induction of the expression of enzymes such as superoxide dismutase (SOD) and catalase that inactivate ROS. Hence, anti-oxidants are thought to exert an anti-aging influence when given on a regular basis. The combination of antioxidant, anti-inflammatory, and antiproliferative/pro-differentiation activities in the NRBAs of this invention may make them particularly potent chemopreventative agents for a variety of age-related diseases.

SUMMARY OF THE PRESENT INVENTION

In one embodiment, this invention provides a nuclear receptor binding agent (NRBA) or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula I:

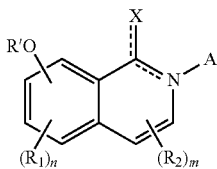

I wherein
A is

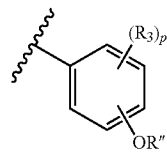

and X is O or S; or

A is nothing, N forms a double bond with the cyclic carbon and X is OH or OCH$_2$CH$_2$-heterocycle in which the heterocycle is a 3-7 member saturated or unsaturated, substituted or unsubstituted heterocyclic ring;

R$_1$, R$_2$, R$_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 member saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

R' is hydrogen, Alk or —COR;

R'' is hydrogen, Alk or —COR;

R$_4$ and R$_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

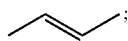;

Q is SO$_3$H, CO$_2$H, CO$_2$R, NO$_2$, tetrazole, SO$_2$NH$_2$ or SO$_2$NHR;
n is an integer between 1-3;
m is an integer between 1-2;
p is an integer between 1-4; and
Alk is a linear alkyl of 1-7 carbons, branched alkyl of 1-7 carbons, or cyclic alkyl of 3-8 carbons.

In one embodiment of the compound of Formula I, A is nothing, N forms a double bond with the cyclic carbon and X is OCH$_2$CH$_2$-heterocycle in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when R$_1$, R$_2$, R$_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when R$_4$ and R$_5$ are independently a 3 to 7 membered heterocycloalkyl, either heterocycle may be substituted or unsubstituted piperidine, pyrrolidine, morpholine or piperazine. In another embodiment, the term "heterocycle" is to be understood to refer to any heterocycle, which may be optionally substituted by one or more substituents, comprising: a halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula I.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula II:

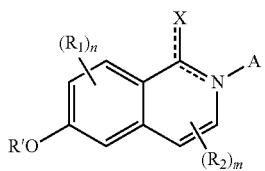

II wherein
A is

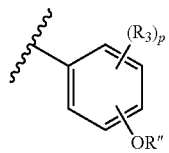

and X is O or S; or
A is nothing, N forms a double bond with the cyclic carbon and X is OH or OCH$_2$CH$_2$-heterocycle in which the heterocycle is a 3-7 membered saturated or unsaturated, substituted or unsubstituted heterocyclic ring;

$R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 membered cycloalkyl, a 3 to 7 member cycloalkyl, heterocycloalkyl, aryl or heteroaryl group;

Z is O, NH, CH$_2$ or $\diagup\!\!\!\diagdown\!\!\!\diagup$ ;

Q is SO$_3$H, CO$_2$H, CO$_2$R, NO$_2$, tetrazole, SO$_2$NH$_2$ or SO$_2$NHR;

n is an integer between 1-3;

m is an integer between 1-2;

p is an integer between 14; and

Alk is a linear alkyl of 1-7 carbons, branched alkyl of 1-7 carbons or cyclic alkyl of 3-8 carbons.

In one embodiment of the compound of Formula II, A is nothing, N forms a double bond with the cyclic carbon and X is OCH$_2$CH$_2$-heterocycle in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula II.

In another embodiment this invention provides a NRBA, its prodrug, analog, isomer, metabolite, derivative, pharmaceutically acceptable salt, pharmaceutical product, polymorph, crystal, impurity, N-oxide, ester, hydrate or any combination thereof, represented by the structure of Formula III:

III wherein

A is and X is O or S; or

A is nothing and N forms a double bond with the cyclic carbon and X is OH or OCH$_2$CH$_2$-heterocycle in which the heterocycle is a 3-7 membered saturated or unsaturated, substituted or unsubstituted heterocyclic ring;

$R_1$, $R_2$, $R_3$, $R_6$, $R_7$, $R_8$, $R_9$, $R_{10}$, $R_{11}$ are independently selected from hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$, or OH;

R' is hydrogen, Alk, or COR;

R" is hydrogen, Alk, or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or $\diagup\!\!\!\diagdown\!\!\!\diagup$ ;

Q is SO$_3$H, CO$_2$H, CO$_2$R, NO$_2$, tetrazole, SO$_2$NH$_2$, or SO$_2$NHR; and Alk is a linear alkyl of 1-7 carbons, branched alkyl of 1-7 carbons, or cyclic alkyl of 3-8 carbon;

wherein if A is

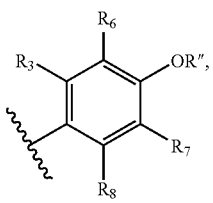

X is an oxo group and $R_{10}$ is a benzene ring, then $R_9$ is not COOR, if R is an ester residue or $CONR_4R_5$.

In one embodiment of the compound of Formula III, A is nothing, N forms a double bond with the cyclic carbon and X is $OCH_2CH_2$-heterocycle in which the heterocycle is a 3-7 membered heterocycloalkyl. In one embodiment, when X is $OCH_2CH_2$-heterocycle, the heterocycle is substituted or unsubstituted piperidine, pyrrolidine, morpholine or piperazine. In another embodiment, when $R_1$, $R_2$, $R_3$, $R_6$, $R_7$, $R_8$, $R_9$, $R_{10}$, $R_{11}$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, haloalkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula III.

In one embodiment, the present invention provides a NRBA, its prodrug, analog, isomer, metabolite, derivative, pharmaceutically acceptable salt, pharmaceutical product, polymorph, crystal, impurity, N-oxide, ester, hydrate or any combination thereof, represented by the structure of Formula X:

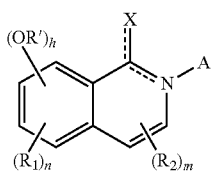

wherein
A is

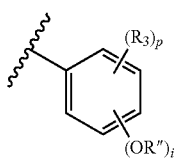

and X is O or S; or

A is nothing, N forms a double bond with the cyclic carbon and X is OH or $OCH_2CH_2$-heterocycle in which the heterocycle is a 3-7 membered saturated or unsaturated, substituted or unsubstituted heterocyclic ring;

$R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NR$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$, or OH;

R' is hydrogen, Alk or COR;
R" is hydrogen, Alk or COR;
$R_4$ and $R_5$ are independently hydrogen, phenyl, an alkyl group of 1 to 6 carbon atoms, a 3 to 7 membered cycloalkyl, a 3 to 7 member cycloalkyl, heterocycloalkyl, aryl or heteroaryl group;
Z is O, NH, CH$_2$ or

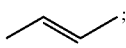

Q is SO$_3$H, CO$_2$H, CO$_2$R, NO$_2$, tetrazole, SO$_2$NH$_2$ or SO$_2$NHR;
h is an integer between 0-3;
i is an integer between 0-4;
n is an integer between 1-4;
m is an integer between 1-2;
p is an integer between 1-5; and
Alk is a linear alkyl of 1-7 carbons, branched alkyl of 1-7 carbons or cyclic alkyl of 3-8 carbons.

In one embodiment of the compound of Formula X, A is nothing, N forms a double bond with the cyclic carbon and X is $OCH_2CH_2$-heterocycle in which the heterocycle is a 3-7 membered heterocycloalkyl. In one embodiment, when X is $OCH_2CH_2$-heterocycle, the heterocycle is substituted or unsubstituted piperidine, pyrrolidine, morpholine or piperazine. In another embodiment, when $R_1$, $R_2$, and $R_3$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula X.

In one embodiment, this invention provides a method of improving a lipid profile in a subject, the method comprising administering a NRBA of this invention, or combinations thereof, to said subject.

In one embodiment, improving a lipid profile in a subject comprises reducing circulating triglyceride levels, low density lipoprotein (LDL) cholesterol levels, or a combination thereof. In another embodiment, improving a lipid profile in a subject comprises increasing circulating high density lipoprotein (HDL) cholesterol levels in the subject. In another embodiment, improving a lipid profile in a subject comprises reducing the ratio of LDL levels to HDL levels in the subject. In some embodiments, such a subject may further suffer from atherosclerosis and its associated diseases, premature aging, Alzheimer's disease, stroke, toxic hepatitis, viral hepatitis, peripheral vascular insufficiency, renal disease, hyperglycemia, or any combination thereof.

In one embodiment, this invention provides a method of treating atherosclerosis, cardiovascular disorders, cerebrovascular disorders, or peripheral vascular disorders, in a subject, comprising administering to said subject a NRBA or its pharmaceutically acceptable salt, hydrate, N-oxide, or any combination thereof.

In one embodiment, this invention provides a method of treating ischemia in a tissue of a subject, comprising administering to said subject a NRBA or its pharmaceutically acceptable salt, hydrate, N-oxide, or any combination thereof.

In another embodiment this invention provides a method of (i) treating, delaying onset, reducing the incidence of or reducing the severity of osteoporosis, bone fractures and/or loss of bone mineral density (BMD) in a subject; (ii) treating, delaying onset, reducing the incidence of or reducing the severity of cardiovascular disease in a subject: (iii) ameliorating symptoms and/or clinical complications associated with menopause in a female subject; (iv) treating, delaying onset, reducing the incidence of or reducing the severity of neurodegenerative diseases including Alzheimer's disease and Parkinson's disease; (v) treating, delaying onset, reducing the incidence of or reducing the severity of hot flashes, breast tenderness, and/or hair loss in a subject; (vi) treating, delaying onset, reducing the incidence of, reducing or delaying relapse of or reducing the severity of prostate cancer in a subject and preventing metastasis from a prostate cancer; (vii) treating, delaying onset, reducing the incidence of or reducing the number of precancerous precursors of prostate adenocarcinoma lesions; (viii) treating, delaying onset, reducing the incidence of, reducing or delaying relapse of or reducing the severity of breast cancer in a subject; (ix) treating, delaying onset, reducing the incidence of, reducing or delaying relapse of or reducing the severity of colon cancer in a subject; (x) treating, delaying onset, reducing the incidence of, reducing or delaying relapse of or reducing the severity of leukemia or lymphoma in a subject; (xi) treating, delaying onset, reducing the incidence of, reducing or delaying relapse of or reducing the severity of bladder cancer in a subject; (xii) treating, delaying onset, reducing the incidence of or reducing the severity of inflammation in a subject; (xiii) treating, delaying onset, reducing the incidence of or reducing the severity of neurological disorders in a subject; (xiv) treating, delaying onset, reducing the incidence of or reducing the severity of ocular disorders in a subject, (xv) treating, suppressing, inhibiting or reducing the risk of atherosclerosis in a subject; (xvi) treating, delaying onset, reducing the incidence of or reducing the severity of ischemia in a subject; (xvii) treating, delaying onset, reducing the incidence of or reducing the severity of oxidative injury in a subject; using the NRBAs of the invention.

In some embodiments, this invention provides a method of treating, ameliorating or preventing generation of reactive oxygen species-mediated damage in a subject, comprising the step of administering a NRBA of this invention to the subject. According to this aspect, and in one embodiment, the damage being treated, ameliorated or prevented is as a consequence of production of reactive oxygen intermediates and administration of the NRBA promotes or enhances the activity of cellular superoxide dismutase catalase, or other antioxidant enzymes.

In some embodiments, the methods of this invention may be carried out via the administration of a composition comprising the NRBAs of the invention.

BRIEF DESCRIPTION OF THE DRAWINGS

FIG. 5 depicts binding constants of 12b (A), 12f (B), 12h (C), 12p (D), 12s (E), 12u (F), 12y (G), 12z (H), and estradiol (I) to ER-α (dashed) and ER-β (full).

DETAILED DESCRIPTION OF THE PRESENT INVENTION

Figure 1:
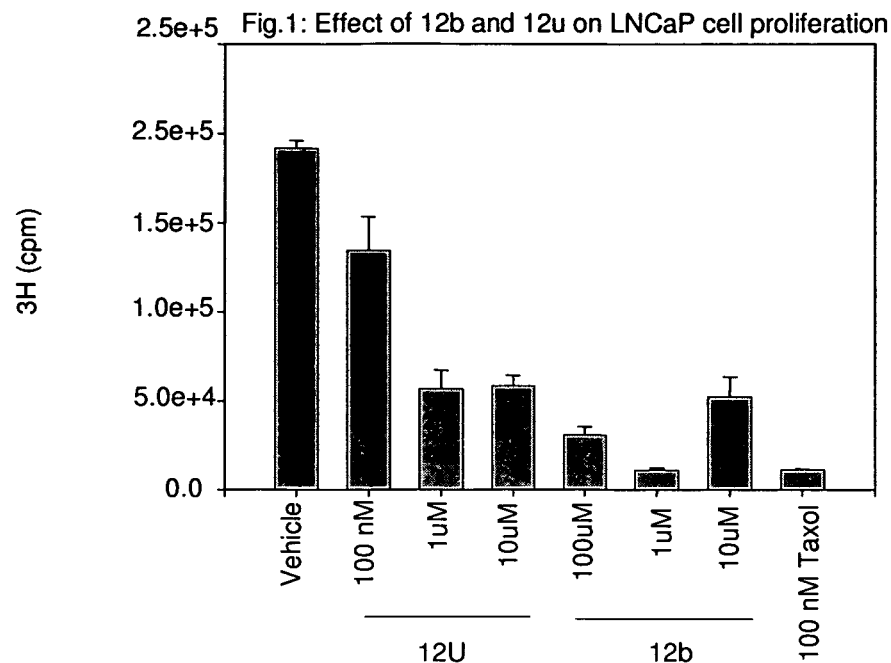
FIG. 1 depicts the effect of 12b and 12u on LNCaP (prostate cancer) cell proliferation.

The present invention provides novel NRBAs and compositions comprising the same.

This invention provides NRBAs. In one embodiment, a NRBA refers to a compound that affects estrogen receptor activity. In one embodiment, a NRBA exhibits activity as an agonist, or, in another embodiment, as an antagonist, or in another embodiment, as a partial agonist, or in another embodiment, as a partial antagonist of the estrogen receptor. In one embodiment, the NRBA exerts its effects on the estrogen receptor (e.g., ERα, ERβ or ERRs) in a tissue-dependent manner. In some embodiments, the NRBA of this invention can act as estrogen receptor agonists in some tissues (e.g., bone, brain, and/or heart) and as antagonists in other tissue types, for example in the breast and/or uterine lining.

In one embodiment, a NRBA of this invention will have an $IC_{50}$ or $EC_{50}$ with respect to ERα and/or ERβ of up to about 10 μM as determined using the ERα and/or ERβ transactivation assays, as known in the art, or, in other embodiments, as described herein. In some embodiments, the NRBA exhibit $EC_{50}$ or $IC_{50}$ values (as agonists or antagonists) of about 5 μM, or less than about 5 μM. Representative compounds of the present invention have been discovered to exhibit agonist or antagonist activity with respect to the estrogen receptor. Compounds of the present invention exhibit, in some embodiments, an antagonist or agonist $IC_{50}$ or $EC_{50}$ with respect to ERα and/or ERβ of about 5 μM or less than about 5 μM, or in some embodiments, up to about 500 nM, or in other embodiments, up to about 1 nM, as measured in ERα and/or ERβ transactivation assays. The term "$IC_{50}$" refers, in some embodiments, to a concentration of the NRBA which reduces the activity of a target (e.g., ERα or ERβ) to half-maximal level. The term "$EC_{50}$" refers, in some embodiments, to a concentration of the NRBA that produces a half-maximal effect.

In some embodiments of this invention, the compounds of this invention are bisphenolic agents. In some embodiments of this invention, the compounds of this invention are mono- or nonphenolic agents. In some embodiments of this invention, the compounds of this invention are substituted isoquinolines. In some embodiments of this invention, the compounds of this invention are substituted isoquinolinones. In some embodiments of this invention, the compounds of this invention are substituted dihydroisoquinolinones. In some embodiments of this invention, the NRBAs have selectivity for ER-β. In some embodiment of this invention, the NRBAs are agonists of ER-β. In some embodiment of this invention, the NRBAs are partial agonists of ER-β. In some embodiment of this invention, the NRBAs are antagonists of ER-β. In some embodiments of this invention, the NRBAs have antioxidant activity. In some embodiments, the antioxidant activity is independent of the nuclear receptor binding activity. In some embodiments, the NRBAs of this invention exhibit non-genomic signaling in cells. In some embodiments, the NRBAs of this invention exhibit mitochondrial signaling.

In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula I:

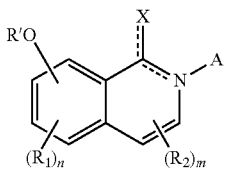

wherein
A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic rings are optionally substituted by 1 to 5 substituents independently selected from $R_3$ or OR"; and X is O or S; or A is nothing, N forms a double bond with the cyclic carbon and X is OH or $OCH_2CH_2$-heterocycle in which the heterocycle is a 3-7 membered saturated or unsaturated substituted or unsubstituted heterocyclic ring;

$R_1$, $R_2$ and $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle, in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, heteroaryl, phenyl, benzyl, -Ph-CF$_3$, -Ph-CH$_2$F, -Ph-CHF$_2$, -Ph-CF$_2$CF$_3$, halogen, alkenyl, CN, NO$_2$, or OH;

R' is hydrogen, Alk, or COR;
R" is hydrogen, Alk, or COR;
$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;
Z is O, NH, CH$_2$ or

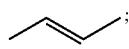

Q is SO$_3$H, CO$_2$H, CO$_2$R, NO$_2$, tetrazole, SO$_2$NH$_2$ or SO$_2$NHR;
n is an integer of between 1-3;
m is an integer between 1-2; and
Alk is a linear alkyl of 1-7 carbons, branched alkyl of 1-7 carbons, or cyclic alkyl of 3-8 carbons.

In one embodiment, the NRBA is represented by the structure of Formula I:

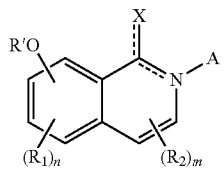

wherein A, X, $R_1$, $R_2$, R', n and m are as described above, wherein if X is oxo and A is phenyl, then A is not substituted with:
  NHCOR and halogen without further substitution, or
  NHCOR and an alkyl without further substitution. According to this aspect, such a NRBA is referred to herein as "a compound of Formula 1".

In one embodiment, A is

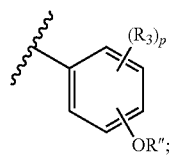

p is an integer between 1-4; R" is hydrogen, Alk, or COR; $R_3$ is hydrogen, aldehyde, COOH, C(=N)—OH, CHNOH, CH=CHCO$_2$H, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle, in which the heterocycle is a 3-7 membered saturated or unsaturated, substituted or unsubstituted heterocyclic ring.

In one embodiment of the compound of Formula I, A is nothing, N forms a double bond with the cyclic carbon and X is OCH$_2$CH$_2$-heterocycle in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula I.

In another embodiment of the compound of Formula I, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH. In another embodiment, $R_2$ is —CH=CH—CH$_3$. In another embodiment, $R_2$ is —CH=CH—COOEt. In another embodiment $R_1$ is a hydroxyl group. In another embodiment $R_1$ is O—(CO)-Ph-CF$_3$. In another embodiment $R_1$ is COOH. In another embodiment $R_1$ is COOMe. In another embodiment $R_1$ is hydrogen. In another embodiment $R_1$ is a hydroxyl group and n is 1. In another embodiment $R_1$ is in position 8 of the isoquinolinone group. In another embodiment $R_3$ is halogen. In another embodiment $R_3$ is hydrogen. In another embodiment R' is H. In another embodiment R' is a methyl group. In another embodiment R' is a COMe group. In another embodiment R" is H. In another embodiment R" is a methyl group. In another embodiment R" is a COMe group.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula II:

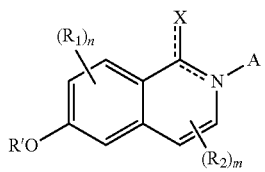

II wherein
A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic ring are optionally substituted by 1 to 5 substituents independently selected from $R_3$ or OR"; and X is O or S; or A is nothing, N forms a double bond with the cyclic carbon and X is OH or OCH$_2$CH$_2$-heterocycle in which the heterocycle is a 3-7 membered saturated or unsaturated, substituted or unsubstituted heterocyclic ring;

$R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

R' is hydrogen, Alk or COR;
R" is hydrogen, Alk or COR;
$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;
Z is O, NH, CH$_2$ or

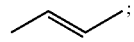;

Q is SO$_3$H, CO$_2$R, CO$_2$R, NO$_2$, tetrazole, SO$_2$NH$_2$ or SO$_2$NHR;
n is an integer between 1-3;
m is an integer between 1-2;
p is an integer between 1-4; and
Alk is a linear alkyl of 1-7 carbons, branched alkyl of 1-7 carbons, or cyclic alkyl of 3-8 carbons.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula II:

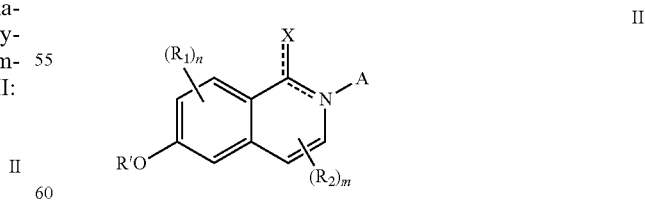

II

A, X, $R_1$, $R_2$, R', n and m are as described above, wherein if X is oxo and A is phenyl, then A is not substituted with:
NHCOR and halogen without further substitution, or
NHCOR and an alkyl without further substitution. According to this aspect, such a NRBA is referred to herein as "a compound of Formula 2".

In one embodiment, A is

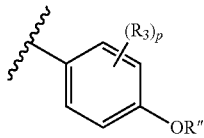

p is an integer between 1-4; R" is hydrogen, Alk, or COR; $R_3$ is hydrogen, aldehyde, COOH, C(=N)—OH, CHNOH, CH=CHCO$_2$H, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle, in which the heterocycle is a 3-7 membered saturated or unsaturated, substituted or unsubstituted heterocyclic ring;

In one embodiment of the compound of Formula II, A is nothing, N forms a double bond with the cyclic carbon and X is OCH$_2$CH$_2$-heterocycle, in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula II.

In another embodiment of the compound of Formula II, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—CH$_3$. In another embodiment, $R_2$ is —CH=CH$_2$. In another embodiment, $R_2$ is —CH=CH—COOEt. In another embodiment $R_1$ is O—(CO)-Ph-CF$_3$. In another embodiment $R_1$ is COOH. In another embodiment $R_1$ is COOMe. In another embodiment $R_1$ is a hydroxyl group. In another embodiment $R_1$ is hydrogen. In another embodiment $R_1$ is a hydroxyl group and n is 1. In another embodiment $R_1$ is in position 8 of the isoquinolinone group. In another embodiment $R_3$ is halogen. In another embodiment $R_3$ is hydrogen. In another embodiment R' is H. In another embodiment R' is a methyl group. In another embodiment R' is a COMe group. In another embodiment R" is H. In another embodiment R" is a methyl group. In another embodiment R" is a COMe group.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula III:

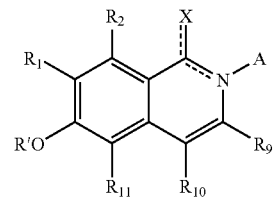

wherein

A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic ring are optionally substituted by 1 to 5 substituents independently selected from $R_3$ or OR"; and X is O or S; or A is nothing and N forms a double bond with the cyclic carbon and X is OH or OCH$_2$CH$_2$-heterocycle in which the heterocycle is a 3-7 membered saturated or unsaturated, substituted or unsubstituted heterocyclic ring;

$R_1$, $R_2$, $R_3$, $R_9$, $R_{10}$, $R_{11}$ are independently selected from hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$, or OH;

R' is hydrogen, Alk, or COR;

R" is hydrogen, Alk, or COR $R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$, or

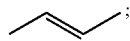

Q is SO$_3$H, CO$_2$H, CO$_2$R, NO$_2$, tetrazole, SO$_2$NH$_2$, or SO$_2$NHR; and Alk is a linear alkyl of 1-7 carbons, branched alkyl of 1-7 carbons, or cyclic alkyl of 3-8 carbons;

wherein if A is a phenyl, X is an oxo group and $R_{10}$ is a benzene ring, then:

$R_9$ is not COOR, if R is a hydrogen or an ester; or $R_9$ is not CONR$_4$R$_5$, if $R_4$ and $R_5$ are as described above.

In another embodiment this invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula III:

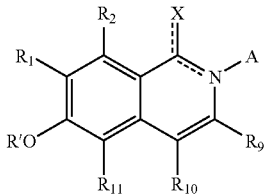

A, X, $R_1$, $R_2$, $R_9$, $R_{10}$, $R_{11}$ and R' are as described above, wherein if X is oxo and A is phenyl, then A is not substituted with:
NHCOR and halogen without further substitution; or
NHCOR and an alkyl without further substitution. According to this aspect, such a NRBA is referred to herein as "a compound of Formula 3".

In one embodiment, A is

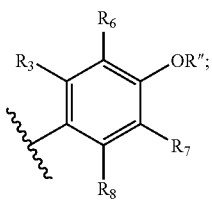

$R_3$, $R_6$, $R_7$, $R_8$, are independently selected from hydrogen, aldehyde, COOH, —C(=NH)—OH, CHNOH, CH=CHCO$_2$H, CH=CHCO$_2$R—CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring; R" is hydrogen, Alk, or COR;
wherein if A is

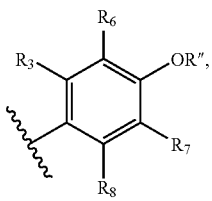

X is an oxo group and $R_{10}$ is a benzene ring, then $R_9$ is not COOR, if R is an ester residue or CONR$_4$R$_5$. In one embodiment of the compound of Formula III, A is nothing, N forms a double bond with the cyclic carbon and X is OCH$_2$CH$_2$-heterocycle in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, wherein R is as defined for Formula III.

In another embodiment of the compound of Formula III, $R_{10}$ is a halogen. In another embodiment $R_{10}$ is a bromide. In another embodiment $R_{10}$ is a chloride. In another embodiment $R_2$ is a fluoride. In another embodiment $R_{10}$ is an iodide. In another embodiment $R_{10}$ is hydrogen. In another embodiment $R_{10}$ is a cyano. In another embodiment, $R_{10}$ is a phenyl. In another embodiment, $R_{10}$ is —CH=CH—CH$_3$. In another embodiment, $R_{10}$ is —CH=CH$_2$. In another embodiment, $R_{10}$ is —CH=CH—COOEt. In another embodiment $R_2$ is a hydroxyl group. In another embodiment $R_2$ is hydrogen. In another embodiment $R_2$ is O—(CO)-Ph-CF$_3$. In another embodiment $R_2$ is COOH. In another embodiment $R_2$ is COOMe. In another embodiment $R_7$ is a halogen. In another embodiment $R_3$, $R_6$, $R_7$ and $R_8$ are hydrogens. In another embodiment R' is H. In another embodiment R' is a methyl group. In another embodiment R' is a COMe. In another embodiment R" is H. In another embodiment R" is a methyl group. In another embodiment R" is COMe. In another embodiment $R_1$, $R_3$, $R_6$, $R_7$, $R_8$, $R_9$ and $R_{11}$ are hydrogens.

In one embodiment, the compound of Formula I may be represented by the structure of Formula IV:

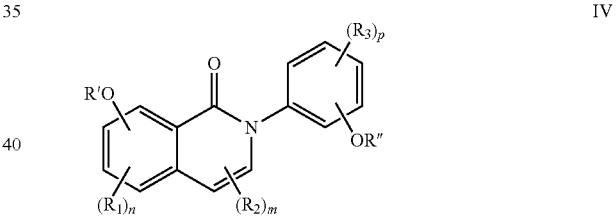

wherein $R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

![alkenyl structure]

Q is SO$_3$H, CO$_2$H, CO$_2$R, NO$_2$, tetrazole, SO$_2$NH$_2$ or SO$_2$NHR;
n is an integer between 1-3;
m is an integer between 1-2;
p is an integer between 1-4; and
Alk is a linear alkyl of 1-7 carbons, branched alkyl of 1-7 carbons, or cyclic alkyl of 3-8 carbons.

In another embodiment of the compound of Formula IV, R$_2$ is a halogen. In another embodiment R$_2$ is a bromide. In another embodiment R$_2$ is a chloride. In another embodiment R$_2$ is a fluoride. In another embodiment R$_2$ is an iodide. In another embodiment R$_2$ is hydrogen. In another embodiment R$_2$ is a cyano. In another embodiment, R$_2$ is a phenyl. In another embodiment, R$_2$ is —CH=CH—CH$_3$. In another embodiment, R$_2$ is —CH=CH$_2$. In another embodiment, R$_2$ is —CH=CH—COOEt. In another embodiment R$_1$ is O—(CO)-Ph-CF$_3$. In another embodiment R$_1$ is COOH. In another embodiment R$_1$ is COOMe. In another embodiment R$_1$ is a hydroxyl group. In another embodiment R$_1$ is hydrogen. In another embodiment R$_3$ is halogen. In another embodiment R$_3$ is hydrogen. In another embodiment R' is H. In another embodiment R' is a methyl group. In another embodiment R' is COMe. In another embodiment R" is H. In another embodiment R" is a methyl group. In another embodiment R" is COMe. In another embodiment, when R$_1$, R$_2$, R$_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when R$_4$ and R$_5$ are independently a 3 to 7 membered heterocycloalkyl, either heterocycle may be substituted or unsubstituted piperidine, pyrrolidine, morpholine or piperazine. In another embodiment, the heterocycles are optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula IV.

In another embodiment, the compound of formula II may be represented by the structure of Formula V:

![Formula V structure]

wherein
R$_1$, R$_2$, R$_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;
R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;
R' is hydrogen, Alk or COR;
R" is hydrogen, Alk or COR;
R$_4$ and R$_5$ are independently hydrogen, phenyl, benzyl, an alkyl group of 1 to 6 carbon atoms, a 3 to 7 member cycloalkyl, heterocycloalkyl, aryl or heteroaryl group;
Z is O, NH, CH$_2$ or ![alkenyl structure]

Q is SO$_3$H, CO$_2$H, CO$_2$R, NO$_2$, tetrazole, SO$_2$NH$_2$ or SO$_2$NHR;
n is an integer between 1-3;
m is an integer between 1-2;
p is an integer between 1-4; and
Alk is a linear alkyl of 1-7 carbons, branched alkyl of 1-7 carbons or cyclic alkyl of 3-8 carbons.

In another embodiment of the compound of Formula V, R$_2$ is a halogen. In another embodiment R$_2$ is a bromide. In another embodiment R$_2$ is a chloride. In another embodiment R$_2$ is a fluoride. In another embodiment R$_2$ is an iodide. In another embodiment R$_2$ is hydrogen. In another embodiment R$_2$ is a cyano. In another embodiment, R$_2$ is a phenyl. In another embodiment, R$_2$ is —CH=CH—CH$_3$. In another embodiment, R$_2$ is —CH=CH$_2$. In another embodiment, R$_2$ is —CH=CH—COOEt. In another embodiment R$_1$ is O—(CO)-Ph-CF$_3$. In another embodiment R$_1$ is COOH. In another embodiment R$_1$ is COOMe. In another embodiment R$_1$ is a hydroxyl group. In another embodiment R$_1$ is hydrogen. In another embodiment R$_3$ is halogen. In another embodiment R$_3$ is hydrogen. In another embodiment R' is H. In another embodiment R' is a methyl group. In another embodiment R' is a COMe group In another embodiment R" is H. In another embodiment R" is a methyl group. In another embodiment R" is a COMe. In another embodiment, when R$_1$, R$_2$, R$_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when R$_4$ and R$_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy; and R is as defined for Formula V.

In another embodiment, the compound of formula III may be represented by the structure of Formula VI:

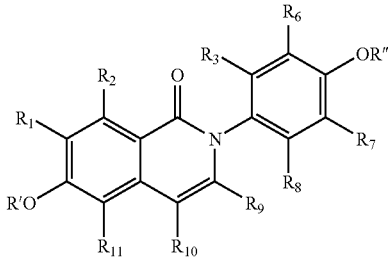

wherein $R_1$, $R_2$, $R_3$, $R_6$, $R_7$, $R_8$, $R_9$, $R_{10}$, $R_{11}$ are independently selected from hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

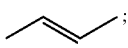

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH and;

and Alk is a linear alkyl of 1-7 carbons, branched alkyl of 1-7 carbons or cyclic alkyl of 3-8 carbons;

Wherein, if $R_{10}$ is a benzene ring, then:

$R_9$ is not COOR, if R is hydrogen or an ester residue; or $R_9$ is not CONR$_4$R$_5$, if $R_4$ and $R_5$ are as described above.

In another embodiment of the compound of Formula VI, $R_{10}$ is a halogen. In another embodiment $R_{10}$ is a bromide. In another embodiment $R_{10}$ is a chloride. In another embodiment $R_2$ is a fluoride. In another embodiment $R_{10}$ is an iodide. In another embodiment $R_{10}$ is hydrogen. In another embodiment $R_{10}$ is a cyano. In another embodiment, $R_{10}$ is a phenyl. In another embodiment, $R_{10}$ is —CH=CH—CH$_3$. In another embodiment, $R_{10}$ is —CH=CH$_2$. In another embodiment, $R_{10}$ is —CH=CH—COOEt. In another embodiment $R_2$ is a hydroxy group. In another embodiment $R_2$ is hydrogen. In another embodiment $R_2$ is O—(CO)-Ph-CF$_3$. In another embodiment $R_2$ is COOH. In another embodiment $R_2$ is COOMe. In another embodiment $R_7$ is a halogen. In another embodiment $R_3$, $R_6$, $R_7$ and $R_8$ are hydrogens. In another embodiment R' is H. In another embodiment R' is a methyl group. In another embodiment R' is a COMe. In another embodiment R" is H. In another embodiment R" is a methyl group. In another embodiment R" is COMe. In another embodiment $R_1$, $R_3$, $R_6$, $R_7$, $R_8$, $R_9$ and $R_{11}$ are hydrogens. In another embodiment, when $R_1$, $R_2$, $R_3$, $R_6$, $R_7$, $R_8$, $R_9$, $R_{10}$, $R_{11}$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, wherein R is as defined for Formula VI.

In one embodiment, the compound of formula I may be represented by the structure of Formula VII:

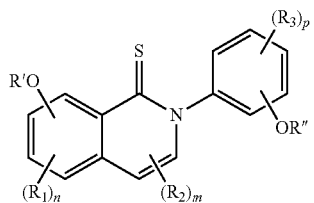

wherein $R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated, substituted or unsubstituted heterocyclic ring;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

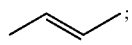

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

n is an integer between 1-3;

m is an integer between 1-2;

p is an integer between 1-4; and

Alk is a linear alkyl of 1-7 carbons, branched alkyl of 1-7 carbons or cyclic alkyl of 3-8 carbons.

In another embodiment of the compound of Formula VII, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—CH$_3$. In another embodiment, $R_2$ is —CH=CH$_2$. In another embodiment, $R_2$ is —CH=CH—COOEt. In another embodiment $R_1$ is O—(CO)-Ph-CF$_3$. In another embodiment $R_1$ is COOH. In another embodiment $R_1$ is COOMe. In another embodiment $R_1$ is a hydroxyl group. In another embodiment $R_1$ is hydrogen. In another embodiment $R_3$ is halogen. In another embodiment $R_3$ is hydrogen. In another embodiment R' is H. In another embodiment R' is a methyl group. In another embodiment R' is COMe. In another embodiment R" is H. In another embodiment R" is a methyl group. In another embodiment R" is a COMe. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, and R is as defined for Formula VII.

In another embodiment, the compound of formula II may be represented by the structure of Formula VIII:

wherein $R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

n is an integer between 1-3;

m is an integer between 1-2;

p is an integer between 1-4; and

Alk is a linear alkyl of 1-7 carbons, branched alkyl of 1-7 carbons or cyclic alkyl of 3-8 carbons.

In another embodiment of the compound of Formula VIII, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—CH$_3$. In another embodiment, $R_2$ is —CH=CH$_2$. In another embodiment, $R_2$ is —CH=CH—COOEt. In another embodiment $R_1$ is O—(CO)-Ph-CF$_3$. In another embodiment $R_1$ is COOH. In another embodiment $R_1$ is COOMe. In another embodiment $R_1$ is a hydroxyl group. In another embodiment $R_1$ is hydrogen. In another embodiment $R_3$ is hydrogen. In another embodiment $R_3$ is halogen. In another embodiment R' is H. In another embodiment R' is a methyl group. In another embodiment R' is COMe. In another embodiment R" is H. In another embodiment R" is a methyl group. In another embodiment R" is COMe. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, and R is as defined for Formula VIII.

In another embodiment, the compound of formula III may be represented by the structure of Formula IX:

wherein $R_1$, $R_2$, $R_3$, $R_6$, $R_7$, $R_8$, $R_9$, $R_{10}$, $R_{11}$ are independently selected from hydrogen, aldehyde, COOH, —C(=NH)—

OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

R$_4$ and R$_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

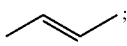

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH; and Alk is a linear alkyl of 1-7 carbons, branched alkyl of 1-7 carbons or cyclic alkyl of 3-8 carbons.

In another embodiment of the compound of Formula IX, R$_{10}$ is a halogen. In another embodiment R$_{10}$ is a bromide. In another embodiment R$_{10}$ is a chloride. In another embodiment R$_2$ is a fluoride. In another embodiment R$_{10}$ is an iodide. In another embodiment R$_{10}$ is hydrogen. In another embodiment R$_{10}$ is a cyano. In another embodiment, R$_{10}$ is a phenyl. In another embodiment, R$_{10}$ is —CH=CH—CH$_3$. In another embodiment, R$_{10}$ is —CH=CH$_2$. In another embodiment, R$_{10}$ is —CH=CH—COOEt. In another embodiment R$_2$ is a hydroxyl group. In another embodiment R$_2$ is hydrogen. In another embodiment R$_2$ is O—(CO)-Ph-CF$_3$. In another embodiment R$_2$ is COOH. In another embodiment R$_2$ is COOMe. In another embodiment R$_7$ is a halogen. In another embodiment R$_3$, R$_6$, R$_7$ and R$_8$ are hydrogens. In another embodiment R' is H. In another embodiment R' is a methyl group. In another embodiment R' is a COMe. In another embodiment R" is H. In another embodiment R" is a methyl group. In another embodiment R" is COMe. In another embodiment R$_1$, R$_3$, R$_6$, R$_7$, R$_8$, R$_9$ and R$_{11}$ are hydrogens. In another embodiment, when R$_1$, R$_2$, R$_3$, R$_6$, R$_7$, R$_8$, R$_9$, R$_{10}$, R$_{11}$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when R$_4$ and R$_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, and R is as defined for Formula IX.

In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula X:

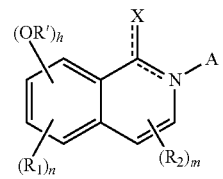

wherein

A is a 5-14 membered saturated or unsaturated, substituted or unsubstituted carbocyclic or heterocyclic ring which is optionally a fused ring system, or a combination thereof; wherein the saturated or unsaturated carbocyclic or heterocyclic ring are optionally substituted by 1 to 5 substituents independently selected from R$_3$ or OR"; and X is O or S; or A is nothing, N forms a double bond with the cyclic carbon and X is OH or OCH$_2$CH$_2$-heterocycle in which the heterocycle is a 3-7 membered saturated or unsaturated, substituted or unsubstituted heterocyclic ring;

R$_1$, R$_2$, R$_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

R$_4$ and R$_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, CH$_2$ or

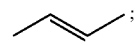

Q is SO$_3$H, CO$_2$H, CO$_2$R, NO$_2$, tetrazole, SO$_2$NH$_2$ or SO$_2$NHR;

R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;

h is an integer between 0-3;

n is an integer between 1-4;

m is an integer between 1-2; and

Alk is a linear alkyl of 1-7 carbons, branched alkyl of 1-7 carbons or cyclic alkyl of 3-8 carbons In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the structure of Formula X:

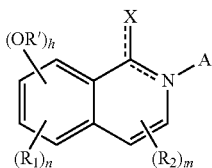

wherein A, X, $R_1$, $R_2$, R', n, m and h are as described above, however,
if X is oxo and A is phenyl, then A is not substituted with:
NHCOR and halogen without further substitution, or
NHCOR and an alkyl without further substitution. According to this aspect, such a NRBA is referred to herein as "a compound of Formula 4".

In one embodiment, A is

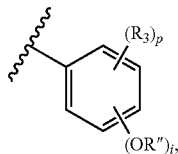

p is an integer between 1-5; i is an integer between 0-4; R" is hydrogen, Alk or COR; and $R_3$ is hydrogen, aldehyde, COOH, C(=NH)—OH, CHNOH, CH=CHCO$_2$H, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring.

In one embodiment of the compound of Formula X, A is nothing, N forms a double bond with the cyclic carbon and X is OCH$_2$CH$_2$-heterocycle in which the heterocycle is a 3-7 membered heterocycloalkyl. In one embodiment, when X is OCH$_2$CH$_2$-heterocycle, the heterocycle is substituted or unsubstituted piperidine, pyrrolidine, morpholine or piperazine. In another embodiment, when $R_1$, $R_2$, $R_3$ are independently Z-Alk-heterocycle or, in another embodiment, OCH$_2$CH$_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, haloalkyl, cycloalkyl, heterocycloalkyl, alkenyl, alkynyl, alkanoyl, alkylthio, alkylamino, N,N dialkylamino, aminoalkyl, haloalkyl, aryl, heteroaryl, alkoxy or haloalkoxy, and R is as defined for Formula X.

In another embodiment of the compound of Formula X, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—CH$_3$. In another embodiment, $R_2$ is —CH=CH$_2$. In another embodiment, $R_2$ is —CH=CH—COOEt. In another embodiment $R_1$ is O—(CO)-Ph-CF$_3$. In another embodiment $R_1$ is COOH. In another embodiment $R_1$ is COOMe. In another embodiment $R_1$ is a hydroxyl group. In another embodiment $R_1$ is hydrogen. In another embodiment $R_3$ is halogen. In another embodiment $R_3$ is hydrogen. In another embodiment R' is H. In another embodiment R' is a methyl group. In another embodiment R' is COMe. In another embodiment R" is H. In another embodiment R" is a methyl group. In another embodiment R" is COMe.

In one embodiment, the compound of Formula X may be represented by the structure of Formula XI:

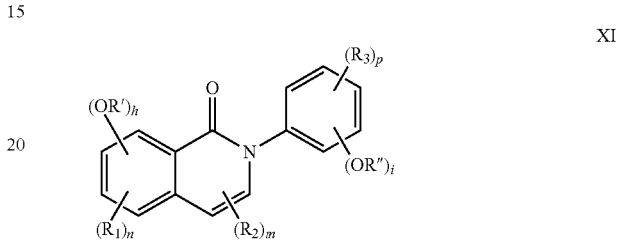

wherein
$R_1$, $R_2$, $R_3$ are independently hydrogen, aldehyde, COOH, —C(=NH)—OH, CHNOH, CH=CHCO$_2$H, CH=CHCO$_2$R, —CH=CH$_2$, hydroxyalkyl, halogen, hydroxyl, alkoxy, cyano, nitro, CF$_3$, NH$_2$, 4-Ph-OMe, 4-Ph-OH, SH, COR, COOR, OCOR, alkenyl, allyl, 2-methylallyl, alkynyl, propargyl, OSO$_2$CF$_3$, OSO$_2$CH$_3$, NHR, NHCOR, N(R)$_2$, sulfonamide, SO$_2$R, alkyl, haloalkyl, aryl, phenyl, benzyl, protected hydroxyl, OCH$_2$CH$_2$NR$_4$R$_5$, Z-Alk-Q, Z-Alk-NR$_4$R$_5$, Z-Alk-heterocycle or OCH$_2$CH$_2$-heterocycle in which the heterocycle is a 3-7 membered saturated or unsaturated, substituted or unsubstituted heterocyclic ring;
R is alkyl, hydrogen, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN, NO$_2$ or OH;
R' is hydrogen, Alk or COR;
R" is hydrogen, Alk or COR;
$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;
Z is O, NH, CH$_2$ or

;

Q is SO$_3$H, CO$_2$H, CO$_2$R, NO$_2$, tetrazole, SO$_2$NH$_2$ or SO$_2$NHR;
h is an integer between 0-3;
i is an integer between 0-4;
n is an integer between 1-4;
m is an integer between 1-2;
p is an integer between 1-5; and
Alk is a linear alkyl of 1-7 carbons, branched alkyl of 1-7 carbons, or cyclic alkyl of 3-8 carbons.

In another embodiment of the compound of Formula XI, $R_2$ is a halogen. In another embodiment $R_2$ is a bromide. In another embodiment $R_2$ is a chloride. In another embodiment $R_2$ is a fluoride. In another embodiment $R_2$ is an iodide. In another embodiment $R_2$ is hydrogen. In another embodiment $R_2$ is a cyano. In another embodiment, $R_2$ is a phenyl. In another embodiment, $R_2$ is —CH=CH—$CH_3$. In another embodiment, $R_2$ is —CH=$CH_2$. In another embodiment, $R_2$ is —CH=CH—COOEt. In another embodiment $R_1$ is O—(CO)-Ph-$CF_3$. In another embodiment $R_1$ is COOH. In another embodiment $R_1$ is COOMe. In another embodiment $R_1$ is a hydroxyl group. In another embodiment $R_1$ is a hydrogen. In another embodiment $R_3$ is a hydrogen. In another embodiment $R_3$ is a halogen. In another embodiment R' is H. In another embodiment R' is a methyl group. In another embodiment R' is a COMe. In another embodiment R" is H. In another embodiment R" is a methyl group. In another embodiment R" is a COMe. In one embodiment h is 1. In another embodiment h is 2. In another embodiment, when $R_1$, $R_2$, $R_3$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, and R is as defined for Formula XI.

In one embodiment, the present invention provides a NRBA or its prodrug, analog, isomer, metabolite, derivative, pharmaceutically acceptable salt, pharmaceutical product, polymorph, crystal, impurity, N-oxide, ester, hydrate or any combination thereof, represented by the following structure:

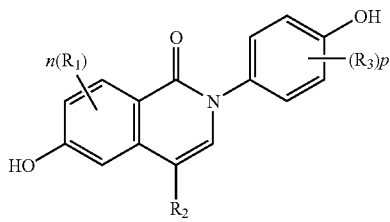

XII wherein $R_1$, $R_2$ and $R_3$ are independently hydrogen, aldehyde, COOH, C(=NH)—OH, CHNOH, CH=$CHCO_2$H, —CH=$CH_2$, hydroxyalkyl, halogen, hydroxyl, alkoxy, cyano, nitro, $CF_3$, $NH_2$, 4-Ph-OMe, 4-Ph-OH, SH, COR, COOR, OCOR, alkenyl, allyl, 2-methylallyl, alkynyl, propargyl, $OSO_2CF_3$, $OSO_2CH_3$, NHR, NHCOR, N(R)$_2$, sulfonamide, $SO_2R$, alkyl, haloalkyl, aryl, phenyl, benzyl, protected hydroxyl, $OCH_2CH_2NR_4R_5$, Z-Alk-Q, Z-Alk-$NR_4R_5$, Z-Alk-heterocycle or $OCH_2CH_2$-heterocycle in which the heterocycle is a 3-7 membered saturated or unsaturated, substituted or unsubstituted heterocyclic ring;

R' is hydrogen, Alk or COR;

R" is hydrogen, Alk or COR;

$R_4$ and $R_5$ are independently hydrogen, phenyl, benzyl, an alkyl group of 1 to 6 carbon atoms, a 3 to 7 member cycloalkyl, heterocycloalkyl, aryl or heteroaryl group;

Z is O, NH, $CH_2$ or

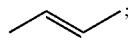;

Q is $SO_3H$, $CO_2H$, $CO_2R$, $NO_2$, tetrazole, $SO_2NH_2$ or $SO_2NHR$;

R is alkyl, hydrogen, haloalkyl, dihaloalkyl, trihaloalkyl, $CH_2F$, $CHF_2$, $CF_3$, $CF_2CF_3$, aryl, phenyl, -Ph-$CF_3$, -Ph-$CH_2F$, -Ph-$CHF_2$, -Ph-$CF_2CF_3$, halogen, alkenyl, CN, $NO_2$ or OH;

n is an integer between 1-3;

p is an integer between 1-4; and

Alk is a linear alkyl of 1-7 carbons, branched alkyl of 1-7 carbons, or cyclic alkyl of 3-8 carbons.

In another embodiment of the compound of Formula XII, $R_2$ is a halogen. In another embodiment $R_2$ is a bromide. In another embodiment $R_2$ is a chloride. In another embodiment $R_2$ is a fluoride. In another embodiment $R_2$ is a iodide. In another embodiment $R_2$ is hydrogen. In another embodiment $R_2$ is a cyano. In another embodiment, $R_2$ is a phenyl. In another embodiment, $R_2$ is —CH=CH—$CH_3$. In another embodiment, $R_2$ is —CH=$CH_2$. In another embodiment, $R_2$ is —CH=CH—COOEt. In another embodiment $R_1$ is O—(CO)-Ph-$CF_3$. In another embodiment $R_1$ is COOH. In another embodiment $R_1$ is COOMe. In another embodiment $R_1$ is an hydroxyl group. In another embodiment $R_1$ is hydrogen. In another embodiment $R_3$ is halogen. In another embodiment $R_3$ is hydrogen. In another embodiment p is 1. In another embodiment, when $R_1$, $R_2$, $R_3$ are independently Z-Alk-heterocycle or, in another embodiment, $OCH_2CH_2$-heterocycle, either heterocycle may be substituted or unsubstituted piperidine, pyrrolidine, morpholine or piperazine. In another embodiment, when $R_4$ and $R_5$ are independently a 3 to 7 membered heterocycloalkyl, either heterocycle may be substituted or unsubstituted piperidine, pyrrolidine, morpholine or piperazine. In another embodiment, any heterocycle is optionally substituted by one or more substituents comprising halogen, cyano, nitro, COOH, COOR, NHCOR, hydroxyl, amine, alkyl, cycloalkyl, heterocycloalkyl, alkenyl, alkynyl, alkanoyl, alkylthio, alkylamino, N,N-dialkylamino, aminoalkyl, haloalkyl, aryl, heteroaryl, alkoxy or haloalkoxy, and R is as defined for Formula XII.

In another embodiment the NRBA of this invention is 1-(2-(piperidin-1-yl)ethoxy)isoquinolin-6-ol. In another embodiment the NRBA of this invention is 6-hydroxy-2-(4-hydroxyphenyl)isoquinolin-1(2H)-one. In another embodiment the NRBA of this invention is 4-bromo-6-hydroxy-2-(4-hydroxyphenyl)isoquinolin-1(2H)-one. In another embodiment the NRBA of this invention is 4-bromo-2-(4-hydroxyphenyl)-6-methoxyisoquinolin-1(2H)-one. In another embodiment the NRBA of this invention is 4-bromo-2-(3-fluoro-4-hydroxyphenyl)-6-hydroxyisoquinolin-1 (2H)-one. In another embodiment the NRBA of this invention is 4-bromo-2-(4-fluorophenyl)-6-hydroxyisoquinolin-1 (2H)-one. In another embodiment the NRBA of this invention is 4-chloro-6-hydroxy-2-(4-hydroxyphenyl)isoquinolin-1 (2H)-one. In another embodiment the NRBA of this invention is 4-chloro-2-(3-fluoro-4-hydroxyphenyl)-6-hydroxyisoquinolin-1(2H)-one. In another embodiment the NRBA of this invention is 6-hydroxy-2-(4-hydroxyphenyl)-4-iodoisoquinolin-1(2H)-one. In another embodiment the NRBA of this invention is 4-bromo-6-hydroxy-2-(3-hydroxyphenyl) isoquinolin-1(2H)-one. In another embodiment the NRBA of this invention is 8-hydroxy-2-(4-hydroxyphenyl)-6-methoxy-isoquinolin-1(2H)-one. In another embodiment the NRBA of this invention is 5-bromo-8-hydroxy-2-(4-hydroxyphenyl)-6-methoxy-isoquinolin-1(2H)-one. In another embodiment the NRBA of this invention is 6,8-dihydroxy-2-(4-hydroxyphenyl)-isoquinolin-1(2H)-one. In another embodiment the NRBA of this invention is 5-bromo-6,8-dihydroxy-2-(4-hydroxyphenyl)isoquinolin-1(2H)-one. In another embodiment the NRBA of this invention is 2-(3-fluoro-4-hydroxyphenyl)-6-hydroxy-4-iodoisoquinolin-1(2H)-one. In another embodiment the NRBA of this invention is 4-bromo-6-hydroxy-2-(4-hydroxy-3-methylphenyl)isoquinolin-1(2H)-one. In another embodiment the NRBA of this invention is 2-(4-hydroxyphenyl)-6,8-dihydroxy-isoquinoline-1(2H)-thione. In another embodiment the NRBA of this invention is 8-hydroxy-2-(4-hydroxyphenyl)-6-methoxy-1-oxo-1,2-dihydroisoquinoline-5-carbonitrile. In another embodiment the NRBA of this invention is 4-bromo-6-hydroxy-2-(4-hydroxyphenyl)isoquinoline-1(2H)-thione. In another embodiment the NRBA of this invention is 2-(3-fluoro-4-hydroxyphenyl)-6,8-dihydroxyisoquinolin-1(2H)-one. In another embodiment the NRBA of this invention is 2-(3-fluoro-4-hydroxyphenyl)-8-hydroxy-6-methoxyisoquinolin-1(2H)-one. In another embodiment the NRBA of this invention is 4-bromo-6,8-dihydroxy-2-(4-hydroxyphenyl)isoquinolin-1(2H)-one. In another embodiment the NRBA of this invention is 4-bromo-8-hydroxy-2-(4-hydroxyphenyl-6-methoxyisoquinolin-1(2H)-one. In another embodiment the NRBA of this invention is 4-chloro-6,8-dihydroxy-2-(4-hydroxyphenyl)isoquinolin-1(2H)-one. In another embodiment the NRBA of this invention is 4-bromo-6,8-dihydroxy-2-(3-fluoro-4-hydroxyphenyl)isoquinolin-1(2H)-one. In another embodiment the NRBA of this invention is 4,5-dibromo-2-(3,5-dibromo-4-hydroxyphenyl)-6-hydroxyisoquinolin-1(2H)-one. In another embodiment the NRBA of this invention is 6,8-dihydroxy-2-(4-hydroxyphenyl)-5-(trifluoromethylsulfonyl)isoquinolin-1(2H)-one. In another embodiment the NRBA of this invention is 4-(1,2-dibromoethyl)-6-hydroxy-2-(4-hydroxyphenyl)isoquinolin-1(2H)-one. In another embodiment the NRBA of this invention is 6-methoxy-2-(4-methoxyphenyl)-1-oxo-1,2-dihydroisoquinolin-8-yl trifluoromethanesulfonate. In another embodiment the NRBA of this invention is 4,5-dibromo-6,8-dihydroxy-2-(4-hydroxyphenyl)isoquinolin-1(2H)-one. In another embodiment the NRBA of this invention is 6-hydroxy-2-(4-hydroxyphenyl)-4-vinylisoquinolin-1(2H)-one. In another embodiment the NRBA of this invention is 6-methoxy-2-(4-methoxyphenyl)-1-oxo-1,2-dihydroisoquinoline-4-carbonitrile. In another embodiment the NRBA of this invention is 6-hydroxy-2-(4-hydroxyphenyl)-1-oxo-1,2-dihydroisoquinoline-4-carbonitrile. In another embodiment the NRBA of this invention is 6-methoxy-2-(4-methoxyphenyl)-1-oxo-1,2-dihydroisoquinoline-8-carbonitrile. In another embodiment the NRBA of this invention is 4-bromo-6-methoxy-2-(4-methoxyphenyl)-1-oxo-1,2-dihydroisoquinoline-8-carbonitrile. In another embodiment the NRBA of this invention is 4-bromo-6-hydroxy-2-(4-hydroxyphenyl)-1-oxo-1,2-dihydroisoquinoline-8-carbonitrile. In another embodiment the NRBA of this invention is 6,8-dihydroxy-2-(4-hydroxyphenyl)-4-vinylisoquinolin-1(2H)-one. In another embodiment the NRBA of this invention is 6,8-dihydroxy-2-(4-hydroxyphenyl)-1-oxo-1,2-dihydroisoquinoline-4-carbonitrile. In another embodiment the NRBA of this invention is 6-hydroxy-2-(4-hydroxyphenyl)-1-oxo-1,2-dihydroisoquinoline-8-carbonitrile. In another embodiment the NRBA of this invention is 6-hydroxy-2-(4-hydroxyphenyl)-1-oxo-4-vinyl-1,2-dihydroisoquinoline-8-carbonitrile. In another embodiment the NRBA of this invention is 4-chloro-6-hydroxy-2-(4-hydroxyphenyl)-1-oxo-1,2-dihydroisoquinoline-8-carbonitrile. In another embodiment the NRBA of this invention is 4-bromo-6-methoxy-2-(4-methoxyphenyl)isoquinolin-1(2H)-one. In another embodiment the NRBA of this invention is 8-hydroxy-6-methoxy-2-(4-methoxyphenyl)isoquinolin-1(2H)-one. In another embodiment the NRBA of this invention is 4-chloro-6-methoxy-2-(4-methoxyphenyl)-1-oxo-1,2-dihydroisoquinolin-8-yl trifluoromethanesulfonate. In another embodiment the NRBA of this invention is 4-chloro-6-methoxy-2-(4-methoxyphenyl)-1-oxo-1,2-dihydroisoquinoline-8-carbonitrile. In another embodiment the NRBA of this invention is isoquinoline-1,6-diol. In another embodiment the NRBA of this invention is 4-bromo-6-hydroxy-2-(4-methoxyphenyl)isoquinolin-1(2H)-one. In another embodiment the NRBA of this invention is 4-(6-acetoxybromo-1-oxoisoquinolin-2(1H)-yl)phenyl acetate. In another embodiment the NRBA of this invention is 4-(4-bromo-6-methoxy-1-oxoisoquinolin-2(1H)-yl)phenyl acetate. In another embodiment the NRBA of this invention is 4-bromo-6-hydroxy-2-(4-hydroxyphenyl)-1-oxo-1,2-dihydroisoquinoline-8-carbimidic acid. In another embodiment the NRBA of this invention is methyl 4-bromo-6-hydroxy-2-(4-hydroxyphenyl)-1-oxo-1,2-dihydroisoquinoline-8-carboxylate. In another embodiment the NRBA of this invention is 4-bromo-6-hydroxy-2-(4-hydroxyphenyl)-1-oxo-1,2-dihydroisoquinoline-8-carboxylic acid. In another embodiment the NRBA of this invention is 6-hydroxy-2-(4-hydroxyphenyl)-4-phenylisoquinolin-1(2H)-one. In another embodiment the NRBA of this invention is 6-hydroxy-2-(4-hydroxyphenyl)-4-(4-methoxyphenyl)isoquinolin-1(2H)-one. In another embodiment the NRBA of this invention is 2-(3-fluoro-4-hydroxyphenyl)-6,8-dihydroxy-4-vinylisoquinolin-1(2H)-one. In another embodiment the NRBA of this invention is 2-(3-fluoro-4-hydroxyphenyl)-6,8-dihydroxy-1-oxo-1,2-dihydroisoquinoline-4-carbonitrile. In another embodiment the NRBA of this invention is 6-hydroxy-2-(4-hydroxyphenyl)-8-vinylisoquinolin-1(2H)-one. In another embodiment the NRBA of this invention is 4-bromo-6-hydroxy-2-(4-hydroxyphenyl)-8-vinylisoquinolin-1(2H)-one. In another embodiment the NRBA of this invention is 6,8-dihydroxy-2-(4-hydroxyphenyl)-4-(4-methoxyphenyl)isoquinolin-1(2H)-one. In another embodiment the NRBA of this invention is 6,8-dihydroxy-2-(4-hydroxyphenyl)-4-phenylisoquinolin-1(2H)-one. In another embodiment the NRBA of this invention is (E)-6,8-dihydroxy-2-(4-hydroxyphenyl)-4-(prop-1-enyl)isoquinolin-1(2H)-one. In another embodiment the NRBA of this invention is (E)-ethyl 3-(8-hydroxy-6-methoxy-2-(4-methoxyphenyl)-1-oxo-1,2-dihydroisoquinolin-4-yl)acrylate. In another embodiment the NRBA of this invention is (E)-3-(6-hydroxy-2-(4-hydroxyphenyl)-1-oxo-1,2-dihydroisoquinolin-4-yl)acrylic acid. In another embodiment the NRBA of this invention is (E)-3-(6,8-dihydroxy-2-(4-hydroxyphenyl)-1-oxo-1,2-dihydroisoquinolin-4-yl)acrylic acid. In another embodiment the NRBA of this invention is 4-chloro-6-methoxy-2-(4-methoxyphenyl)-1-oxo-1,2-dihydroisoquinolin-8-yl 4-(trifluoromethyl)benzoate, 1-(2-(piperidin-1-yl)ethoxy)isoquinolin-6-ol or any combination thereof.

In some embodiments, the NRBA of this invention, compositions of this invention or uses thereof may comprise any combinations of such NRBA as described herein.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 14 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, cyano, alkoxy carbonyl, amido, alkylamido, dialkylamido, nitro, amino, alkylamino, dialkylamino, carboxyl, thio and/or thioalkyl.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 24 carbons. In another embodiment the alkenyl group is vinyl (—CH=CH$_2$) Examples of alkenyl groups are vinyl, propenyl, butenyl, cyclohexenyl, etc. The alkenyl group may be unsubstituted or substituted by a halogen, hydroxy, cyano, alkoxy carbonyl, amido, alkylamido, dialkylamido, nitro, amino, alkylamino, dialkylamino, carboxyl, thio and/or thioalkyl.

A "haloalkyl" group refers, in another embodiment, to an alkyl group as defined above, which is substituted by one or more halogen atoms, e.g. by F, Cl, Br or I.

An "aryl" group refers, in another embodiment, to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers, in another embodiment, to an OH group. In some embodiments, when R$_1$, R$_2$ or R$_3$ of the compounds of the present invention is OR, then R is not OH.

In one embodiment, the term "halo" refers to a halogen, such as F, Cl, Br or I.

In another embodiment, the phrase "phenol" refers to an alcohol (OH) derivative of benzene.

A "heterocycle" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, CO$_2$H, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. Examples of a heterocycle group comprise pyridine, piperidine, morpholine, piperazine, thiophene, pyrrole or indole.

In one embodiment the 5-14 member saturated or unsaturated, substituted or unsubstituted carbocyclic or heterocyclic ring comprises a phenyl, naphthalene, anthracene, pyridine, piperidine, thiophene, morpholine, piperazine, pyrimidine, cyclohexyl, cycloheptyl, pyrrole, pyrazole, furan, oxazole, quinoline, pyrazine or indole groups.

In one embodiment unsaturated cycloalkyl or heterocycloalkyl groups refer to cycloalkyl or heterocycloalkyl comprising at list one double bond. In another embodiment unsaturated cycloalkyl or heterocycloalkyl refer to an aryl or heteroaryl group.

In some embodiments, protected hydroxyl includes the incorporation of a substituent bonded to an oxygen atom bound to a benzene ring, wherein the substituent may be readily removed. In some embodiments, phenolic protecting groups may comprise a: methyl ether, methoxymethyl (MOM) ether, benzoyloxymethyl (BOM) ether, methoxyethoxymethyl (MEM) ether, 2-(trimethylsilyl)ethoxymethyl (SEM) ether, methylthiomethyl (MTM) ether, phenylthiomethyl (PTM) ether, azidomethyl ether, cyanomethyl ether, 2,2-dichloro-1,1-difluoroethyl ether, 2-chloroethyl ether, 2-bromoethyl ether, tetrahydropyranyl (THP) ether, 1-ethoxyethyl (EE) ether, phenacyl ether, 4-bromophenacyl ether, cyclopropylmethyl ether, allyl ether, propargyl ether, isopropyl ether, cyclohexyl ether, t-butyl ether, benzyl ether, 2,6-dimethylbenzyl ether, 4-methoxybenzyl ether, o-nitrobenzyl ether, 2,6-dichlorobenzyl ether, 3,4-dichlorobenzyl ether, 4-(dimethylamino)carbonylbenzyl ether, 4-methylsulfinylbenzyl ether, 4-anthrylmethyl ether, 4-picolyl ether, heptafluoro-p-tolyl, tetrafluoro-4-pyridyl ether, trimethylsilyl (TMS) ether, t-butyldimethylsilyl (TBDMS) ether, t-butyldiphenylsilyl (TBDPS) ether, triisopropylsilyl (TIPS) ether, aryl formate, arylacetate, aryl levulinate, arylpivaloate, aryl benzoate, aryl 9-fluorencarboxylate, aryl methyl carbonate, 1-adamantyl carbonate, t-butyl carbonate, 4-methylsulfinylbenzyl carbonate, 2,4-dimethylpent-3-yl carbonate, aryl 2,2,2-trichloroethyl carbonate, aryl benzyl carbonate, aryl carbamate, dimethylphosphinyl ester (Dmp-OAr), dimethylphosphinothionyl ester (Mpt-OAr), diphenylphosphinothionyl ester (Dpt-OAr), aryl methanesulfonate, aryl toluenesulfonate or aryl 2-formylbenzenesulfonate.

In one embodiment, this invention provides a NRBA and/or its analog, derivative, isomer, metabolite, pharmaceutically acceptable salt, pharmaceutical product, hydrate, N-oxide, prodrug, ester, polymorph, impurity or crystal or combinations thereof. In one embodiment, this invention provides an analog of the NRBA. In another embodiment, this invention provides a derivative of the NRBA. In another embodiment, this invention provides an isomer of the NRBA. In another embodiment, this invention provides a metabolite of the NRBA. In another embodiment, this invention provides a pharmaceutically acceptable salt of the NRBA. In another embodiment, this invention provides a pharmaceutical product of the NRBA. In another embodiment, this invention provides a hydrate of the NRBA. In another embodiment, this invention provides an N-oxide of the NRBA. In another embodiment, this invention provides a prodrug of the NRBA. In another embodiment, this invention provides an ester of the NRBA. In another embodiment, this invention provides a polymorph of the NRBA. In another embodiment, this invention provides a crystal of the NRBA. In another embodiment, this invention provides an impurity of the NRBA. In another embodiment, this invention provides composition comprising a NRBA, as described herein, or, in another embodiment, a combination of an analog, derivative, isomer, metabolite, pharmaceutically acceptable salt, pharmaceutical product, hydrate, N-oxide, prodrug, polymorph, ester, impurity or crystal of the NRBA of the present invention.

In one embodiment, the term "isomer" includes, but is not limited to, optical isomers and analogs, structural isomers and analogs, conformational isomers and analogs, and the like.

In one embodiment, the NRBAs are the pure (E)-isomers. In another embodiment, the NRBAs are the pure (Z)-isomers. In another embodiment, the NRBAs are a mixture of the (E) and the (Z) isomers. In one embodiment, the NRBAs are the pure (R)-isomers. In another embodiment, the NRBAs are the pure (S)-isomers. In another embodiment, the NRBAs are a mixture of the (R) and the (S) isomers.

The invention includes "pharmaceutically acceptable salts" of the compounds of this invention, which may be produced, by reaction of a compound of this invention with an acid or base.

Suitable pharmaceutically-acceptable salts of amines of Formula I-XII may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoate, hydrofluorate, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, mitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the pharmaceutically acceptable salt of a NRBA comprising a piperidine ring is an HCl salt or an amine salt as described herein. In another embodiment, the pharmaceutically acceptable salt of a NRBA comprising a pyrrolidine ring is an HCl salt, or an amine salt as described herein. In another embodiment, the pharmaceutically acceptable salt of a NRBA comprising a morpholine ring is an HCl salt or an amine salt as described herein. In another embodiment, the pharmaceutically acceptable salt of a NRBA comprising a piperazine ring is an HCl salt, or an amine salt as described herein or others as will be appreciated by one skilled in the art.

Pharmaceutically acceptable salts can be prepared from the phenolic compounds, in other embodiments, by treatment with inorganic bases, for example, sodium hydroxide. In another embodiment, esters of the phenolic compounds can be made with aliphatic and aromatic carboxylic acids, for example, acetic acid and benzoic acid esters.

This invention provides, in some embodiments, derivatives of the NRBAs. In one embodiment, the term "derivatives" refers to ether derivatives, acid derivatives, amide derivatives, ester derivatives or others, as known in the art. In another embodiment, this invention further includes hydrates of the NRBAs. In one embodiment, the term "hydrate" refers to hemihydrate, monohydrate, dihydrate, trihydrate or others, as known in the art.

This invention provides, in other embodiments, metabolites of the NRBAs. In one embodiment, the term "metabolite" refers to any substance produced from another substance by metabolism or a metabolic process.

In some embodiments, a NRBA this invention will comprise the compounds listed in Table 1. In some embodiments, the NRBAs of this invention will have a selective affinity for a particular nuclear hormone receptor, with varying affinities at other nuclear receptors. In some embodiments of this invention, NRBAs of this invention will vary in terms of their activity, for example, some NRBAs possess greater activity in terms of stimulating bone growth, while some exhibit greater antagonistic activity, etc. It is to be understood that all such NRBAs are to be considered as part of this invention.

In some embodiments, the NRBAs of this invention may exhibit nonselective affinity for or binding to a nuclear receptor, which in some embodiments, is an estrogen receptor α and/or estrogen receptor β molecule. In some embodiments, the NRBAs of this invention may exhibit selective affinity for a nuclear receptor such as ER-β. In some embodiment, the NRBAs of this invention may exhibit selective affinity for receptors that do not translocate to the cell nucleus. In some embodiments, the NRBAs of this invention may exhibit agonist activity. In some embodiments, the NRBAs of this invention may exhibit antagonist activity. In some embodiments, the NRBAs of this invention may exhibit anti-proliferative activity. In some embodiments, the NRBAs of this invention may exhibit anti-inflammatory activity. In some embodiments, the NRBAs of this invention may exhibit anti-oxidant activity. In some embodiments, the NRBAs of this invention may exhibit vasodilatory activity. In some embodiments, the NRBAs of this invention may exhibit pro-differentiation activity. ER-α and ER-β binding and agonist and antagonist activities, anti-proliferative and anti-inflammatory activities for representative NRBAs are exemplified in hereinbelow, where such activity is described in the context of specific experimental conditions employed, representing only certain embodiments of this invention, and in no way to be taken to limiting the invention. It is to be understood that while the indicated compounds may exhibit a particular activity under certain experimental conditions employed, as a function, in some embodiments, of the particular cells utilized, etc., such compounds may possess alternate, varied, or partial activity in different experimental settings. In some embodiments, the NRBAs of this invention may exhibit agonist activity for a particular receptor, and antagonist activity for a different receptor, or vice versa, or in some embodiments, the NRBAs of this invention may exhibit agonist activity for a particular receptor under certain experimental conditions, yet exhibit antagonist activity for the same receptor under different experimental conditions, or vice versa, or in some embodiments, the NRBAs of this invention may exhibit agonist activity for a particular receptor in a particular tissue, yet exhibit antagonist activity for the same receptor in a different tissue, or vice versa, etc. It is to be understood that a single described activity for a NRBA this invention is not to be taken as limiting the compound to such activity/condition/tissue exclusively, but rather to represent an embodiment of one such activity for the indicated NRBA.

Steroid nuclear hormone receptors are known to have rapid, tissue-specific effects that are mediated by cell-surface and cytosolic receptors through protein-protein interaction or phosphorylation of kinases, which are known as non-genomic effects. For instance, NRBAs are known to have distinct rapid effects in the cardiovascular and central nervous systems which may be mediated by distinct receptors. Putative receptors for these non-genomic effects include a variety of G-protein coupled receptors (GPCRs) such as GPR130, as well as cell-membrane associated or cytosolic nuclear receptors. NRBAs of this invention may also bind to receptors involved in these non-genomic effects allowing differential pharmacological exploitation of genomic, non-genomic, and tissue-selective steroid receptor activities. As such these NRBAs may have a wide variety of specific and targeted steroid responses broadening their potential to have beneficial medical properties.

In some embodiments, a NRBA of this invention is a non-genomic agonist, or in some embodiments, a non-genomic antagonist, or in some embodiments, a non-genomic partial agonist of a nuclear receptor. In some embodiments, the NRBAs of this invention are tissue selective, non-genomic nuclear receptors, such as for example, estrogen or androgen receptor agonists, or in some embodiments, tissue selective, non-genomic nuclear receptor antagonists, or in some embodiments, tissue selective, non-genomic nuclear receptor partial agonists. In some embodiments, the NRBAs of this invention are non-selective non-genomic nuclear receptor agonists, such as for example, estrogen or androgen receptor agonists, or in some embodiments, non-selective non-genomic nuclear receptor antagonists, or in some embodiments, non-selective non-genomic nuclear receptor partial agonists. In some embodiments, the NRBAs of this invention are non-selective genomic nuclear receptor agonists, such as for example, estrogen or androgen receptor agonists, or in some embodiments, antagonists, or in some embodiments, partial agonists. In some embodiments, the NRBAs of this invention are tissue selective genomic nuclear receptor modulators, such as for example, estrogen or androgen receptor agonists, or in some embodiments, antagonists, or in some embodiments, partial agonists. In some embodiments, the NRBAs of this invention are genomic agents which selectively transactivate nuclear receptor-regulated genes. In some embodiments, selective transactivation is in a tissue selective manner. In some embodiments, the NRBAs of this invention are genomic agents which selectively transrepress nuclear receptor-regulated genes. In some embodiments, selective tranrepression is in a tissue selective manner. In some embodiments, the NRBAs are dissociated in their ability to affect non-genomic process but not genomic processes, or vice versa. In some embodiments, NRBA's are dissociated in their ability to affect transactivation but not transrepression, or vice versa.

This invention provides, in other embodiments, pharmaceutical products of the NRBAs. The term "pharmaceutical product" refers, in other embodiments, to a composition suitable for pharmaceutical use (pharmaceutical composition), for example, as described herein.

In one embodiment, this invention provides a method of binding any NRBA of this invention to an estrogen receptor or an estrogen related receptors, comprising the step of contacting an estrogen receptor with said NRBA. In another embodiment, this invention provides a method of binding any NRBA of this invention to a nuclear hormone receptor or one related thereto.

In one embodiment, this invention provides general and specific synthetic routes for embodiments of isoquinolinones and isoquinolin-6-ols.

Some embodiments of a synthetic procedure for some of the NRBAs are provided below:

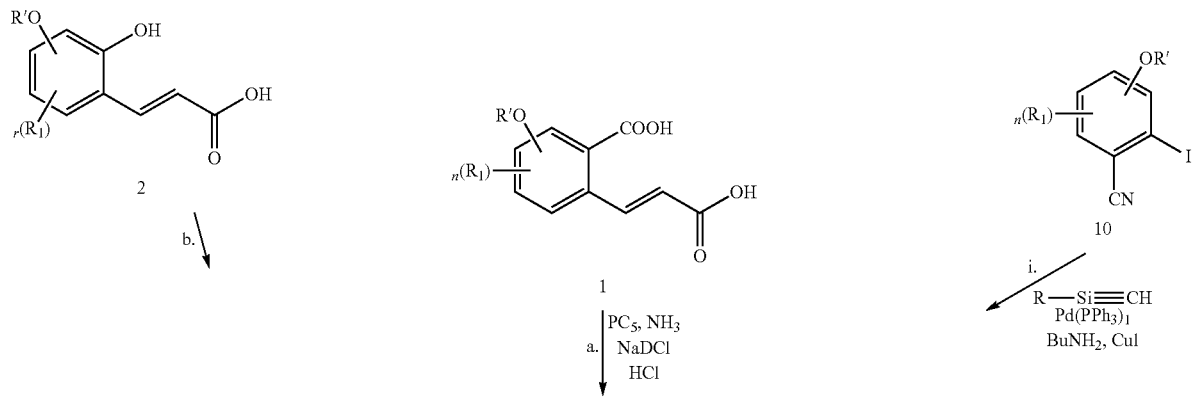

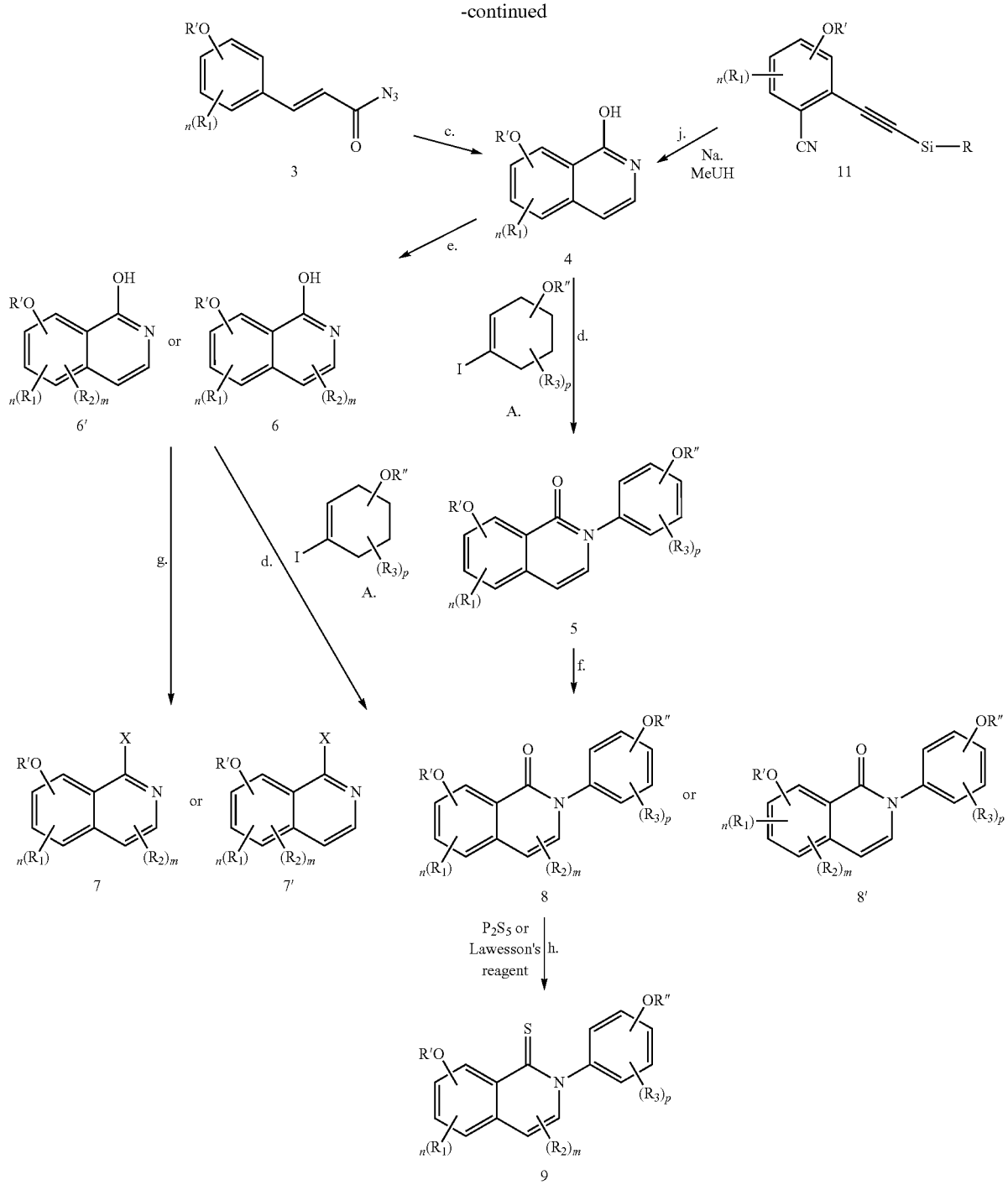

Intermediate compound 4 can be prepared by three different paths starting from 2-(2-carboxy-vinyl)benzoic acid (compound 1) via step a; or starting with 3-phenyl-acrylic acid, (compound 2) together with sodium azide (step b) to obtain an acyl derivative of compound 3, followed by Curtius rearrangement and a cyclization step (step c) in the presence of diphenyl ether and tributylamine at 230° C. to obtain compound 4; or starting with 2-iodo benzonitrile (compound 10) via the Sonogashira reaction (step i) followed by methanolysis (step j) to obtain compound 4.

Compound 4 is further coupled with an iodo substituted formula A (step d), yielding compound 5, which may be further brominated, chlorinated, or iodinated (using NBS, NCS, or NIS, respectively) followed by further substitutions to obtain the desired $R_2$ group (step f) compound 8 or compound 8', or obtain the sulfone compound 9 using $P_2S_5$ reagent (step h). Compounds 8 or 9 can be optionally demethylated with $BBr_3$ to yield the phenolic products, however if step h is executed, then the phenol must be protected.

Alternatively, compound 4 may be brominated, chlorinated, or iodinated (using NBS, NCS, or NIS, respectively)

and further substituted (step e) to obtain the desired R₂ of compound 6 or 6'. Compound 6 or 6' may be coupled together with an iodo substituted formula A (step d), yielding compound 8 or 8', or the OH group of compound 6 or 6' is further substituted (step g) to obtain the desired X group of compound 7 or compound 7'.

In some embodiments this invention provides synthetic route for embodiments of 4-halogenated isoquinolinones. For example, one embodiment of a synthetic procedure for a compound of this invention, 4-bromo-6-hydroxy-2-(4-hydroxyphenyl)isoquinolin-1(2H)-one (12b), is as follows:

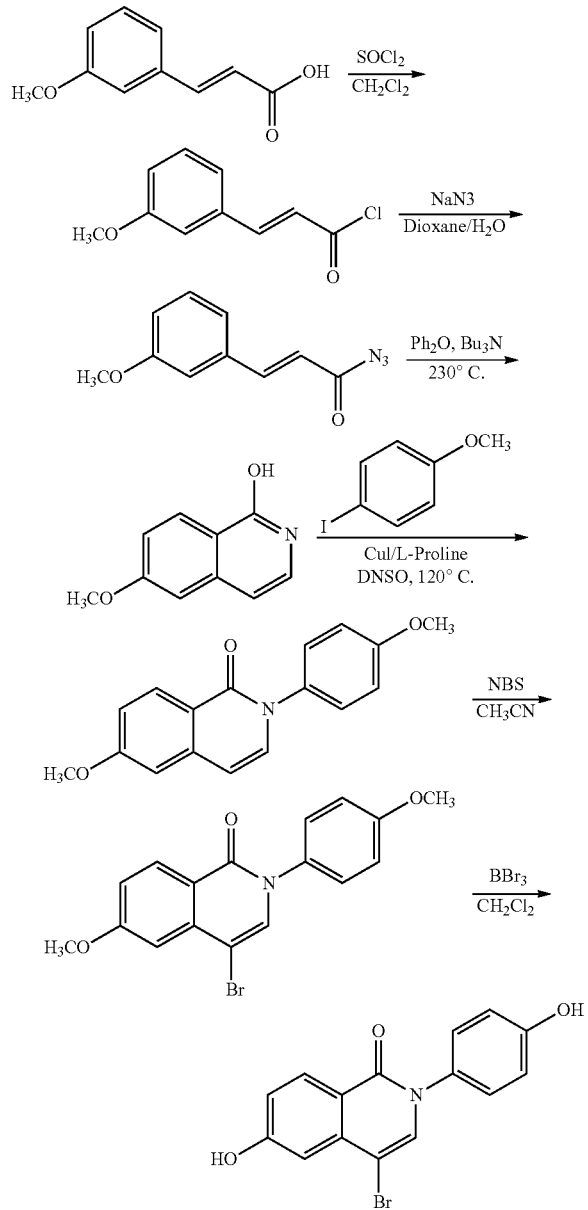

Synthesis of 6-methoxyisouinolinemethoxyisoquinoline-1-ol

A mixture of 17.82 g (0.10 mol) of trans-3-methoxycinnamic acid and thionyl chloride (14.28 g, 0.12 mol) were placed in a 250 mL single-necked round-bottomed flask fitted with a stirring bar and reflux condenser. 80 mL of dry methylene chloride was added to the flask. The resulting mixture was heated to reflux for 3 hours and then the solvent was removed under reduced pressure. The residue oil was dried under vacuum overnight.

The pale-yellow solid acid chloride was dissolved in 20 mL of 1,4-dioxane and added dropwise with stirring to a 0° C. suspension of 19.50 g (0.30 mol) of sodium azide in 80 mL of 1,4-dioxane/water (1:1 mixture). During the addition the temperature was maintained at 0° C. After complete addition of the acid chloride, the mixture was stirred at 0° C. for an additional hour, and then diluted with 75 mL of water. The mixture was extracted with methylene chloride (2×40 mL). The combined extracts were dried over anhydrous magnesium sulfate, filtered and concentrated to approximately 100 mL. The solution was diluted with 20 mL of phenyl ether and further concentrated to remove the remaining methylene chloride. A 500 mL 3-necked round-bottomed flask fitted with an argon inlet, reflux condenser, additional funnel and an internal thermometer was charged with 29 mL of tributylamine and 80 mL of phenyl ether. The solution was heated to 230° C., and the acyl azide in 20 mL of phenyl ether was added dropwise with stirring over 3 hours from an addition funnel. During the addition, the reflux temperature gradually decreased to 200° C. After completion of the addition, the distillate was collected in the addition funnel (15 mL of a 1:1 mixture of tributylamine/phenyl ether) until the temperature reached 230° C. After heating for an additional hour at 230° C., the mixture was cooled to room temperature. The mixture was then combined with 500 mL hexane with stirring. The solid was filtered and washed with hexanes (2×100 mL). The pale-yellow solid was recrystallized from ethyl acetate/methanol (9/1 v/v) to give a pure pale-yellow crystalline material, 15.28 g, 87.2% yield. MS: 198.1 [M+Na]⁺. ¹H NMR (DMSO-d₆, 300 MHz): δ 11.06 (s, 1H), 8.08 (d, 1H, J=8.5 Hz), 7.14-7.14 (m, 1H), 7.10 (d, 1H, J=2.5 Hz), 7.05-7.03 (m, 1H), 7.04 (dd, 1H, J₁=9.0 Hz, J₂=2.5 Hz), 6.47 (d, 1H, J=7.0 Hz), 3.86 (s, 3H).

Synthesis of 6-methoxy-2-(4-methoxyphenyl)isoquinolin-1(2H)-one

6-Methoxyisoquinoline-1-ol (2.00 g, 11.42 mmol), 4-iodoanisole (4.01 g, 17.13 mmol), copper (1) iodide (0.44 g, 2.28 mmol). L-proline (0.53 g, 4.57 mmol) and anhydrous potassium carbonate (3.16 g, 22.84 mmol) were placed in a dry 250 mL three-necked round-bottomed flask fitted with a stirring bar and reflux condenser. The reaction flask was vacuumed and refilled with dry argon. 50 mL of anhydrous methyl sulfoxide was added via syringe. The reaction mixture was stirred and heated to 130° C. for 20 hours. 50 mL of water was added to quench the reaction, and yellow solid precipitated out. The pale-yellow solid was filtered, washed with water (2×20 mL) and dried in air. This pale-yellow solid was purified by flash column chromatography (silica gel, ethyl acetate) to give a pale-yellow solid product, 2.90 g, 90.3% yield. MS: 282.2 [M+H]⁺. ¹H NMR (DMSO-d₆, 300 MHz): δ 8.14 (d, 1H, J=8.7 Hz), 7.39-7.34 (m, 3H), 7.19 (d, 1H, J=2.4 Hz), 7.13-7.03 (m, 3H), 6.62 (dd, 1H, J=7.5 Hz), 3.89 (s, 3H), 3.81 (s, 3H).

Synthesis of 4-bromo-6-methoxy-2-(4-methoxyphenyl)isoquinolin-1(2H)-one (14q)

6-Methoxy-2-(4-methoxyphenyl)isoquinolin-1(2H)-one (0.50 g, 1.78 mmol) was placed in a dry 250 mL single-necked round-bottomed flask fitted with a stirring bar and septa. Acetonitrile (10 mL) was added via a syringe under argon atmosphere at room temperature. N-Bromosuccinimide or NBS (0.33 g, 1.87 mmol) was added portionwise under argon atmosphere at room temperature. The reaction mixture was allowed to stir at room temperature for 2 hours. 20 mL of saturated sodium bicarbonate solution was then added. The mixture was extracted with ethyl acetate (3×10 mL). Organic layers were separated, dried over anhydrous magnesium sulfate and concentrated under vacuum. The residue was purified by flash column chromatography (silica gel, hexanes/EtOAc=2/3 v/v) to give a white solid product, 0.55 g, 85.9% yield. MS: 360.4 [M+H]$^+$. $^1$H NMR (DMSO-d$_6$, 300 MHz): δ 8.14 (d, 1H, J=8.7 Hz), 7.39-7.34 (m, 3H), 7.19 (d, 1H, J=2.4 Hz), 7.13-7.03 (m, 3H), 6.62 (dd, 1H, J=7.5 Hz), 3.89 (s, 3H), 3.81 (s, 3H).

Synthesis of 4-Bromo-6-hydroxy-2-(4-hydroxyphenyl)isoquinolin-1(2H)-one (12b)

4-Bromo-6-methoxy-2-(4-methoxyphenyl)isoquinolin-1 (2H)-one (0.22 g, 0.61 mmol) was placed in a dry 150 mL single-necked flask fitted with a stirring bar and septa. Methylene chloride (30 mL) was added via a syringe. Boron tribromide (1.83 mL of 1.0 M methylene chloride solution) was added dropwise with stirring under argon atmosphere at room temperature. The reaction mixture was allowed to stir at room temperature for 20 hours. Then, 20 mL of water was added to quench the reaction. The mixture was extracted with 50 mL of ethyl acetate. The organic layer was separated, dried over anhydrous magnesium sulfate and concentrated under vacuum. The residue was subjected to flash column chromatography (silica gel, CH$_2$Cl$_2$/MeOH=9/1 v/v) to give a white solid product, 0.10 g, 49.4% yield. MS: 334.2 [M+H]$^+$. $^1$H NMR (DMSO-d$_6$, 300 MHz): δ 10.58 (s, 1H), 9.83 (s, 1H), 8.12 (d, 1H, J=8.7 Hz), 7.71 (s, 1H), 7.22 (d, 2H, J=8.7 Hz), 7.09 (d, 1H, J=21. Hz), 7.04 (dd, 1H, J$_1$=8.7 Hz, J$_2$=2.4 Hz), 6.84 (d, 2H, J=8.7 Hz).

In some embodiments this invention provides synthetic route for embodiments of 6,8-dihydroxy-isoquinolinones. An example of these embodiments of this invention provides a synthetic route for 4-bromo-6,8-dihydroxy-2-(4-hydroxyphenyl) isoquinolin-1(2H)-one.

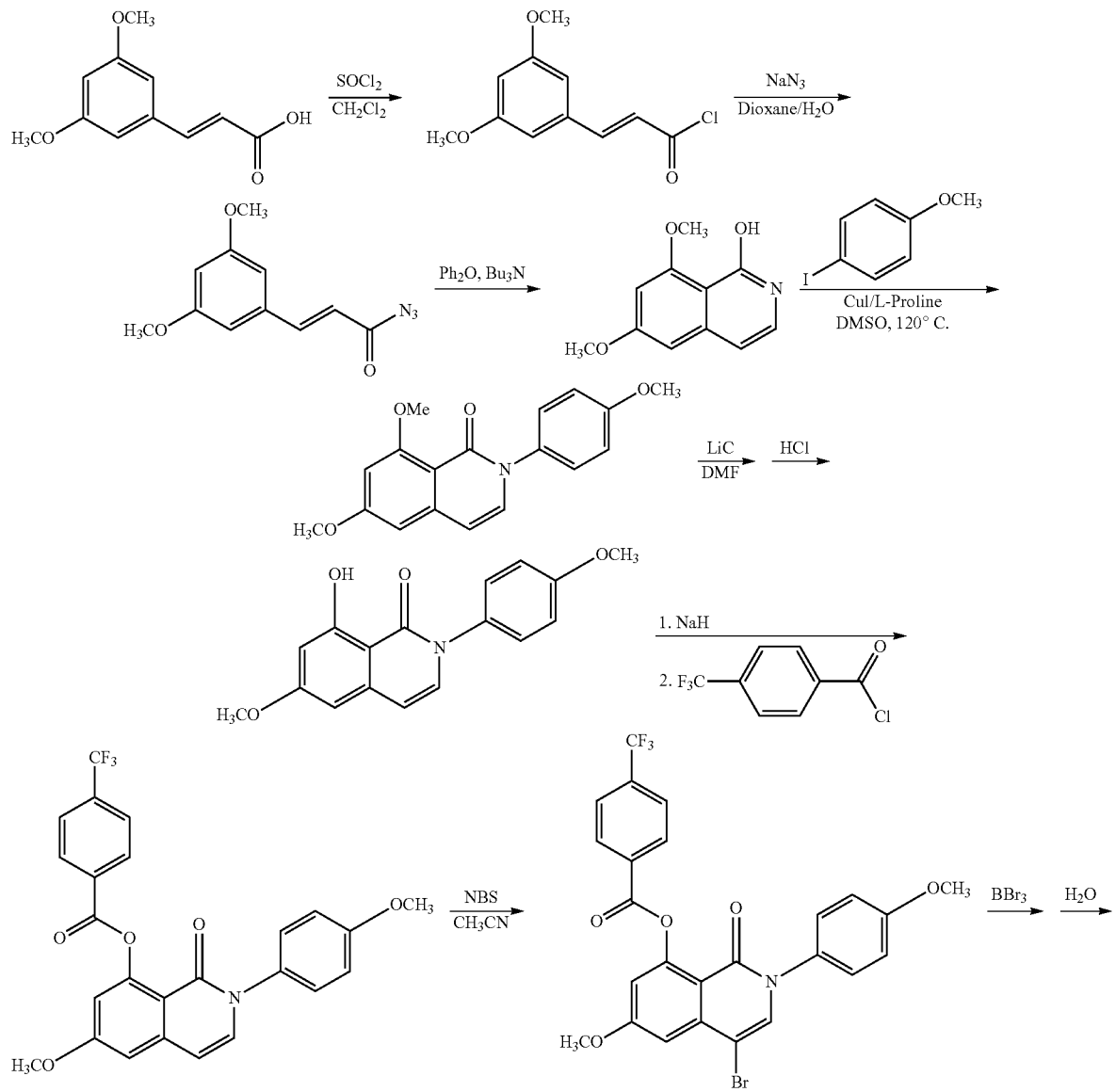

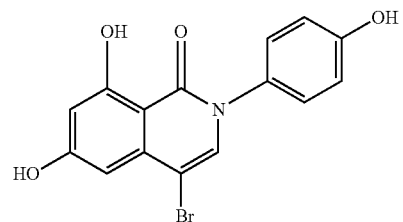

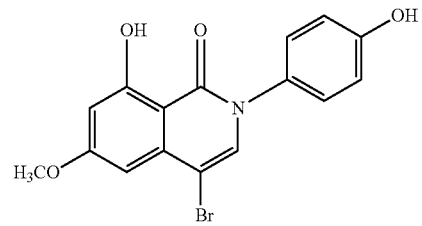

Synthesis of 6,8-dimethoxyisoquinolin-1-ol

A mixture of trans-3,5-dimethoxycinnamic acid (15.30 g, 73.48 mmol) and thionyl chloride (13.11 g, 0.11 mol) were placed in a 250 mL single-necked round-bottomed flask fitted with a magnetic stirring bar and reflux condenser. Dry methylene chloride (80.0 mL) was added to the above mixture. The resulting solution was heated to reflux for 3 hours. Then, the solvent was removed under reduced pressure. The residue was dried under vacuum overnight to give a pale-yellow solid, trans-3,5-dimethoxycinnamic acid chloride.

The pale-yellow solid acid chloride was dissolved in 20 mL of 1,4-dioxane and added drop wise over 1 h to a 0° C. suspension of 14.33 g (0.22 mol) of sodium azide in 80 mL of 1:1 (v/v) 1,4-dioxane/water. During the addition the temperature was maintained at 0° C. in an ice-bath. After complete addition of the acid chloride, the mixture was stirred for 1 h at 0° C., and then diluted with 75 mL of water. The mixture was extracted with methylene chloride (3×40 mL); the combined extracts were dried over anhydrous magnesium sulfate followed by filtration and concentration to approximately 100 mL. The solution was diluted with 20 mL of phenyl ether and further concentrated to remove the remaining methylene chloride (trans-3,5-dimethoxycinnamic acyl azide).

A 500 mL three-necked round-bottomed flask fitted with a nitrogen inlet, reflux condenser, an addition funnel, internal thermometer and magnetic stirring bar was charged with 29 mL of tributylamine and 80 mL of phenyl ether. The solution was heated to 230° C. and the acyl azide in 40 mL of phenyl ether was added drop wise over 3 h from an addition funnel. During the addition, the reflux temperature gradually decreased to about 200° C. Hence, after completion of the addition, the temperature was raised to 230° C. After heating for an additional hour at 230° C., the mixture was cooled to room temperature. The mixture was poured to 500 mL of hexanes with stirring. The solid was filtered and washed with hexanes (2×100 mL). The pale-yellow solid was dried and recrystallized from ethyl acetate/methanol mixture to give a pale-yellow crystalline material, 10.58 g, 70.2% yield. MS: nm/z 228.2 [M+Na]$^+$. $^1$H NMR (DMSO-d$_6$, 300 MHz): δ 10.71 (s, 1H), 7.02 (d, 1H, J=6.9 Hz), 6.63 (d, 1H, J=2.4 Hz), 6.47 (d, 1H, J=2.4 Hz), 6.31 (d, 1H, J=6.9 Hz), 3.83 (s, 3H), 3.79 (s, 3H).

Synthesis of 6,8-dimethoxy-2-(4-methoxyphenyl)isoquinolin-1(2H)-one 6,8-Dimethoxyisoquinolin-1-ol (1.59 g, 7.75 mmol), 4-iodoanisole (2.72, 11.62 mmol), copper(I) iodide (0.30 g, 1.55 mmol), L-proline (0.36 g, 3.10 mmol) and anhydrous potassium carbonate (2.14 g, 15.50 mmol) were placed in a dry 250 mL three-necked round-bottomed flask fitted with a stirring bar and reflux condenser. The system was vacuumed and refilled with dry argon. Then, anhydrous methyl sulfoxide (50 mL) was added via a syringe under argon atmosphere. The reaction solution was stirred and heated to 120° C. for 20 h. Water (20 mL) was added to quench the reaction. The mixture was extracted with ethyl acetate (5×20 mL). The extracts were combined, washed with brine (3×10 mL) and dried over anhydrous MgSO$_4$ followed by filtration and concentration to give a yellow residue. The yellow residue was purified by flash column chromatography (silica-gel, EtOAc) to give a pale-yellow solid product, 2.12 g, 88.0% yield. MS: m/z 312.9 [M+H]$^+$. $^1$H NMR (DMSO-d$_6$, 300 MHz): δ 7.31-7.26 (m, 3H), 7.02 (d, 2H, J=8.7 Hz), 6.71 (d, 1H, J=2.4 Hz), 6.54 (d, 1H, J=2.4 Hz), 6.45 (d, 1H, J=7.8 Hz), 3.87 (s, 3H), 3.81 (s, 3H), 3.79 (s, 3H).

Synthesis of 8-hydroxy-6-methoxy-2-(4-methoxyphenyl)isoquinolin-1(2H)-one 6,8-Dimethoxy-2-(4-methoxyphenyl)isoquinolin-1(2H)-one (2.25 g, 7.23 mmol) and LiCl (6.12 g, 144.54 mmol) were placed in a dry, argon flushed 150 mL three-necked flask fitted with a stirring bar and reflux condenser. Anhydrous DMF (30 mL) was added via a syringe. The reaction mixture was heated to 140° C. under vacuum for 20 h. Then, the reaction was quenched by addition of 30 mL of 2N HCl solution. The solution was extracted with EtOAc (3×30 mL). The extracts were combined and dried over anhydrous MgSO$_4$. The solvent was removed under reduced pressure. The residue was purified by flash column chromatography (silica-gel, EtOAc) to give a white solid product, 1.80 g, 83.7% yield. $^1$H NMR (DMSO-d$_6$, 300 MHz): δ 12.98 (s, 1H), 7.42-7.35 (m, 3H), 7.06 (d, 2H, J=9.0 Hz), 6.70-6.67 (m, 2H), 6.45 (d, 1H, J=2.1 Hz), 3.85 (s, 3H), 3.82 (s, 3H).

Synthesis of 6-methoxy-2-(4-methoxyphenyl)-1-oxo-1,2-dihydroisoquinolin-8-yl-4-(trifluoromethyl)benzoate 8-Hydroxy-6-methoxy-2-(4-methoxyphenyl)isoquinolin-1(2H)-one (0.60 g, 2.02 mmol) was placed in a dry 250 mL three-necked flask fitted with a stirring bar and sealed with septa. Anhydrous DMF (15 mL) was added via a syringe under argon atmosphere. The solution was cooled to 0° C. in an ice-bath. NaH (0.12 g, 3.03 mmol, 60% dispersion in mineral oil) was added. The reaction mixture was stirred at 0° C. for 30 minutes. Then, it was warmed to room temperature for 30 minutes. The mixture was cooled to 0° C. again in an ice bath. 4-Trifluormethylbenzoyl chloride was added via a syringe with stirring at 0° C. The reaction mixture was stirred at 0° C. for 30 minutes and at room temperature for additional 30 minutes. The reaction was quenched by adding 20 mL of saturated $NH_4Cl$ solution. The solution was diluted with 20 mL of water and stirred for one hour at room temperature. It was extracted with ethyl acetate (3×20 mL). The extracts were washed with brine (20 mL) and dried over anhydrous $MgSO_4$. The solvent was removed under reduced pressure. The residue was subjected to flash column chromatography (silica-gel, hexanes/EtOAc=1/1 v/v) to give a white solid product, 0.93 g, 98.1% yield. MS: m/z 492.1 $[M+Na]^+$. $^1H$ NMR (DMSO-$d_6$, 300 MHz): δ 8.25 (d, 2H, J=8.7 Hz), 7.93 (d, 2H, J=8.4 Hz), 7.40 (d, 1H, J=7.5 Hz), 7.23 (d, 2H, J=8.7 Hz), 7.21 (d, 1H, J=2.4 Hz), 7.01 (d, 1H, J=2.4 Hz), 6.98 (d, 2H, J=8.7 Hz), 6.67 (d, 1H, J=7.5 Hz), 3.93 (s, 3H), 3.76 (s, 3H).

Synthesis of 4-bromo-6-methoxy-2-(4-methoxyphenyl)-1-oxo-1,2-dihydroisoquinolin-8-yl-4-(trifluoromethyl)benzoate 6-Methoxy-2-(4-methoxyphenyl)-1-oxo-1,2-dihydroisoquinolin-8-yl-4-(trifluoromethyl)benzoate (0.51 g, 1.09 mmol) and N-bromosuccinimide (0.23 g, 1.30 mmol) were placed in a dry, argon flushed 150 mL single-necked flask fitted with a stirring bar and sealed with a septa. Acetonitrile (15 mL) was added via a syringe at room temperature under argon atmosphere. After the mixture was stirred at room temperature for 5 h, the solvent was removed under reduced pressure. The residue was purified by flash column chromatography (silica-gel, hexanes/EtOAc=1/1 v/v) to give a white solid product, 0.54 g, 90.0% yield. MS: m/z 572.1 $[M+Na]^+$. $^1H$ NMR (DMSO-$d_6$, 300 MHz): δ 8.26 (d, 2H, J=8.1 Hz), 7.93 (d, 2H, J=8.4 Hz), 7.28 (d, 2H, J=8.7 Hz), 7.21 (d, 1H, J=2.1 Hz), 7.20 (d, 1H, J=2.4 Hz), 6.97 (d, 2H, J=9.0 Hz), 3.98 (s, 3H), 3.76 (s, 3H).

Synthesis of 4-bromo-6,8-dihydroxy-2-(4-hydroxyphenyl) isoquinolin-1(2H)-one

4-Bromo-6-methoxy-2-(4-methoxyphenyl)-1-oxo-1,2-dihydroisoquinolin-8-yl-4-(trifluoromethyl)benzoate (0.47 g, 0.86 mmol) was placed in a dry 250 mL single-necked round-bottomed flask fitted with a stirring bar and sealed with a septa. Anhydrous methylene chloride (20 mL) was added via a syringe at room temperature. $BBr_3$ (8.60 mL of 1.0 M $CH_2Cl_2$ solution, 8.60 mmol) was added drop wise with stirring at room temperature. The resulting solution was heated to reflux for 20 hours and then stirred at room temperature for 3 days. 20 mL of water was added to quench the reaction. $CH_2Cl_2$ layer was separated and the aqueous layer was extracted with EtOAc (3×20 mL). The organic layers were combined and dried over anhydrous $MgSO_4$. The solvent was removed under reduced pressure. The residue was purified by column chromatography (silica-gel, $CH_2Cl_2$/MeOH=9/1 v/v) to give a white solid product, 0.05 g, 16.7% yield. MS: m/e 347.8 $[M-H]^-$. $^1H$ NMR (DMSO-$d_6$, 300 MHz): δ 13.12 (s, 1H), 10.78 (s, 1H), 9.81 (s, 1H), 7.75 (s, 1H), 7.28 (d, 2H, J=8.7 Hz), 6.85 (d, 2H, J=8.7 Hz), 6.61 (d, 1H, J=2.1 Hz), 6.37 (d, 1H, J=2.1 Hz).

In some embodiments this invention provides synthetic route for embodiments of 4-alkenyl isoquinolinones. An example of these embodiments of this invention provides a synthetic route for 6-hydroxy-2-(4-hydroxyphenyl)-4-vinyl-isoquinolin-1(2H)-one (14f) compound.

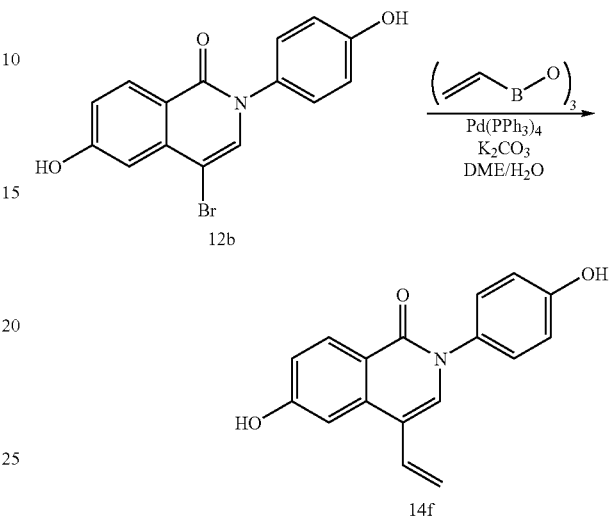

Synthesis of 6-hydroxy-2-(4-hydroxyphenyl)-4-vinylisoquinolin-1(2H)-one (14f)

4-Bromo-6-hydroxy-2-(4-hydroxyphenyl)-isoquinolin-1 (2H)-one (0.60 g, 1.81 mmol), tetrakis(triphenylphosphine) palladium (42 mg, 0.036 mmol), potassium carbonate (0.25 g, 1.81 mmol) and vinylboronic anhydride pyridine complex (0.22 g, 0.91 mmol) were placed in a dry and argon flushed 150 mL three-necked round-bottomed flask fitted with a stirring bar and reflux condenser. Anhydrous 1,2-dimethoxyethane (10 mL) and water (3 mL) were added via a syringe under argon atmosphere. The reaction solution was stirred and heated to reflux for 4 hours. The reaction was quenched by adding 20 mL of water at room temperature. The mixture was extracted with ethyl acetate/methanol (9/1 v/v) (2×20 mL). The extracts were combined, washed with brine (2×10 mL) and dried over anhydrous $MgSO_4$ followed by filtration and concentration to give a yellow residue. The yellow residue was purified by flash column chromatography (silica-gel, $CH_2Cl_2$/MeOH=19/1 v/v) to give a white solid product, 0.44 g, 87.0% yield. M.p. ° C. (decomposed). MS: m/z 280.0 $[M+H]^+$. $^1H$ NMR (DMSO-$d_6$, 300 MHz) δ 10.43 (s, 1H), 9.71 (s, 1H), 8.13 (d, 1H, J=8.7 Hz), 7.41 (s, 1H), 7.24 (d, 2H, J=8.7 Hz), 7.10 (d, 1H, J=2.1 Hz), 7.01 (dd, 1H, $J_1$=8.7 Hz, $J_2$=2.1 Hz), 6.88 (dd, 1H, $J_1$=17.4 Hz, $J_2$=10.8 Hz), 6.85 (d, 2H, J=8.7 Hz), 5.64 (dd, 1H, $J_1$=17.4 Hz, $J_2$=1.2 Hz), 5.26 (dd, 1H, $J_1$=10.8 Hz, $J_2$=1.2 Hz).

In some embodiments this invention provides synthetic route for embodiments of 4-carbonitrile derivatives of 1-oxo-1,2-dihydroisoquinolines. For example, this invention provides synthetic routes for 6-hydroxy-2-(4-hydroxyphenyl)-1-oxo-1,2-dihydroisoquinoline-4-carbonitrile (14h).

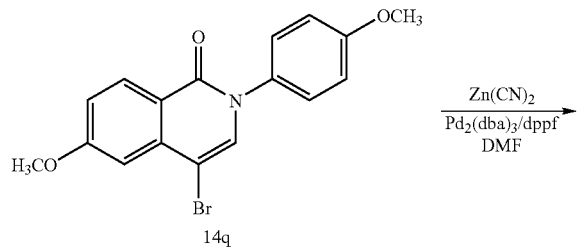

of water. The solution was stirred at room temperature for one hour, extracted with EtOAc (3×20 mL). The organic layers were separated, combined and dried over anhydrous MgSO$_4$. The solvent was removed under reduced pressure. The residue was purified by column chromatography (silica-gel, CH$_2$Cl$_2$/MeOH=9/1 v/v) to give a white solid product, 0.28 g, 68.5% yield. M.p. ° C. (decomposed). MS: m/z 279.0 [M+H]$^+$. $^1$H NMR (DMSO-d$_6$, 300 MHz) δ 10.86 (s, 1H), 9.80 (s, 1H), 8.38 (s, 1H), 8.13 (d, 1H, J=8.7 Hz), 7.25 (d, 2H, J=8.7 Hz), 7.09 (dd, 1H, J$_1$=8.7 Hz, J$_2$=2.4 Hz), 7.04 (d, 1H, J=2.4 Hz), 6.85 (d, 2H, J=8.7 Hz).

In some embodiments this invention provides synthetic route for embodiments of 8-carbonitrile derivatives of 1-oxo-1,2-dihydroisoquinolines. For example, this invention provides synthetic routes for 4-bromo-6-hydroxy-2-(4-hydroxyphenyl)-1-oxo-1,2-dihydroisoquinoline-8-carbonitrile (14k):

Synthesis of 6-methoxy-2-(4-methoxyphenyl)-1-oxo-1,2-dihydroisoquinoline-4-carbonitrile (14g)

4-Bromo-6-Methoxy-2-(4-methoxyphenyl)-isoquinolin-1 (2H)-one (0.80 g, 2.22 mmol), Zn(CN)$_2$ (0.40 g, 3.42 mmol), tris(dibenzylideneacetone)dipalladium (0.20 g, 0.22 mmol) and 1,1'-bis(diphenylphosphino)ferrocene (0.49 g, 0.89 mmol) were placed in a dry and argon flushed 150 mL three-necked round-bottomed flask fitted with a stirring bar and reflux condenser. Then, anhydrous dimethylformamide (30 mL) was added via a syringe under argon atmosphere. The reaction solution was stirred and heated to 100° C. for 5 hours. Water (30 mL) was added to quench the reaction. The mixture was extracted with ethyl acetate (2×20 mL). The extracts were combined, washed with brine (3×10 mL) and dried over anhydrous MgSO$_4$ followed by filtration and concentration to give a yellow residue. The yellow residue was purified by flash column chromatography (silica-gel, EtOAc/hexanes=1/1 v/v) to give a pale-yellow solid product, 0.63 g, 92.6% yield. M.p. ° C. (decomposed). MS: m/z 307.0 [M+H]$^+$. $^1$H NMR (DMSO-d$_6$, 300 MHz) (8.48 (s, 1H), 8.22 (d, 1H, J=9.0 Hz), 7.43 (d, 2H, J=8.7 Hz), 7.27 (dd, 1H, J$_1$=8.7 Hz, J$_2$=2.4 Hz), 7.08 (d, 1H, J=2.4 Hz), 7.06 (d, 2H, J=8.7 Hz), 3.97 (s, 3H), 3.82 (s, 3H).

Synthesis of 6-hydroxy-2-(4-hydroxyphenyl)-1-oxo-1,2-dihydroisoquinoline-4-carbonitrile (14h)

6-Methoxy-2-(4-methoxyphenyl)-isoquinoline-4-carbonitrile (0.45 g, 1.47 mmol) was placed in a dry and argon flushed 150 mL single-necked round-bottomed flask fitted with a stirring bar and an argon inlet. BBr$_3$ (9.0 mL of 1.0M CH$_2$Cl$_2$ solution, 9.0 mmol) was added via a syringe with stirring at room temperature. After stirred at room temperature for 24 hours, the reaction was quenched by adding 20 mL

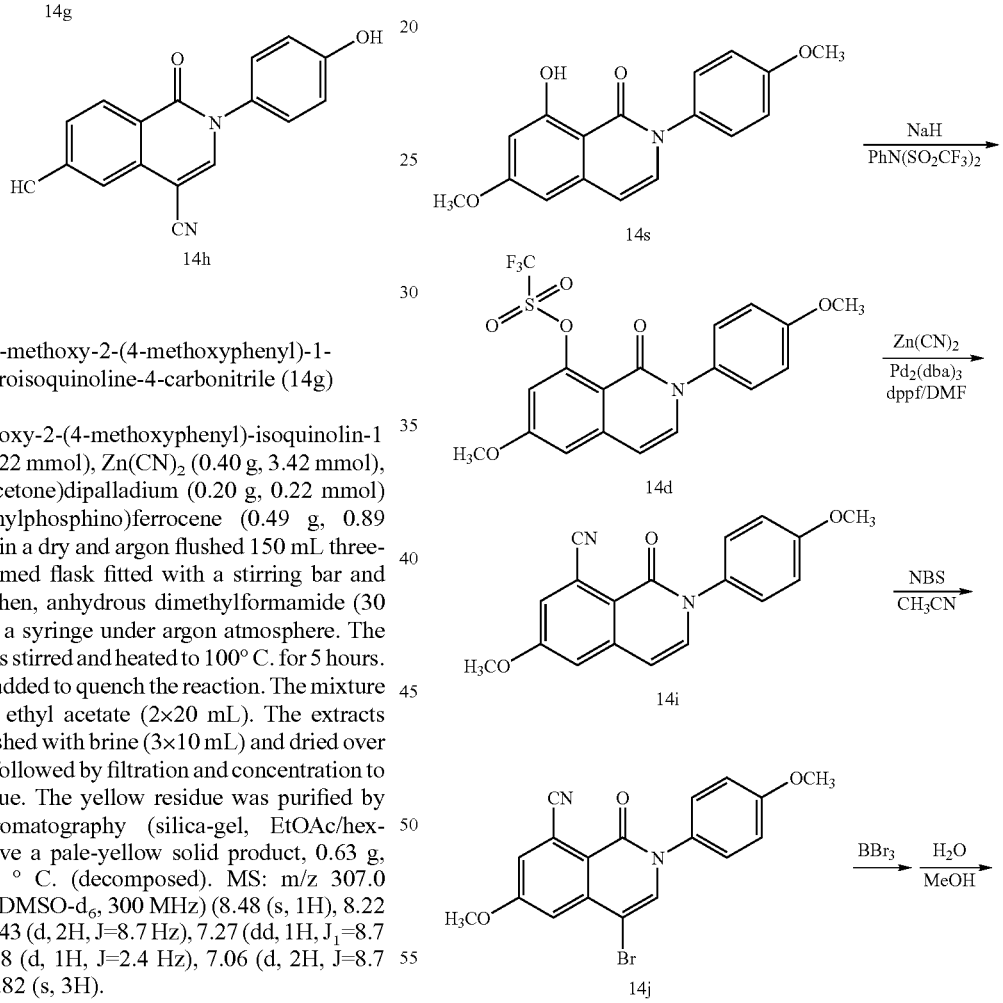

Synthesis of 6-methoxy-2-(4-methoxyphenyl)-1-oxo-1,2-dihydroisoquinolin-8-yl trifluoromethanesulfonate (14d)

8-hydroxy-6-methoxy-2-(4-methoxyphenyl)isoquinolin-1(2H)-one (2.10 g, 7.06 mmol) was dissolved in 30 mL of anhydrous dimethylformide in a 250 mL three-necked round-bottomed flask fitted with a magnetic stirring bar, an argon inlet and sealed with rubber stoppers. The solution was cooled to 0° C. in an ice-bath. Sodium hydride (0.37 g of 60% wt. in mineral oil, 9.18 mmol) was added in 4 portions under argon atmosphere. The reaction mixture was stirred at 0° C. for 30 minutes, then at room temperature for 30 minutes. After the solution was cooled to 0° C. again, N-phenyl-bis(trifluoromethanesulfonamide) (2.65 g, 7.41 mmol) was added in portions under argon protection. The reaction mixture was stirred at 0° C. for 30 minutes and at room temperature for one hour. The reaction was quenched by adding 50 mL of saturated ammonia chloride solution, and diluted with 50 mL of water. The solution was extracted with ethyl acetate (3×50 mL). The organic layers were separated, combined, washed with brine, dried over anhydrous $MgSO_4$, filtered and concentrated under reduced pressure. The residue was purified by flash column chromatography (silica gel, hexanes/EtOAc=1/1 v/v) to give a white solid product, 2.85 g, 94.1% yield. M.p. ° C. (decomposed). MS: m/z 452.1 $[M+Na]^+$. $^1H$ NMR (DMSO-$d_6$, 300 MHz) δ 7.52 (d, 1H, J=7.2 Hz), 7.38 (d, 1H, J=2.4 Hz), 7.34 (d, 2H, J=9.0 Hz), 7.07 (d, 2H, J=9.0 Hz), 7.02 (d, 1H, J=1.8 Hz), 6.72 (d, 1H, J=7.5 Hz), 3.94 (s, 3H), 3.82 (s, 3H).

Synthesis of 6-methoxy-2-(4-methoxyphenyl)-1-oxo-1,2-dihydroisoquinoline-8-carbonitrile (14i)

6-Methoxy-2-(4-methoxyphenyl)-1-oxo-1,2-dihydroisoquinolin-8-yl trifluoromethanesulfonate (0.43 g, 1.00 mmol), $Zn(CN)_2$ (0.14 g, 1.20 mmol), tris(dibenzylideneacetone)dipalladium (92 mg, 0.1 mmol) and 1,1'-bis(diphenylphosphino)ferrocene (0.22 g, 0.40 mmol) were placed in a dry and argon flushed 150 mL three-necked round-bottomed flask fitted with a stirring bar and reflux condenser. Then, anhydrous dimethylformide (20 mL) was added via a syringe under argon atmosphere. The reaction solution was stirred and heated to 100° C. for 4 hours. Water (20 mL) was added to quench the reaction. The mixture was extracted with ethyl acetate (4×30 mL). The extracts were combined, washed with brine (3×10 mL) and dried over anhydrous $MgSO_4$ followed by filtration and concentration to give a yellow residue. The yellow residue was purified by flash column chromatography (silica-gel, EtOAc/hexanes=3/2 v/v) to give a white solid product, 0.23 g, 75.2% yield. M.p. ° C. (decomposed). MS: m/z 307.2 $[M+H]^+$. $^1H$ NMR (DMSO-$d_6$, 300 MHz) δ 7.63 (d, 1H, J=2.1 Hz), 7.54 (d, 1H, J=2.1 Hz), 7.51 (d, 1H, J=7.5 Hz), 7.38 (d, 2H, J=8.7 Hz), 7.06 (d, 2H, J=8.7 Hz), 6.71 (d, 1H, J=7.5 Hz), 3.95 (s, 3H), 3.82 (s, 3H).

Synthesis of 4-bromo-6-methoxy-2-(4-methoxyphenyl)-1-oxo-1,2-dihydroisoquinoline-8-carbonitrile (14j)

Compound 6-methoxy-2-(4-methoxyphenyl)-1-oxo-1,2-dihydroisoquinoline-8-carbonitrile (0.22 g, 0.72 mmol) and N-bromosuccinimide (0.15 g, 0.86 mmol) were placed in a dry, argon flushed 150 mL single-necked flask fitted with a stirring bar and sealed with a rubber stopper. Acetonitrile (10 mL) was added via a syringe at room temperature under argon atmosphere. After the mixture was stirred at room temperature for 4 hours, the solvent was removed under reduced pressure. The residue was purified by flash column chromatography (silica-gel, hexanes/EtOAc=2/3 v/v) to give a white solid product, 0.23 g, 83.3% yield. M.p. ° C. (decomposed). MS: m/z 387.1 $[M+H]^+$. $^1H$ NMR (DMSO-$d_6$, 300 MHz), δ 8.01 (s, 1H), 7.81 (d, 1H, J=2.4 Hz), 7.43 (d, 1H, J=2.4 Hz), 7.42 (d, 2H, J=8.7 Hz), 7.07 (d, 2H, J=8.7 Hz), 4.02 (s, 3H), 3.82 (s, 3H).

Synthesis of 4-bromo-6-hydroxy-2-(4-hydroxyphenyl)-1-oxo-1,2-dihydroisoquinoline-8-carbonitrile (14k)

4-Bromo-6-methoxy-2-(4-methoxyphenyl)-1-oxo-1,2-dihydroisoquinoline-8-carbonitrile (0.15 g, 0.39 mmol) was placed in a dry and argon flushed 100 mL single-necked round-bottomed flask fitted with a stirring bar, reflux condenser and an argon inlet. Anhydrous chlorobenzene (10 mL) was added via a syringe at room temperature. $BBr_3$ (0.59, 2.33 mmol) was added via a syringe with stirring at room temperature. The resulting solution was heated to 120° C. for 4 hours. 10 mL of water was added to quench the reaction. After stirred at room temperature for one hour, the solution was extracted with EtOAc (5×20 mL). The organic layers were combined and dried over anhydrous $MgSO_4$. The solvent was removed under reduced pressure. The residue was purified by column chromatography (silica-gel, $CH_2C_2$/MeOH=9/1 v/v) to give a white solid product, 0.05 g, 36.0% yield. M.p. ° C. (decomposed). MS: m/z 357.1 $[M+H]^+$. $^1H$ NMR (DMSO-$d_6$, 300 MHz) δ 11.40 (s, 1H), 9.79 (s, 1H), 7.91 (s, 1H), 7.48 (d, 1H, J=2.1 Hz), 7.38 (d, 1H, J=2.1 Hz), 7.26 (d, 2H, J=8.7 Hz), 6.86 (d, 2H, J=8.7 Hz).

In some embodiments this invention provides synthetic route for 14o compound

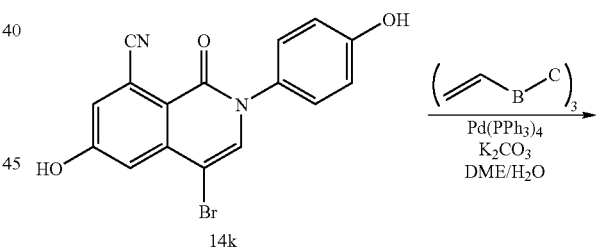

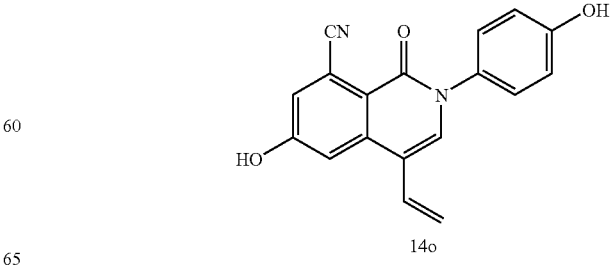

53
In some embodiments this invention provides synthetic route for 14p compound
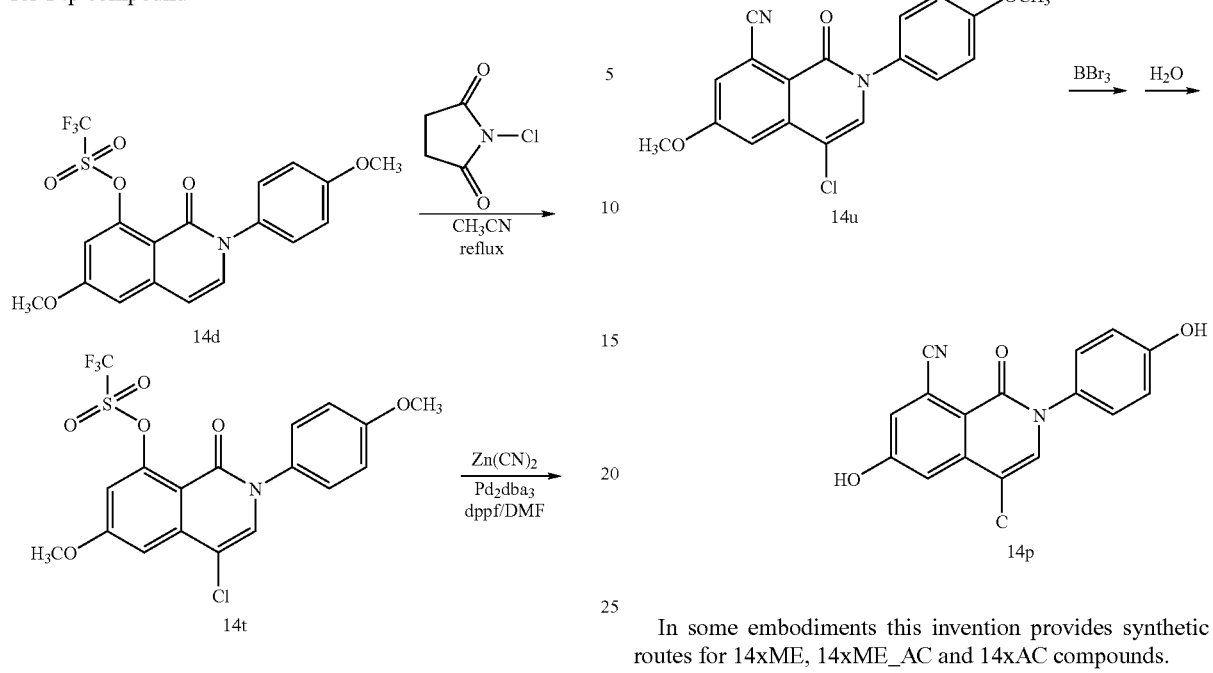
54
In some embodiments this invention provides synthetic routes for 14xME, 14xME_AC and 14xAC compounds.
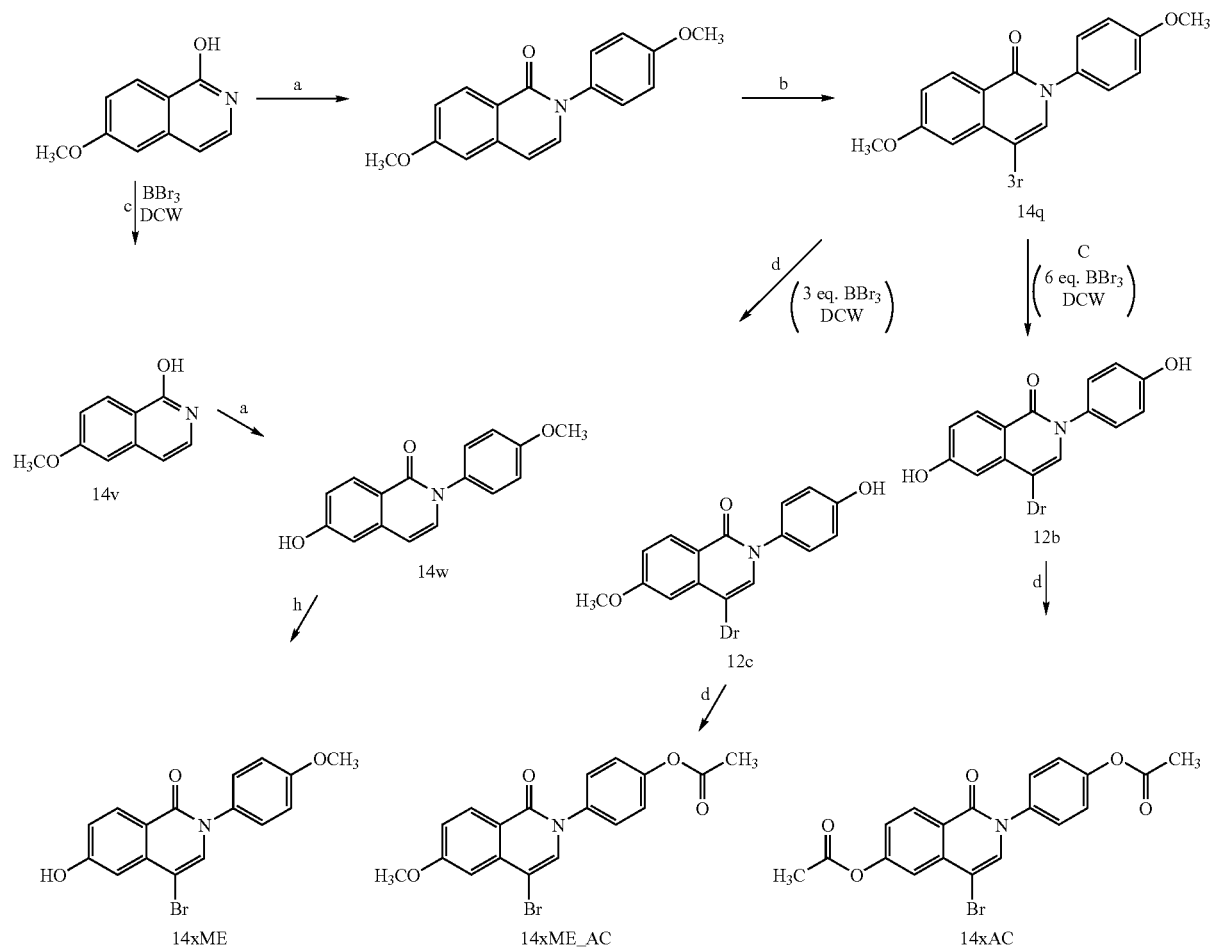

Synthesis of 4-bromo-6-hydroxy-2-(4-hydroxyphenyl)isoquinolin-1(2H)-one (12b)

4-Bromo-6-methoxy-2-(4-methoxyphenyl)isoquinolin-1 (2H)-one (14q) was prepared as described above. 14q was placed in a dry 150 mL single-necked flask fitted with a stirring bar and septa. Chlorobenzene (30 mL) was added via a syringe. Boron tribromide (6 equivalents, neat) was added dropwise with stirring under argon atmosphere at room temperature. The reaction mixture was allowed to stir at room temperature for 20 hours. Then, 20 mL of water was added to quench the reaction. The mixture was extracted with 50 mL of ethyl acetate. The organic layer was separated, dried over anhydrous magnesium sulfate and concentrated under vacuum. The residue was subjected to flash column chromatography (silica gel, $CH_2Cl_2$/MeOH=9/1 v/v) to give a white solid product, 0.10 g, 49.4% yield. MS: 334.2 $[M+H]^+$. $^1$H NMR (DMSO-$d_6$, 300 MHz): δ 10.58 (s, 1H), 9.83 (s, 1H), 8.12 (d, 1H, J=8.7 Hz), 7.71 (s, 1H), 7.22 (d, 2H, J=8.7 Hz), 7.09 (d, 1H, J=21. Hz), 7.04 (dd, 1H, J=8.7 Hz, $J_2$=2.4 Hz), 6.84 (d, 2H, J=8.7 Hz).

Synthesis of 4-Bromo-2-(4-hydroxyphenyl)-6-methoxy-isoquinolin-1(2H)-one (12c)

4-Bromo-6-methoxy-2-(4-methoxyphenyl)isoquinolin-1 (2H)-one (14q) was prepared as described above. 14q was placed in a dry 150 mL single-necked flask fitted with a stirring bar and septa. Chlorobenzene (30 mL) was added via a syringe. Boron tribromide (3 equivalents, neat) was added dropwise with stirring under argon atmosphere at room temperature. The reaction mixture was allowed to stir at room temperature for 20 hours. Then, 20 mL of water was added to quench the reaction. The mixture was extracted with 50 mL of ethyl acetate. The organic layer was separated, dried over anhydrous magnesium sulfate and concentrated under vacuum. The residue was subjected to flash column chromatography (silica gel, $CH_2Cl_2$/MeOH=9/1 v/v) to give a white solid product, 0.10 g, 49.4% yield. MS: 334.2 $[M+H]^+$. $^1$H NMR (DMSO-$d_6$, 300 MHz): δ 10.58 (s, 1H), 9.83 (s, 1H), 8.12 (d, 1H, J=8.7 Hz), 7.71 (s, 1H), 7.22 (d, 2H, J=8.7 Hz), 7.09 (d, 1H, J=21. Hz), 7.04 (dd, 1H, J=8.7 Hz, $J_2$=2.4 Hz), 6.84 (d, 2H, J=8.7 Hz).

Synthesis of 4-(6-acetoxy-4-bromo-1-oxoisoquinolin-2(1H)-yl)phenyl acetate (14xAC) and 4-(4-bromo-6-methoxy-1-oxoisoquinolin-2(1H)-yl)phenyl acetate (14xME_AC)

To a solution of 12b or 12c (0.3 mmol) in dry 10 mL dichloromethane was added anhydrous acetyl chloride (0.9 mmol), and then triethyl amine (0.9 mmol) dropwise at 0° C. under argon atmosphere. The reaction mixture was stirred for 30 minutes at room temperature. Water (30 mL) was added for quenching the reaction. The organic layer was washed with saturated $NH_4Cl$ solution and brine, dried with anhydrous $MgSO_4$, concentrated under reduced pressure, purified by flash column chromatography as an eluent of EtOAc/hexane (1/3, v/v) to get the desired product.

Synthesis of 4-bromo-6-hydroxy-2-(4-methoxyphenyl)isoquinolin-1(2H)-one (14xME)

6-Methoxyisoquinoline-1-ol was prepared as described above, followed by deprotection of the methoxy group using chlorobenzene and boron tribromide (6 equivalents, neat) added dropwise under argon atmosphere at room temperature, to obtain isoquinoline-1,6-diol (14v). Compound 14v (11.5 mmol) reacted with 4-iodoanisole (4.01 g, 17.13 mmol), copper (I) iodide (0.44 g, 2.28 mmol). L-proline (0.53 g, 4.57 mmol) and anhydrous potassium carbonate (3.16 g, 22.84 mmol) were placed in a dry 250 mL three-necked round-bottomed flask fitted with a stirring bar and reflux condenser. The reaction flask was vacuumed and refilled with dry argon. 50 mL of anhydrous methyl sulfoxide was added via syringe. The reaction mixture was stirred and heated to 130° C. for 20 hours. 50 mL of water was added to quench the reaction, and solid precipitated out. The solid was filtered, washed with water (2×20 mL) and dried in air. This solid was purified by flash column chromatography (silica gel, ethyl acetate) to give 6-hydroxy-2-(4-methoxyphenyl)isoquinolin-1(2H)-one (14w) a brown solid product. Compound 14w (1.8 mmol) was placed in a dry 250 mL single-necked round-bottomed flask fitted with a stirring bar and septa. Acetonitrile (10 mL) was added via a syringe under argon atmosphere at room temperature. N-Bromosuccinimide or NBS (0.33 g, 1.87 mmol) was added portionwise under argon atmosphere at room temperature. The reaction mixture was allowed to stir at room temperature for 2 hours. 20 mL of saturated sodium bicarbonate solution was then added. The mixture was extracted with ethyl acetate (3×10 mL). Organic layers were separated, dried over anhydrous magnesium sulfate and concentrated under vacuum. The residue was purified by flash column chromatography (silica gel, hexanes/EtOAc=2/3 v/v) to give white solid of 4-bromo-6-hydroxy-2-(4-methoxyphenyl)isoquinolin-1(2H)-one (14xME)

In some embodiments this invention provides synthetic routes for 4-bromo-6-hydroxy-2-(4-hydroxyphenyl)-1-oxo-1,2-dihydroisoquinoline-8-carbimidic acid (14yAM), methyl 4-bromo-6-hydroxy-2-(4-hydroxyphenyl)-1-oxo-1,2-dihydroisoquinoline-8-carboxylate (14yME), and 4-bromo-6-hydroxy-2-(4-hydroxyphenyl)-1-oxo-1,2-dihydroisoquinoline-8-carboxylic acid (14z) compounds.

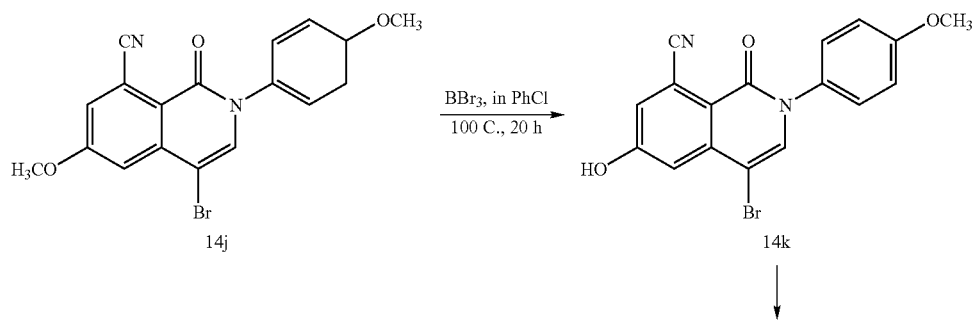

-continued
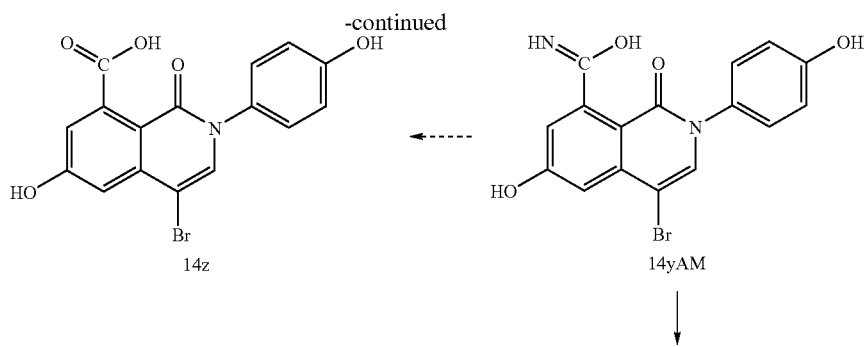
14z
14yAM
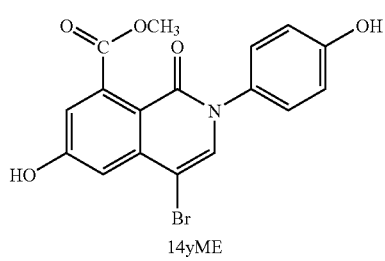
14yME
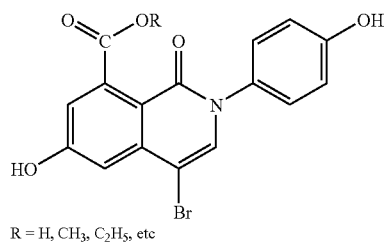
R = H, CH$_3$, C$_2$H$_5$, etc
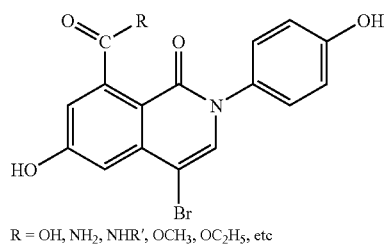
R = OH, NH$_2$, NHR', OCH$_3$, OC$_2$H$_5$, etc
In some embodiments this invention provides synthetic routes for 6-hydroxy-2-(4-hydroxyphenyl)-4-phenylisoquinolin-1(2H)-one (15a).
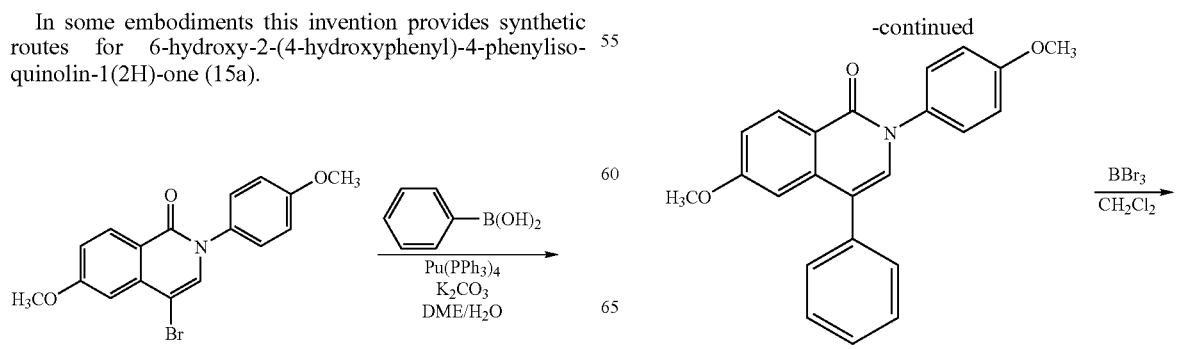

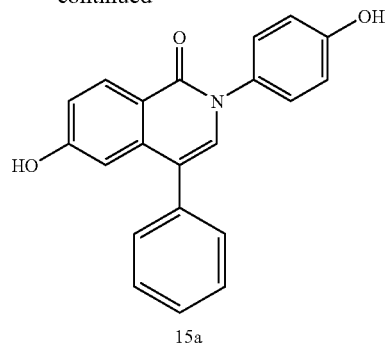

15a

Synthesis of 6-methoxy-2-(4-methoxyphenyl)-4-phenylisoquinolin-1(2H)-one

4-Bromo-6-methoxy-2-(4-methoxyphenyl)-isoquinolin-1 (2H)-one (0.52 g, 1.44 mmol), tetrakis(triphenylphosphine) palladium (83 mg, 0.07 mmol), potassium carbonate (0.22 g, 1.00 mmol) and phenylboronic acid (0.21 g, 1.73 mmol) were placed in a dry and argon flushed 150 mL three-necked round-bottomed flask fitted with a stirring bar and reflux condenser. 1,2-Dimethoxyethane (10 mL) and water (3 mL) were added via a syringe under argon atmosphere. The reaction solution was stirred and heated to reflux for 20 hours. The reaction was quenched by adding 30 mL of water at room temperature. The mixture was extracted with ethyl acetate (3×20 mL). The extracts were combined, washed with brine (2×10 mL) and dried over anhydrous MgSO$_4$ and 2 g of 3-(diethylenetri-amino)propylfunctionalized silica gel followed by filtration and concentration to give a yellow residue. The yellow residue was purified by flash column chromatography (silica-gel, hexanes/ethyl acetate=2/3 v/v) to give a white solid product, 0.50 g, 98.0% yield. MS: m/z 358.3 [M+H]$^+$. $^1$H NMR (DMSO-d$_6$, 300 MHz) (8.30 (d, 2H, J=9.0 Hz), 7.55-7.40 (m, 8H), 7.29 (s, 1H), 7.21 (dd, 1H, J$_1$=9.0 Hz, J$_2$=2.4 Hz), 7.05 (d, 2H, J=9.0 Hz), 6.94 (d, 1H, J=2.4 Hz), 3.81 (s, 3H), 3.78 (s, 3H).

Synthesis of 6-hydroxy-2-(4-hydroxyphenyl)-4-phenylisoquinolin-1(2H)-one (15a)

6-Methoxy-2-(4-methoxyphenyl)-4-phenylisoquinolin-1 (2H)-one (0.36 g, 1.01 mmol) was placed in a dry 150 mL single-necked flask fitted with a stirring bar and septa. Methylene chloride (30 mL) was added via a syringe. Boron tribromide (5.0 mL of 1.0 M methylene chloride solution) was added dropwise with stirring under argon atmosphere at room temperature. The reaction mixture was allowed to stir at room temperature for 16 hours. Then, 20 mL of water was added to quench the reaction. The mixture was extracted with ethyl acetate (3×20 mL). The organic layers were separated, dried over anhydrous magnesium sulfate and concentrated under vacuum. The residue was subjected to flash column chromatography (silica gel, CH$_2$Cl$_2$/MeOH=9/1 v/v) to give a white solid product, 0.29 g, 87.9% yield. MS: 330.2 [M+H]$^+$. $^1$H NMR (DMSO-d$_6$, 300 MHz): δ 10.31 (s, 1H), 9.69 (s, 1H), 8.19 (d, 1H, J=8.7 Hz), 7.52-7.39 (m, 5H), 7.28 (d, 2H, J=8.7 Hz), 7.18 (s, 1H), 7.00 (dd, 1H, J$_1$=8.7 Hz, J$_2$=2.4 Hz), 6.87-6.82 (m, 3H).

In some embodiments the following compounds are synthesized via Suzuki coupling reactions as described for compound 15a.

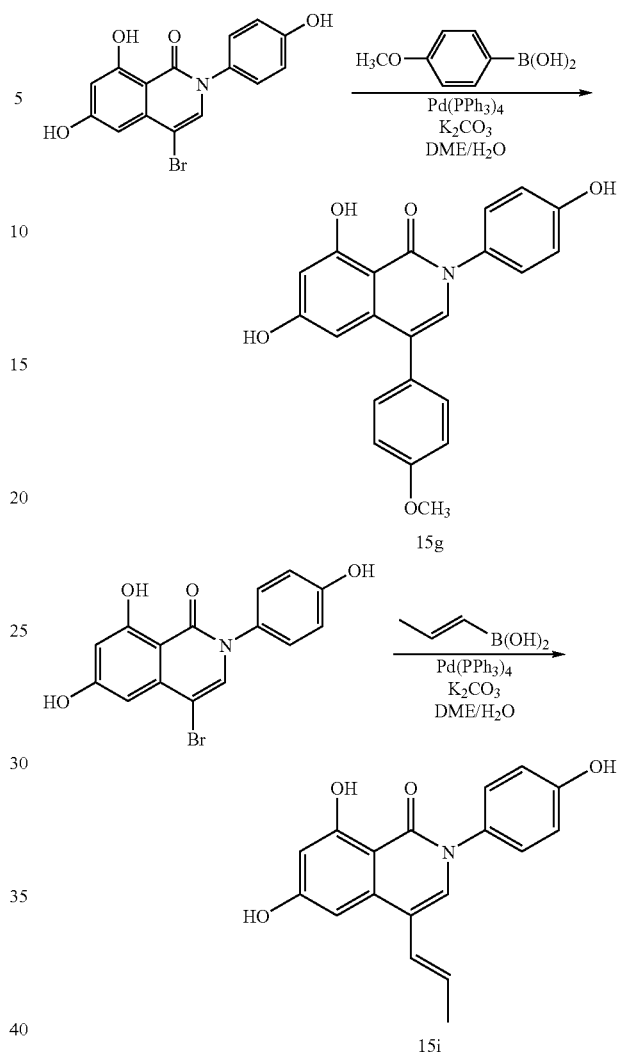

Synthesis of Compound 1-(2-(piperidin-1-yl)ethoxy)isoquinolin-6-ol (13a)

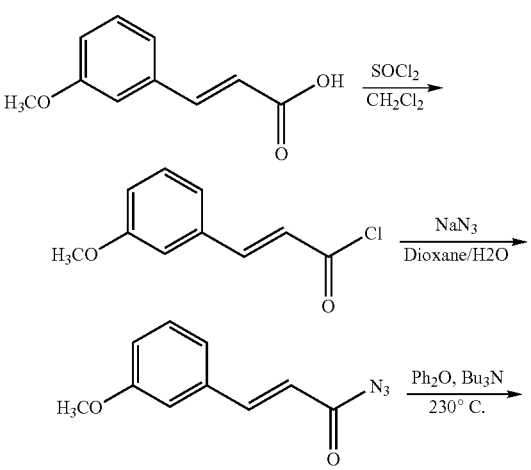

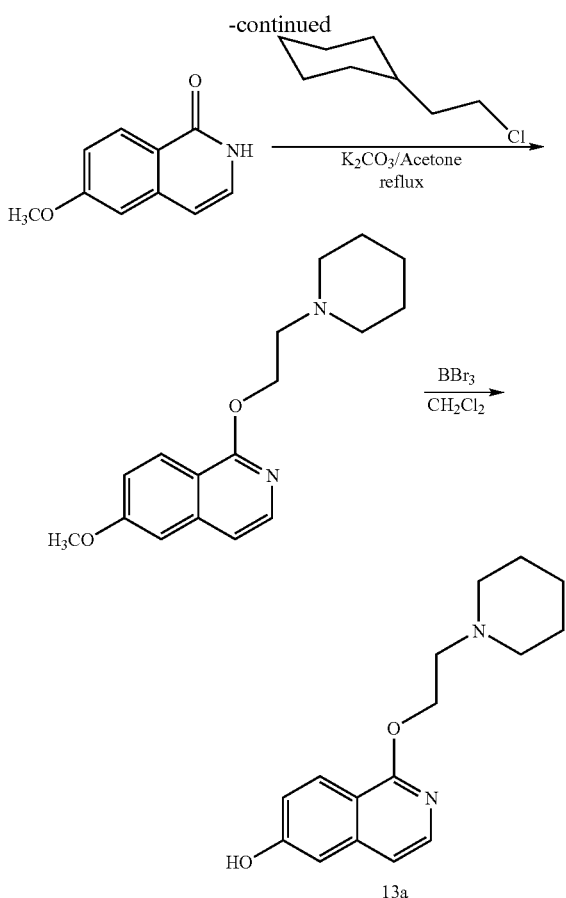

Synthesis of 6-methoxyisoquinoline-1-ol

A mixture of 17.82 g (0.10 mol) of trans-3-methoxycinnamic acid and thionyl chloride (14.28 g, 0.12 mol) were placed in a 250 mL single-necked round-bottomed flask fitted with a stirring bar and reflux condenser. 80 mL of dry methylene chloride was added to the flask. The resulted mixture was heated to reflux for 3 hours. Then, the solvent was removed under reduced pressure. The residue oil was dried under vacuum overnight. The pale-yellow solid acid chloride was dissolved in 20 mL of 1,4-dioxane and added dropwise with stirring to a 0° C. suspension of 19.50 g (0.30 mol) of sodium azide in 80 mL of 1,4-dioxane/water (1:1 mixture). During the addition the temperature was maintained at 0° C. After complete addition of the acid chloride, the mixture was stirred at 0° C. for an additional hour, then diluted with 75 mL of water. The mixture was extracted with methylene chloride (2×40 mL). The combined extracts were dried over anhydrous magnesium sulfate, filtered and concentrated to ca. 100 mL. The solution was diluted with 20 mL of phenyl ether and further concentrated to remove the remaining methylene chloride.

A 500 mL 3-necked round-bottomed flask fitted with an argon inlet, reflux condenser, additional funnel and an internal thermometer was charged with 29 mL of tributylamine and 80 mL of phenyl ether. The solution was heated to 230° C., and the acyl azide in 20 mL of phenyl ether was added dropwise with stirring over 3 hours from an addition funnel. During the addition, the reflux temperature gradually decreased to 200° C. After, completion of the addition, the distillate was collected in the addition funnel (15 mL of a 1:1 mixture of tributylamine/phenyl ether) until the temperature reached 230° C. After heating for an additional hour at 230° C., the mixture was cooled to room temperature. The mixture was then poured to 500 mL of hexanes with stirring. The solid was filtered and washed with hexanes (2×100 mL). The pale-yellow solid was recrystallized from ethyl acetate/methanol (9/1 v/v) to give a pure pale-yellow crystalline material, 15.28 g, 87.2% yield. MS: 198.1 [M+Na]$^+$. $^1$H NMR (DMSO-d$_6$, 300 MHz): δ 11.06 (s, 1H), 8.08 (d, 1H, J=8.5 Hz), 7.14-7.14 (m, 1H), 7.10 (d, 1H, J=2.5 Hz), 7.05-7.03 (m, 1H), 7.04 (dd, 1H, J$_1$=9.0 Hz, J$_2$=2.5 Hz), 6.47 (d, 1H, J=7.0 Hz), 3.86 (s, 3H).

Synthesis of 6-methoxy-1-(2-(piperidin-1-yl)ethoxy)isoquinoline

To a solution of 6-methoxyisoquinoline-1-ol (1.00 g, 5.71 mmol) in acetone, K$_2$CO$_3$ (4.73 g, 34.26 mmol) and N-chloroethyl-piperidine hydrochloride salt (1.37 g, 7.42 mmol) were added. The solution was heated to reflux for 6 hours. The solution was evaporated to dryness. The residue was hydrolyzed by adding water, then extracted with ethyl acetate. The organic layers were separated and dried over anhydrous MgSO$_4$. The solvent was removed under reduced pressure. The residue was purified by flash chromatography (silica-gel; methylene chloride/methanol=9/1 v/v) to give a yellow oil product, 1.50 g, 92.0% yield. MS: 287.2 [M+H]$^+$. $^1$H NMR (DMSO-d$_6$, 300 MHz) δ 8.11 (d, 1H, J=9.0 Hz), 7.39 (d, 1H, J=7.5 Hz), 7.10-7.13 (m, 2H), 6.51 (d, 1H, J=7.5 Hz), 4.02 (t, 2H, J=6.6 Hz), 3.86 (s, 3H), 2.55 (t, 2H, J=6.5 Hz), 2.41 (br, 4H), 1.52-1.44 (m, 4H), 1.37-114 (m, 2H).

Synthesis of 1-(2-(piperidin-1-yl)ethoxy)isoquinolin-6-ol (13a)

6-Methoxy-1-(2-(piperidin-1-yl)ethoxy)isoquinoline (0.60 g, 2.10 mmol) was dissolved in 30 mL of dry CH$_2$Cl$_2$ at room temperature. BBr$_3$ (10.50 mmol, 10.50 mL of 1.0 M CH$_2$Cl$_2$ solution) was added dropwise with stirring via a syringe at room temperature. The reaction solution was allowed to stir overnight at room temperature. The mixture was cooled to 0° C. in an ice bath and hydrolyzed by adding water. EtOAc was added to partition the solution. The organic layer was separated; the aqueous layer was extracted with EtOAc twice. The organic layers were combined, washed with brine and dried over anhydrous MgSO$_4$. The solvent was removed under vacuum. The residue was purified by flash column chromatography using silica-gel with CH$_3$OH/CH$_2$Cl$_2$ (1/9 v/v) to give a white solid product, 40 g, 70.2% yield. MS: 273.2 [M+H]$^+$. $^1$H NMR (DMSO-d$_6$, 300 MHz) δ 10.29 (s, 1H), 8.05 (d, 1H, J=8.7 Hz), 7.32 (d, 1H, J=7.2 Hz), 6.93 (d, 1H, J=8.4 Hz), 6.87 (s, 1H), 6.43 (d, 1H, J=7.2 Hz), 4.03 (s, br, 2H), 2.62 (s, br, 2H), 2.50 (s, br, 2H), 1.49-1.39 (m, 6H).

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention.

As used herein, administration can be accomplished in vitro, i.e. in a test tube, or in vivo, i.e. in cells or tissues of living organisms, for example humans. In one embodiment, the present invention encompasses administering the compounds of the present invention to a subject.

The pharmaceutical compositions containing the compounds of this invention can be administered to a subject by any method known to a person skilled in the art, such as orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the recombinant virus/composition can be delivered to tissue (e.g., needle or catheter). Alternatively, topical administration may be desired for application to mucosal cells, for skin or ocular application. Another method of administration is via aspiration or aerosol formulation.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment of the present invention, the NRBA compounds are formulated in a capsule. In accordance with this embodiment, the compositions of the present invention comprise in addition to a compound of this invention and the inert carrier or diluent, a hard gelatin capsule.

In one embodiment, the micronized capsules comprise particles containing a compound of this invention, wherein the term "micronized" used herein refers to particles having a particle size is of less than 200 microns, or in another embodiment less than 100 microns, or in another embodiment, less than 60 microns, or in another embodiment, less than 36 microns, or in another embodiment, less than 16 microns, or in another embodiment, less than 10 microns, or in another embodiment, less than 6 microns.

Further, in another embodiment, the pharmaceutical compositions are administered by intravenous, intraarterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of a compound as herein described over a period of time. In a further embodiment, the pharmaceutical compositions are administered intravaginally.

In another embodiment, the active compound can be delivered in a vesicle, in particular a liposome (see Langer, Science 249:1627-1633 (1990); Treat et al., in Liposomes in the Therapy of Infectious Disease and Cancer, Lopez-Berestein and Fidler (eds.), Liss, New York, pp. 363-366 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In one embodiment, the compositions of this invention may include, a compound of this invention or any combination thereof, together with one or more pharmaceutically acceptable excipients.

It is to be understood that this invention encompasses any embodiment of a compound as described herein, which in some embodiments is referred to as "a compound of this invention".

Suitable excipients and carriers may be, according to embodiments of the invention, solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, coloring agents, flavoring agents, flow-inducing agents, and melting agents. Liquid dosage forms may contain, for example, suitable solvents, preservatives, emulsifying agents, suspending agents, diluents, sweeteners, thickeners, and melting agents. Parenteral and intravenous forms should also include minerals and other materials to make them compatible with the type of injection or delivery system chosen. Of course, other excipients may also be used.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzalkonium chloride, benzyl benzoate, cyclodextrins, sorbitan esters, stearic acids), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweetners (e.g. aspartame, citric acid), preservatives (e.g., Thimerosal, benzyl alcohol, parabens), coloring agents, lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound of this invention is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery-88:607 (1980); Saudek et al., N. Engl. J. Med. 321: 674 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 116-138 (1984). Other controlled release systems are discussed in the review by Langer (Science 249:1627-1633 (1990).

The compositions may also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds of this invention or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds of this invention or their physiologically tolerated derivatives such as salts, esters, N-oxides, and the like are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicine, the salts of the compound will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In one embodiment, this invention provides pharmaceutical compositions comprising a compound of this invention. In one embodiment, such compositions are useful for oral testosterone replacement therapy.

In one embodiment, this invention also provides a composition comprising two or more compounds of this invention, or polymorphs, isomers, hydrates, salts, N-oxides, etc., thereof. The present invention also relates to compositions and pharmaceutical compositions which comprise a compound of this invention alone or in combination with a progestin or estrogen, or in another embodiment, chemotherapeutic compound, osteogenic or myogenic compound, or other agents suitable for the applications as herein described. In one embodiment, the compositions of this invention will comprise a suitable carrier, diluent or salt.

In one embodiment, the methods of this invention may comprise administration of a compound of this invention at various dosages. In one embodiment, the compound of this invention is administered at a dosage of 0.1-200 mg per day. In one embodiment, the compound of this invention is administered at a dose of 0.1-10 mg, or in another embodiment, 0.1-26 mg, or in another embodiment, 0.1-60 mg, or in another embodiment, 0.3-16 mg, or in another embodiment, 0.3-30 mg, or in another embodiment, 0.6-26 mg, or in another embodiment, 0.6-60 mg, or in another embodiment, 0.76-16 mg, or in another embodiment, 0.76-60 mg, or in another embodiment, 1-6 mg, or in another embodiment, 1-20 mg, or in another embodiment, 3-16 mg, or in another embodiment, 30-60 mg, or in another embodiment, 30-76 mg, or in another embodiment, 100-2000 mg.

In one embodiment, the methods of this invention may comprise administration of a compound of this invention at various dosages. In one embodiment, the compound of this invention is administered at a dosage of 1 mg. In another embodiment the compound of this invention is administered at a dosage of 6 mg, 10 mg, 16 mg, 20 mg, 26 mg, 30 mg, 36 mg, 40 mg, 46 mg, 50 mg, 56 mg, 60 mg, 66 mg, 70 mg, 76 mg, 80 mg, 86 mg, 90 mg, 96 mg or 100 mg.

In one embodiment, the present invention provides methods of use comprising the administration of a pharmaceutical composition comprising a) any embodiment of a compound as described herein; and b) a pharmaceutically acceptable carrier or diluent; which is to be understood to include an analog, isomer, metabolite, derivative, pharmaceutically acceptable salt, N-oxide, hydrate or any combination thereof of a compound as herein described.

In some embodiments, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) a pharmaceutically acceptable carrier or diluent; c) a flow-aid; and d) a lubricant.

In another embodiment, the present invention provides methods of use of a pharmaceutical composition comprising a) any embodiment of the compounds as described herein, including an analog, isomer, metabolite, derivative, pharmaceutically acceptable salt, pharmaceutical product, N-oxide, hydrate thereof or any combination thereof; b) lactose monohydrate; c) microcrystalline cellulose; d) magnesium stearate; and e) colloidal silicon dioxide.

In some embodiments, the methods of this invention make use of compositions comprising compounds of this invention, which offer the advantage that the compounds are nonsteroidal ligands for the estrogen receptor, and exhibit estrogenic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention, as described herein. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the methods of this invention make use of compositions comprising compounds of this invention, which offer the advantage that the compounds are nonsteroidal ligands for the estrogen receptor, and exhibit estrogenic activity in vivo. According to this aspect, such compounds are unaccompanied by serious side effects, provide convenient modes of administration, and lower production costs and are orally bioavailable, lack significant cross-reactivity with other undesired steroid receptors, and may possess long biological half-lives.

For administration to mammals, and particularly humans, it is expected that the physician will determine the actual dosage and duration of treatment, which will be most suitable for an individual and can vary with the age, weight and response of the particular individual.

In one embodiment, the compositions for administration may be sterile solutions, or in other embodiments, aqueous or non-aqueous, suspensions or emulsions. In one embodiment, the compositions may comprise propylene glycol, polyethylene glycol, injectable organic esters, for example ethyl oleate, or cyclodextrins. In another embodiment, compositions may also comprise wetting, emulsifying and/or dispersing agents. In another embodiment, the compositions may also comprise sterile water or any other sterile injectable medium.

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In some embodiments, the compositions will further comprise a 5α-Reductase Inhibitors (5ARI), a SARM or SARMs, a Selective Estrogen Receptor Modulator (SERM), an aromatase inhibitor, such as but not limited to anastrozole, exemestane, or letrozole; a gonadotropin releasing hormone (GnRH) agonist or antagonist, a steroidal or nonsteroidal GR ligand, a steroidal or nonsteroidal PR ligand, a steroidal or nonsteroidal AR antagonist, a 17-aldoketoreductase inhibitor or 17-β-hydroxysteroid dehydrogenase inhibitor. Such compositions may be used, in some embodiments, for treating a hormone dependent condition, such as, for example, infertility, neoplasia of a hormone-responsive cancer, for example, a gonadal cancer, or a urogenital cancer.

In some embodiments, the composition will comprise the compounds as described herein, as well as another therapeutic compound, including inter alia, a 5ARI such as finasteride, dutasteride, izonsteride; other SARMs, such as, RU-58642, RU-56279, WS9761 A and B, RU-59063, RU-58841, bexlosteride, LG-2293, L-245976, LG-121071, LG-121091, LG-121104, LGD-2226, LGD-2941, LGD-3303, YM-92088, YM-175735, LGD-1331, BMS-357597, BMS-391197, S-40503, BMS-482-404, EM-4283, EM-4977, BMS-564929, BMS-391197, BMS434588, BMS487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, ACP-105; a SERM, such as tamoxifene, 4-hydroxytamoxifene, idoxifene, toremifene, ospemifene, droloxifene, raloxifene, arzoxifene, bazedoxifene, PPT (1,3,5-tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstilbestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERB-002, ERB-037, ERB-017, BE-1060, BE-380, BE-381, WAY-358, [18F]FEDNP, LSN-500307, AA-102, Ban zhi lian, CT-101, CT-102, VG-101; GnRH agonists or antagonists, such as, leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, acyline; FSH agonist/antagonist, LH agonist/antagonists, aromatase inhibitors, such as, letrozole, anastrazole, atamestane, fadrozole, minamestane, exemestane, plomestane, liarozole, NKS-01, vorozole, YM-511, finrozole, 4-hydroxyandrostenedione, aminoglutethimide, rogletimide; Steroidal or nonsteroidal glucocorticoid receptor ligands, such as, ZK-216348, ZK-243149, ZK-243185, LGD-5552, mifepristone, RPR-106541, ORG-34517, GW-215864X, Sesquicillin, CP-472555, CP-394531, A-222977, AL-438, A-216054, A-276575, CP-394531, CP-409069, UGR-07; Steroidal or nonsteroidal progesterone receptor ligands; Steroidal or nonsteroidal AR antagonists such as flutamide, hydroxyflutamide, bicalutamide, nilutamide, hydroxysteroid dehydrogenase inhibitors, PPARα ligand such as bezafibrate, fenofibrate, gemfibrozil; PPARγ ligands such as darglitazone, pioglitazone, rosiglitazone, isaglitazone, rivoglitazone, netoglitazone; Dual acting PPAR ligands, such as naveglitazar, farglitazar, tesaglitazar, ragaglitazar, oxeglitazar, PN-2034, PPAR δ; a 17-ketoreductase inhibitors, 3β-DHΔ4,6-isomerase inhibitors, 3β-DHΔ4,5-isomerase inhibitors, 17,20 desmolase inhibitors, p450c17 inhibitors, p450ssc inhibitors, 17,20-lyase inhibitors, or combinations thereof.

In some embodiments, the compositions will further comprise Ghrelin receptor ligand or growth hormone analogues and secretagogues, IGF-1, IGF-1 analogues and secretagogues, insulins, myostatin analogues, proteasome inhibitors, androgenic/anabolic steroid, Enbrel, melanocortin 4 receptor agonist, insulins or combinations thereof.

In some embodiments, the composition will comprise the compounds as described herein, as well as another therapeutic compound, including inter alia, Ghrelin receptor ligand or growth hormone analogues and secretagogues, such as, pralmorelin, examorelin, tabimorelin, capimorelin, capromorelin, ipamorelin, EP-01572, EP-1572, JMV-1843, an androgenic/anabolic steroid such as testosterone/oxandrolone; a melanocortin 4 receptor agonist, such as bremelanotide, a Ghrelin or analogue thereof, such as human ghrelin, CYT-009-GhrQb, L-692429, GHRP-6, SK&F-110679, U-75799E), leptin (metreleptin, pegylated leptin; a leptin receptor agonist, such as LEP(116-130), OB3, [D-Leu4]-OB3, rAAV-leptin, AAV-hOB, rAAVhOB; an insulin (short-, intermediate-, and long acting formulations; a cortisol or corticosteroid, or a combination thereof.

The invention contemplates, in some embodiments, administration of compositions comprising the individual agents, administered separately and by similar or alternative routes, formulated as appropriately for the route of administration. The invention contemplates, in some embodiments, administration of compositions comprising the individual agents, administered in the same formulation. The invention contemplates, in some embodiments, staggered administration, concurrent administration, of administration of the various agents over a course of time, however, their effects are synergistic in the subject.

It is to be understood that any of the above means, timings, routes, or combinations thereof, of administration of two or more agents is to be considered as being encompassed by the phrase "administered in combination", as described herein.

In one embodiment, the compound of this invention is administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof. In one embodiment, anti-cancer monoclonal antibodies are conjugated or linked to a compound of this invention as described hereinabove.

In another embodiment, the present invention includes compounds and compositions in which a compound of the invention is either combined with, or covalently bound to, an agent bound to a targeting agent, such as a monoclonal antibody (e.g., a murine or humanized monoclonal antibody). In one embodiment, the agent bound to a targeting agent is a cytotoxic agent. It will be appreciated that the latter combination may allow the introduction of cytotoxic agents into for example cancer cells with greater specificity. Thus, the active form of the cytotoxic agent (i.e., the free form) will be present only in cells targeted by the antibody. Of course, the compounds of the invention may also be combined with monoclonal antibodies that have therapeutic activity against cancer.

In one embodiment, the compound is administered in combination with a selective tyrosine kinase inhibitor. In some embodiments, the selective tyrosine kinase inhibitor inhibits catalytic sites of cancer promoting receptors thereby inhibiting tumor growth. In one embodiment, a selective tyrosine kinase inhibitor modulates growth factor signaling. In some embodiments, the selective tyrosine kinase inhibitor targets EGFR (ERB B/HER) family members. In one embodiment, the selective tyrosine kinase inhibitor is a BCR-ABL tyrosine kinase inhibitor. In one embodiment, the selective tyrosine kinase inhibitor is an epidermal growth factor receptor tyrosine kinase inhibitor. In one embodiment, the selective tyrosine kinase inhibitor is a vascular endothelial growth factor tyrosine kinase inhibitor. In one embodiment, the selective tyrosine kinase inhibitor is a Platelet Derived Growth Factor (PDGF) inhibitor.

In one embodiment, the compound is administered in combination with a cancer vaccine. In one embodiment, the cancer vaccine is a therapeutic vaccine thus, treating an existing cancer. In some embodiments, the cancer vaccine is a prophylactic vaccine thus, preventing the development of cancer. In one embodiment, both types of vaccines have the potential to reduce the burden of cancer. In one embodiment, treatment or therapeutic vaccines are administered to cancer patients and are designed to strengthen the body's natural defenses against cancers that have already developed. In one embodiment, therapeutic vaccines may prevent additional growth of existing cancers, prevent the recurrence of treated cancers, or eliminate cancer cells not killed by prior treatments. In some embodiments, prevention or prophylactic vaccines are administered to healthy individuals and are designed to target cancer in individuals who present high risk for the disease. In one embodiment, the cancer vaccine is an antigen/adjuvant vaccine. In one embodiment, the cancer vaccine is a whole cell tumor vaccine. In one embodiment, the cancer vaccine is a dendritic cell vaccine. In one embodiment, the cancer vaccine comprises viral vectors and/or DNA vaccines. In one embodiment, the cancer vaccine is an idiotype vaccine.

In one embodiment, the compound is administered in combination with an anti-cancer chemotherapeutic agent. In one embodiment, the anti-cancer chemotherapeutic agent is an alkylating agent, such as but not limited to cyclophosphamide. In one embodiment, the anti-cancer chemotherapeutic agent is a cytotoxic antibiotic such as but not limited to doxorubicin. In one embodiment, the anti-cancer chemotherapeutic agent is an antimetabolite, such as but not limited to methotrexate. In one embodiment, the anti-cancer chemotherapeutic agent is a vinca alkaloid, such as but not limited to vindesine. In some embodiments, the anti-cancer chemotherapeutic agents include platinum compounds such as but not limited to carboplatin, and taxanes such as docetaxel. In one embodiment, the anti-cancer chemotherapeutic agent is an aromatase inhibitor such as but not limited to anastrazole, exemestane, or letrozole.

In one embodiment, the compound is administered in combination with a Bax activity modulator such as alisol B acetate. In one embodiment, the compound is administered in combination with an angiotensin II receptor blocker such as losartan. In one embodiment, the compound is administered in combination with selenium, green tea cachecins, saw palmetto, lycopene, vitamin D, dietary soy, genistein or isoflavone.

In one embodiment, the compound is administered in combination with antineoplastic agents, such as alkylating agents, antibiotics, hormonal antineoplastics and antimetabolites. Examples of useful alkylating agents include alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophos-phoramide and trimethylolomelamine; nitrogen mustards such as chlorambucil, chlomaphazine, cyclophosphamide, estramustine, iphosphamide, mechlore-thamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, ranimustine, dacarbazine, mannomustine, mitobronitol, mitolactol and pipobroman. More such agents will be known to those having skill in the medicinal chemistry and oncology arts.

In some embodiments, other agents suitable for combination with the compounds of this invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine, modeccin, neomycin, norvaline, pactamycin, paromomycine, puromycin, ricin, α-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine, β-1-D-arabinoside, amethopterin, aminopterin, 2-aminopurine, aphidicolin, 8-aza-guanine, azaserine, 6-azauracil, 2'-azido-2'-deoxynucliosides, 5-bromodeoxycytidine, cytosine, β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In one embodiment, the compound is administered in combination with a vaccine for prostate cancer, alisol B acetate, angiotensin II receptor blocker, or others known in the art. In one embodiment, the compound is administered in combination with an agent to decrease prostate (benign or malignant) hypertrophy, such as, for example, selenium, green tea cachecins, saw palmetto, lycopene, vitamin D, dietary soy, genistein and isoflavone food product and others.

In one embodiment, the compound is administered in combination with an immunomodulating agent. In one embodiment, the immunomodulating agent is an immunosuppressive agent. In one embodiment, immunosuppressive agents comprise corticosteroids, cyclosporine, azathioprine, methotrexate, cyclophosphamide, tacrolimus—FK-506, anti-thymocyte globulin, mycophenylate moeftil, or a combination thereof. In one embodiment, the corticosteroid is a glucocorticoid.

In one embodiment, the immunomodulating agent is an immunostimulatory agent. In one embodiment, the immunostimulatory agent is a specific immunostimulator thus, provides antigenic specificity during an immune response, such as a vaccine or any antigen. In one embodiment, the immunostimulatory agent is a non-specific immunostimulator thus, acting irrespective of antigenic specificity to augment immune response of other antigen or stimulate components of the immune system without antigenic specificity. In one embodiment, the non-specific immunostimulator is Freund's complete adjuvant. In one embodiment, the non-specific immunostimulator is Freund's incomplete adjuvant. In one embodiment, the non-specific immunostimulator is a montanide ISA adjuvant. In one embodiment, the non-specific immunostimulator is a Ribi's adjuvant. In one embodiment, the non-specific immunostimulator is a Hunter's TiterMax. In one embodiment, the non-specific immunostimulator is an aluminum salt adjuvant. In one embodiment, the non-specific immunostimulator is a nitrocellulose-adsorbed protein. In one embodiment, the non-specific immunostimulator is a Gerbu Adjuvant.

In one embodiment, the compound is administered in combination with an agent, which treats bone diseases, disorders or conditions, such as osteoporosis, bone fractures, etc., and this invention comprises methods of treating the same, by administering the compounds as herein described, alone or in combination with other agents.

In one embodiment, bone turnover markers have been demonstrated as an effective, validated tool for the clinical scientist to monitor bone activity. In another embodiment, urinary hydroxyproline, serum alkaline phosphatase, tartrate-resistant acid phosphatase, and osteocalcin levels, along with the urinary calcium-creatinine ratio are used as bone turnover markers. In another embodiment osteocalcin levels is used as a bone formation marker. In another embodiment c-telopeptide is used as a bone resorption marker.

In one embodiment, this invention provides for the treatment, prevention, suppression or inhibition of, or the reduction of the risk of developing a skeletal-related event (SRE), such as bone fractures, surgery of the bone, radiation of the bone, spinal cord compression, new bone metastasis, bone loss, or a combination thereof in a subject with cancer, comprising administering to the subject a compound of formula 1-4, IV-IX or XI-XII and/or its analog, derivative, isomer, metabolite, pharmaceutically acceptable salt, pharmaceutical product, hydrate, N-oxide, or any combination thereof. The invention relates, inter alia to treatment of an SRE with the compound of this invention in a subject with prostate cancer undergoing or having undergone androgen deprivation therapy (ADT).

In one embodiment, the skeletal-related events treated using the methods provided herein and/or utilizing the compositions provided herein, are fractures, which in one embodiment, are pathological fractures, non-traumatic fractures, vertebral fracture, non-vertebral fractures, morphometric fractures, or a combination thereof.

In another embodiment, the methods and/or compositions provided herein, are effective in treatment, prevention, suppression, inhibition or reduction of the risk of skeletal-related events such as pathologic fractures, spinal cord compression, hypercalcemia, bone-related pain, or their combination.

In another embodiment, the skeletal-related events sought to be treated using the methods provided herein and/or utilizing the compositions provided herein, comprise the necessity for bone surgery and/or bone radiation, which in some embodiments, is for the treatment of pain resulting in one embodiment from bone damage, or nerve compression. In another embodiment, the skeletal-related events sought to be treated using the methods provided herein and/or utilizing the compositions provided herein, comprise spinal cord compression, or the necessity for changes in antineoplastic therapy, including changes in hormonal therapy, in a subject. In some embodiments, skeletal-related events sought to be treated using the methods provided herein and/or utilizing the compositions provided herein, comprise treating, suppressing, preventing, reducing the incidence of, or delaying progression or severity of bone metastases, or bone loss. In one embodiment, bone loss may comprise osteoporosis, osteopenia, or a combination thereof. In one embodiment, skeletal-related events may comprise any combination of the embodiments listed herein.

In one embodiment, the methods provided herein and/or utilizing the compositions provided herein, are effective in reducing metastases to the bone, such as in terms of number of foci, the size of foci, or a combination thereof. In another embodiment, the compositions comprise a compound of formula 1-4, IV-IX or XI-XII. According to this aspect of the invention and in one embodiment, provided herein is a method of preventing or inhibiting cancer metastasis to bone in a subject, comprising the step of administering to the subject a composition comprising toremifene, raloxifene, tamoxifen or an analogue, functional derivative, metabolite or a combination thereof, or a pharmaceutically acceptable salt thereof. In one embodiment, such metabolites may comprise ospemifene, fispemifene or their combination. In one embodiment, the cancer is prostate cancer.

A person skilled in the art would readily recognize that changes in the antineoplastic therapy according to the methods provided herein, utilizing the compositions provided herein may be conducted as a function of, or adjusted or varied as a function of, inter alia, the severity of the underlying disease, the source of the underlying disease, the extent of the patients' pain and source of the patients' pain, as well as the stage of the disease. The therapeutic changes may include in certain embodiments, changes in the route of administration (e.g. intracavitarily, intraartiarly, intratumorally etc.), forms of the compositions administered (e.g. tablets, elixirs, suspensions etc.), changes in dosage and the like. Each of these changes are well recognized in the art and are encompassed by the embodiments provided herein.

In one embodiment, the skeletal-related events are a result of cancer therapy. In one embodiment, the skeletal-related events are a result of hormone deprivation therapy, while in another embodiment, they are a product of ADT.

In one embodiment, the compounds of this invention are useful in prevention or reversal of ADT induced side effects such as reduced muscle mass, reduced muscle strength, frailty, hypogonadism, osteoporosis, osteopenia, decreased BMD and/or decreased bone mass. In another embodiment the compounds comprise a compound of formula 1-4, IV-IX or XI-XII.

In males, while the natural decline in sex-hormones at maturity (direct decline in androgens as well as lower levels of estrogens derived from peripheral aromatization of androgens) is associated with the frailty of bones, this effect is more pronounced in males who have undergone androgen deprivation therapy.

Such agents for combined use may comprise a, as herein described, a bisphosphonate, for example, alendronate, tiludroate, clodroniate, pamidronate, etidronate, alendronate, zolendronate, cimadronate, neridronate, minodronic acid, ibandronate, risedronate, homoresidronate, a calcitonin, for example, salmon, Elcatonin, SUN-8577, TJN-135; a vitamin D or derivative (ZK-156979); a vitamin D receptor ligand or analogues thereof, such as calcitriol, topitriol, ZK-150123, TEI-9647, BXL-628, Ro-26-9228, BAL-2299, Ro-65-2299, DP-035, an estrogen, estrogen derivative, or conjugated estrogen; an antiestrogen, progestin, synthetic estrogen/progestin; a RANK ligand mAb, for example, denosumab or AMG162 (Amgen); an $\alpha v\beta 3$ integrin receptor antagonist; an osteoclast vacuolar ATPase inhibitor; an antagonist of VEGF binding to osteoclast receptors; a calcium receptor antagonist; PTh (parathyroid hormone) or analogues thereof, PTHrP analogues (parathyroid hormone-related peptide), cathepsin K inhibitors (AAE581); Strontium ranelate; tibolone; HCT-1026, PSK3471; gallium maltolate; Nutropin AQ; prostaglandins, p38 protein kinase inhibitor; a bone morphogenetic protein; an inhibitor of BMP antagonism, an. HMG-CoA reductase inhibitor, a vitamin K or derivative, an antiresorptive, an Ipriflavone, a fluoride salt, dietary calcium supplement, osteoprotegerin, or any combination thereof. In one embodiment, the combined administration of a SARM as herein described, Osteoprotegerin and parathyroid hormone is contemplated for treating any disease, disorder or condition of the bone.

In one embodiment, the immunomodulating agent is an anti-inflammatory agent. In one embodiment, the anti-inflammatory agent is a non-steroidal anti-inflammatory agent. In one embodiment, the non-steroidal anti-inflammatory agent is a cox-1 inhibitor. In one embodiment, the non-steroidal anti-inflammatory agent is a cox-2 inhibitor. In one embodiment, the non-steroidal anti-inflammatory agent is a cox-1 and cox-2 inhibitor. In some embodiments, non-steroidal anti-inflammatory agents include but are not limited to aspirin, salsalate, diflunisal, ibuprofen, fenoprofen, flubiprofen, fenamate, ketoprofen, nabumetone, piroxicam, naproxen, diclofenac, indomethacin, sulindac, tolmetin, etodolac, ketorolac, oxaprozin, or celecoxib. In one embodiment, the anti-inflammatory agent is a steroidal anti-inflammatory agent. In one embodiment, the steroidal anti-inflammatory agent is a corticosteroid.

In one embodiment, the immunomodulating agent is an anti-rheumatic agent. In one embodiment, the anti-rheumatic agent is a non-steroidal anti-inflammatory agent. In one embodiment, the anti-rheumatic agent is a corticosteroid. In one embodiment, the corticosteroid is prednisone or dexamethasone. In one embodiment, the anti-rheumatic agent is a disease modifying anti-rheumatic drug. In one embodiment, the disease modifying anti-rheumatic drug is a slow-acting anti-rheumatic drug. In one embodiment, the disease modifying anti-rheumatic drug is an antimalarial agent. In one embodiment, disease modifying anti-rheumatic drugs include but are not limited to chloroquine, hydroxychloroquine, methotrexate, sulfasalazine, cyclosporine, azathioprine, cyclophosphamide, azathioprine, sulfasalazine, penicillamine, aurothioglucose, gold sodium thiomalate, or auranofin. In one embodiment, the anti-rheumatic agent is an immunosuppressive cytotoxic drug. In one embodiment, immunosuppressive cytotoxic drugs include but are not limited to methotrexate, mechlorethamine, cyclophosphamide, chlorambucil, or azathioprine.

In one embodiment, the compound is administered in combination with an antidiabetic agent. In one embodiment, the antidiabetic agent is a sulfonylurea. In one embodiment, sulfonylureas include but are not limited to tolbutamide, acetohexamide, tolazamide, chlorpropamide, glipizide, glyburide, glimepiride, or gliclazide. In one embodiment, the antidiabetic agent is a meglitinide. In one embodiment, meglitinides include but are not limited to prandin or nateglinide. In one embodiment, the antidiabetic agent is a biguanide. In one embodiment, biguanides include but are not limited to metformin. In one embodiment, the antidiabetic agent is a thiazolidinedione. In one embodiment, thiazolidinediones include but are not limited to rosiglitazone, pioglitazone, or troglitazone. In one embodiment, the antidiabetic agent is an alpha glucosidase inhibitor. In one embodiment, alpha glucosidase inhibitors include but are not limited to miglitol or acarbose. In one embodiment, the antidiabetic agent is PPARα/γ ligand, dipeptidylpeptidase 4 (DPP-4) inhibitor, SGLT (sodium-dependent glucose transporter 1) inhibitor, or FBPase (fructose 1,6-bisphosphatase) inhibitor. In one embodiment, the antidiabetic agent is insulin. In one embodiment, the insulin is rapid-acting insulin. In one embodiment, the insulin is short-acting insulin. In one embodiment, the insulin is intermediate-acting insulin. In one embodiment, the insulin is intermediate- and short-acting insulin mixtures. In one embodiment, the insulin is long-acting insulin. In one embodiment, the antidiabetic agents are inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603, which are incorporated by reference.

In one embodiment, the compound is administered in combination with an agent treating the nervous system. In one embodiment, the agent treating the nervous system is an agent treating the autonomic nervous system. In one embodiment, the agent treating the autonomic nervous system is an adrenomimetic drug. In one embodiment, the adrenomimetic drug is a beta-adrenoceptor agonist, alpha-adrenoceptor agonist, or a combination thereof. In one embodiment, the adrenomimetic drug is a catecholamine. In one embodiment, adrenomimetic drugs include but are not limited to isoproterenol, norepinephrine, epinephrine, amphetamine, ephedrine, or dopamine. In one embodiment, the adrenomimetic drug is a directly acting adrenomimetic drug. In some embodiments, directly acting adrenomimetic drugs include but are not limited to phenylephrine, metaraminol, or methoxamine.

In one embodiment, the agent treating the autonomic nervous system is an adrenoceptor antagonist. In one embodiment, the adrenoceptor antagonist is a haloalkylamine, imidazoline, or quinazoline. In one embodiment, haloalkylamines include but are not limited to phenoxybenzamine. In one embodiment, imidazolines include but are not limited to phentolamine or tolazoline. In one embodiment, quinazolines include but are not limited to prazosine, terazosin, doxazosin, or trimazosin.

In one embodiment, the adrenoceptor antagonist has a combined alpha and beta blocking activity. In one embodiment, the combined alpha and beta blocking agent is labetalol, bucindolol, carvedilol, or medroxalol In one embodiment, the agent treating the autonomic nervous system is a cholinomimetic agent. In one embodiment, the cholinomimetic agent is a direct-acting parasympathomimetic drug. In one embodiment, direct-acting parasympathomimetic drugs include but are not limited to methacholine, pilocarpine, carbachol, or bethanechol.

In one embodiment, the agent treating the autonomic nervous system is a cholinesterase inhibitor. In one embodiment, the cholinesterase inhibitor is a quaternary ammonium agent. In one embodiment, quaternary ammonium agents include but are not limited to edrophonium or ambenonium. In one embodiment, the cholinesterase inhibitor is a carbamate such as physostigmine, pyridostigmine, neostigmine, or rivastigmine. In one embodiment, the cholinesterase inhibitor is an organophosphate agent. In one embodiment, the inhibitor targets acetylcholine in the central nervous system such as tacrine, donepezil, or galantamine.

In one embodiment, the agent treating the autonomic nervous system is a muscarinic blocking agent. In one embodiment, the muscarinic blocking agent is a belladonna alkaloid such as atropine or scopolamine.

In one embodiment, the agent treating the autonomic nervous system is a ganglionic blocking agent. In one embodiment, ganglionic blocking agents include but are not limited to nicotine, trimethaphan, or mecamylamine.

In one embodiment, the agent treating the nervous system is an agent treating the central nervous system. In one embodiment, the agent treating the central nervous system is a local anesthetic agent. In one embodiment, local anesthetic agents include but are not limited to benzocaine, chloroprocaine, cocaine, procaine, bupivacaine, levobupivacaine, lidocaine, mepivacaine, prilocaine, or ropivacaine. In one embodiment, the agent treating the central nervous system is a general anaesthetic agent. In one embodiment, general anesthetic agents include but are not limited to esflurane, sevoflurane, isoflurane, halothane, enflurane, methoxyflurane, xenon, propofol, etomidate, methohexital, midazolam, diazepamor, ketamine, thiopentone/thiopental, or lidocaine/prilocaine.

In one embodiment, the agent treating the central nervous system is an analgesic agent. In some embodiments, analgesic agents include but are not limited to paracetamol or non-steroidal anti-inflammatory agent. In some embodiments, analgesic agents include opiates or morphinomimetics such as morphine, pethidine, oxycodone, hydrocodone, diamorphine, tramadol, or buprenorphine. In some embodiments, a combination of two or more analgesics is desired.

In one embodiment, the agent treating the central nervous system is a muscle relaxant or vasoconstrictor agent. In one embodiment, muscle relaxants include but are not limited to methocarbamol, baclofen, carisoprodol, chlorzoxazone, cyclobenzaprine, dantrolene, metaxalone, orphenadrine, amyl nitrite, pancuronium, tizanidine, clonidine, or gabapentin. In one embodiment, vasoconstrictor agents include but are not limited to antihistamines, adrenalin dimethylarginine, caffeine, *cannabis*, catecholamines, decongestants, pseudoephedrinse, norepinephrines, tetrahydrozoline, or thromboxane.

In one embodiment, the agent treating the central nervous system is an antiemetic drug. In one embodiment, the antiemetic drug is a 5-HT3 receptor antagonist such as dolasetron, granisetron, ondensetron, or tropisetron. In one embodiment, the antiemetic drug is a dopamine antagonist such as domperidone droperidol, haloperidol, chlorpromazine, promethazine, or metoclopramide. In one embodiment, the antiemetic drug is an antihistamine such as cyclizine, diphenhydramine, dimenhydrinate, or meclizine. In one embodiment, the antiemetic drug is a cannabinoid such as *cannabis* or marinol.

In one embodiment, the agent treating the central nervous system is a sedative agent. In one embodiment, the sedative agent is an antidepressant agent such as mirtazapine or trazodone. In one embodiment, the sedative agent is a barbiturate such as secobarbital, pentobarbital, or amobarbital. In one embodiment, the sedative agent is a benzodiazepine such as diazepam, clonazepam, alprazolam, temazepam, chlordiazepoxide, flunitrazepam, lorazepam, or clorazepate. In one embodiment, the sedative agent is an imidazopyridines such as zolpidem or alpidem. In one embodiment, the sedative agent is a pyrazolopyrimidine such as zaleplon. In one embodiment, the sedative agent is an antihistamine such as diphenhydramine, dimenhydrinate, or doxylamine. In one embodiment, the sedative agent is an antipsychotic agent such as ziprasidone, risperidone, quetiapene, clozapine, prochlorperazine, perphenazine, loxapine, trifluoperazine, thiothixene, haloperidol, or fluphenazine. In one embodiment, the sedative agent is an herbal sedative such as valerian plant mandrake, or kava. In some embodiments, the sedative agent is eszopiclone, ramelteon, methaqualone, ethchlorvynol, chloral hydrate, meprobamate, glutethimide, methyprylon, gamma-hydroxybutyrate, ethyl alcohol, methyl trichloride, zopiclone, or diethyl ether.

In one embodiment, the agent treating the central nervous system is a neurodegenerative disorder medication. In one embodiment, the neurodegenerative disorder medication is an acetylcholinesterase inhibitor such as tacrine, donepezil, galanthamine, or rivastigmine. In one embodiment, the neurodegenerative disorder medication is an N-methyl-D-aspartate (NMDA) antagonist such as memantine. In one embodiment, the neurodegenerative disorder medication reduces damage to motor neurons such as riluzole. In one embodiment, the neurodegenerative disorder medication silences the gene that causes the progression of the disease. In one embodiment, the agent treating the central nervous system is an antiepileptic drug (AED). In some embodiments, antiepileptic agents include sodium channel blockers, GABA receptor agonists, GABA reuptake inhibitors, GABA transaminase inhibitor, AEDs with a potential GABA mechanism of action, glutamate blockers, or AEDs with other mechanisms of action. In some embodiments, antiepileptic agents include but are not limited to phenyloin, carbamazepine, fosphenyloin, oxcarbazepine, lamotrigine, zonisamide, clobazam, clonazepam, phenobarbital, primidone, tiagabine, vigabatrin, gabapentin, valproate, felbamate, topiramate, levetiracetam, or pregabalin.

In one embodiment, the agent treating the central nervous system is an anti-addiction drug. In one embodiment, the anti-addiction is an anti-alcoholism drug such as disulfuram. In one embodiment, the anti-addiction drug is a serotonin uptake inhibitor, dopaminergic agonist, or opioid antagonist.

In one embodiment, the agent treating the central nervous system is an agent treating Alzheimer disease. In some embodiments, agents treating Alzheimer's disease include but are not limited to a cholinesterase inhibitor, gamma secretase inhibitor, or A beta lowering drug.

In one embodiment, the agent treating the central nervous system is an agent treating mild cognitive impairment. In some embodiments, agents treating mild cognitive impairment include but are not limited to an AMPA regulator.

In one embodiment, the agent treating the central nervous system is an agent treating Parkinson's disease. In some embodiments, agents treating Parkinson's disease include but are not limited to a dopaminergic drugs, amantadine, benztropine, biperiden, bromocriptine, entacapone, carbidopa/levodopa, selegiline/deprenyl, diphenhydramine, pergolide, procyclidine, selegiline, or trihexyphenidyl.

In one embodiment, the compound is administered with an agent, which treats Alzheimer's disease, such as cholinesterase inhibitors, gamma secretase inhibitors, A-beta lowering drugs; or an agent, which treats mild cognitive impairment (MCI)—such as AMPA regulators, or an agent, which treats Parkinson's Disease, such as dopaminergic drugs, or an agent, which treats major depression, such as SSRI's, SNRI's, for example, duloxetine, or an agent, which treats sexual dysfunction, such as PDE5 inhibitors.

In one embodiment, the compound is administered in combination with an agent treating the cardiovascular system. In one embodiment, the agent treating the cardiovascular system is treating a congestive heart failure. In one embodiment, the agent treating congestive heart failure is an angiotensin converting enzyme (ACE) inhibitor such as benazepril, captopril, cilazapril, enalapril, fosinopril, lisinopril, moexipril, perindopril, quinapril, ramipril, trandolapril, or enalaprilat. In one embodiment, the agent treating congestive heart failure is a beta-blocker such as acebutolol, atenolol, betaxolol hydrochloride, bisoprolol fumarate, carteolol hydrochloride, carvedilol, celiprolol hydrochloride, esmolol hydrochloride, labetalol hydrochloride, levobunolol, metoprolol tartrate, metipranolol, nadolol, nebivolol, oxprenolol hydrochloride, pindolol, propranolol hydrochloride, sotalol hydrochloride, or timolol maleate. In one embodiment, the agent treating congestive heart failure is digoxin. In one embodiment, the agent treating congestive heart failure is a diuretic such as thiazide diuretic, loop diuretic, potassium-sparing diuretic, or a combination thereof. In some embodiments, thiazide diuretics include but are not limited to bendrofluazide, bendroflumethiazide, benzthiazide, chlorothiazide, chlorthalidone, cyclopenthiazide, Diucardin®, Diuril®, Enduron®, Esidrix®, Exna®, HCTZ, hydrochlorothiazide, HydroDIURIL®, HYDROFLUMETHLAZIDE, Hydromox®, Hygroton®, indapamide, Lozol®, methylclothiazide, metolazone, Mykrox®, Naqua®, Naturetin®, Oretic®, polythiazide, quinethazone, Renese®, trichloromethiazide, xipamide, or Zaroxolyn®. In some embodiments, loop diuretics include but are not limited to furosemide, bumetamide, or torsemide. In some embodiments, potassium-sparing diuretics include but are not limited to amiloride, triamterene, aldosterone antagonists, or spironolactone.

In one embodiment, the agent treating the cardiovascular system is an anti-arrhythmic agent. In one embodiment, the anti-arrhythmic agent is a sodium channel blocker, beta-adrenergic blocker, calcium channel blocker, or an agent that prolong repolarization. In one embodiment, sodium channel blockers include but are not limited to quinidine, procainamide, diisopyramide, lidocaine, tocamide, mexiletine, encamide, or flecamide. In one embodiment, beta-adrenergic blockers include but are not limited to propranolol, acebutolol, esmolol, or sotalol. In one embodiment, agents that prolong repolarization include but are not limited to sotalol or amiodarone. In one embodiment, calcium channel blockers include but are not limited to verapamil, diltiazem, nifedipine, or mebefradil. In one embodiment, the anti-arrhythmic agent is adenosine or digoxin.

In one embodiment, the agent treating the cardiovascular system is an anti-anginal agent. In one embodiment, the anti-anginal agent is an antiplatelet agent, adrenoceptor antagonist, calcium channel blocker, or a vasodilator. In some embodiments, the adrenoceptor antagonists and calcium channel blockers comprise agents as described hereinabove. In one embodiment, the antiplatelet agent is a cyclooxygenase inhibitor, ADP inhibitor, phosphodiesterase (1) inhibitor, glycoprotein IIb/IIIa inhibitor, or an adenosine reuptake inhibitor. In one embodiment, cyclooxygenase inhibitors include but are not limited to acetylsalicylic acid or an acetylsalicylic acid in combination with dipyridamole. In one embodiment, ADP inhibitors include but are not limited to clopidogrel, CS-747, or ticlopdipine. In one embodiment, phosphodiesterase III inhibitors include but are not limited to cilostazol. In one embodiment, glycoprotein IIb/IIIa inhibitors include but are not limited to abciximab, rheopro, eptifibatide, intergrilin, tirofiban, or aggrastat. In one embodiment, adenosine reuptake inhibitors include but are not limited to dipyridamole. In one embodiment, vasodilator agents include but are not limited to isosorbide dinitrate, isosorbide mononitrate, or nitroglycerine. In one embodiment, cardiac glycosides such as digitalis or ouabain may be used in combination with a SARM compound.

In one embodiment, the agent treating the cardiovascular system is a vasoactive agent or an inotrope. In one embodiment, vasoactive agents or inotropes include but are not limited to digoxin, dopamine, dobutamine, hydralazine, prazosin, carvedilol, nitroprusside, nitroglycerin, captopril, lisinopril, nifedipine, diltiazem, hydrochlorothiazide, furosemide, spironolactone, AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), or nitrates.

In one embodiment, the agent treating the cardiovascular system is an anticoagulant agent. In one embodiment, the anticoagulant agent is a coumarin derivative or an unfractionated heparin. In one embodiment, coumarin derivatives include but are not limited to warfarin.

In one embodiment, the agent treating the cardiovascular system is a fibrinolytic agent such as streptokinase, urokinase, alteprase, antistreplase, prourokinase, reteplase, tenecteplase, lanoteplase, staphylokinase, vampire, or alfimeprase.

In one embodiment, the agent treating the cardiovascular system is a hypercholesterolemic agent such as niacin-lovastatin, colestipol HCl, fluvastatin sodium, atorvastatin calcium, simvastatin, gemfibrozil, lovastatin, pravastatin sodium, cholestyramine, cholestyramine light, fenofibrate, colesevelam HCl, or ezetimibe.

In one embodiment, the compound of this invention is administered in combination with an agent treating a metabolic disease, disorder or condition, which in some embodiments refers to metabolic syndrome. In some embodiments, such agents comprise, inter alia, pancreatic lipase inhibitors, such as for example, orlistat, cetilistat, serotonin and norepinephrine reuptake inhibitors, such as sibutramine, insulin-sensitizers such as biguanides (metformin) or PPAR agonists, dual-acting PPAR agonists (muraglitazar, tesaglitazar, naveglitazar). PPAR-delta agonists (GW-501516), DPP-IV inhibitors (vildagliptin, sitagliptin), alpha glucosidase inhibitors (acarbose), anti-diabetic combinations (ActoPlusMet, AvandaMet, metformin/pioglitazone, metformin/rosiglitazone, Glucovance, etc.), glucagon-like peptide-1 analogues (exenatide, liraglutide), amylin analogues (pramlintide), statins (atorvastatin, simvastatin, rosuvastatin, pravastatin, fluvastatin, lovastatin, pitavastatin), cholesterol absorption inhibitors (ezetimibe), nicotinic acid derivatives (immediate release and controlled release niacins, niaslo, etc.), antidyslipidemic fixed combinations (simvastatin/ezetimibe, lovastatin/nicotinic acid, atorvastatin/amlodipine, atorvastatin/torcetrapib, simvastatin/nicotinic acid (ER), ACE inhibitors (ramipril, captopril, lisinopril), AT-II receptor antagonists (valsartan, telmisartan), cannabinoid receptor antagonists (rimonabant), cholesteryl ester transfer protein or CETP Inhibitors (JTT-705, CETi-1), beta3 adrenergic agonists, PPARα ligands, or combinations thereof.

In one embodiment, the compound is administered in combination with an agent treating a dermatological disorder. In one embodiment, the agent treating a dermatological disorder is a corticosteroid or glucocorticosteroid such as betamethasone dipropionate, clobetasol, diflorasone, amcinonide, desoximetasone, fluocinonide, aclometasone, desonide triamcinolone, fluticasone, halobetasol, mometasone, or hydrocortisone. In one embodiment, the agent treating a dermatological disorder is a retinoid such as isotretinoin, acitretin, tretinoin, adapalene, tazarotene, bexarotene, alitretinoin, or beta-carotene.

In one embodiment, the agent treating a dermatological disorder is photochemotherapy agent. In one embodiment, the photochemotherapy agent is PUVA or psoralen such as oxsoralen. In one embodiment, the agent treating a dermatological disorder is a photodynamic agent such as porphyrin.

In one embodiment, the agent treating a dermatological disorder is daspone, thalidomide, anti-malarial agent, antimicrobial agent, or antifungal agent. In one embodiment, the anti-malarial agent is chloroquine or hydroxychloroquine.

In one embodiment, the agent treating a dermatological disorder is an antibiotic. In one embodiment, the antibiotic is a systemic antibiotic such as griseofulvin, ketoconazole, fluconazole, itraconazole, terbinafine, or potassium iodide. In one embodiment, the antibiotic is a topical antifungal agent. In some embodiment, topical antifungal agents include but are not limited to ciclopirox, clotrimazole, econazole, ketoconazole, miconazole, naftifine, oxiconazole, terbinafine, or tolnaftate.

In one embodiment, the agent treating a dermatological disorder is an antiviral agent such as interferon alpha. In one embodiment, the agent treating a dermatological disorder is an antiscabies agent such as pyrethrin or pyrethroid. In one embodiment, the agent treating a dermatological disorder is an immunosuppressive agent such as mycophenolate motefil or 6-thioguanine. In one embodiment, the agent treating a dermatological disorder is a topical immunosuppressive agent such as tacrolimus, pimecrolimus, imiquimod, 5-fluorouracil, or mechlorethamine. In one embodiment, the agent treating a dermatological disorder is an antihistamine such as doxepin. In one embodiment, the agent treating a dermatological disorder is treating pigmentation such as hydroquinone or monobenzone. In one embodiment, the agent treating a dermatological disorder is a protein or a recombinant protein such as becaplermin, etanercept, denileukin diftitox, or botulinum toxin. In one embodiment, the agent treating a dermatological disorder is capsaicin, anthralin, benzoyl peroxide, or calcipotriene.

In one embodiment, the agent treating a dermatological disorder is a keratolytic agent. In one embodiment, the agent treating a dermatological disorder is selenium sulfide. In one embodiment, the agent treating or preventing a dermatological disorder is a sunscreen. In one embodiment, the sunscreen absorbs UVB, UVA, or a combination thereof.

In one embodiment, the agent treating a dermatological disorder may be a growth factor such as epidermal growth factor (EGF), transforming growth factor-$\alpha$ (TGF-$\alpha$), platelet derived growth factor (PDGF), fibroblast growth factors (FGFs) including acidic fibroblast growth factor ($\alpha$-FGF) and basic fibroblast growth factor ($\beta$-FGF), transforming growth factor-$\beta$ (TGF-$\beta$) and insulin like growth factors (IGF-1 and IGF-2), or any combination thereof.

In one embodiment, the compound is administered in combination with an anti-infective agent. In one embodiment, the anti-infective agent is an antibiotic agent. In one embodiment the antibiotic is a beta-lactam antibiotic. In one embodiment beta-lactam antibiotics include but are not limited to penicillin, benzathine penicillin, benzylpenicillin, amoxicillin, procaine penicillin, dicloxacillin, amoxicillin, flucloxacillin, ampicillin, methicillin, azlocillin, carbenicillin, ticarcillin, mezlocillin, piperacillin, phenoxymethylpenicillin, co-amoxiclav, cephalosporin, cefalexin, cephalothin, cefazolin, cefaclor, cefuroxime, cefamandole, cefotetan, cefoxitin, ceftriaxone, cefotaxime, ceftazidime, cefepime, cefpirome, imipenem, meropenem, ertapenem, faropenem, monobactam, aztreonam, or carbapenem.

In one embodiment the antibiotic is a tetracycline antibiotic. In one embodiment tetracycline antibiotics include but are not limited to tetracycline, chlortetracycline, demeclocycline, doxycycline, lymecycline, minocycline, or oxytetracycline.

In one embodiment the antibiotic is a macrolide antibiotic. In one embodiment macrolide antibiotics include but are not limited to erythromycin, azithromycin, oxithromycin, dirithromycin, clarithromycin, josamycin, oleandomycin, kitasamycin, spiramycin, tylosin/tylocine, troleandomycin, carbomycin, cethromycin, or telithromycin.

In one embodiment the antibiotic is an aminoglycoside antibiotic. In one embodiment, aminoglycoside antibiotics include but are not limited to gentamicin, tobramycin, faropenem, imipenem, kanamycin, neomycin, ertapenem, apramycin, paromomycin sulfate, streptomycin, or amikacin.

In one embodiment the antibiotic is a quinolone antibiotic. In one embodiment quinolone antibiotics include but are not limited to ciprofloxacin, norfloxacin, lomefloxacin, enoxacin, ofloxacin, ciprofloxacin, levofloxacin, sparfloxacin, gatifloxacin, moxifloxacin, trovafloxacin, or alatrofloxacin.

In one embodiment the antibiotic is a cyclic peptide antibiotic. In one embodiment cyclic peptide antibiotics include but are not limited to vancomycin, streptogramins, Microcin J25, Bacteriocin AS-48, RTD-1, or polymyxins.

In one embodiment the antibiotic is a lincosamide antibiotic. In one embodiment lincosamide antibiotics include but are not limited to clindamycin.

In one embodiment, the antibiotic is an oxazolidinone antibiotic. In one embodiment oxazolidinone antibiotics include but are not limited to linezolid, U-100592, DA-7867, AZD2563, or U-100766.

In one embodiment, the antibiotic is a sulfa antibiotic. In one embodiment, sulfa antibiotics include but are not limited to sulfisoxazole.

In one embodiment, the antibiotic is an antiseptic agent. In one embodiment, antiseptic agents include but are not limited to alcohols, chlorhexidine, chlorine, hexachlorophene, iodophors, chloroxylenol (PCMX), quaternary ammonium compounds, or triclosan.

In one embodiment, the antibiotic is an anti-tuberculosis agent. In one embodiment an anti-tuberculosis agents include but are not limited to ethambutol, rifabutin, isoniazid, rifampicin, pyrazinamide, or rifampin In one embodiment, the antibiotic is an antifungal agent. In one embodiment, antifungal agents include but are not limited to terbinafine, flucytosine, fluconazole, itraconazole, ketoconazole, ravuconazole, posaconazole, voriconazole, caspofungin, micafungin, v-echinocandin, amphotericin B, amphotericin B lipid complex (ABLC), amphotericin B colloidal dispersion (ABCD), liposomal amphotericin b (1-Amb), liposomal nystatin, or griseofulvin.

In one embodiment, the antibiotic is an antiprotozoal agent. In one embodiment the antiprotozoal agent is an anti-malarial agent. In one embodiment, antimalarial agents include but are not limited to chloroquine, mefloquine, proguanil, pyrimethamine with dapsone, pyrimethamine with sulfadoxine, quinine, or primaquine. In one embodiment, the antiprotozoal agent is an amoebicide. In one embodiment, amoebicides include but are not limited to metronidazole, timidazole, or diloxanide furoate. In one embodiment, the antiprotozoal agent is an antigiadial agent. In one embodiment, antigiadial agents include but are not limited to metronidazole, tinidazole, or mepacrine. In one embodiment, the antiprotozoal agent is a leishmanicide. In one embodiment, leishmanicides include but are not limited to sodium stibogluconate. In one embodiment, the antibiotic is an nticanthelmintic agent.

In one embodiment, the antibiotic is an antiviral agent. In one embodiment, antiviral agents include but are not limited to abacavir, acyclovir, amantadine, didanosine, emtricitabine, enfuvirtide, entecavir, lamivudine, nevirapine, oseltamivir, ribavirin, rimantadine, stavudine, valaciclovir, vidarabine, zalcitabine, or zidovudine. In one embodiment, the antiviral agent is a nucleotide analog reverse transcriptase inhibitor. In one embodiment, nucleotide analog reverse transcriptase inhibitors include but are not limited totenofovir or adefovir. In one embodiment, the antiviral agent is a protease inhibitor. In one embodiment, protease inhibitors include but are not limited to saquinavir, ritonavir, indinavir, nelfinavir, amprenavir, lopinavir, fosamprenavir, or tipranavir. In one embodiment, the antiviral agent is a fusion inhibitor such as enfuvirtide. In one embodiment, a combination of antiviral or antiretroviral agents is desired. In one embodiment, antiviral or antiretroviral agents or a combination thereof, further comprise hydroxyurea, resveratrol, grapefruit, ritonavir, leflunomide, or a combination thereof.

In one embodiment, the compound is administered in combination with an agent treating the liver. In one embodiment, the compound is administered in combination with a statin. In some embodiment, statins include but are not limited to atorvastatin, fluvastatin, lovastatin, pravastatin, simvastatin, or rosuvastatin.

In one embodiment, the compound is administered in combination with a bile acid sequestrant. In some embodiment, bile acid sequestrants include but are not limited to cholestyramine, colestipol, or colesevelam.

In one embodiment, the compound is administered in combination with a cholesterol absorption inhibitor. In some embodiment, cholesterol absorption inhibitors include but are not limited to ezetimibe.

In one embodiment, the compound is administered in combination with a nicotinic acid agent. In some embodiments, nicotinic acid agents include but are not limited to niacin, niacor, or slo-niacin.

In one embodiment, the compound is administered in combination with a fibrate. In some embodiments, fibrates include but are not limited to gemfibrozil, or fenofibrate.

In one embodiment, the agent treating the liver is cortisone, cortisol or corticosterone. In some embodiments, the agent treating the liver is colchicine, methotrexate, ursodeoxycholic acid, or penicillamine.

In one embodiment, the compound is administered in with an agent treating a metabolic disease. In some embodiments, agents treating a metabolic disease include but are not limited to a vitamin, Coenzyme Q10, glucosidase alfa, sodium bicarbonate, bisphosphonate, biotin, allopurinol, levodopa, diazepam, phenobarbital, haloperidol, folic acid, antioxidants, activators of cation channels haptoglobin, or carnitine.

In one embodiment, the agent treating a metabolic disease is a pancreatic lipase inhibitor such as orlistat or cetilistat, serotonin or norepinephrine reuptake inhibitor such as sibutramine, insulin-sensitizers such as biguanide, PPAR agonist, dual-acting PPAR agonist such as muraglitazar, tesaglitazar, or naveglitazar, PPAR-delta agonist such as GW-501516, DPP-IV Inhibitor such as vildagliptin or sitagliptin, alpha glucosidase inhibitor such as acarbose, antidiabetic combination such as ActoPlusMet, AvandaMet, metformin/pioglitazone, metformin/rosiglitazone, or Glucovance, Glucagon-like peptide-1 analogue such as exenatide or liraglutide, Amylin analogue such as pramlintide, statin such as atorvastatin, simvastatin, rosuvastatin, pravastatin, fluvastatin, lovastatin, or pitavastatin, cholesterol absorption inhibitor such as ezetimibe, nicotinic acid derivative such as niacin or niaslo, antidyslipidemic fixed combination such as simvastatin/ezetimibe, lovastatin/nicotinic acid, atorvastatin/amlodipine, or atorvastatin/torcetrapib, simvastatin/nicotinic acid, ACE inhibitor such as ramipril, captopril, or lisinopril, AT-II receptor antagonist such as valsartan or telmisartan, cannabinoid receptor antagonist such as rimonabant, cholesteryl ester transfer protein or CETP Inhibitor such as JTT-705, CETi-1, or beta-3 adrenergic agonist.

In one embodiment, the compound is administered in with an agent treating the endocrine system. In some embodiments, agents treating the endocrine system include but are not limited to radioactive iodine, antithyroid agent, thyroid hormone supplement, growth hormone, cabergoline, bromocriptine, thyroxine, gonadotropin, glucocorticoid, glucocorticoid analogue, corticotrophin, metyrapone, aminoglutethimide, mitotane, ketoconazole, mifepristone, dexamethasone somatostatin analogue, gonadotropin-releasing hormone analogue, leuprolide, goserelin, antidiuretic hormone, antidiuretic hormone analogue, oxytocin, calcium supplement, vitamin D, or a combination thereof.

In one embodiment, the agent treating the endocrine system is a 5-alpha-reductase inhibitor. In some embodiments, 5-alpha-reductase inhibitors include but are not limited to finasteride, dutasteride, or izonsteride.

In one embodiment, the agent treating the endocrine system is a SARM compound. In some embodiments, SARMs include but are not limited to RU-58642, RU-56279, WS9761 A and B, RU-59063, RU-58841, bexlosteride, LG-2293, L-245976, LG-121071, LG-121091, LG-121104, LGD-2226, LGD-2941, LGD-3303, YM-92088, YM-175735, LGD-1331, BMS-357597, BMS-391197, S-40503, BMS-482-404, EM-4283, EM-4977, BMS-564929, BMS-391197, BMS-434588, BMS487745, BMS-501949, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105.

In one embodiment, the agent treating the endocrine system includes but is not limited to tamoxifen, 4-hydroxytamoxifen, idoxifene, toremifene, ospemifene, droloxifene, raloxifene, arzoxifene, bazedoxifene, PPT (1,3,5-Tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstibestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In one embodiment, the agent treating the endocrine system is a gonadotropin-releasing hormone agonist or antagonist. In some embodiments, gonadotropin-releasing hormone agonists or antagonists include but are not limited to leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, or acyline.

In one embodiment, the agent treating the endocrine system is a steroidal or nonsteroidal glucocorticoid receptor ligand. In some embodiments, nonsteroidal glucocorticoid receptor ligands include but are not limited to ZK-216348, ZK-243149, ZK-243185, LGD-5552, mifepristone, RPR-106541, ORG-34517, GW-215864X, Sesquicillin, CP-472555, CP-394531, A-222977, AL-438, A-216054, A-276575, CP-394531, CP-409069, or UGR-07.

In one embodiment, the agent treating the endocrine system is a steroidal or non-steroidal progesterone receptor ligand. In one embodiment, the agent treating the endocrine system is a steroidal or nonsteroidal androgen receptor antagonist. In some embodiments, steroidal or nonsteroidal androgen receptor antagonists include but are not limited to flutamide, hydroxyflutamide, bicalutamide, nilutamide, or hydroxysteroid dehydrogenase inhibitor.

In one embodiment, the agent treating the endocrine system is a peroxisome proliferator-activated receptor ligand. In some embodiments, peroxisome proliferator-activated receptor ligands include but are not limited to bezafibrate, fenofibrate, gemfibrozil, darglitazone, pioglitazone, rosiglitazone, isaglitazone, rivoglitazone, netoglitazone, naveglitazar, farglitazar, tesaglitazar, ragaglitazar, oxeglitazar, or PN-2034.

In one embodiment, an agent treating the endocrine system is a human growth hormone. In some embodiments, human growth hormones include but are not limited to somatotropin or analogues.

In one embodiment, the agent treating the endocrine system is a ghrelin. In some embodiments, ghrelins include but are not limited to human ghrelin, CYT-009-GhrQb, L-692429, GHRP-6, SK&F-110679, or U-75799E.

In one embodiment, the compound of this invention is administered with an agent treating osteoporosis. In some embodiments, osteoporosis is induced by alcohol and/or smoking. In some embodiments, agents treating osteoporosis include but are not limited to, calcitonin, vitamin D, vitamin D derivatives, vitamin D receptor ligand, vitamin D receptor ligand analogue, estrogen, estrogen derivative, conjugated estrogen, antiestrogen, progestin, synthetic estrogen, synthetic progestin, RANK ligand monoclonal antibody, integrin receptor antagonist, osteoclast vacuolar ATPase inhibitor, antagonist of VEGF binding to osteoclast receptors, calcium receptor antagonist, parathyroid hormone, parathyroid hormone analogue, parathyroid hormone-related peptide, cathepsin K inhibitor, strontium ranelate, tibolone, HCT-1026, PSK3471, gallium maltolate, Nutropin AQ, prostaglandin, p38 protein kinase inhibitor, bone morphogenetic protein (BMP), inhibitor of BMP antagonism, HMG-CoA reductase inhibitor, vitamin K, vitamin K derivative, ipriflavone, fluoride salts, dietary calcium supplement, or osteoprotegerin.

In one embodiment, the agent treating osteoporosis is a calcitonin. In some embodiments, calcitonins include but are not limited to salmon, elcatonin, SUN-8577, or TJN-135.

In one embodiment, the agent treating osteoporosis is a vitamin D receptor ligand or analogue. In some embodiments, vitamin D receptor ligands or analogues include but are not limited to calcitriol, topitriol, ZK-150123, TEI-9647, BXL-628, Ro-26-9228, BAL-2299, Ro-65-2299, or DP-035.

In one embodiment, the compound of this invention is administered with an agent treating pharmacotherapy induced hypogonadal and/or osteopenic and/or sarcopenic state. In some embodiments, agents treating pharmacotherapy induced hypogonadal and/or osteopenic and/or sarcopenic states include but are not limited to opioids, narcotics, opiates, opioids, methadone, kadian, D2 dopamine receptor antagonist, zotepine, haloperidol, amisulpride, risperidone, anti-epileptic agent, valproic acid, carbamazepine, oxcarbamazepine, chemotherapeutic agent, methotrexate, cyclophosphamide, ifosfamide, adriamycin, doxorubicin, glucocorticoids, cyclosporine, L-thyroxine, SERMs, aromatase inhibitor (AI), fulvestrant, gonadotropin-releasing hormone agent, androgen depravation agent, prolactinemia-inducing agent, serotonergic antidepressant, selective serotonin reuptake inhibitor, monoamine oxidase inhibitor, tricyclic antidepressant, antihypertensive agents, methyldopa, reserpine, clonidine, verapamil, antidopaminergic agent, antiemetic agent, metoclopramide, H2 receptor antagonist, cimetidine, ranitidine, estrogen, or amphetamine.

In one embodiment, the compound of this invention is administered with a vitamin. In some embodiments, vitamins include but are not limited to vitamin D, vitamin E, vitamin K, vitamin B, vitamin C, or a combination thereof.

In one embodiment, the compound of this invention is administered with a behavior-modulating agent. In some embodiments, behavior-modulating agents include but are not limited to an anti-anxiety agent, anti-psychotic agent, anti-depressant, beta-blocker, beta-2 agonist, anticholinergic bronchodilator, theophylline, aminophylline, nedocromil sodium, sodium cromoglycate, leukotriene receptor antagonist, corticosteroid, expectorant, mucolytic agent, antihistamine, pseudoephedrine, methylphenidate, amphetamine, buspirone, benzodiazepine, dextroamphetamine, tricyclic antidepressant, serotonin reuptake inhibitor, phenothiazines, benztropine, bupropion, propranolol, lithium, venlafaxine, haloperidol, buspirone, or a neuraminidase inhibitor.

In one embodiment, the behavior-modulating agent is a benzodiazepine. In one embodiment, benzodiazepines comprise alprazolam, chlordiazepoxide, diazepam, flurazepam, lorazepam, oxazepam, temazepam, or triazolam.

In one embodiment, the behavior-modulating agent is a phenothiazine. In one embodiment, phenothiazines comprise fluphenazine, perphenazine, thioridazine, or trifluoperazine.

In one embodiment, the behavior-modulating agent is a tricyclic antidepressant or a serotonin reuptake inhibitor. In one embodiment, tricyclic antidepressants or serotonin reuptake inhibitors comprise phenothiazine, protriptyline, fluoxetine, paroxetine, or sertraline.

In one embodiment, the compound of this invention is administered with an agent including but not limited to an anti-malaria agent, a cytotoxic agent, a steroid, corticosteroid, lupus medication, imuran, cytoxan, anti-rheumatic agent, corticosteroid, nifedipine, aspirin, colchicine, captopril, penicillamine, azathioprine, methotrexate, cyclophosphamide, prednisone, nicardipine, or a non-steroidal anti-inflammatory agent.

In one embodiment, the compound of this invention is administered with an agent treating an ophthalmic disease. In some embodiments, agents treating an ophthalmic disease include but are not limited to Betagan, Betimol, Timoptic, Betoptic, Ocupress, Optipranolol, Xalatan, Alphagan, Azopt, Trusopt, Cospot, Pilocar, Pilagan, Propine, Opticrom, Acular, Livostin, Alomide, Emadine, Patanol, Alrex, Poly-Pred, Pred-G, Dexacidin, eythromycin, Maxitrol, Tobradex, Blephamide, FML Ocufen, Voltaren, Profenal, Pred Forte, Econpred Plus, Eflone, Flarex, Inflamase Forte betadine, gramicidin, prednisolone, betaxolol, humorsol, proparacaine, betoptic, hylartin, inflamase mild, lotemax, flurbiprofen, chloramphenicol, methazolamide, timolol, ciloxan, terramycin, ciprofloxacin, miostat, triamcinolone, miconazole, tobramycin, physostimine, gentamicin, pilocarpine, bacitracin, goniosol, polymyxin, oxytetracycline, viroptic, vexol, suprofen, celluvisc, polytrim, illotycin, ciloxan, Ocuflox, brinzolamide, cefazolin, Tobrex, latanoprost, indocyanine, trifluridine, phenylephrine, demecarium, neomycin, tropicamide, dexamethasone, neptazane, dipivefrin, ocuflox, vidarabine, dorzolamide, ofloxacin, epinephrine, acyclovir, carbonic anhydrase inhibitor, antihistamine vitamin A, vitamin C, vitamin E, zinc, copper, atropine, or garamycin.

In one embodiment, the compound of this invention is administered in with a gene therapy agent. In some embodiments, gene therapy agents include but are not limited to an antisense agent, or a replacement gene.

In some embodiments, any of the compositions of this invention will comprise a compound of this invention, in any form or embodiment as described herein. In some embodiments, any of the compositions of this invention will comprise a compound of formula 1-4, IV-IX or XI-XII of this invention, in any form or embodiment as described herein. In some embodiments, any of the compositions of this invention will consist of a compound of this invention, in any form or embodiment as described herein. In some embodiments, any of the compositions of this invention will consist of a compound of formula 1-4, IV-IX or XI-XII of this invention, in any form or embodiment as described herein. In some embodiments, of the compositions of this invention will consist essentially of a compound of this invention, in any form or embodiment as described herein. In some embodiments, of the compositions of this invention will consist essentially of a compound of formula 1-4, IV-IX or XI-XII of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, the present invention provides combined preparations. In one embodiment, the term "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

Biological Activity of NRBA Compounds

It is to be understood that this invention is directed to compositions and combined therapies as described herein, for any disease, disorder or condition, as appropriate, as will be appreciated by one skilled in the art. Certain applications of such compositions and combined therapies have been described hereinabove, for specific diseases, disorders and conditions, representing embodiments of this invention, and methods of treating such diseases, disorders and conditions in a subject by administering a compound as herein described, or a compound of formula 1-4, IV-IX or XI-XII, or a compound of formula X, alone or as part of the combined therapy or using the compositions of this invention represent additional embodiments of this invention.

In one embodiment, appropriately substituted compounds are useful for a) depression, hypogonadism, osteoporosis, hair loss, osteopenia, benign prostate hyperplasia, and alterations in mood and cognition; b) treatment of endometriosis, breast cancer, uterine cancer and ovarian cancer; c) treatment of diabetic nephropathy; d) treatment of diabetic neuropathy; e) treatment of diabetic retinopathy; and/or other clinical therapeutic and/or diagnostic areas, including any embodiment of what is encompassed by the term "treating" as described herein.

In one embodiment, this invention provides: a) a method of treating a bone-related disorder in a subject; b) a method of increasing a bone mass in a subject; c) a method of improving the lipid profile in a subject; d) a method of treating atherosclerosis and its associated diseases; e) a method of improving dexterity and movement in a subject; f) a method of treating a subject having dysmenorrhea comprising the step of administering to said subject a compound of this invention and/or an analog, derivative, isomer, metabolite, pharmaceutically acceptable salt, pharmaceutical product, hydrate, N-oxide, prodrug, polymorph, impurity or crystal of said compound, or any combination thereof.

In some embodiments, the compounds as described herein and/or compositions comprising the same may be used for applications and treating diseases in which the improvement of cognition, reduction or treatment of depression, or other neuroportective effects are desired.

In one embodiment, "Cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind. As contemplated herein, alterations mean any change for the positive or negative, in cognition and/or mood.

In one embodiment, "depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, the methods of this invention are useful a subject, which is a human. In another embodiment, the subject is a mammal. In another embodiment the subject is an animal. In another embodiment the subject is an invertebrate. In another embodiment the subject is a vertebrate.

In one embodiment, the subject is male. In another embodiment, the subject is female. In some embodiments, while the methods as described herein may be useful for treating either males or females, females may respond more advantageously to administration of certain compounds, for certain methods, as described and exemplified herein.

In some embodiments, while the methods as described herein may be useful for treating either males or females, males may respond more advantageously to administration of certain compounds, for certain methods, as described herein.

In some embodiments, the compounds as described herein and/or compositions comprising the same may be used for applications in and/or treating diseases and/or conditions associated with problems with a subject's libido, or erectile dysfunction in a subject. In another embodiment, the subject is a male or female. In one embodiment, "libido", may refer to sexual desire.

In one embodiment, the term "erectile" refers to the ability to be erect or upright. An erectile tissue is a tissue, which is capable of being greatly dilated and made rigid by the distension of the numerous blood vessels, which it contains. In some embodiments, the NRBA of this invention relax the smooth muscles in the cavernosus tissues of the clitoris or penis.

In another embodiment of the present invention, a method is provided for hormonal therapy in a patient (i.e., one suffering from an androgen-dependent condition) which includes contacting an nuclear hormone receptor of a patient with a compound and/or a non steroidal agonist of the present invention and/or its analog, derivative, isomer, metabolite, pharmaceutically acceptable salt, pharmaceutical product, polymorph, crystal, impurity, hydrate, N-oxide or any combination thereof, in an amount effective to bind the compound to the receptor and effect a change in an hormone-dependent condition.

In one embodiment of this invention, a method is provided for hormone replacement therapy in a patient, which includes administering a compound as herein described and/or its analog, derivative, isomer, metabolite, pharmaceutically acceptable salt, pharmaceutical product, polymorph, crystal, impurity, hydrate, N-oxide or any combination thereof, to a subject, in an amount sufficient to effect a change in a hormone-dependent condition in the subject.

Hormone-dependent conditions which may be treated with the compounds and/or compositions as herein described, comprising the methods of the present invention include those conditions which are associated with aging, hypogonadism, diminished erythropoiesis, osteoporosis, and any other conditions dependent upon low estrogen levels.

Hormone-dependent conditions which may be treated with the compounds and/or compositions as herein described, and comprising a method of the invention, may comprise conditions characterized by elevated estrogen levels, including hirsutism, infertility, polycystic ovarian syndrome, endometrial carcinoma, breast cancer, male pattern baldness, prostate cancer, testicular cancer, and others, as will be known to one skilled in the art. For such conditions, the subject may be administered a compound as herein described, alone or in combination with another therapeutic agent, as will be appreciated by one skilled in the art.

In one embodiment, this invention provides methods for the treatment of a cancer in a subject, reduction of incidence or severity or pathogenesis of a cancer in a subject, delaying progression, prolonging remission or delaying onset of cancer in a subject, comprising the step of administering to the subject a compound as herein described and/or its analog, derivative, isomer, metabolite, pharmaceutically acceptable salt, pharmaceutical product, polymorph, crystal, impurity, hydrate, N-oxide or any combination thereof. In another embodiment the compound used herein is a compound of formula 1-4, IV-IX or XI-XII. In some embodiments, such cancers are hormone-dependent or androgen receptor dependent tumors (malignant or benign) associated with reproductive tissue in males or females, such as cancer of the prostate, ovary, breast, uterus, testicle, or others.

In some embodiments, the NRBA of this invention suppresses angiogenesis in a patient suffering from cancer. In some embodiments, the NRBA of this invention suppresses angiogenesis thereby treating diseases related thereto, including, in some embodiments, macular degeneration and other related conditions, as will be appreciated by the skilled artisan.

In some embodiments, this invention provides methods for the treatment of a precancerous precursor or lesion in a subject, reduction of incidence of precancerous precursors or lesions in a subject, comprising the step of administering to the subject a compound as herein described and/or its analog, derivative, isomer, metabolite, pharmaceutically acceptable salt, pharmaceutical product, polymorph, crystal, impurity, hydrate, N-oxide or any combination thereof. In some embodiments, such precancerous precursors are androgen receptor dependent tumors found in hormone-responsive tissue or are associated with reproductive tissue in males or females, such as in the prostate, ovary, breast, uterus, testicle, or others. In some embodiments, such precancerous precursors comprise any local intraepithelial neoplasia, for example, of the prostate, the cervix, etc. In some embodiments, such methods are useful in treating neoplasia or pre-neoplasia, dysplasia or hyperplasia in a tissue, such as in reproductive tissue in males or females.

In one embodiment, this invention provides compounds, compositions and/or methods of use thereof in treating benign prostate hyperplasia (BPH). "BPH (benign prostate hyperplasia)" is a nonmalignant enlargement of the prostate gland, and is the most common non-malignant proliferative abnormality found in any internal organ and the major cause of morbidity in the adult male. BPH occurs in over 75% of men over 50 years of age, reaching 88% prevalence by the ninth decade. BPH frequently results in a gradual squeezing of the portion of the urethra which traverses the prostate (prostatic urethra). This causes patients to experience a frequent urge to urinate because of incomplete emptying of the bladder and urgency of urination. The obstruction of urinary flow can also lead to a general lack of control over urination, including difficulty initiating urination when desired, as well as difficulty in preventing urinary flow because of the inability to empty urine from the bladder, a condition known as overflow urinary incontinence, which can lead to urinary obstruction and to urinary failure. In another embodiment, this invention provides a method of treating overflow urinary incontinence.

In one embodiment, this invention provides compounds, compositions and/or methods of use thereof in inhibiting LH production in males or females. In some embodiments, such inhibition thereby reduces circulating testosterone and prostate size, in males, or in some embodiments, such inhibition results in treatment of infertility in males or females.

In another embodiment, the invention provides a method of treating, delaying onset, reducing the incidence of or reducing the severity of prostate cancer in a subject with prostate cancer comprising administering a compound of formula 1-4, IV-IX or XI-XII to said subject.

In some embodiments ER-β agonists are useful treating, delaying onset, reducing the incidence of or reducing the severity of prostate cancer in a subject. In another embodiment, ERβ agonist of this invention is compound 12b, listed in Table 1. In another embodiment, ERβ agonist of this invention is compound 12f, listed in Table 1. In another embodiment, ERβ agonist of this invention is compound 12h, listed in Table 1. In another embodiment, ERβ agonist of this invention is compound 12p, listed in Table 1. In another embodiment, ERβ agonist of this invention is compound 12s, listed in Table 1. In another embodiment, ERβ agonist of this invention is compound 12u, listed in Table 1. In another embodiment, ERβ agonist of this invention is compound 12z, listed in Table 1, or any combination thereof.

In one embodiment, the method comprises administering prodrug, ester, analog, isomer, metabolite, derivative, pharmaceutically acceptable salt, pharmaceutical product, polymorph, crystal, impurity, N-oxide, hydrate or any combination thereof of the compound of formula (I)-(XII) to the subject. In another embodiment, the compound is of formula 1-4, IV-IX or XI-XII. In another embodiment, the compound is 12b, 12f, 12h, 12p, 12s, 12u, 12y, or 12z.

In some embodiments, the method comprises administering a composition comprising a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, to the subject. In another embodiment the compound is a compound of formula 1-4, IV-IX or XI-XII. In another embodiment, the compound is 12b, 12f, 12h, 12p, 12s, 12u, 12y, or 12z.

In another embodiment, the invention provides a method of reducing the risk of developing prostate cancer in a mammalian subject comprising administering a compound of formula (I)-(XII) or its prodrug, analog, isomer, metabolite, derivative, pharmaceutically acceptable salt, pharmaceutical product, ester, polymorph, crystal, impurity, N-oxide, hydrate or any combination thereof to the subject. In another embodiment the compound is a compound of formula 1-4, IV-IX or XI-XII. In some embodiments ER-β agonists are useful in reducing the risk of developing prostate cancer in a mammalian subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ERβ agonist of this invention is compound 12z, listed in Table 1, or any combination thereof.

In another embodiment, the invention provides a method of treating, delaying onset, reducing the incidence of or reducing the number precancerous precursors of prostate adenocarcinoma lesions in a mammalian subject comprising administering a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof to the subject. In another embodiment the compound is a compound of formula 1-4, IV-IX or XI-XII. In another embodiment, the precancerous precursor of prostate adenocarcinoma is prostate intraepithelial neoplasia (PIN). In some embodiments ER-β agonists are useful in treating, delaying onset, reducing the incidence of or reducing the number precancerous precursors of prostate adenocarcinoma lesions in a mammalian subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ERβ agonist of this invention is compound 12p, listed in Table 1. In another embodiment, ERβ agonist of this invention is compound 12s, listed in Table 1. In another embodiment, ERβ agonist of this invention is compound 12u, listed in Table 1. In another embodiment, ERβ agonist of this invention is compound 12z, listed in Table 1, or any combination thereof.

In another embodiment, the invention provides a method of treating, preventing, suppressing, inhibiting, or reducing the incidence of testicular cancer in a mammalian subject comprising administering a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof to the subject. In another embodiment the compound is a compound of formula 1-4, IV-IX or XI-XII. In another embodiment, the invention provides a method of treating, preventing, suppressing, inhibiting, or reducing the incidence of a urogenital disorder, disease or condition in a mammalian subject comprising administering a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof to the subject. In some embodiments ER-β agonists are useful in treating, preventing, suppressing, inhibiting, or reducing the incidence of testicular cancer in a mammalian subject. In another embodiment, ERβ agonist of this invention is compound 12b, listed in Table 1. In another embodiment, ERβ agonist of this invention is compound 12f, listed in Table 1. In another embodiment, ER-β, agonist of this invention is compound 12h, listed in Table 1. In another embodiment, ERβ agonist of this invention is compound 12p, listed in Table 1. In another embodiment, ER-β agonist of this invention is compound 12s, listed in Table 1. In another embodiment, ERβ agonist of this invention is compound 12u, listed in Table 1. In another embodiment, ERβ agonist of this invention is compound 12z, listed in Table 1, or any combination thereof.

In one embodiment, according to these aspects of the invention, the methods are appropriate for treating, suppressing, inhibiting, reducing the risk of developing latent prostate cancer. In one embodiment, this invention provides a method of treating, delaying onset, reducing the incidence of, reducing the recurrence of or reducing the severity of a disease, disorder or condition of the prostate in a subject, the method comprising administering the NRBA compound of this invention, to said subject. In another embodiment the compound is a compound of formula 1-4, IV-IX or XI-XII. In another embodiment the disease, disorder or condition of the prostate is prostatic dysplasia, prostatic hyperplasia or prostatitis.

It is to be understood that any of the methods may be effected via the administration of a composition comprising the indicated compound or compounds, and represents embodiments of this invention.

In some embodiments, this invention provides compounds, compositions and methods of use thereof in the treatment of a cancer, or a precancerous precursor thereof or a hyperplasia. In some embodiments, such neoplasia, preneoplasias or hyperplasias may be of any cell type, such as, for example, an epithelial cell. In some embodiments, such cancers, precancerous lesions or hyperplastic lesions, which may be positively affected by the NRBAs or compositions of this invention may comprise those of thyroid, liver, bladder, kidney, head and neck tissue, pancreas, urogenital tract, GI tract, nervous and supporting tissue, or combinations thereof. In some embodiments, compounds and compositions of this invention are beneficial when administered at an early, pre-neoplastic stage. In some embodiments, the compounds and compositions of this invention are beneficial when administered at latter stages of disease, for example, in the prevention of metastasis from a primary focus. In some embodiments, the compounds, compositions and methods of this invention are beneficial when administered at any, or at multiple stages of carcinogenesis in a subject, or pre-cancerous stages or combinations thereof. In another embodiment the compound is a compound of formula 1-4, IV-IX or XI-XII.

In one embodiment, the invention provides a method of treating, preventing the recurrence, inhibiting, reducing the incidence of, delaying onset, reducing the recurrence of, or reducing the severity of a carcinoma in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

In another embodiment of the present invention, the method for treating benign prostate hyperplasia (BPH) in a subject, comprises the step of administering to the subject a compound as herein described and/or its analog, derivative, isomer, metabolite, pharmaceutically acceptable salt, pharmaceutical product, polymorph, crystal, impurity, hydrate, N-oxide or any combination thereof, in an amount effective to treat BPH in the subject. In another embodiment the compound is a compound of formula 1-4, IV-IX or XI-XII.

In some embodiments, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cachexia and/or cachexia associated with cancer in a subject. In another embodiment, the cancer comprise adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of lung cancer. In another embodiment the compound is a compound of formula 1-4, IV-IX or XI-XII.

In another embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, delaying the onset of non small cell lung cancer.

Colon cancer is the second most frequently diagnosed malignancy in the United States, as well as the second most common cause of cancer death. Cholesterol-rich diets have had a significant epidemiological association with cancers of the colon, which in turn may be influenced by the administration of compounds which modulate nuclear hormone binding agents, in particular, compounds which modulate receptors binding components of the steroidogenic pathway, in particular, as described herein.

In one embodiment, the invention provides a method of treating, preventing the recurrence, inhibiting, reducing the incidence of, delaying onset, reducing the recurrence of, or reducing the severity of colon cancer in a subject, comprising administering a compound of formula (I)-(XII), which in some embodiments is a, or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII. In some embodiments ER-$\beta$ agonists are useful in treating, preventing the recurrence, inhibiting, reducing the incidence of, delaying onset, reducing the recurrence of, or reducing the severity of colon cancer in a subject. In another embodiment, ER-$\beta$ agonist of this invention is compound 12b, listed in Table 1. In another embodiment, ER-$\beta$ agonist of this invention is compound 12f, listed in Table 1. In another embodiment, ER-$\beta$ agonist of this invention is compound 12h, listed in Table 1. In another embodiment, ER$\beta$ agonist of this invention is compound 12p, listed in Table 1. In another embodiment, ER-$\beta$ agonist of this invention is compound 12s, listed in Table 1. In another embodiment, ER-$\beta$ agonist of this invention is compound 12u, listed in Table 1. In another embodiment, ER-$\beta$ agonist of this invention is compound 12z, listed in Table 1, or any combination thereof.

In one embodiment, the invention provides a method of treating, preventing the recurrence, inhibiting, reducing the incidence of, delaying onset, reducing the recurrence of, or reducing the severity of head and neck cancer in a subject, comprising administering a compound of formula (I)-(XII), which in some embodiments is a, or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

In one embodiment, the invention provides a method of treating, preventing the recurrence, inhibiting, reducing the incidence of, delaying onset, reducing the recurrence of, or reducing the severity of liver cancer in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

In one embodiment, the invention provides a method of treating, preventing the recurrence, inhibiting, reducing the incidence of, delaying onset, reducing the recurrence of, or reducing the severity of thyroid cancer in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

In one embodiment, the invention provides a method of treating, preventing the recurrence, inhibiting, reducing the incidence of, delaying onset, reducing the recurrence of, or reducing the severity of kidney cancer in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

In one embodiment, the invention provides a method of treating, preventing the recurrence, inhibiting, reducing the incidence of, delaying onset, reducing the recurrence of, or reducing the severity of pancreatic cancer in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

Melanomas are aggressive, frequently metastatic tumors derived from either melanocytes or melanocyte related nevus cells ("Cellular and Molecular Immunology" (1991) (eds) Abbas A. K., Lechtman, A. H., Pober, J. S.; W. B. Saunders Company, Philadelphia: pages 340-341). Melanomas make up approximately three percent of all skin cancers and the worldwide increase in melanoma is unsurpassed by any other neoplasm with the exception of lung cancer in women ("Cellular and Molecular Immunology" (1991) (eds) Abbas, A. K., Lechtiman, A. H., Pober, J. S.; W. B. Saunders Company Philadelphia pages: 340-342; Kirkwood and Agarwala (1993) *Principles and Practice of Oncology* 7:1-16). Even when melanoma is apparently localized to the skin, up to 30% of the patients will develop systemic metastasis and the majority will die (Kirkwood and Agarwala (1993) *Principles and Practice of Oncology* 7:1-16). Classic modalities of treating melanoma include surgery, radiation and chemotherapy. In the past decade immunotherapy and gene therapy have emerged as new and promising methods for treating melanoma.

In one embodiment, the invention provides a method of treating, preventing the recurrence, inhibiting, reducing the incidence of, delaying onset, reducing the recurrence of, or reducing the severity of melanoma in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

In one embodiment, the invention provides a method of treating, preventing the recurrence, inhibiting, reducing the incidence of, delaying onset, reducing the recurrence of, or reducing the severity of skin disorder, disease or condition in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. In another embodiment the compound is a compound of formula 1-4, IV-IX or XI-XII.

In one embodiment, skin disorder, disease or condition may comprise dermatitis, melanoma, pruritis, psoriasis, and skin atropy.

In one embodiment, this invention provides methods of 1) improving the lipid profile of a subject; 2) reducing the circulating lipid levels in a subject; 3) increasing high density lipoprotein (HDL) cholesterol levels in a subject; 4) altering ratios of low density lipoprotein to high density lipoprotein levels in a subject; wherein said subject has prostate cancer and is undergoing or has undergone ADT, wherein said method comprises administering to said subject a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof. In another embodiment, the method comprises administering a composition comprising the compound of this invention.

In another embodiment, the subject is undergoing or has undergone ADT. The terms "has undergone," "undergoing", and the like refer, in one embodiment, to subjects that have recently (within the last 6 months) or are currently receiving any treatment or therapy known in the art that reduces androgen levels in general or testosterone levels in particular. In another embodiment, the terms refer to a subject that received such a treatment or therapy more than 6 months previously. In one embodiment, the treatment or therapy is surgical. In another embodiment, the treatment or therapy is medical. In another embodiment, the treatment or therapy eliminates an androgen or a testosterone entirely, or below detectable levels. In another embodiment, the ADT is a side effect of a treatment or therapy not intended to reduce androgen or testosterone levels. Each of these possibilities represents a separate embodiment of the present invention.

In another embodiment, ADT is used for treating prostate cancer, for delaying the progression of prostate cancer, and for preventing and/or treating the recurrence of prostate cancer, which comprise administering LHRH analogs, reversible anti-androgens (such as bicalutamide or flutamide), anti-estrogens, anticancer drugs, 5-alpha reductase inhibitors, aromatase inhibitors, progestins, selective androgen receptor modulators (SARMS) or agents acting through other nuclear hormone receptors. In another embodiment, ADT is administered monthly, or every 3, 4, 6 or 12 months. In another embodiment, ADT is administered every two weeks in the first month, then every four weeks.

In some embodiments, according to this aspect, such methods comprise administering a compound of this invention to a subject that has prostate cancer and is undergoing or has undergone ADT. In one embodiment, the compound can be administered prior to the ADT. In another embodiment, the compound can be administered concurrent with ADT. In another embodiment, the compound can be administered following ADT.

In some embodiments, the methods of this invention comprise administering a compound of this invention in combination with the ADT, prior to the ADT or after the ADT as a preventive for all diseases in this invention. In one embodiment the NRBA is administered between 1-2 weeks before ADT. In another embodiment the NRBA is administered between 2-4 weeks prior to ADT. In another embodiment the NRBA is administered between 1-2 months before ADT. In another embodiment the NRBA is administered between 2-4 months before ADT. In another embodiment the NRBA is administered between 4-6 months before ADT. In one embodiment the NRBA is administered between 1-2 weeks after ADT. In another embodiment the NRBA is administered between 2-4 weeks after ADT. In another embodiment the NRBA is administered between 1-2 months after ADT. In another embodiment the NRBA is administered between 24 months after ADT. In another embodiment the NRBA is administered between 4-6 months after ADT.

In other embodiments, the present invention provides a method of treating any disease, disorder, or symptom associated with ADT. In other embodiments, the present invention provides a method of treating any disease, disorder, or symptom associated with testosterone deprivation. Each disease, disorder, or symptom represents a separate embodiment of the present invention.

Papilloma viruses are non-enveloped DNA viruses that induce hyperproliferative lesions of the epithelia. The papilloma viruses are widespread in nature and have been identified in higher vertebrates. Viruses have been characterized, amongst others, from humans, cattle, rabbits, horses, and dogs. Human papilloma viruses (HPV) have been classified into more than 80 types (Epidemiology and Biology of Cervical Cancer. Seminars in Surgical Oncology 1999 16:203-211).

In one embodiment, the invention provides a method of treating, preventing the recurrence, inhibiting, reducing the incidence of, delaying onset, reducing the recurrence of, or reducing the severity of papilloma in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject. Cross-talk has been shown to occur between endocrine-disrupting chemicals and cytokine signaling through estrogen receptors, suggesting a role for other nuclear hormone binding agents in the modulation of the immune system and/or diseases thereof.

For example, tamoxifen, clomiphene and nafoxidine cause a decrease in viability of the estrogen receptor-negative T-lymphoblastic leukemia cell line CCRF/CEM, suggesting a role for antiestrogens in the clinical treatment of leukemia.

Leukemia is a malignant cancer of the bone marrow and blood and comprises acute or chronic myelogenous, or acute or chronic lymphocytic type disease.

Standard treatment for leukemia usually involves chemotherapy and/or bone marrow transplantation and/or radiation therapy. Chemotherapy usually involves a combination of two or more anti-cancer drugs, with common combinations including cytarabine with either doxorubicin or daunorubicin or mitoxantrone or thioguanine, mercaptopurine with methotrexate, mitroxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine and daunorubicin with vincristine and prednisone.

In one embodiment, the invention provides a method of treating, preventing the recurrence, inhibiting, reducing the incidence of, delaying onset or reducing the severity of leukemia in a subject, comprising administering a compound of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, to the subject.

In some embodiments, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for treating reducing the severity of, reducing the incidence of, or reducing pathogenesis of cancer. In another embodiment, the cancer comprises androgen AR dependent tumors (malignant or benign) such as prostate cancer, breast cancer (male or female, operable or inoperable). In another embodiment the compounds adjunct to ADT for treating prostate cancer; bladder cancers; brain cancers; bone tumors, colon cancer, endometrial cancer, liver cancer, lung cancer, lymphatic cancer, kidney cancer, osteosarcoma cancer, ovarian cancer, pancreas cancer, penis cancer, skin cancer, thyroid cancer; and/or hormone-dependent cancers.

In some embodiments this invention provides a method of treating, suppressing, reducing the incidence or severity of, or prolonging remission of bladder cancer in a subject, the method comprising administering a NRBA of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof to the subject. In another embodiment the NRBA is a compound of formula 1-4, IV-IX or XI-XII.

Existing therapies for bladder cancer may be combined with the therapies provided herein, including, cystectomy with or without administration of methotrexate, vinblastine, doxorubicin, or cisplatin (M-VAC), or others as known in the art.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) treating a bone related disorder; b) preventing a bone related disorder; c) suppressing a bone related disorder, d) inhibiting a bone related disorder; e) increasing a strength of a bone of a subject; f) increasing a bone mass in a subject; g) use for osteoclastogenesis inhibition.

In one embodiment, this invention provides for the use of a compound as herein described, or its prodrug, analog, isomer, metabolite, derivative, pharmaceutically acceptable salt, pharmaceutical product, polymorph, crystal, impurity, N-oxide, hydrate or any combination thereof, for a) Accelerate bone repair; b) treating bone disorders; c) treating bone density loss; d) treating low bone mineral density (BMD); e) treating reduced bone mass; f) treating metabolic bone disease; g) promoting bone growth or regrowth; h) promoting bone restoration; i) promoting bone fracture repair; j) promoting bone remodeling; k) treating bone damage following reconstructive surgery including of the face, hip, or joints; l) enhancing of bone strength and function; m) increasing cortical bone mass; n) increasing trabecular connectivity.

In one embodiment, the invention provides a method of treating, preventing, reducing the severity of, delaying onset, reducing the recurrence of a bone-related disease or disorder in a subject, comprising administering a NRBA of this invention to the subject. In one embodiment, the subject is administered a NRBA or composition comprising the same, wherein the NRBA is a of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof. In another embodiment the NRBA is a compound of formula 1-4, IV-IX or XI-XII. In some embodiments ER-β agonists are useful in treating, preventing, reducing the severity of, delaying onset, reducing the recurrence of a bone-related disease or disorder in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ERβ agonist of this invention is compound 12s, listed in Table 1. In another embodiment, ER-β agonist of this invention is compound 12u, listed in Table 1. In another embodiment, ER-β agonist of this invention is compound 12z, listed in Table 1, or any combination thereof.

In one embodiment, the bone related disorder is a genetic disorder, or in another embodiment, is induced as a result of a treatment regimen for a given disease. For example, and in one embodiment, the compounds as herein described are useful in treating a bone-related disorder that arises as a result of cancer metastasis to bone, or in another embodiment, as a result of androgen-deprivation therapy, for example, given in response to prostate carcinogenesis in the subject.

In one embodiment, the bone-related disorder is osteoporosis. In another embodiment, the bone-related disorder is osteopenia. In another embodiment, the bone-related disorder is increased bone resorption. In another embodiment, the bone-related disorder is bone fracture. In another embodiment, the bone-related disorder is bone frailty.

In another embodiment, the bone-related disorder is a loss of bone mineral density (BMD). In another embodiment, the bone-related disorder is any combination of osteoporosis, osteopenia, increased bone resorption, bone fracture, bone frailty and loss of BMD. Each disorder represents a separate embodiment of the present invention.

"Osteoporosis" refers, in one embodiment, to a thinning of the bones with reduction in bone mass due to depletion of calcium and bone protein. In another embodiment, osteoporosis is a systemic skeletal disease, characterized by low bone mass and deterioration of bone tissue, with a consequent increase in bone fragility and susceptibility to fracture. In osteoporotic patients, bone strength is abnormal, in one embodiment, with a resulting increase in the risk of fracture. In another embodiment, osteoporosis depletes both the calcium and the protein collagen normally found in the bone, in one embodiment, resulting in either abnormal bone quality or decreased bone density. In another embodiment, bones that are affected by osteoporosis can fracture with only a minor fall or injury that normally would not cause a bone fracture. The fracture can be, in one embodiment, either in the form of cracking (as in a hip fracture) or collapsing (as in a compression fracture of the spine). The spine, hips, and wrists are common areas of osteoporosis-induced bone fractures, although fractures can also occur in other skeletal areas. Unchecked osteoporosis can lead, in another embodiment, to changes in posture, physical abnormality, and decreased mobility.

In one embodiment, the osteoporosis results from androgen deprivation. In another embodiment, the osteoporosis follows androgen deprivation. In another embodiment, the osteoporosis is primary osteoporosis. In another embodiment, the osteoporosis is secondary osteoporosis. In another embodiment, the osteoporosis is postmenopausal osteoporosis. In another embodiment, the osteoporosis is juvenile osteoporosis. In another embodiment, the osteoporosis is idiopathic osteoporosis. In another embodiment, the osteoporosis is senile osteoporosis.

In another embodiment, the primary osteoporosis is Type I primary osteoporosis. In another embodiment, the primary osteoporosis is Type II primary osteoporosis. Each type of osteoporosis represents a separate embodiment of the present invention.

According to this aspect of the invention and in one embodiment, the bone-related disorder is treated with a compound as herein described, or a combination thereof. In another embodiment, other bone-stimulating compounds can be provided to the subject, prior to, concurrent with or following administration of a compound or compounds as herein described. In one embodiment, such a bone stimulating compound may comprise natural or synthetic materials.

In another embodiment, the invention provides, a method of reducing the incidence, inhibiting, suppressing, and treating osteoporosis, bone fractures and/or loss of bone mineral density (BMD) in a subject, comprising administering a NRBA/ of formula (I)-(XII), or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby reducing the incidence, inhibiting, suppressing, and treating osteoporosis, bone fractures and/or loss of bone mineral density (BMD) in the subject. In another embodiment the NRBA is a compound of formula 1-4, IV-IX or XI-XII. In some embodiments ER-β agonists are useful in reducing the incidence, inhibiting, suppressing, and treating osteoporosis, bone fractures and/or loss of bone mineral density (BMD) in a subject. In another embodiment, ERβ agonist of this invention is compound 12b, listed in Table 1. In another embodiment, ERβ agonist of this invention is compound 12f, listed in Table 1. In another embodiment, ER-β agonist of this invention is compound 12h, listed in Table 1. In another embodiment, ERβ agonist of this invention is compound 12p, listed in Table 1. In another embodiment, ERβ agonist of this invention is compound 12s, listed in Table 1. In another embodiment, ERβ agonist of this invention is compound 12u, listed in Table 1. In another embodiment, ER-β agonist of this invention is compound 12z, listed in Table 1, or any combination thereof.

In one embodiment, the bone stimulating compound may comprise a bone morphogenetic protein (BMP), a growth factor, such as epidermal growth factor (EGF), a fibroblast growth factor (FGF), a transforming growth factor (TGF, an insulin growth factor (IGF), a platelet-derived growth factor (PDGF) hedgehog proteins such as sonic, indian and desert hedgehog, a hormone such as follicle stimulating hormone, parathyroid hormone, parathyroid hormone related peptide, activins, inhibins, follistatin, frizzled, frzb or frazzled proteins, BMP binding proteins such as chordin and fetuin, a cytokine such as IL-3, IL-7, GM-CSF, a chemokine, such as eotaxin, a collagen, osteocalcin, osteonectin and others, as will be appreciated by one skilled in the art.

In another embodiment, the compositions for use in treating a bone disorder of this invention may comprise a compound or compounds as herein described, an additional bone stimulating compound, or compounds, and osteogenic cells. In one embodiment, an osteogenic cell may be a stem cell or progenitor cell, which may be induced to differentiate into an osteoblast. In another embodiment, the cell may be an osteoblast. In another embodiment, nucleic acids which encode bone-stimulating compounds may be administered to the subject, which is to be considered as part of this invention.

In one embodiment, the methods of the present invention comprise administering the compound for treating osteoporosis. In another embodiment, the methods of this invention comprise administering a compound in combination with SERMs for treating osteoporosis. In another embodiment, the SERMs are tamoxifene, 4-hydroxytamoxifene, idoxifene, toremifene, ospemifene, droloxifene, raloxifene, arzoxifene, bazedoxifene, PPT (1,3,5-Tris(4-hydroxyphenyl)-4-propyl-1H-pyrazole), DPN, lasofoxifene, pipendoxifene, EM-800, EM-652, nafoxidine, zindoxifene, tesmilifene, miproxifene phosphate, RU 58,688, EM 139, ICI 164,384, ICI 182,780, clomiphene, MER-25, diethylstilbestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE- 424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, Ban zhi lian, CT-101, CT-102, or VG-101.

In another embodiment, the methods of the present invention comprise administering the compounds of this invention, in combination with bisphosphonates such as alendronate, tiludroate, clodroniate, pamidronate, etidronate, alendronate, zolendronate, cimadronate, neridronate, minodronic acid, ibandronate, risedronate, or homoresidronate for treating osteoporosis.

In another embodiment, the methods of the present invention comprise administering the compound, in combination with Calcitonin such as salmon, Elcatonin, SUN-8577 or TJN-135 for treating osteoporosis.

In another embodiment, the methods of treating osteoporosis of the present invention comprise administering the compound of this invention, in combination with a) vitamin D or derivative such as ZK-156979; b) vitamin D receptor ligand and analogues such as calcitriol, topitriol, ZK-150123, TEI-9647, BXL-628, Ro-26-9228, BAL-2299, Ro-65-2299 or DP-035; c) estrogen, estrogen derivative, or conjugated estrogens; d) antiestrogen, progestins, or synthetic estrogen/progestins; e) RANK ligand mAb such as denosumab formerly AMG162 (Amgen); f) αvβ3 Integrin receptor antagonist; g) osteoclast vacuolar ATPase inhibitor; h) antagonist of VEGF binding to osteoclast receptors; i) calcium receptor antagonist; j) PTh (parathyroid hormone) and analogues, PTHrP analogues (parathyroid hormone-related peptide); k) Cathepsin K inhibitors (ME581, etc.); l) strontium ranelate; m) tibolone; n) HCT-1026, PSK3471; o) gallium maltolate; p) nutropin AQ; q) prostaglandins (for osteo); r) p38 protein kinase inhibitor; s) bone morphogenetic protein; t) inhibitor of BMP antagonism; u) HMG-CoA reductase inhibitor; v) vitamin K or derivative; w) ipriflavone; x) fluoride salts; y) dietary calcium supplement, and z) osteoprotegerin.

In one embodiment, the methods of this invention are useful in treating diseases or disorders caused by, or associated with a hormonal disorder, disruption or imbalance. In one embodiment, the hormonal disorder, disruption or imbalance comprises an excess of a hormone. In another embodiment, the hormonal disorder, disruption or imbalance comprises a deficiency of a hormone. In one embodiment, the hormone is a steroid hormone. In another embodiment, the hormone is an estrogen. In another embodiment, the hormone is an androgen. In another embodiment, the hormone is a glucocorticoid. In another embodiment, the hormone is a cortico-steroid. In another embodiment, the hormone is Luteinizing Hormone (LH). In another embodiment, the hormone is Follicle Stimulating Hormone (FSH). In another embodiment, the hormone is any other hormone known in the art. In another embodiment, the hormonal disorder, disruption or imbalance is associated with menopause. In another embodiment, the hormonal disorder, disruption or imbalance is associated with andropause, andropausal vasomotor symptoms, andropausal gynecomastia, muscle strength and/or function, bone strength and/or function and anger. In another embodiment, hormone deficiency is a result of specific manipulation, as a byproduct of treating a disease or disorder in the subject. For example, the hormone deficiency may be a result of androgen depletion in a subject, as a therapy for prostate cancer in the subject. Each possibility represents a separate embodiment of the present invention.

Injuries or damage to the central nervous system (CNS) are also associated with muscle wasting and other wasting disorders. Injuries or damage to the CNS can be, for example, caused by diseases, trauma or chemicals. Examples are central nerve injury or damage, peripheral nerve injury or damage and spinal cord injury or damage. In one embodiment CNS damage or injury comprise Alzheimer's diseases (AD); anger (mood); anorexia, anorexia nervosa, anorexia associated with aging and/or assertiveness (mood).

In some embodiments, the present invention provides a method for treating, reducing the incidence, delaying the onset or progression, or reducing and/or abrogating the symptoms associated with an infection in a subject. In one embodiment, the method comprises administering to a subject a composition comprising a compound and an immunomodulating agent, an anti-infective agent, a gene therapy agent, or a combination thereof. In some embodiments, infections comprise actinomycosis, anaplasmosis, anthrax, aspergillosis, bacteremia, bacterial mycoses, *bartonella* infections, botulism, brucellosis, *burkholderia* infections, *campylobacter* infections, candidiasis, cat-scratch disease, chlamydia infections, cholera, *clostridium* infections, coccidioidomycosis, cross infection, cryptococcosis, dermatomycoses, diphtheria, ehrlichiosis, *Escherichia coli* infections, fasciitis, necrotizing, *Fusobacterium* infections, gas gangrene, gram-negative bacterial infections, gram-positive bacterial infections, histoplasmosis, impetigo, Klebsiella infections, legionellosis, leprosy, leptospirosis, *Listeria* infections, lyme disease, maduromycosis, melioidosis, mycobacterium infections, mycoplasma infections, mycoses, *nocardia* infections, onychomycosis, plague, pneumococcal infections, pseudomonas infections, psittacosis, q fever, rat-bite fever, relapsing fever, rheumatic fever, *Rickettsia* infections, rocky mountain spotted fever, *salmonella* infections, scarlet fever, scrub typhus, sepsis, sexually transmitted diseases, Staphylococcal infections, Streptococcal infections, tetanus, tick-borne diseases, tuberculosis, tularemia, typhoid fever, typhus, louse-borne, *vibrio* infections, yaws, *yersinia* infections, zoonoses, zygomycosis, acquired immunodeficiency syndrome, adenoviridae infections, alphavirus infections, arbovirus infections, boma disease, bunyaviridae infections, caliciviridae infections, chickenpox, coronaviridae infections, coxsackievirus infections, cytomegalovirus infections, dengue, DNA virus infections, eethyma, contagious, encephalitis, arbovirus, Epstein-barr virus infections, erythema infectiosum, hantavirus infections, hemorrhagic fevers, viral hepatitis, viral human herpes simplex, herpes zoster, herpes zoster oticus, herpesviridae infections, infectious mononucleosis, human-lassa fever, measles, molluscum, contagiosum, mumps, paramyxoviridae infections, phlebotomus fever, polyomavirus infections, rabies, respiratory syncytial virus infections, rift valley fever, RNA virus infections, rubella, slow virus diseases, smallpox, subacute sclerosing panencephalitis, tumor virus infections, warts, west nile fever, virus diseases, yellow fever, amebiasis, anisakiasis, *ascariasis*, babesiosis, blastocystis hominis infections, bug bite, cestode infections, chagas disease, cryptosporidiosis, cyclosporiasis, cysticercosis, dientamoebiasis, diphyllobothriasis, dracunculiasis, echinococcosis, ectoparasitic infestations, filariasis, giardiasis, helminthiasis, hookworm infections, larva migrans, leishmaniasis, lice infestations, loiasis, malaria, mite infestations, myiasis, onchocerciasis, protozoan infections, scabies, schistosomiasis, skin diseases, parasitic, strongyloidiasis, taeniasis, toxocariasis, toxoplasmosis, trichinosis, trichomonas infections, trypanosomiasis, trypanosomiasis, african, or whipworm infections.

In some embodiments, the present invention provides a method for treating, reducing the incidence, delaying the onset or progression, or reducing and/or abrogating the symptoms associated with a respiratory tract disease in a subject. In one embodiment, the method comprises administering to a subject a composition comprising a compound of this invention and an anti-cancer agent, an immunomodulating agent, an agent treating the central nervous system, an agent treating the cardiovascular system, an anti-infective agent, an agent treating a wasting disease, a gene therapy agent, an agent treating the endocrine system, vitamins, or a combination thereof. In some embodiments, respiratory tract diseases comprise airway obstruction, apnea, asbestosis, asthma, asthma-induced muscle weakness or bone weakness, atelectasis, berylliosis, bronchial diseases, bronchiectasis, bronchiolitis, bronchiolitis obliterans organizing pneumonia, bronchitis, bronchopulmonary dysplasia, chronic obstructive pulmonary disease (COPD), common cold, cough, empyema, pleural, epiglottitis, glucocorticoid (GC)-induced myopathy or osteopenia hemoptysis, hypertension, pulmonary, hyperventilation, kartagener syndrome, lung abscess, lung diseases, meconium aspiration syndrome, pleural effusion, pleurisy, pneumonia, pneumothorax, pulmonary alveolar proteinosis, pulmonary disease, chronic obstructive, pulmonary edema, pulmonary embolism, pulmonary emphysema, pulmonary fibrosis, respiratory distress syndrome, newborn-respiratory hypersensitivity, respiratory tract infections, rhinoscleroma, scimitar syndrome, severe acute respiratory syndrome, silicosis, sleep apnea, central stridor, tracheal stenosis, decreased muscle mass or bone mass due to asthma, wasting in chronic obstructive pulmonary disease (COPD), Wegener's granulomatosis, or whooping cough.

Lung diseases include diseases such as chronic obstructive pulmonary disease (COPD), cystic fibrosis and interstitial lung disease. A common characteristic of these diseases is the decreased capacity of lungs to exchange oxygen and carbon dioxide. This causes the patient to breathe faster which increases the energy the patient must expend in order to obtain enough oxygen. Various respiratory syndromes interfere with the ability of the lungs to adequately exchange gas with the atmosphere. These respiratory problems are a major cause of mortality and morbidity.

In another embodiment, the invention provides a method of treating, preventing, inhibiting reducing the incidence of lung diseases, disorders or conditions in a subject, comprising administering a pharmaceutical composition comprising a NRBA of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of inflammatory conditions in a subject. In another the NRBA/ is of formula 1-4, IV-IX or XI-XII.

In some embodiments, the lung diseases, disorders or conditions may comprise asthma, chronic obstructive pulmonary disease (COPD), cystic fibrosis, hemorrhagic shock, lung cancer or pleurisy.

In some embodiments, the present invention provides a method for treating, reducing the incidence, delaying the onset or progression, or reducing and/or abrogating the symptoms associated with a nervous system disease in a subject. In one embodiment, the method comprises administering to a subject a composition comprising a compound and an anti-cancer agent, an immunomodulating agent, an agent treating the central nervous system, an anti-infective agent, an agent treating a metabolic disease, an agent treating a wasting disease, a gene therapy agent, an agent treating the endocrine system, vitamins, or a combination thereof. In some embodiments, nervous system diseases comprise autonomic nervous system diseases, central nervous system diseases, cranial nerve diseases, demyelinating diseases, nervous system malformations, neurologic manifestations, or neuromuscular diseases.

In some embodiments, autonomic nervous system diseases comprise causalgia, or reflex sympathetic dystrophy.

In some embodiments, central nervous system diseases comprise Alzheimer's disease, arachnoiditis, brain abscess, brain ischemia, central nervous system infections, cerebral palsy, cerebrovascular disorders, corticobasal ganglionic degeneration (CBGD), Creutzfeldt-Jakob syndrome, Dandy-Walker syndrome, dementia, encephalitis, encephalomyelitis, epilepsy, epilepsy induced hypogonadal and/or hypermetabolic state, essential tremor, Friedreich ataxia, Gerstmann-Straussler-Scheinker disease, Hallervorden-Spatz syndrome, Huntington disease, hydrocephalus, hypoxia, insomnia, ischemic attack, kuru, Landau-Kleffner syndrome, Lewy Body disease, Machado-Joseph disease, meige syndrome, meningitis, bacterial meningitis, viral, migraine disorders, movement disorders, multiple system atrophy, myelitis, olivopontocerebellar atrophies, Parkinson's disease, parkinsonian disorders, poliomyelitis, postpoliomyelitis syndrome, prion diseases, pseudotumor cerebri, Shy-Drager syndrome, spasms, infantile, spinal cord diseases, supranuclear palsy, syringomyelia, thalamic diseases, tic disorders, tourette syndrome, or uveomeningoencephalitic syndrome. In some embodiments, the central nervous system disease is cystic fibrosis induced hypogonadal state.

In some embodiments, cranial nerve diseases comprise bell palsy, cranial nerve diseases, facial hemiatrophy, facial neuralgia, glossopharyngeal nerve diseases, Moebius syndrome, or trigeminal neuralgia.

In some embodiments, central nervous system diseases comprise injuries or damage to the central nervous system (CNS). In some embodiments, injuries or damage to the CNS may be associated with muscle wasting disorders. Injuries or damage to the CNS can be, for example, caused by diseases, trauma or chemicals. Examples are central nerve injury or damage, peripheral nerve injury or damage and spinal cord injury or damage.

Studies involving patients with spinal cord injuries (SCI) have shown that central neurotransmitters may be altered after SCI causing hypothalamus-pituitary-adrenal axis dysfunction, whose disruption led to a significant decrease in testosterone and other hormone levels. SCI or other acute illness or trauma characteristically includes heightened catabolism in conjunction with the lowered anabolic activity resulting in a condition that is prone to loss of lean body tissue, which is often accompanied by disturbed nutrient utilization. The effects of the loss of lean body mass include the development of wounds and impaired healing mechanisms, further compounding the problem. Because of poor nutrition and protein combined with immobilization, patients with spinal cord injury are at high risk for bed sores.

In one embodiment, a wide variety of injuries of the CNS may be treated by the methods of the present invention. CNS injury may refer, in one embodiment, to a breakdown of the membrane of a nerve cell, or, in another embodiment, to the inability of the nerve to produce and propagate nerve impulses, or in another embodiment, to the death of the cell. An injury includes damage that directly or indirectly affects the normal functioning of the CNS. The injury may be a structural, physical, or mechanical impairment and may be caused by physical impact, as in the case of a crushing, compression, or stretching of nerve fibers. Alternatively, the cell membrane may be destroyed by or degraded by an illness, a chemical imbalance, or a physiological malfunction such as anoxia (e.g., stroke), aneurysm, or reperfusion. A CNS injury includes, for example and without limitation, damage to retinal ganglion cells, a traumatic brain injury, a stroke-related injury, a cerebral aneurism-related injury, a spinal cord injury, including monoplegia, diplegia, paraplegia, hemiplegia and quadriplegia, a neuroproliferative disorder, or neuropathic pain syndrome.

In another embodiment, the invention provides a method of treating, preventing, suppressing, inhibiting, or reducing the incidence of central nervous system (CNS) disorder, disease or condition in a mammalian subject comprising administering a compound of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof to the subject. In another embodiment the compounds used herein is of formula 1-4, IV-IX or XI-XII.

With injury to the spinal cord of a mammal, connections between nerves in the spinal cord are broken. Such injuries block the flow of nerve impulses for the nerve tracts affected by the injury, with a resulting impairment to both sensory and motor function. Injuries to the spinal cord may arise from compression or other contusion of the spinal cord, or a crushing or severing of the spinal cord. A severing of the spinal cord, also referred to herein as a "transection," may be a complete severing or, may be an incomplete severing of the spinal cord.

In some embodiments, the methods of treating a subject suffering form a CNS injury or, in other embodiments, spinal cord injury, may be accompanied by treatment of the subject with electrical stimulation of the injured site and the administration of a purine nucleoside, or analog thereof, for example as described in United States Patent Application Publication Number 20040214790A1.

In some embodiments, demyelinating diseases comprise adrenoleukodystrophy, alexander disease, canavan disease, demyelinating disease, diffuse cerebral sclerosis of schilder, leukodystrophy-globoid cell, leukodystrophy-metachromatic, multiple sclerosis, or neuromyelitis optica.

In some embodiments, nervous system malformations comprise Arnold-Chiari malformation, Charcot-Marie-Tooth disease, encephalocele, hereditary motor and sensory neuropathies, septo-optic dysplasia, spina bifida occulta, or spinal dysraphism.

In some embodiments, neurologic manifestations comprise agnosia, amnesia, anomia, aphasia, apraxias, back pain, Brown-Sequard syndrome, cerebellar ataxia, chorea, communication disorders, confusion, dizziness, dyslexia, dystonia, facial paralysis, fasciculation, gait disorders, neurologic-headache, hemiplegia, memory disorders, mental retardation, mutism, myoclonus, neck pain, nonverbal learning disorder, olfaction disorders, pain, paralysis, phantom limb, prosopagnosia, quadriplegia, seizures, spasm, speech disorders, synesthesia tardive dyskinesia, taste disorders, torticollis, tremor, trismus, unconsciousness, or vertigo.

In some embodiments, neuromuscular diseases comprise. amyotrophic lateral sclerosis, brachial plexus neuritis, brachial plexus neuropathies, bulbar palsy, carpal tunnel syndrome, cubital tunnel syndrome, diabetic neuropathies, dysautonomia, guillain, barre syndrome, hereditary sensory and autonomic neuropathies, miller fisher syndrome, motor neuron disease, muscular atrophy, spinal, myasthenia gravis, myopathies, structural, congenital, nerve compression syndromes, neuralgia, neuromuscular diseases, paralyses, familial periodic, peripheral nervous system diseases, poems syndrome, polyneuropathies, polyradiculopathy, refsum disease, sciatica, spinal muscular atrophies of childhood, stiff-person syndrome, thoracic outlet syndrome, or ulnar nerve compression syndromes.

In one embodiment, methods of treating a subject with a nervous system disease encompass treating any secondary conditions in the subject, which arise due to the subject having a nervous system disease, some of which are described herein.

The compounds of this invention may be useful for the treatment or amelioration of conditions affecting the neural retina. Estrogen may have neuroprotective effects in the retina (see for example Invest Ophthal V is Sci 38:1193-1202 (1997) and Invest Ophthal V is Sci 44(7):3155-3162 (2003)), and estrogen receptors are found in the inner retina as well as the choroid (Br J Opthalmol 85:877-882 (2001). The NRBAs of the present invention may be useful in treating the eye for, or protecting against local ischemia or degenerative events that include, but are not limited to, macular degeneration, glaucoma, diabetic retinopathy, macular edema, retinitis pigmentosa and other retinal degeneration resulting from genetic defects, trauma or environmental exposure.

In some embodiments, the present invention provides a method for treating, reducing the incidence, delaying the onset or progression, or reducing and/or abrogating the symptoms associated with an ophthalmic disease in a subject. In one embodiment, the method comprises administering to a subject a composition comprising a NRBA compound. In one embodiment, the method comprises administering to a subject a composition comprising a NRBA compound and an anti-cancer agent, an immunomodulating agent, an agent treating the cardiovascular system, an anti-infective agent, an agent treating a wasting disease, a gene therapy agent, an agent treating the endocrine system, vitamins, or a combination thereof. In some embodiments ophthalmic disease comprise acute zonal occult outer retinopathy, abnormal color vision, Adie syndrome, albinism, ocular-amaurosis, fugax, amblyopia, aniridia, anisocoria, anterior ischemic optic neuropathy, anopthalmos, aphakia, asthenopia astigmatism, autoimmune disease blepharitis, blepharoptosis, blepharospasm, blindness, cataract, senile cataract central chorioretinopathy chalazion, chorioretinitis, chorioretinal hemorrhage, choroideremia, coloboma, color vision defects, conjunctivitis, corneal diseases, corneal dystrophies, corneal edema, corneal ulcer, corneal opacity, corneal erosion, corneal endothelial cell degeneration and dystrophy or loss of endothelial cell, corneal dystrophy or degeneration, detachment of corneal epithelium, epidemic keratoconjunctivitis, chalazion, central nerve diseases, central retinal artery or vein occlusion, arteriosclerosis of retinal artery, photopsia, diabetic retinopathy, chorioretinal atrophy, diabetic retinopathy, diplopia, distichiasis, dry eye syndromes, Duane retraction syndrome, ectropion, entropion, esotropia, exfoliation syndrome, exotropia, eye hemorrhage, eye neoplasms, eyelid diseases, floaters, general fibrosis syndrome, glaucoma, high tension glaucoma, normal tension glaucoma, gyrate atrophy, hemianopsia, Hermanski-Pudlak syndrome, hordeolum, Horner syndrome, hysteria hyperopia, hyphema, iridocyclitis iritis, Kearns-Sayer syndrome, keratitis, keratoconus, lacrimal apparatus diseases, lacrimal duct obstruction, lens diseases, lowering in dynamic visual activity, macular degeneration, macular hole micropthalmos, myopia, nystagmus, narrowing of visual field due to various kinds of diseases pathologic, ocular motility disorders, oculomotor nerve diseases, opthalmoplegia, optic atrophies, optic nerve diseases, optic neuritis, optic neuropathy, optic nerve atrophy orbital cellulitis, papilledema, peter's anomaly, presbyopia, psychosis pterygium, pupil disorders, refractive errors, retinal detachment, retinal diseases, retinal vein occlusion, retinal and choroidal neovascular diseases, cataract due to removal of ovary, cataract due to TGFβ, macular fibrosis, macular epiretinal membrane, refractive error retinal tear, retinitis proliferans, pigmentary retinal degeneration retinitis pigmentosa, retinopathy of prematurity, retinoschisis, scleritis, senile macular degeneration scotoma, strabismus, Thygeson's superficial punctate keratitis, trachoma, uveitis, white dot syndrome, vision disorders, or vitreous disorders, diseases due to cerebral pituitary gland disorder and imbalance of hormones, diseases due to gene disorder and diseases due to immune disorder, the method comprising administering a NRBA of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof to the subject. In another embodiment the NRBA is of formula 1-4, IV-IX or XI-XII.

In some embodiments ER-β agonists are useful in treating, reducing the incidence, delaying the onset or progression, or reducing and/or abrogating the symptoms associated with an ophthalmic disease in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12z, listed in Table 1, or any combination thereof.

In another embodiment, the methods of treating eye diseases comprise administering a composition comprising the compounds of this invention to the subject, wherein the composition is in the form of eye drops, eye wash, ointments, conjunctival injections, or contact lens adsorbents. In another embodiment, the methods of treating eye diseases comprises administering a composition comprising the compounds of this invention in the form of a tablet, capsule, liquid, syrup, injection, hap, ointment, eye drops, and the like, and administered orally, or non-orally such as injection, locally such as dropping to eye, etc. The effective ingredient may be vaporized and inhaled, for example through the nose, mouth or trachea.

In some embodiment, the methods of treating eye diseases comprise administering a composition comprising the compounds of this invention and any other compound, which is useful in treating the indicated conditions, as known in the art.

In some embodiment, eye drops and eye wash comprise water-solubilized compounds (I)-(XII) of this invention, which are, in one embodiment, dissolved in sterilized distilled water, BSS Plus, and/or physiological saline. In another embodiment, the compounds are of formula 1-4, IV-IX or XI-XII. In another embodiment, additives are added comprising excipients, carriers, pH controllers, isotonic agents, preservatives, glutathione, glucose, various kind of salt(s), stabilizers, refrigerants, antioxidants, antiseptic agents, or any combination thereof. In another embodiment, the eye drops and eye wash comprise hydroxypropylmethyl cellulose, carboxymethyl cellulose or its sodium salt, polypyrrolidone, polyvinylpyrrolidone (this is added and heated), or any combination thereof.

In some embodiments, the compounds of this invention have low solubility in water. In one embodiment, the compounds may be water solubilized by using cyclodextrin. In another embodiment α-cyclodextrin is used. In another embodiment β cyclodextrin is used. In another embodiment, γ cyclodextrin is used. In another embodiment, hydroxyalkylated β cyclodextrin is used.

In some embodiments, the present invention provides a method for treating, reducing the incidence, delaying the onset or progression, or reducing and/or abrogating the symptoms associated with a dermatological disorder in a subject. In one embodiment, the method comprises administering to a subject a composition comprising a compound and anti-cancer agent, an immunomodulating agent, an agent treating a dermatological disorder, an anti-infective agent, a gene therapy agent, an agent treating the endocrine system, vitamins, or a combination thereof. In some embodiments, dermatological disorders comprise acne, actinic keratosis, alopecia, androgenic alopecia, alopecia greata, alopecia secondary to chemotherapy, alopecia secondary to radiation therapy, alopecia induced by scarring, alopecia induced by stress, angioma, athlete's foot, aquagenic pruritus, atopic dermatitis, baldness, premature baldness, male pattern baldness, androgenic baldness, basal cell carcinoma, burns, bed sore, Behcet's disease, blepharitis, boil, Bowen's disease, bullous pemphigoid, canker sore, carbuncles, cellulitis, chloracne, chronic dermatitis of the hands and feet, dyshidrosis, cold sores, contact dermatitis, creeping eruption, dandruff, dermatitis, dermatitis herpetiformis, dermatofibroma, diaper rash, eczema, epidermolysis bullosa, erysipelas, erythroderma, friction blister, genital wart, hidradenitis, suppurativa, hives, hyperhidrosis, ichthyosis, impetigo, jock itch, Kaposi's sarcoma, keloid, keratoacanthoma, keratosis pilaris, lice infection, lichen planus, lichen simplex chronicus, lipoma, lymphadenitis, malignant melanoma, melasma, miliaria, molluscum contagiosum, nummular dermatitis, paget's disease of the nipple, pediculosis, pemphigus, perioral dermatitis, photoallergy, photosensitivity, pityriasis rosea, pityriasis rubra pilaris, psoriasis, raynaud's disease, ring worm, rosacea, scabies, scleroderma, sebaceous cyst, seborrheic keratosis, seborrhoeic dermatitis, shingles, skin cancer, skin tags, spider veins, squamous cell carcinoma, stasis dermatitis, tick bite, tinea barbae, tinea capitis, tinea corporis, tinea cruris tinea pedis, tinea unguium, tinea versicolor, tinea, tungiasis, vitiligo, or warts.

In some embodiments, the present invention provides a method for treating, reducing the incidence, delaying the onset or progression, or reducing and/or abrogating the symptoms associated with an endocrine disorder in a subject. In one embodiment, the method comprises administering to a subject a composition comprising a compound and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, endocrine disorders comprise acromegaly, Addison disease, adrenal gland diseases, adrenal hyperplasia, congenital, androgen-insensitivity syndrome, congenital hypothyroidism, Cushing syndrome, diabetes insipidus, diabetes mellitus, diabetes mellitus-type 1, diabetes mellitus-type 2, diabetic, ketoacidosis, empty Sella syndrome, endocrine gland neoplasms, endocrine system diseases, gigantism, gonadal disorders, graves disease, hermaphroditism, hyperaldosteronism, hyperglycemic hyperosmolar nonketotic coma, hyperpituitarism, hyperprolactinemia, hyperthyroidism, hypogonadism, hypopituitarism, hypothyroidism, Kallmann syndrome, Nelson syndrome, parathyroid diseases, pituitary diseases, polyendocrinopathies, autoimmune, puberty, delayed, puberty, precocious, renal osteodystrophy, thyroid diseases, thyroid hormone resistance syndrome, thyroid neoplasms, thyroid nodule, thyroiditis, thyroiditis, autoimmune, thyroiditis, subacute, or Wolfram syndrome.

In one embodiment, "Hypogonadism" is a condition resulting from or characterised by abnormally decreased functional activity of the gonads, with retardation of growth and sexual development.

In some embodiments, the present invention provides a method for treating, reducing the incidence, delaying the onset or progression, or reducing and/or abrogating the symptoms associated with urogenital disease and/or fertility in a subject. In one embodiment, the method comprises administering to a subject a composition comprising a compound of this invention and anti-cancer agent, an immunomodulating agent, an anti-infective agent, an agent treating the kidney, gene therapy agent, an agent treating the endocrine system, vitamins, or a combination thereof. In some embodiments, urogenital diseases and/or fertility diseases comprise abortion, spontaneous-adhesions-pelvic, candidiasis, vulvovaginal, depression-postpartum, diabetes, gestational, dyspareunia, dystocia, eclampsia, endometriosis, fetal death, fetal growth retardation, fetal membranes, premature rupture, genital diseases, female, genital neoplasms, female, hydatidiform mole, hyperemesis gravidarum, infertility, ovarian cysts, ovarian torsion, pelvic inflammatory disease, placenta diseases, placental insufficiency, polycystic ovary syndrome, polyhydramnios, postpartum hemorrhage, pregnancy complications, pregnancy, ectopic, pruritus vulvae, puerperal disorders, puerperal infection, salpingitis, trophoblastic neoplasms, uterine cervix incompetence, uterine inversion, uterine prolapse, vaginal diseases, vulvar diseases, vulvar lichen sclerosis.

In one embodiment, the method comprises administering to a subject a composition comprising a compound of this invention and anti-cancer agent, an immunomodulating agent, an antidiabetic agent, an agent treating the cardiovascular system, an agent treating the gastrointestinal system, an agent treating a dermatological disorder, an agent treating the central nervous system, an anti-infective agent, an agent treating the liver, an agent treating the kidney, an agent treating a metabolic disease, an agent treating a wasting disease, a gene therapy agent, an agent treating the endocrine system, vitamins, or a combination thereof. In some embodiments, disorders of environmental origin comprise barotrauma, bites and stings, brain concussion, burns, central cord syndrome, craniocerebral trauma, electric injuries, fractures, bone, frostbite, heat stress disorders, motion sickness, occupational diseases, poisoning, shaken baby syndrome, shoulder injuries, space motion sickness, spinal cord injuries, tick paralysis, or wounds (penetrating and non-penetrating).

In some embodiments, the present invention provides a method for treating, reducing the incidence, delaying the onset or progression, or reducing and/or abrogating the symptoms associated with a behavior mechanism in a subject. In one embodiment, the method comprises administering to a subject a composition comprising a compound of this invention and an agent treating the cardiovascular system, an agent treating the central nervous system, a gene therapy agent, an agent treating the endocrine system, vitamins, or a combination thereof. In some embodiments, behavior mechanisms comprise aggression, attitude to death, codependency, self-injurious behavior, sexual behavior, or social behavior.

In some embodiments, the present invention provides a method for treating, reducing the incidence, delaying the onset or progression, or reducing and/or abrogating the symptoms associated with a mental disorder in a subject. In one embodiment, the method comprises administering to a subject a composition comprising a compound of this invention and an agent treating the central nervous system, a gene therapy agent, an agent treating the endocrine system, vitamins, or a combination thereof. In some embodiments, mental disorders comprise Asperger syndrome, attention deficit disorder with hyperactivity, autistic disorder, bipolar disorder, borderline personality disorder, capgras syndrome, child behavior disorders, combat disorders, cyclothymic disorder, dependent personality disorder, depressive disorder, dissociative disorders, dysthymic disorder, eating disorders, firesetting behavior, hypochondriasis, impulse control disorders, Kleine-Levin syndrome, mental disorders, mental disorders diagnosed in childhood, multiple personality disorder, Munchausen syndrome, Munchausen syndrome, narcissistic personality disorder, narcolepsy, obsessive-compulsive disorder, paraphilias, phobic disorders, psychotic disorders, restless legs syndrome, schizophrenia, seasonal affective disorder, sexual and gender disorders, sexual dysfunctions, psychological, sleep disorders, somatoform disorders, stress disorders, post-traumatic, substance-related disorders, suicidal behavior, or trichotillomania.

In one embodiment, "depression" refers to an illness that involves the body, mood and thoughts that affects the way a person eats, sleeps and the way one feels about oneself, and thinks about things. The signs and symptoms of depression include loss of interest in activities, loss of appetite or overeating, loss of emotional expression, an empty mood, feelings of hopelessness, pessimism, guilt or helplessness, social withdrawal, fatigue, sleep disturbances, trouble concentrating, remembering, or making decisions, restlessness, irritability, headaches, digestive disorders or chronic pain.

In one embodiment, "cognition" refers to the process of knowing, specifically the process of being aware, knowing, thinking, learning and judging. Cognition is related to the fields of psychology, linguistics, computer science, neuroscience, mathematics, ethology and philosophy. In one embodiment, "mood" refers to a temper or state of the mind. As contemplated herein, alterations mean any change for the positive or negative, in cognition and/or mood.

In some embodiments, the present invention provides a method for treating, reducing the incidence, delaying the onset or progression, or reducing and/or abrogating the symptoms associated with a liver disease in a subject. In one embodiment, the method comprises administering to a subject a composition comprising a compound of this invention and anti-cancer agent, an immunomodulating agent, an agent treating the gastrointestinal system, an anti-infective agent, an agent treating the liver, an agent treating a metabolic disease, an agent treating a wasting disease, a gene therapy agent, an agent treating the endocrine system, vitamins, or a combination thereof. In some embodiments, liver diseases comprise liver cancer, primary biliary cirrhosis, autoimmune hepatitis, chronic liver disease, cirrhosis of the liver, hepatitis, viral hepatitis (hepatitis a, hepatitis b, chronic hepatitis b, hepatitis c, chronic hepatitis c, hepatitis d, hepatitis e, hepatitis x), liver failure, jaundice, neonatal jaundice, hepatoma, liver cancer, liver abscess, alcoholic liver disease, hemochromatosis, Wilson's disease, portal hypertension, primary sclerosing cholangitis, sarcoidosis, tapeworms, alveolar hydatid disease, fascioliasis, schistosomiasis, gaucher disease, Zellweger syndrome, alcoholism, food poisoning, pneumococcal pneumonia' or *vibrio* vulnificus.

In some embodiments, the present invention provides a method for treating, reducing the incidence, delaying the onset or progression, or reducing and/or abrogating the symptoms associated with nerve injury, neuropathy, diabetic neuropathy, alcoholic neuropathy, subacute combined degeneration of the spinal cord, diabetes, rheumatoid arthritis, In some embodiments this invention provides a method of treating kidney disease or disorder, wherein the efficacy of such methods are detected by known clinical indications such as but not limited to urinary casts, GFR, or other markers of renal function.

In some embodiments, the present invention provides a method for treating, reducing the incidence, delaying the onset or progression, or reducing and/or abrogating the symptoms associated with a hypogonadal state in a subject. In one embodiment, the present invention provides a method for treating, reducing the incidence, delaying the onset or progression, or reducing and/or abrogating the symptoms associated with a pharmacotherapy induced hypogonadal state in a subject. In some embodiments, hypogonadism is caused by treatments which alter the secretion of hormones from the sex glands in both women and men. In some embodiments, hypogonadism may be "primary" or "central". In primary hypogonadism, the ovaries or testes themselves do not function properly. In some embodiments, hypogonadism may be induced by surgery, radiation, genetic and developmental disorders, liver and kidney disease, infection, or certain autoimmune disorders. In some embodiments, menopause is a form of hypogonadism. Menopause may cause, in some embodiments, amenorrhea, hot flashes, vaginal dryness, or irritability due to woman's estrogen levels fall. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In another embodiment, the invention provides a contraceptive, and/or a method of use thereof, the contraceptive comprising a composition comprising a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof. In one embodiment, the invention provides a method for providing post-coital contraception by administering the composition comprising a NRBA, which in one embodiment is a of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof.

In one embodiment this invention provides a method of treating a subject suffering from post menopausal conditions, said method comprising the step of administering to said subject a NRBA and/or its pharmaceutically acceptable salt, hydrate, N-oxide, or any combination thereof.

In another embodiment this invention provides a method of suppressing, inhibiting or reducing the risk of post menopausal conditions, said method comprising the step of administering to said subject a NRBA and/or its pharmaceutically acceptable salt, hydrate, N-oxide, or any combination thereof.

In another embodiment, the invention provides a method of treating, preventing, suppressing, inhibiting, or reducing the incidence of hot flashes, gynecomastia, and/or hair loss in female subjects, or in another embodiment, in male human subjects. In one embodiment, invention provides a method of treating, preventing, suppressing, inhibiting, or reducing the incidence of hot flashes, gynecomastia, and/or hair loss in a male subject having prostate cancer, comprising administering a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby treating, preventing, suppressing, inhibiting, or reducing the incidence of hot flashes, gynecomastia, and/or hair loss in said male human subjects. In another embodiment, the compound is of formula 1-4, IV-IX or XI-XII.

In one embodiment, the term "hot flashes" refers to the following: sudden feeling of heat in the upper part or all of the body, face and neck flush, red blotches appearing on the chest, back and arms, heavy sweating, cold shivering, etc.

It is to be understood that any sex hormone-dependent disease, disorder or condition may be treated via the methods of this invention, using the compositions of this invention.

In one embodiment, hot flashes can be treated with any NRBA, which has a structure characterized by any of the formulas, as described herein. In one embodiment, hot flashes may be treated, prevented, alleviated with the following NRBAs chosen based on their pharmacologic activity as demonstrated in receptor binding studies, estrogen receptor transactivation, in vitro studies of osteoblast and osteoclast activity, and in vivo studies.

Hot flash is mediated by both ER-α and ER-β. In some embodiments, to overcome this, tissue selective agonists of both the isoforms can be used. In some embodiments, side effects associated with some ER-α agonists such as thromboembolism, mammary carcinogenesis and uterine cancer, may be avoided via selection of specific ER-β agonists for this indication.

In some embodiments, the present invention provides a method for treating, reducing the incidence, delaying the onset or progression, or reducing and/or abrogating the symptoms associated with osteopenic state in a subject. In one embodiment, the present invention provides a method for treating, reducing the incidence, delaying the onset or progression, or reducing and/or abrogating the symptoms associated with a pharmacotherapy induced osteopenic state in a subject. In some embodiments, osteopenia is a mild thinning of the bone mass. In some embodiments, osteopenia is a precursor to osteoporosis. In some embodiments osteopenia is defined as a bone density between one standard deviation (SD) and 2.5 SD below the bone density of a normal young adult. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

In some embodiments, the present invention provides a method for treating, reducing the incidence, delaying the onset or progression, or reducing and/or abrogating the symptoms associated with a combination of diseases and/or disorders in a subject as described hereinabove. In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, or a combination thereof.

It is to be understood that any method of this invention, as herein described, encompasses the administration of a compound as herein described, or a composition comprising the same, to the subject, in order to treat the indicated disease, disorder or condition. The methods as herein described each and/or all may further comprise administration of an additional therapeutic agent as herein described, and as will be appreciated by one skilled in the art.

In one embodiment, the method comprises administering to a subject a composition comprising a compound of this invention and an anti-cancer agent, an immunomodulating agent, an antidiabetic agent, an agent treating the cardiovascular system, an agent treating the gastrointestinal system, an agent treating the central nervous system, an agent treating a metabolic disease, an agent treating a wasting disease, a gene therapy agent, an agent treating the endocrine system, an agent treating a dermatological disorder, an anti-infective agent, an agent treating the liver, an agent treating the kidney, vitamins, nutritional additives, hormones, each and/or all as herein described, or any other therapeutic agent as herein described, or a combination thereof.

In another embodiment, this invention provides methods of treatment of cystic fibrosis and induced hypogonadal states as a result of the same, epilepsy and induced hypogonadal and/or hypermetabolic states as a result of the same, hereditary angioedema, lupus erythematosus and decreased BMD as a result of the same, alcohol and smoking induced osteoporosis, in a subject the methods comprising administering a compound as herein described to the subject.

In another embodiment, this invention provides a method of treating a nervous system disease, disorder or condition, the method comprising administering to the subject a compound as herein described, and optionally anti-psychotics, such as, for example, zotepine, haloperidol, amisulpride, risperidone, other D2 dopamine receptor antagonists; anti-epileptics, such as valproic acid, carbamazepine, oxcarbamazepine, etc. or combinations thereof.

In another embodiment, this invention provides a method of treating a hormone dependent disease, disorder or condition, the method comprising administering to the subject a compound as herein described, and optionally chemotherapeutics agents and therapies (methotrexate, cyclophosphamide, ifosfamide, adriamycin, doxorubicin, glucocorticoids, cyclosporine, L-thyroxine, AI, fulvestrant, GnRH agents, ADT, discontinuation of hormone replacement therapy, cranial irradiation, peripheral irradiation, etc.; prolactinemia-inducing pharmacotherapeutics (serotonergic antidepressants acting through 5HT2 receptors, selective serotonin reuptake inhibitors, monoamine oxidase inhibitors, tricyclic antidepressants, antihypertensives such as methyldopa, reserpine, clonidine, and verapamil; antidopaminergic anti-emetics such as metoclopramide, H2 receptor antagonists such as cimetidine and ranitidine, estrogens, amphetamines, AR partial antagonists (ketoconazole, spironolactone, eplerenone)

In one embodiment, the present invention provides a use of a compound as described herein for reducing a fat mass in a subject. In another embodiment the invention provides such methods for use of the compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same.

In another embodiment, this invention provides for the use of a compound as described herein or its prodrug, analog, isomer, metabolite, derivative, pharmaceutically acceptable salt, pharmaceutical product, polymorph, crystal, impurity, N-oxide, hydrate or any combination thereof, or a composition comprising the same, improving blood lipid profile, increasing bone mass/BMD/strength/function; lowering body fat in a subject.

In another embodiment, the subject has a hormonal imbalance, disorder, or disease. In another embodiment the subject has menopause.

In one embodiment, the present invention provides a use of a compound as described herein for increasing a lean mass in a subject. In another embodiment such use comprises administration of a compound as described herein or its prodrug, analog, isomer, metabolite, derivative, pharmaceutically acceptable salt, pharmaceutical product, polymorph, crystal, impurity, N-oxide, hydrate or any combination thereof.

In one embodiment the subject has a hormonal imbalance, disorder, or disease. In another embodiment the subject has menopause.

Cholesterol, triacylglycerol and other lipids are transported in body fluids by lipoproteins which may be classified according to their density, for example, the very low density lipoproteins (VLDL), intermediate density lipoproteins (IDL), low density lipoproteins (LDL) and high density lipoproteins (HDL).

It has been shown that high levels of LDL-Cholesterol in the blood correlate with atherosclerosis which is a progressive disease characterized in part by sedimentation of lipids in inner walls of arteries, particularly of coronary arteries. It has also been shown that a high blood level of LDL-Cholesterol correlates with coronary heart disease. Also, a negative correlation exists between blood levels of HDL cholesterol and coronary heart disease.

The level of total cholesterol in blood, which is the sum of HDL-Cholesterol, LDL-Cholesterol, VLDL-Cholesterol and chylomicron-Cholesterol, is not necessarily predictive of the risk of coronary heart disease and atherosclerosis.

The correlation between atherosclerosis and LDL cholesterol levels, however, is much higher than a similar correlation between atherosclerosis and total serum cholesterol levels.

In one embodiment, this invention provides methods of use of the compounds as herein described for improving the lipid profile and/or reducing the circulating lipid levels in a subject. In some embodiments, according to this aspect of the invention, the subject suffers from one or more conditions selected from the group consisting of: atherosclerosis and its associated diseases, premature aging, Alzheimer's disease, stroke, toxic hepatitis, viral hepatitis, peripheral vascular insufficiency, renal disease, and hyperglycemia, and the invention provides for the administration of a compound or composition comprising the same, as herein described, which in some embodiments positively affects a lipid profile in the subject, which is one means by which the method is useful in treating the indicated diseases, disorders and conditions.

In one embodiment the invention provides for the treatment of atherosclerosis and its associated diseases, such as for example, cardiovascular disorders, cerebrovascular disorders, peripheral vascular disorders, intestinal vascular disorders, or combinations thereof.

In one embodiment cardiovascular disorders comprise of hypertension (HTN), coronary artery disease (CAD) or myocardial perfusion. In another embodiment this invention provides methods of use of the NRBA compounds as herein described for promoting aortic smooth muscle cell proliferation. In another embodiment this invention provides methods of use of the compounds as herein described for treating arteriosclerosis. In one embodiment this invention provides methods of use of the compounds as herein described in conjunction with vascular stents. In some embodiments the compounds of this embodiment could be incorporated onto the stent as a coating to retard vascular fibrosis and remodeling, vascular cell proliferation and migration, etc. that often cause stent failure or restenosis. In another embodiment this invention provides methods of use of the compounds as herein described for lowering blood pressure. In another embodiment this invention provides methods of use of the compounds as herein described for treating cardiac diseases and disorders comprising cardiomyopathy, cardiac dysfunctions such as myocardial infarction, cardiac hypertrophy and congestive heart failure. In another embodiment this invention provides methods of use of the compounds as herein described for cardioprotection comprising cardioprotection in insulin resistance; treating diabetes type I and II, metabolic syndrome, syndrome X and/or high blood pressure.

In one embodiment, the invention provides a method of treating, preventing, reducing the risk of mortality from cardiovascular and/or cerebrovascular disease in a subject, comprising administering a compound of this invention or its prodrug, ester, analog, isomer, metabolite, derivative, pharmaceutically acceptable salt, pharmaceutical product, polymorph, crystal, impurity, N-oxide, hydrate or any combination thereof, or a pharmaceutical composition comprising the same.

In one embodiment, compounds of this invention reduce LDL and total cholesterol levels.

In another embodiment the compound of this invention reduces LDL and total cholesterol levels in a subject.

In another embodiment, compounds of this invention are co-administered with HDL-elevating agents. In another embodiment, a compound of this invention is co-administered with an HDL-elevating agent. In another embodiment, HDL-elevating agents include niacin. In another embodiment the HDL-elevating agents include fibrates including gemfibrozil (Lopid), thiourea based gemfibrozil analogues, and fenofibrate (TriCor). In another embodiment, HDL-elevating agents include statins. In another embodiment, HDL-elevating agents include 1-hydroxyalkyl-3-phenylthiourea, and analogs thereof.

In one embodiment, this invention provides a method of reducing circulating lipid levels in a subject, said method comprising administering a compound of this invention or its pharmaceutically acceptable salt, hydrate, N-oxide, or any combination thereof, or a composition comprising the same. In one embodiment, the subject suffers from atherosclerosis and its associated diseases, premature aging, Alzheimer's disease, stroke, toxic hepatitis, viral hepatitis, peripheral vascular insufficiency, renal disease, hyperglycemia, or any combination thereof.

In one embodiment, this invention provides a method of treating atherosclerosis and its associated diseases, such as, for example, cardiovascular disorders, cerebrovascular disorders, peripheral vascular disorders, or intestinal vascular disorders in a subject, the method comprising the step of administering to the subject compound of this invention or its pharmaceutically acceptable salt, hydrate, N-oxide, or any combination thereof, or a composition comprising the same. In another embodiment, the compound is of formula 1-4, IV-IX or XI-XII. The method may further comprise co-administration, subsequent or prior administration with an agent or agents, which are known to be useful in treating cardiovascular disorders, cerebrovascular disorders, peripheral vascular disorders, or intestinal vascular disorders.

Cardiovascular cells, as well as reproductive tissues, bone, liver, and brain, express both of the known estrogen receptors, estrogen receptor-α (ER-α) and estrogen receptor-β (ER-β). These receptors are important targets for endogenous estrogen, estrogen replacement therapy (ERT), and pharmacological estrogen agonists. Estrogen-estrogen receptor complexes serve as transcription factors that promote gene expression with a wide range of vascular effects, including regulation of vasomotor tone and response to injury, which may be protective against development of atherosclerosis and ischemic diseases. Estrogen receptors in other tissues, such as the liver, may mediate both beneficial effects (e.g., changes in apoprotein gene expression that improve lipid profiles) and adverse effects (e.g., increases in gene expression of coagulation proteins and/or decreases in fibrinolytic proteins). Two general estrogen-mediated vascular effects are recognized. Rapid, transient vasodilation occurs within a few minutes after estrogen exposure, independently of changes in gene expression. Longer-term effects of estrogen on the vasculature, such as those related to limiting the development of atherosclerotic lesions or vascular injury, occur over hours to days after estrogen treatment and have as their hallmark alterations in vascular gene expression. Progesterone and other hormonal receptors are also expressed in the vasculature.

In another embodiment, the invention provides a method of improving a lipid profile in a subject, comprising administering a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same, thereby improving the lipid profile in said subject. In another embodiment, the NRBA is of formula 1-4, IV-IX or XI-XII. In some embodiments ER-β agonists are useful in improving a lipid profile in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ERβ agonist of this invention is compound 12p, listed in Table 1. In another embodiment, ER-β agonist of this invention is compound 12s, listed in Table 1. In another embodiment, ER-3 agonist of this invention is compound 12u, listed in Table 1. In another embodiment, ER-β agonist of this invention is compound 12z, listed in Table 1, or any combination thereof.

In some embodiments, the phrase "improving a lipid profile" may refer to lowering pathogenic circulating lipid levels, lowering plaque formation in vasculature, altering circulating HDL/LDL ratios, ratios reducing the ratio of LDL levels to HDL levels, lowering circulating cholesterol levels, preventing lipid accumulation in vasculature, or any combination thereof, or other therapeutic effects related thereto, as will be appreciated by one skilled in the art.

In one embodiment, the invention provides a method of treating, preventing, reducing the risk of mortality from vasculature disease disorder or condition in a subject, comprising administering a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same.

In one embodiment, vasculature disease disorder or condition may comprise, inter alia, aortic smooth cell proliferation, restenosis, reperfusion injury, vascular smooth muscle cell proliferation or vasospasm.

Estrogen receptor receptors ER-α and ER-β mediates many of the known cardiovascular effects of estrogen and is expressed in male and female vascular cells. In one embodiment, estrogen deficiency is associated with increased risk of developing coronary artery disease. Estrogen replacement therapy attenuates this risk in postmenopausal women. In one embodiment the NRBA compounds of this invention mediate gene expression in vascular cells, mediate ion channel function, elaborate the response to vasoactive substances, as well as vascular smooth muscle cell proliferation and migration, and endothelial cell proliferation. ERα and ER-β are expressed in vascular smooth muscle cells derived from both women and men.

In one embodiment, this invention provides a method of improving coronary artery function. In one embodiment, this invention provides a method of: a) inducing rapid, NO-dependent and endothelium smooth muscle dependent relaxation; b) inducing rapid, NO-independent independent smooth muscle relaxation; and c) attenuating the constriction of smooth muscle. In some embodiments the smooth muscle is vascular smooth muscle. In some embodiments, the vascular smooth muscle is aortic. In some embodiments of this invention vascular smooth muscle is in an artery. In some embodiments of this invention the vascular smooth muscle is a vein. In other embodiments of this invention, the vascular smooth muscle is in the intrarenal artery, pulmonary arteries, microcirculation, coronary artery, hepatic portal vein, etc. According to these aspects, such methods are effected by administering a NRBA of this invention or a composition comprising the same.

In another embodiment, this invention provides a method for nitric oxide formation and inhibiting $O_2^-$. In another embodiment this invention provides a method of controlling coronary artery vasoreactivity in males and females and regulate vascular NO and $O_2^-$ formation. According to these aspects, such methods are affected by administering a NRBA of this invention or a composition comprising the same.

Vascular effects of estrogens can be divided in nongenomic and chronic effects. Nongenomic vascular effects may be applied to stimulate or enhance epicardial coronary arterial circulation. According to these aspects, such methods are affected by administering a NRBA of this invention or a composition comprising the same.

In one embodiment, the compounds of this invention involve activation of NO synthase. In one embodiment, the compounds of this invention activate BK channels in native smooth muscle cells via a non-genomic mechanism. BK channels refer to large conductance $Ca^{2+}$-sensitive potassium channels. According to these aspects, administering a NRBA of this invention or a composition comprising the same is useful in applications related thereto.

In one embodiment, the invention provides a method of treating, preventing, reducing the risk of mortality from cardiovascular and/or cerebrovascular disease in a subject, comprising administering a NRBA of formula (I)-(XII) or its prodrug, ester, analog, isomer, metabolite, derivative, pharmaceutically acceptable salt, pharmaceutical product, polymorph, crystal, impurity, N-oxide, hydrate or any combination thereof, or a composition comprising the same. In another embodiment, the NRBA is of formula 1-4, IV-IX or XI-XII. In some embodiments ER-β agonists are useful in treating, preventing, reducing the risk of mortality from cardiovascular and/or cerebrovascular disease in a subject. In another embodiment, ER-β agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ERβ agonist of this invention is compound 12z, listed in Table 1, or any combination thereof.

In one embodiment, cardiovascular disease comprises, inter alia, atherosclerosis of the coronary arteries, angina pectoris, and myocardial infarction. In one embodiment, cerebrovascular disease comprises, inter alia, atherosclerosis of the intracranial or extracranial arteries, stroke, syncope, and transient ischemic attacks.

In one embodiment, this invention provides a method of improving the dexterity and movement in a subject, for example, by treating arthritis in the subject.

The term "arthritis" refers, in another embodiment, to a non-inflammatory degenerative joint disease occurring chiefly in older people, characterized by degeneration of the articular cartilage, hypertrophy of bones and the margins, changes in the synovial membrane, etc. It is accompanied, in other embodiments, by pain and stiffness, particularly after prolonged activity.

The term "increased blood pressure" or "hypertension" refers, in other embodiments, to a repeatedly high blood pressure above 140 over 90 mmHg. Chronically-elevated blood pressure can cause blood vessel changes in the back of the eye, thickening of the heart muscle, kidney failure, and brain damage.

The term "stroke" refers, in other embodiments, to damage to nerve cells in the brain due to insufficient blood supply often caused by a bursting blood vessel or a blood clot. The term "heart disease", in other embodiments, refers to a malfunction in the heart normal function and activity, including heart failure.

In another embodiment, this invention relates to a method of promoting, increasing or facilitating weight loss in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to promote, increase or facilitate weight loss in the subject.

In another embodiment, this invention relates to a method of decreasing, suppressing, inhibiting or reducing appetite of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to decrease, suppress, inhibit or reduce the appetite of the subject.

In another embodiment, this invention relates to a method of altering the body composition of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the body composition of the subject. In one embodiment, altering the body composition comprises altering the lean body mass, the fat free body mass of the subject, or a combination thereof.

In another embodiment, this invention relates to a method of altering lean body mass or fat free body mass of a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter the lean body mass or fat free body mass of the subject.

In another embodiment, this invention relates to a method of converting fat to lean muscle in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to convert fat to lean muscle in the subject.

In another embodiment, this invention relates to a method of treating an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to treat the obesity-associated metabolic disorder in the subject.

In another embodiment, this invention relates to a method of preventing, suppressing, inhibiting or reducing an obesity-associated metabolic disorder in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to prevent, suppress, inhibit or reduce the obesity-associated metabolic disorder in the subject.

In one embodiment, the obesity-associated metabolic disorder is hypertension. In another embodiment, the disorder is osteoarthritis. In another embodiment, the disorder is increased blood pressure. In another embodiment, the disorder is stroke. In another embodiment, the disorder is heart disease.

In another embodiment, this invention relates to a method of decreasing, suppressing, inhibiting or reducing adipogenesis in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof.

In another embodiment, this invention relates to a method of altering stem cell differentiation in a subject, comprising the step of administering to the subject a compound as herein described and/or its analog, derivative, isomer, metabolite, pharmaceutically acceptable salt, pharmaceutical product, hydrate, N-oxide, prodrug, polymorph, crystal, or any combination thereof, in an amount effective to alter stem cell differentiation in the subject.

In one embodiment, the compounds as herein described are useful in treating, preventing, suppressing, inhibiting, or reducing an obesity-associated metabolic disorder, for example hypertension, osteoarthritis, increased blood pressure, stroke, or heart disease.

In one embodiment, the compounds as herein described find utility in treating or halting the progression of, or treating symptoms of diabetes. In another embodiment, the compounds as herein described are useful in treating co-morbidities related to diabetes. These conditions include: hypertension (HTN), cerebrovascular disease, atherosclerotic coronary artery disease, macular degeneration, diabetic retinopathy (eye disease) and blindness, cataracts—systemic inflammation (characterized by elevation of inflammatory markers such as erythrocyte sedimentation rate or C-reactive protein), birth defects, pregnancy related diabetes, pre-eclampsia and hypertension in pregnancy, kidney disease (renal insufficiency, renal failure etc.), nerve disease (diabetic neuropathy), superficial and systemic fungal infections, congestive heart failure, gout/hyperuricemia, obesity, hypertriglyceridemia, hypercholesterolemia, fatty liver disease (non-alcoholic steatohepatitis, or NASH), and diabetes-related skin diseases such as Necrobiosis Lipoidica Diabeticorum (NLD), Blisters of diabetes (Bullosis Diabeticorum), Eruptive Xanthomatosis, Digital Sclerosis, Disseminated Granuloma Annulare, and Acanthosis Nigricans.

In one embodiment, this invention provides a method of treating diabetic nephropathy. Diabetic nephropathy is a complication of diabetes that evolves early, typically before clinical diagnosis of diabetes is made. The earliest clinical evidence of nephropathy is the appearance of low but abnormal levels (>30 mg/day or 20 µg/min) of albumin in the urine (microalbuminuria), followed by albuminuria (>300 mg/2-4 h or 200 µg/min) that develops over a period of 10-15 years. In patients with type 1 diabetes, diabetic hypertension typically becomes manifest early on, by the time that patients develop microalbuminuria. Once overt nephropathy occurs, the glomerular filtration rate (GFR) falls over a course of times, which may be several years, resulting in End Stage Renal Disease (ESRD) in diabetic individuals.

In one embodiment, this invention provides a method of treating diabetic neuropathy. Diabetic neuropathy is a family of nerve disorders caused by diabetes. Diabetic neuropathies cause numbness and sometimes pain and weakness in the hands, arms, feet, and legs. Neurologic problems in diabetes may occur in every organ system, including the digestive tract, heart, and genitalia. Diabetic neuropathies are classified as peripheral, autonomic, proximal, and focal. Peripheral neuropathy causes pain or loss of feeling in the toes, feet, legs, hands, and arms. Autonomic neuropathy causes changes in digestion, bowel and bladder function, sexual response, and perspiration and can also affect the nerves that serve the heart and control blood pressure. Proximal neuropathy causes pain in the thighs, hips, or buttocks and leads to weakness in the legs. Focal neuropathy results in the sudden weakness of one nerve, or a group of nerves, causing muscle weakness or pain. Any nerve in the body may be affected.

In one embodiment, the subject for whom treatment is sought via the methods of this invention is one with hyperinsulinemia. Hyperinsulinemia is a sign of an underlying problem that is causing the pancreas to secrete excessive amounts of insulin. The most common cause of hyperinsulinemia is insulin resistance, a condition in which your body is resistant to the effects of insulin and the pancreas tries to compensate by making more insulin. hyperinsulinemia is associated with type II diabetes In one embodiment, the subject for whom treatment is sought via the methods of this invention is one with insulin resistance. Insulin resistance is a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to the metabolic syndrome and type II diabetes.

In one embodiment, this invention provides a method of treating vascular disease in a human subject, comprising the step of administering to said subject a compound of this invention or its isomer, pharmaceutically acceptable salt, pharmaceutical product, hydrate, N-oxide, or any combination thereof.

In one embodiment this invention provides a method for a) treating, preventing, suppressing inhibiting atherosclerosis b) treating, preventing, suppressing inhibiting liver damage due to fat deposits comprising the step of administering to the subject a compound as described herein and/or its analog, derivative, isomer, metabolite, pharmaceutically acceptable salt, pharmaceutical product, hydrate, N-oxide, prodrug, polymorph, crystal, or any combination thereof, or a composition comprising the same, in an amount effective to treat, prevent or inhibit atherosclerosis and liver damage due to fat deposit. In another embodiment, the compound is of formula 1-4, IV-IX or XI-XII.

In one embodiment, the compound as described herein is useful in a) treating, preventing, suppressing, inhibiting, or reducing atherosclerosis; b) treating, preventing, suppressing inhibiting liver damage due to fat deposits. In another embodiment, the compound is of formula 1-4, IV-IX or XI-XII.

In one embodiment atherosclerosis refers to a slow, complex disease that may begin with damage to the innermost layer of the artery. In another embodiment the causes of damage to the arterial wall may include a) elevated levels of cholesterol and in the blood; b) high blood pressure; c) tobacco smoke d) diabetes. In another embodiment, the condition is treatable in a smoker, despite the fact that tobacco smoke may greatly worsen atherosclerosis and speed its growth in the coronary arteries, the aorta and arteries in the legs. Similarly, in another embodiment, the methods of this invention may be useful in treating subjects with a family history of premature cardiovascular disease who have an increased risk of atherosclerosis.

In one embodiment, liver damage due to fat deposits refer to the build-up of fat in the liver cells forming a Fatty Liver which may be associated with or may lead to inflammation of the liver. This can cause scarring and hardening of the liver. When scarring becomes extensive, it is called cirrhosis.

In another embodiment the fat accumulates in the liver as obesity. In another embodiment fatty liver is also associated with diabetes mellitus, high blood triglycerides, and the heavy use of alcohol. In another embodiment fatty Liver may occur with certain illnesses such as tuberculosis and malnutrition, intestinal bypass surgery for obesity, excess vitamin A in the body, or the use of certain drugs such as valproic acid (trade names: Depakene/Depakote) and corticosteroids (cortisone, prednisone). Sometimes fatty liver occurs as a complication of pregnancy.

Hypertension is another comorbid factor for renal disease. In some embodiments, treatment of renal disease according to the present invention may comprise concomitant treatment with a compound of this invention and an agent which treats hypertension.

In one embodiment, the compound as described herein is useful in treating inflammation and related disorders such as: a) prevention, treatment, or reversal of arthritis; b) prevention, treatment, or reversal of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjögrens' syndrome, tendonitis or ulcerative colitis; c) preventing, treatment, or reversing an autoimmune disease.

In one embodiment, the compound as described herein is useful in prevention of iatrogenic effects comprising acute fatigue syndrome (post-surgical) or androgen-deprivation therapy (ADT) induced side effects such as reduced muscle mass, reduced muscle strength, frailty, hypogonadism, osteoporosis, osteopenia, decreased BMD and/or decreased bone mass.

In one embodiment, the compounds and/or compositions and/or methods of use thereof are for the treatment of human subjects, wherein, in one embodiment, the subject is male, or in another embodiment, the subject is female.

In one embodiment, the methods of the present invention comprise administering a compound of this invention as the sole active ingredient. However, also encompassed within the scope of the present invention are methods for, hormone therapy, dry eye, treating prostate cancer, delaying the progression of prostate cancer, and for preventing and/or treating the recurrence of prostate cancer, treatment of osteoporosis, which comprise administering the compounds in combination with one or more therapeutic agents. These agents include, but are not limited to: antiestrogens, anticancer drugs, 5-alpha reductase inhibitors, aromatase inhibitors, progestins, agents acting through other nuclear hormone receptors, progesterone, estrogen, PDE5 inhibitors, apomorphine, bisphosphonate, and one or more additional NRBAs.

Thus, in one embodiment, the methods of the present invention comprise administering the compound of this invention in combination with diabetes drug such as troglitazone, rosiglitazone, and pioglitazone. In another embodiment, the methods of the present invention comprise administering the compound in combination with an LHRH analog. In another embodiment, the methods of the present invention comprise administering the compound, in combination with a reversible antiandrogen. In another embodiment, the methods of the present invention comprise administering the compound, in combination with an antiestrogen. In another embodiment, the methods of the present invention comprise administering the compound, in combination with an anticancer drug. In another embodiment, the methods of the present invention comprise administering the compound, in combination with a 5-alpha reductase inhibitor. In another embodiment, the methods of the present invention comprise administering the compound, in combination with an aromatase inhibitor. In another embodiment, the methods of the present invention comprise administering the compound, in combination with a progestin. In another embodiment, the methods of the present invention comprise administering the compound, in combination with an agent acting through other nuclear hormone receptors. In another embodiment, the methods of the present invention comprise administering the compound, in combination with a selective estrogen receptor modulators (SERM). In another embodiment, the methods of the present invention comprise administering the compound, in combination with a progesterone. In another embodiment, the methods of the present invention comprise administering the compound, in combination with an estrogen. In another embodiment, the methods of the present invention comprise administering the compound, in combination with a PDE5 inhibitor. In another embodiment, the methods of the present invention comprise administering the compound, in combination with apomorphine. In another embodiment, the methods of the present invention comprise administering the compound, in combination with a bisphosphonate. In another embodiment, the methods of the present invention comprise administering the compound, in combination with one or more SARMs. In some embodiments, the methods of the present invention comprise combined preparations comprising the compound and an agent as described hereinabove. In some embodiments, the combined preparations can be varied, e.g., in order to cope with the needs of a patient subpopulation to be treated or the needs of the single patient which different needs can be due to the particular disease, severity of the disease, age, sex, or body weight as can be readily determined by a person skilled in the art. In some embodiments, the methods of the present invention comprise personalized medicine methods which treat the needs of a single patient. In one embodiment, different needs can be due to the particular disease, severity of the disease, the overall medical state of a patient, or the age of the patient. In some embodiments, personalized medicine is the application of genomic data to better target the delivery of medical interventions. Methods of personalized medicine, in some embodiments, serve as a tool in the discovery and clinical testing of new products of the present invention. In one embodiment, personalized medicine involves the application of clinically useful diagnostic tools that may help determine a patient's predisposition to a particular disease or condition. In some embodiments, personalized medicine is a comprehensive approach utilizing molecular analysis of both patients and healthy individuals to guide decisions throughout all stages of the discovery and development of pharmaceuticals and diagnostics; and applying this knowledge in clinical practice for a more efficient delivery of accurate and quality healthcare through improved prevention, diagnosis, treatment, and monitoring methods.

Oxidative damage can comprise damage to cells and tissue, caused by oxidation of various cellular products, which through the production of peroxides and free radicals damage components of the cell and tissue, for example, damaging cell integrity, cell membranes, DNA, etc.

In another embodiment, the invention provides a method of treating, preventing, inhibiting reducing the incidence of oxidative damage-related diseases, disorders or conditions in a subject, comprising administering a pharmaceutical composition comprising a of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of oxidative damage-related diseases in a subject.

In some embodiments, the oxidative damage-related diseases, disorders or conditions may comprise cancers; skin disorders; neurodegenerative diseases such as Alzheimer's disease, Parkinson's disease, Huntington's disease, multiple sclerosis, and amytrophic lateral sclerosis; vascular diseases such as stroke and various age-related dementias, and atherosclerosis; or age-related macular degeneration.

Inflammation is a common and potentially debilitating condition that occurs when the white blood cells and endogenous chemicals that can protect us from infection and foreign substances such as bacteria and viruses act on tissue surrounding a wound or infection. In some diseases, however, the body's defense system (immune system) triggers an inflammatory response when there are no foreign substances to fight off. In these diseases, called autoimmune diseases, the body's normally protective immune system causes damage to its own tissues. The body responds as if normal tissues are infected or somehow abnormal. Some, but not all types of arthritis are the result of misdirected inflammation. Arthritis is a general term that describes inflammation in joints and affects more than 2-4% of the world's population. There are many medications available to decrease swelling and inflammation and hopefully prevent or minimize the progression of the inflammatory disease. The medications include non-steroidal anti-inflammatory drugs (NSAIDs—such as aspirin, ibuprofen or naproxen), corticosteroids (such as prednisone), anti-malarial medications (such as hydroxychloroquine), and other medications including gold, methotrexate, sulfasalazine, penicillamine, cyclophosphamide and cyclosporine.

The role of estrogen receptor and its ligands as therapy for inflammation has been under consideration. The effects are regarded to be mediated by the isoform ER-β. Treatment of rats with estradiol or SERMs such as raloxifene and tamoxifen has been shown to reduce the incidence of lipo-polysachamide induced inflammatory responses. One of the pathways through which inflammatory responses are mediated is through the activation of NFκB pathway. Nuclear receptor ligands inhibit the NFκB activity through protein protein interaction. Recently it was shown that SERMs inhibit the inflammatory responses by inhibiting the NFκB function without having estrogenic effects on other reproductive tissues.

In one embodiment, the NRBA compounds as described herein are useful in treating inflammation and related disorders such as: a) prevention, treatment, or reversal of arthritis; b) prevention, treatment, or reversal of an arthritic condition such as Behcet's disease (autoimmune vasculitis), bursitis, calcium pyrophosphate dihydrate crystal (CPPD), deposition disease (or pseudogout), carpal tunnel syndrome, connective tissue disorders, Crohn's diseases, Ehlers-Danlos syndrome (EDS), fibromyalgia, gout, infectious arthritis, inflammatory bowel disease (IBD), juvenile arthritis, systemic lupus erythematosus (SLE), Lyme's disease, Marfan syndrome, myositis, osteoarthritis, polyarteritis nodosa, polymyalgia rheumatica, psoriasis, psoriatic arthritis, Raynaud's phenomenon, reflex sympathetic dystrophy syndrome, Reiter's syndrome, rheumatoid arthritis, scleroderma, Sjögrens' syndrome, tendonitis or ulcerative colitis; c) preventing, treatment, or reversing an autoimmune disease; d) chronic kidney disease (CKD).

In another embodiment, the invention provides a method of treating, preventing, inhibiting reducing the incidence of inflammatory diseases, disorders or conditions in a subject, comprising administering a pharmaceutical composition comprising a of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of inflammatory conditions in a subject. In some embodiments ER-β agonists are useful in treating, preventing, inhibiting reducing the incidence of inflammatory diseases, disorders or conditions in a subject. In another embodiment, ERβ agonist of this invention is compound 12b, listed in Table 1. In another embodiment, ER-β agonist of this invention is compound 12f, listed in Table 1. In another embodiment, ER-β agonist of this invention is compound 12h, listed in Table 1. In another embodiment, ER-β agonist of this invention is compound 12p, listed in Table 1. In another embodiment, ER-β agonist of this invention is compound 12s, listed in Table 1. In another embodiment, ER-β agonist of this invention is compound 12u, listed in Table 1. In another embodiment, ER-β agonist of this invention is compound 12z, listed in Table 1, or any combination thereof.

In some embodiments, ER-β agonists of this invention inhibit stroma-epithelial proliferation (FIG. 3, Example 4) which can affect the development of anatomic obstruction, which can reduce inflammation and thereby, treat inflammation. In one embodiment, ER-β agonists of this invention relax smooth muscle which can lower urine tract symptoms, affect the development of BPH, which can reduce inflammation and thereby, treat inflammation.

In some embodiments, the inflammatory diseases disorders or conditions which may comprise acute inflammation, arthropathies (in general), rheumatoid arthritis, systemic lupus erythema, asthma, acute inflammation, chronic inflammation, joint damage, joint swelling, joint erosion, sepsis, or any combination thereof.

In one embodiment, joint inflammation is one of the most common causes of pain, lameness, and loss of physical activity, not only in humans but in animals, particularly horses. This debilitating condition is marked by edema, redness, heat and pain. If left untreated, joint inflammation also can lead to destruction of the joint synovium and the articular cartilage producing a permanent debilitating condition. The edema, redness, and pain that occur during inflammation are the result of physiological changes in the joint. For example, the permeability of the synovial membrane increases during inflammation allowing synovial fluid to leak into the tissues of the joint. Alterations in blood flow and pressure in the vascular system of the joint also occur during inflammation. In addition, the metabolic activity of the cells of the joint increases during inflammation.

In another embodiment, the invention provides a method of treating, preventing, inhibiting reducing the incidence of joint inflammation in a subject, comprising administering a pharmaceutical composition comprising a NRBA of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof, thereby treating, preventing, inhibiting reducing the incidence of joint inflammation in a subject. In another embodiment, the NRBA is of formula 1-4, IV-IX or XI-XII.

In one embodiment, the NRBAs of this invention bind their cognate receptor at the cell surface, translocate to the cell's nucleus, and exerts their effects. In one embodiment, such effects may comprise, inter alia, regulation of particular gene expression, and may in turn play a role in the inhibition of apoptosis, activation of protein kinase pathways, and others.

In another embodiment, the NRBAs of this invention bind cognate receptors and translocate within the mitochondria, whereupon they associate with mitochondrial DNA, and in turn play a role in the increased respiratory chain activity, inhibition of TGFβ-induced apoptosis and/or activation of manganese superoxide dismutase, and others.

Superoxide dismutases (SODs) are key enzymes in the cellular defence against free radical oxidation. By catalyzing the degradation of the superoxide free radical to water and hydrogen peroxide, SODs, play an important role in reducing the damage associated with, for example ischemic injury, chronic lung disease, Alzheimer's disease, Down syndrome, inflammatory disorders, cardiovascular disease, immune-system decline, brain dysfunction, cataracts, and other aspects of aging and degenerative disease.

In one embodiment, this invention provides a method of treating, ameliorating and/or preventing reactive species-mediated damage in a subject, comprising the step of administering a NRBA of formula (I)-(XII) or its prodrug, analog, isomer, metabolite, derivative, pharmaceutically acceptable salt, pharmaceutical product, polymorph, crystal, impurity, N-oxide, ester, hydrate or any combination thereof to the subject. In one embodiment, the reactive species comprises reactive oxygen intermediates and the NRBA promotes or enhances the activity of cellular superoxide dismutase. In one embodiment, the reactive species comprises reactive nitrogen intermediates and the NRBA promotes or enhances the activity of cellular nitric oxide synthase.

In some embodiments, such damage is associated with a variety of diseases, such as, but not limited to cardiovascular disease, such as coronary heart disease and atherosclerosis, neurodegenerative disease, such as Alzheimer's disease and/or multiple sclerosis, infection, for example, HCV infection and complications thereof, autoimmune disease, such as lupus, cancer, and others, as appreciated by one skilled in the art.

In some embodiments, such activity results in suppression of pathogenic apoptosis, for example, as occurs in various disease states, such as neurodegenerative diseases or disorders, glaucoma, autoimmune disease, and others as will be appreciated by one skilled in the art.

In some embodiments, the compounds of this invention, characterized by the structures of formulae I-XII, and including any embodiment thereof, localize within the cytosol of a cell, or within cytosolic organelles, such as mitochondrion, wherein such compounds may affect cellular signaling pathways, and thereby effect the methods as described herein. For example, and in one embodiment, the compounds may interact with cellular proteins and thereby synergize a desired effect, in some embodiments, in signaling pathways within the cell, producing the desired effect. In other embodiments, the compounds of formulae I-XII antagonize a particular response or pathway in the cell, which otherwise produces an undesired effect, for example, exacerbating disease, and thus the compounds as described herein are effective in such methods by their ability to disrupt or interfere or antagonize pathogenic mechanisms in a cell or in a subject.

In some embodiments, the agents of this invention, may alter intracellar signaling pathways or responsiveness to such pathways or cascades.

In some embodiments, downstream effects of the compounds of this invention, characterized by the structures of formulae I-XII, and including any embodiment thereof, may be controlled by intracellular kinase signaling pathways activated by growth factors. In some embodiments, the compounds may affect signaling downstream of binding of a hormone to its receptor, for example, with the case of glycogen synthase kinase 3 (GSK3), an effector kinase of the phosphatidylinositol 3-kinase (PI3K) pathway, may be activated by administration of a compound of this invention and in turn affect ERalpha activity in specific cells, for example in neuroblastoma cells, and thereby effect some of the methods of this invention. In some embodiments, the compounds of this invention may result in greater expression of GSK3, which in turn stimulates or increases ER-dependent gene expression.

It is to be understood that any use of any of the compounds as herein described may be used in the treatment of any disease, disorder or condition as described herein, and represents an embodiment of this invention.

The following examples are presented in order to more fully illustrate the preferred embodiments of the invention. They should in no way, however, be construed as limiting the broad scope of the invention.

EXAMPLES

Example 1

Estrogen Receptor Binding Affinities, Agonist and Antagonist Activity of Some Embodiments of NRBAs of the Invention Materials and Methods ER binding affinity was determined via one of the following methods:
Method 1:
Human recombinant estrogen receptor (ER) was expressed in insect Sf9 cells and a radioactive competitive binding assay was performed using tritiated estradiol. If the NRBAs tested showed a ≥≥50% inhibition of [$^3$H] estradiol binding at 1 µM (1000 nM) concentration, the compounds were assayed using four concentrations to determine $IC_{50}$ and $K_i$ estimates.
Method 2:
Estrogen receptor (ER) binding affinity of the NRBAs was also determined using an in vitro competitive radioligand-binding assay with [$^3$H]-estradiol ([$^3$H]-$E_2$, PerkinElmer), a high affinity ligand for both ERα and ERβ. The equilibrium dissociation constant ($K_d$) of [$^3$H]-$E_2$ was determined by incubating increasing concentrations of [$^3$H]-$E_2$ (0.01 to 10 nM) with bacterially expressed ERα or β ligand binding domain (LBD) at 4° C. for 18 hours (h). Non-specific binding was determined by adding 1000 nM $E_2$ to the incubation mixture. It was determined that the minimum concentration of [$^3$H]-$E_2$ required to saturate ERα and ERβ binding sites in the incubation mixture was 1 nM, respectively. The binding affinity of the NRBAs was determined under identical conditions by incubating increasing concentrations ($3 \times 10^{-2}$ to 1,000 nM) of ligand with isolated ER LBD and 1 nM [$^3$H]-$E_2$. Following incubation, bound and free [$^3$H]-$E_2$ was separated by using vacuum filtration with the Harvester (PerkinElmer). Briefly, the incubation mixture was filtered through a high affinity protein binding filter, and washed several times to remove any unbound radioactivity. The filter plate was air dried and sealed on the bottom. Scintillation cocktail was added to each well and the top of the plate was sealed. Radioactivity was counted in a TopCount NXT Microplate Scintillation Counter.

Specific binding of [$^3$H]-$E_2$ (B) at each concentration of NRBA was obtained by subtracting the nonspecific binding of [$^3$H]-$E_2$, and expressed as a percentage of the specific binding of [$^3$H]-$E_2$ in the absence of the NRBA ($B_0$). The concentration of the NRBA that reduced the specific binding of [$^3$H]-$E_2$ by 50% ($IC_{50}$) was determined by computer-fitting the data by nonlinear regression analysis using SigmaPlot (SPSS Inc., Chicago, Ill.) to the following equation:

$$B = B_0[1 - C/(IC_{50} + C)]$$

where C is the concentration of SERM.

The equilibrium dissociation constant ($K_i$) of the NRBA was calculated by:

$$K_i = K_d * IC_{50}/(K_d + L)$$

where $K_d$ is the equilibrium dissociation constant of [$^3$H]-$E_2$ (ERα=0.65 µM, ERβ=1.83 nM), and L is the concentration of [$^3$H]-$E_2$ (1 nM).

Table 1 presents a series of NRBAs. Representative NRBAs are described hereinbelow, whose activity under specific experimental conditions is provided. It is to be understood that while the indicated compounds may exhibit a particular activity (for example, compound 12b is an agonist) under the experimental conditions employed, as a function, in some embodiments of the particular cells utilized, etc., such compounds may possess alternate or varied activity in different experimental settings. Representative examples of the NRBAs of this invention and their activity under the indicated conditions are as follows:

TABLE 1

| COMPOUND # and IUPAC NAME | PHYSICAL CHARACTERIZATION |
|---|---|
| Estradiol (E2) | |
| Propyl pyrazole triol (PPT) | |
| Dipropionitrile (DPN) | |
| 12a<br>6-hydroxy-2-(4-hydroxyphenyl)-isoquinolin-1(2H)-one | white solid. 67% yield. M.p. 312.3-313.4° C. $^1$H NMR (DMSO-$d_6$, 300 MHz) δ 10.30 (s, 1H), 9.77 (s, 1H), 8.08 (d, 1H, J = 8.7 Hz), 7.26 (d, 1H, J = 7.2 Hz), 7.20 (d, 2H, J = 8.7 Hz), 6.97 (dd, 1H, $J_1$ = 8.7 Hz, $J_2$ = 2.4 Hz), 6.93 (d, 1H, J = 2.4 Hz), 6.85 (d, 2H, J = 8.7 Hz), 6.49 (d, 1H, J = 7.5 Hz). MS m/z 276 (M + Na)$^+$. |
| 12b<br>4-bromo-6-hydroxy-2-(4-hydroxyphenyl)-isoquinolin-1(2H)-one; | white solid. 49% yield. M.p. 264.0-266.0° C. $^1$H NMR (DMSO-$d_6$, 300 MHz) δ 10.58 (s, 1H), 9.83 (s, 1H), 8.12 (d, 1H, J = 8.7 Hz), 7.71 (s, 1H), 7.22 (d, 2H, J = 8.7 Hz), 7.09 (d, 1H, J = 2.1 Hz), 7.04 (dd, 1H, $J_1$ = 8.7 Hz, $J_2$ = 2.4 Hz), 6.84 (d, 2H, J = 8.7 Hz). MS m/z 334 (M + H)$^+$. |
| 12c<br>4-bromo-2-(4-hydroxyphenyl)-6-methoxy-isoquinolin-1(2H)-one | white solid. 24% yield. M.p. 266.3-266.8° C. $^1$H NMR (DMSO-$d_6$, 300 MHz) δ 9.78 (s, 1H), 8.20 (d, 1H, J = 8.7 Hz), 7.79 (s, 1H), 7.25 (d, 2H, J = 9.0 Hz), 7.22 (dd, 1H, $J_1$ = 9.0 Hz, $J_2$ = 2.4 Hz), 6.85 (d, 2H, J = 8.7 Hz). MS m/z 345 (M + H)$^+$. |
| 12d<br>4-bromo-2-(3-fluoro-4-hydroxyphenyl)-6-hydroxy-isoquinolin-1(2H)-one | white solid. 79% yield. M.p. 254.3-254.6° C. $^1$H NMR (DMSO-$d_6$, 300 MHz) δ 10.74 (s, 1H), 10.20 (s, 1H), 8.13 (d, 1H, J = 8.7 Hz), 7.77 (s, 1H), 7.36 (dd, 1H, $J_1$ = 11.7 Hz, $J_2$ = 2.4 Hz), 7.11-6.99 (m, 4H). MS m/z 351 (M + H)$^+$. |
| 12e<br>4-bromo-2-(4-fluorophenyl)-6-hydroxy-isoquinolin-1(2H)-one | white solid. 83% yield. M.p. 250.4-250.9° C. $^1$H NMR (DMSO-$d_6$, 300 MHz) δ 10.76 (s, 1H), 8.14 (d, 1H, J = 8.7 Hz), 7.71 (s, 1H), 7.56-7.51 (m, 2H), 7.37-7.31 (m, 2H), 7.11 (d, 1H, J = 2.1 Hz), 7.06 (dd, 1H, $J_1$ = 8.7 Hz, $J_2$ = 2.4 Hz). MS m/z 336 (M + H)$^+$. |
| 12f<br>4-chloro-6-hydroxy-2-(4-hydroxyphenyl)-isoquinolin-1(2H)-one | white solid. 67% yield. M.p. 288.6-289.6° C. $^1$H NMR (DMSO-$d_6$, 300 MHz) δ 10.72 (s, 1H), 9.74 (s, 1H), 8.13 (d, 1H, J = 8.7 Hz), 7.67 (s, 1H), 7.23 (d, 2H, J = 8.7 Hz), 7.11 (d, 1H, J = 2.1 Hz), 7.06 (dd, 1H, $J_1$ = 8.7 Hz, $J_2$ = 2.1 Hz), 6.84 (d, 2H, J = 8.7 Hz). MS m/z 288 (M + H)$^+$. |
| 12g<br>4-chloro-2-(3-fluoro-4-hydroxyphenyl)-6-hydroxy- | white solid. 50% yield. M.p. 264.0-264.5° C. $^1$H NMR (DMSO-$d_6$, 300 MHz) δ 10.75 (s, 1H), 10.20 (s, 1H), 8.14 (d, 1H, J = 8.7 Hz), 7.71 (s, 1H), 7.36 (dd, 1H, $J_1$ = 12.0 Hz, $J_2$ = 2.4 Hz), 7.12-7.00 (m, 4H). MS m/z |

TABLE 1-continued

| COMPOUND # and IUPAC NAME | PHYSICAL CHARACTERIZATION |
| --- | --- |
| isoquinolin-1(2H)-one | 304 (M + H)+. |
| 12h<br>6-hydroxy-2-(4-hydroxyphenyl)-4-iodoisoquinolin-1(2H)-one | white solid. 80% yield. M.p. 249.3-249.8° C. $^1$H NMR (DMSO-$d_6$, 300 MHz) δ 10.66 (s, 1H), 9.73 (s, 1H), 8.08 (d, 1H, J = 8.4 Hz), 7.74 (s, 1H), 7.21 (d, 2H, J = 8.7 Hz), 7.02-6.98 (m, 2H), 6.84 (d, 2H, J = 8.7 Hz). MS m/z 378 (M − H)−. |
| 12i<br>4-bromo-6-hydroxy-2-(3-hydroxyphenyl)-isoquinolin-1(2H)-one | white solid. 84% yield. M.p. 274.2-274.8° C. $^1$H NMR (DMSO-$d_6$, 300 MHz) δ 10.74 (s, 1H), 9.80 (s, 1H), 8.14 (d, 1H, J = 8.7 Hz), 7.75 (s, 1H), 7.32-7.27 (m, 1H), 7.10 (d, 1H, J = 2.1 Hz), 7.05 (dd, 1H, $J_1$ = 8.7 Hz, $J_2$ = 2.4 Hz), 6.86-6.83 (m, 3H). MS m/z 332 (M − H)−. |
| 12j<br>8-hydroxy-2-(4-hydroxyphenyl)-6-methoxy-isoquinolin-1(2H)-one | white solid. 86% yield. M.p. 223.7-224.2° C. $^1$H NMR (DMSO-$d_6$, 300 MHz) δ 13.02 (s, 1H), 9.80 (s, 1H), 7.34 (d, 1H, J = 7.8 Hz), 7.25 (d, 2H, J = 8.7 Hz), 6.87 (d, 2H, J = 8.7 Hz), 6.68 (d, 1H, J = 2.4 Hz), 6.66 (d, 1H, J = 7.5 Hz), 6.44 (d, 1H, J = 2.1 Hz), 3.85 (s, 3H). MS m/z 282 (M − H)−. |
| 12k<br>5-bromo-8-Hydroxy-2-(4-hydroxyphenyl)-6-methoxy-isoquinolin-1(2H)-one | white solid. 89% yield. M.p. 254.7-255.2° C. $^1$H NMR (DMSO-$d_6$, 300 MHz) δ 13.35 (s, 1H), 9.83 (s, 1H), 7.50 (d, 1H, J = 7.8 Hz), 7.27 (d, 2H, J = 8.7 Hz), 6.88 (d, 2H, J = 8.7 Hz), 6.83 (d, 1H, J = 7.8 Hz), 6.75 (s, 1H), 3.96 (s, 3H). MS m/z 360 (M − H)−. |
| 12l<br>6,8-dihydroxy-2-(4-hydroxyphenyl)-isoquinolin-1(2H)-one | white solid. 42% yield. M.p. 322.9-323.5° C. $^1$H NMR (DMSO-$d_6$, 300 MHz) δ 13.98 (s, 1H), 10.40 (s, 1H), 9.78 (s, 1H), 7.27-7.21 (m, 3H), 6.86 (d, 2H, J = 8.7 Hz), 6.57 (d, 1H, J = 7.5 Hz), 6.43 (d, 1H, J = 2.4 Hz), 6.27 (d, 1H, J = 2.1 Hz). MS m/z 268 (M − H)−. |
| 12m<br>5-bromo-6,8-dihydroxy-2-(4-hydroxyphenyl)isoquinolin-1(2H)-one | white solid. 52.6% yield. $^1$H NMR (DMSO-$d_6$, 300 MHz) δ 13.17 (s, 1H), 11.34 (s, 1H), 9.83 (s, 1H), 7.46 (d, 1H, J = 7.5 Hz), 7.26 (d, 2H, J = 8.4 Hz), 6.87 (d, 2H, J = 8.4 Hz), 6.79 (d, 1H, J = 7.8 Hz), 6.51 (s, 1 Hz). MS m/e 347.5 (M − H)−. |
| 12n<br>2-(3-fluoro-4-hydroxyphenyl)-6-hydroxy-4-iodoisoquinolin-1(2H)-one | pale-yellow solid. 76.7% yield. $^1$H NMR (DMSO-$d_6$, 300 MHz) δ 10.69 (s, 1H), 10.20 (s, 1H), 8.18 (d, 1H, J = 8.7 Hz), 7.78 (s, 1H), 7.34 (dd, 1H, $J_1$ = 8.7 Hz, $J_2$ = 1.8 Hz), 7.07-6.99 (m, 4H). MS m/e 395.8 (M − H)−. |
| 12o<br>4-bromo-6-hydroxy-2-(4-hydroxy-3-methylphenyl)isoquinolin-1(2H)-one | Synthesized by a method similar to Example 14. white solid. 87.5% yield. M.p. 243.5-244.0° C. (decomposed). H NMR (DMSO-$d_6$, 300 MHz) δ 10.70 (s, 1H), 9.63 (s, 1H), 8.12 (d, 1H, J = 8.4 Hz), 7.70 (s, 1H), 7.13-7.02 (m, 4H), 6.85 (d, 1H, J = 8.4 Hz), 2.15 (s, 3H). MS m/e: 345.7 [M − H]−. |
| 12p<br>2-(4-hydroxyphenyl)-6,8-dihydroxy-isoquinoline-1(2H)-thione | yellow solid. 65.8% yield. M.p. 289.9-300.2° C. (decomposed). H NMR (DMSO-$d_6$, 300 MHz) δ 14.18 (s, 1H), 10.69 (s, 1H), 9.83 (s, 1H), 7.55 (d, 1H, J = 7.2 Hz), 7.13 (d, 2H, J = 8.7 Hz), 7.00 (d, 1H, J = 7.2 Hz), 6.87 (d, 2H, J = 8.7 Hz), 6.55 (d, 1H, J = 2.4 Hz), 6.42 (d, 1H, J = 2.7 Hz). |
| 12q<br>8-hydroxy-2-(4-hydroxyphenyl)-6-methoxy-1-oxo-1,2-dihydroisoquinoline-5-carbonitrile | white solid. 54.3% yield. M.p. 328.6-330.0° C. (decomposed). $^1$H NMR (DMSO-$d_6$, 300 MHz) δ 13.89 (s, 1H), 9.86 (s, 1H), 7.65 (d, 1H, J = 7.5 Hz), 7.29 (d, 2H, J = 8.7 Hz), 6.88 (d, 2H, J = 8.7 Hz), 6.79 (d, 1H, J = 7.8 Hz), 6.76 (s, 1H), 4.00 (s, 3H). |
| 12r<br>4-bromo-6-hydroxy-2-(4-hydroxyphenyl)isoquinoline-1(2H)-thione | yellow solid. 27.1% yield. M.p. 238.7-240.1° C. (decomposed). $^1$H NMR (DMSO-$d_6$, 300 MHz) δ 11.01 (s, 1H), 9.78 (s, 1H), 8.82 (d, 1H, J = 8.7 Hz), 8.05 (s, 1H), 7.20-7.16 (m, 4H), 6.85 (d, 2H, J = 8.7 Hz). |
| 12s<br>2-(3-fluoro-4-hydroxyphenyl)-6,8-dihydroxyisoquinolin-1(2H)-one | Synthesized by a method similar to Example 14. yellow solid. 21.2% yield. M.p. 316.8-318.2° C. (decomposed). MS: m/e 285.8 [M − H]−. $^1$H NMR (DMSO-$d_6$, 300 MHz) δ 12.87 (s, 1H), 10.33 (s, 2H), 7.39-7.34 (m, 1H), 7.28 (d, 1H, J = 7.2 Hz), 7.11-7.02 (m, 2H), 6.58 (d, 1H, J = 7.5 Hz), 6.44 (d, 1H, J = 2.1 Hz), 6.28 (d, 1H, J = 2.1 Hz). |
| 12t<br>2-(3-fluoro-4-hydroxyphenyl)-8-hydroxy-6-methoxyisoquinolin-1(2H)-one | Synthesized by a method similar to Example 14. white solid. 76.3% yield. M.p. 204.2-205.0° C. (decomposed). MS: m/z 324.2 [M + Na]+. $^1$H NMR (DMSO-$d_6$, 300 MHz) δ 12.91 (s, 1H), 10.27 (s, 1H), 7.41-7.35 (m, 2H), 7.13-7.03 (m, 2H), 6.69-6.65 (m, 2H), 6.44 (d, 1H, J = 2.4 Hz), 3.85 (s, 3H). |
| 12u<br>4-bromo-6,8-dihydroxy-2-(4-hydroxyphenyl)isoquinolin-1(2H)-one | white solid. 67.7% yield. $^1$H NMR (DMSO-$d_6$, 300 MHz) δ 13.12 (s, 1H), 10.76 (s, 1H), 9.81 (s, 1H), 7.75 (s, 1H), 7.27 (d, 2H, J = 8.7 Hz), 6.86 (d, 2H, J = 8.7 Hz), 6.61 (d, 1H, J = 2.1 Hz), 6.37 (d, 1H, J = 2.1 Hz). MS m/e 347.8 (M − H)−. |
| 12v<br>4-bromo-8-hydroxy-2-(4-hydroxyphenyl)-6-methoxyisoquinolin-1(2H)-one | . white solid. 27.7% yield. M.p. 248.6-245.0° C. (decomposed). MS: m/e 361.8 [M − H]−. $^1$H NMR (DMSO-$d_6$, 300 MHz) δ 13.20 (s, 1H), 9.83 (s, 1H), 7.82 (s, 1H), 7.29 (d, 2H, J = 8.7 Hz), 6.86 (d, 2H, J = 8.7 Hz), 6.66 (d, 1H, J = 2.1 Hz), 6.60 (d, 1H, J = 2.4 Hz), 3.90 (s, 3H). |
| 12y<br>4-chloro-6,8-dihydroxy-2-(4-hydroxyphenyl) isoquinolin-1(2H)-one | white solid. 49.4% yield. $^1$H NMR (DMSO-$d_6$, 300 MHz) δ 13.09 (s, 1H), 10.77 (s, 1H), 9.81 (s, 1H), 7.70 (s, 1H), 7.27 (d, 2H, J = 8.7 Hz), 6.85 (d, 2H, J = 8.7 Hz), 6.62 (d, 1H, J = 2.1 Hz), 6.38 (d, 1H, J = 2.1 Hz). MS m/e 301.8 (M − H)−. |
| 12z<br>4-bromo-6,8-dihydroxy-2-(3-fluoro-4-hydroxyphenyl)isoquinolin-1(2H)-one | white solid. 48.2% yield. $^1$H NMR (DMSO-$d_6$, 300 MHz) δ 13.02 (s, 1H), 10.78 (s, 1H), 10.27 (s, 1H), 7.79 (s, 1H), 7.41 (dd, 1H, $J_1$ = 11.7 Hz, $J_2$ = 2.4 Hz), 7.16-7.01 (m, 2H), 6.61 (d, 1H, J = 2.1 Hz), 6.38 (d, 1H, J = 2.1 Hz). MS m/e 363.9 (M − H)−. |
| 14a<br>4,5-dibromo-2-(3,5-dibromo-4-hydroxyphenyl)-6-hydroxyisoquinolin-1(2H)-one | white solid. 49.4% yield. MS: m/z 567.0 [M − H]−. $^1$H NMR (DMSO-$d_6$, 300 MHz) δ 11.49 (s, 1H), 10.30 (s, 1H), 8.22 (d, 1H, J = 8.7 Hz), 7.86 (s, 1H), 7.76 (s, 2H), 7.25 (d, 1H, J = 8.7 Hz). |

TABLE 1-continued

| COMPOUND # and IUPAC NAME | PHYSICAL CHARACTERIZATION |
|---|---|
| 14b<br>6,8-dihydroxy-2-(4-hydroxyphenyl)-5-(trifluoromethylsulfonyl)isoquinolin-1(2H)-one | white solid. 47.6% yield. Mp. 330.0-332.1° C. (decomposed). $^1$H NMR (DMSO-$d_6$, 300 MHz) δ 13.09 (s, 1H), 11.23 (s, 1H), 9.81 (s, 1H), 7.46 (d, 1H, J = 7.5 Hz), 7.25 (d, 2H, J = 8.7 Hz), 6.87 (d, 2H, J = 8.7 Hz), 6.79 (d, 1H, J = 7.5 Hz), 6.51 (s, 1H). |
| 14c<br>4-(1,2-dibromoethyl)-6-hydroxy-2-(4-hydroxyphenyl)isoquinolin-1(2H)-one | white solid. 10.5% yield. MS: m/z 277.8 [M − 2HBr]−. 1H NMR (DMSO-$d_6$, 300 MHz) δ 10.42 (s, 1H), 9.72 (s, 1H), 8.14 (d, 1H, J = 8.7 Hz), 7.34 (s, 1H), 7.24-7.21 (m, 3H), 7.00 (dd, 1H, $J_1$ = 8.7 Hz, $J_2$ = 2.4 Hz), 6.89 (d, 2H, J = 8.7 Hz), 4.66 (t, 1H, J = 5.7 Hz), 2.82 (d, 2H, J = 5.7 Hz). |
| 14d<br>6-methoxy-2-(4-methoxyphenyl)-1-oxo-1,2-dihydroisoquinolin-8-yl trifluoromethanesulfonate | white solid. 94.1% yield. MS: m/z 452.1 [M + Na]$^+$. $^1$H NMR (DMSO-$d_6$, 300 MHz) δ 7.52 (d, 1H, J = 7.2 Hz), 7.38 (d, 1H, J = 2.4 Hz), 7.34 (d, 2H, J = 9.0 Hz), 7.07 (d, 2H, J = 9.0 Hz), 7.02 (d, 1H, J = 1.8 Hz), 6.72 (d, 1H, J = 7.5 Hz), 3.94 (s, 3H), 3.82 (s, 3H). |
| 14e<br>4,5-dibromo-6,8-dihydroxy-2-(4-hydroxyphenyl)isoquinolin-1(2H)-one | white solid. 45.6% yield. MS: m/z 428.0 [M + H]$^+$. $^1$H NMR (DMSO-$d_6$, 300 MHz) δ 14.06 (s, 1H), 11.64 (s, 1H), 9.83 (s, 1H), 7.83 (s, 1H), 7.28 (d, 2H, J = 8.7 Hz), 6.87 (d, 2H, J = 8.7 Hz), 6.86 (s, 1H). |
| 14f<br>6-hydroxy-2-(4-hydroxyphenyl)-4-vinylisoquinolin-1(2H)-one | white solid. 87.0% yield. MS: m/z 280.0 [M + H]$^+$. $^1$H NMR (DMSO-$d_6$, 300 MHz) δ 10.43 (s, 1H), 9.71 (s, 1H), 8.13 (d, 1H, J = 8.7 Hz), 7.41 (s, 1H), 7.24 (d, 2H, J = 8.7 Hz), 7.10 (d, 1H, J = 2.1 Hz), 7.01 (dd, 1H, $J_1$ = 8.7 Hz, $J_2$ = 2.1 Hz), 6.88 (dd, 1H, $J_1$ = 17.4 Hz, $J_2$ = 10.8 Hz), 6.85 (d, 2H, J = 8.7 Hz), 5.64 (dd, 1H, $J_1$ = 17.4 Hz, $J_2$ = 1.2 Hz), 5.26 (dd, 1H, $J_1$ = 10.8 Hz, $J_2$ = 1.2 Hz). |
| 14g<br>6-methoxy-2-(4-methoxyphenyl)-1-oxo-1,2-dihydroisoquinoline-4-carbonitrile | white solid. 92.6% yield. MS: m/z 307.0 [M + H]$^+$. $^1$H NMR (DMSO-$d_6$, 300 MHz) δ 8.41 (s, 1H), 8.22 (d, 1H, J = 9.0 Hz), 7.43 (d, 2H, J = 8.7 Hz), 7.27 (dd, 1H, $J_1$ = 8.7 Hz, $J_2$ = 2.4 Hz), 7.08 (d, 1H, J = 2.4 Hz), 7.06 (d, 2H, J = 8.7 Hz), 3.97 (s, 3H), 3.82 (s, 3H). |
| 14h<br>6-hydroxy-2-(4-hydroxyphenyl)-1-oxo-1,2-dihydroisoquinoline-4-carbonitrile | White solid. 68.5% yield. MS: m/z 279.0 [M + H]$^+$. $^1$H NMR (DMSO-$d_6$, 300 MHz) δ 10.86 (s, 1H), 9.80 (s, 1H), 8.38 (s, 1H), 8.13 (d, 1H, J = 8.7 Hz), 7.25 (d, 2H, J = 8.7 Hz), 7.09 (dd, 1H, $J_1$ = 8.7 Hz, $J_2$ = 2.4 Hz), 7.04 (d, 1H, J = 2.4 Hz), 6.85 (d, 2H, J = 8.7 Hz). |
| 14i<br>6-methoxy-2-(4-methoxyphenyl)-1-oxo-1,2-dihydroisoquinoline-8-carbonitrile | white solid. 75.2% yield. MS: m/z 307.2 [M + H]$^+$. $^1$H NMR (DMSO-$d_6$, 300 MHz) δ 7.63 (d, 1H, J = 2.1 Hz), 7.54 (d, 1H, J = 2.1 Hz), 7.51 (d, 1H, J = 7.5 Hz), 7.38 (d, 2H, J = 8.7 Hz), 7.06 (d, 2H, J = 8.7 Hz), 6.71 (d, 1H, J = 7.5 Hz), 3.95 (s, 3H), 3.82 (s, 3H). |
| 14j<br>4-bromo-6-methoxy-2-(4-methoxyphenyl)-1-oxo-1,2-dihydroisoquinoline-8-carbonitrile | white solid. 83.3% yield. MS: m/z 387.1 [M + H]$^+$. $^1$H NMR (DMSO-$d_6$, 300 MHz) δ 8.01 (s, 1H), 7.81 (d, 1H, J = 2.4 Hz), 7.43 (d, 1H, J = 2.4 Hz), 7.42 (d, 2H, J = 8.7 Hz), 7.07 (d, 2H, J = 8.7 Hz), 4.02 (s, 3H), 3.82 (s, 3H). |
| 14k<br>4-bromo-6-hydroxy-2-(4-hydroxyphenyl)-1-oxo-1,2-dihydroisoquinoline-8-carbonitrile | pale-yellow solid. 36.0% yield. MS: m/z 357.1 [M + H]$^+$. $^1$H NMR (DMSO-$d_6$, 300 MHz) δ 11.40 (s, 1H), 9.79 (s, 1H), 7.91 (s, 1H), 7.48 (d, 1H, J = 2.1 Hz), 7.38 (d, 1H, J = 2.1 Hz), 7.26 (d, 2H, J = 8.7 Hz), 6.86 (d, 2H, J = 8.7 Hz). |
| 14l<br>6,8-dihydroxy-2-(4-hydroxyphenyl)-4-vinylisoquinolin-1(2H)-one | pale-yellow solid. 75.3% yield. MS: m/e 293.9 [M − H]$^-$. $^1$H NMR (DMSO-$d_6$, 300 MHz) δ 13.22 (s, 1H), 10.48 (s, 1H), 9.79 (s, 1H), 7.38 (s, 1H), 7.28 (d, 2H, J = 8.7 Hz), 6.87 (d, 2H, J = 8.7 Hz), 6.81 (dd, 1H, $J_1$ = 17.1 Hz, $J_2$ = 10.8 Hz), 6.57 (d, 1H, J = 2.1 Hz), 6.33 (d, 1H, J = 2.1 Hz), 5.66 (dd, 1H, $J_1$ = 17.1 Hz, $J_2$ = 1.2 Hz), 5.30 (dd, 1H, $J_1$ = 10.8 Hz, $J_2$ = 1.2 Hz). |
| 14m<br>6,8-dihydroxy-2-(4-hydroxyphenyl)-1-oxo-1,2-dihydroisoquinoline-4-carbonitrile | pale-yellow solid. 72.7% yield. MS: m/z 307.0 [M + Na]$^+$. $^1$H NMR (DMSO-$d_6$, 300 MHz) δ 12.43 (s, 1H), 10.92 (s, 1H), 9.86 (s, 1H), 8.37 (s, 1H), 7.29 (d, 2H, J = 8.7 Hz), 6.86 (d, 2H, J = 8.7 Hz), 6.57 (d, 1H, J = 2.1 Hz), 6.40 (d, 1H, J = 2.1 Hz). |
| 14n<br>6-hydroxy-2-(4-hydroxyphenyl)-1-oxo-1,2-dihydroisoquinoline-8-carbonitrile | white solid. 46.1% yield. MS: m/z 279.0 [M + H]$^+$. $^1$H NMR (DMSO-$d_6$, 300 MHz) δ 11.04 (s, 1H), 9.75 (s, 1H), 7.43 (d, 1H, J = 7.2 Hz), 7.37 (d, 1H, J = 2.1 Hz), 7.23 (d, 2H, J = 8.7 Hz), 7.24 (s, 1H), 6.86 (d, 2H, J = 8.7 Hz), 6.62 (d, 1H, J = 7.5 Hz). |
| 14o<br>6-hydroxy-2-(4-hydroxyphenyl)-1-oxo-4-vinyl-1,2-dihydroisoquinoline-8-carbonitrile | yellow solid. 78.1% yield. MS: m/z 305.0 [M + H]$^+$. $^1$H NMR (DMSO-$d_6$, 300 MHz) δ 11.12 (s, 1H), 9.76 (s, 1H), 7.54 (s, 1H), 7.43 (d, 1H, J = 2.4 Hz), 7.37 (d, 1H, J = 2.4 Hz), 7.27 (d, 2H, J = 8.7 Hz), 6.94-6.84 (m, 3H), 5.68 (dd, 1H, $J_1$ = 17.1 Hz, $J_2$ = 1.2 Hz), 5.31 (dd, 1H, $J_1$ = 11.1 Hz, $J_2$ = 1.2 Hz). |
| 14p<br>4-chloro-6-hydroxy-2-(4-hydroxyphenyl)-1-oxo-1,2-dihydroisoquinoline-8-carbonitrile | yellow solid. 54.5% yield. (MS: m/z 318.8 [M − H]$^-$. $^1$H NMR (DMSO-$d_6$, 300 MHz) δ 11.42 (s, 1H), 9.79 (s, 1H), 7.86 (s, 1H), 7.50 (d, 1H, J = 2.1 Hz), 7.39 (d, 1H, J = 2.1 Hz), 7.26 (d, 2H, J = 8.7 Hz), 6.86 (d, 2H, J = 8.7 Hz). |
| 14q<br>4-bromo-6-methoxy-2-(4-methoxyphenyl)isoquinolin-1(2H)-one | white solid. 85.9% yield. Mp. 153.8-154.3° C. MS: 360.4 [M + H]+. $^1$H NMR (DMSO-d6, 300 MHz): δ 8.14 (d, 1H, J = 8.7 Hz), 7.39-7.34 (m, 3H), 7.19 (d, 1H, J = 2.4 Hz), 7.13-7.03 (m, 3H), 6.62 (dd, 1H, J = 7.5 Hz), 3.89 (s, 3H), 3.81 (s, 3H). |
| 14r<br>6-methoxy-2-(4-methoxyphenyl)-1-oxo-1,2-dihydroisoquinoline-4-carbonitrile | white solid. 92.6% yield. Mp. 204.8° C. (decomposed). MS: m/z 307.0 [M + H]+. $^1$H NMR (DMSO-d6, 300 MHz) δ 8.48 (s, 1H), 8.22 (d, 1H, J = 9.0 Hz), 7.43 (d, 2H, J = 8.7 Hz), 7.27 (dd, 1H, $J_1$ = 8.7 Hz, $J_2$ = 2.4 Hz), 7.08 (d, 1H, J = 2.4 Hz), 7.06 (d, 2H, J = 8.7 Hz), 3.97 (s, 3H), 3.82 (s, 3H). |
| 14s<br>8-hydroxy-6-methoxy-2-(4-methoxyphenyl)isoquinolin-1(2H)-one | white solid. 83.7% yield. Mp. 154.5-155.0° C. $^1$H NMR (DMSO-d6, 300 MHz): δ 12.98 (s, 1H), 7.42-7.35 (m, 3H), 7.06 (d, 2H, J = 9.0 Hz), 6.70-6.67 (m, 2H), 6.45 (d, 1H, J = 2.1 Hz), 3.85 (s, 3H), 3.82 (s, 3H). |

TABLE 1-continued

| COMPOUND # and IUPAC NAME | PHYSICAL CHARACTERIZATION |
| --- | --- |
| 14t<br>4-chloro-6-methoxy-2-(4-methoxyphenyl)-1-oxo-1,2-dihydroisoquinolin-8-yl trifluoromethanesulfonate | white solid. 78.7% yield. MS: m/z 464.0 [M + H]+. 1H NMR (DMSO-d6, 300 MHz) δ 7.97 (s, 1H), 7.39 (d, 2H, J = 9.0 Hz), 7.33 (d, 1H, J = 2.4 Hz), 7.21 (s, 1H), 7.07 (d, 2H, J = 9.0 Hz), 4.02 (s, 3H), 3.82 (s, 3H). |
| 14u<br>4-chloro-6-methoxy-2-(4-methoxyphenyl)-1-oxo-1,2-dihydroisoquinoline-8-carbonitrile | white solid. 69.7% yield. MS: m/z 341.2 [M + H]+. $^1$H NMR (DMSO-d6, 300 MHz) δ 7.95 (s, 1H), 7.80 (d, 1H, J = 2.5 Hz), 7.46 (d, 1H, J = 2.5 Hz), 7.42 (d, 2H, J = 8.5 Hz), 7.07 (d, 2H, J = 8.5 Hz), 4.02 (s, 3H), 3.83 (s, 3H). |
| 14v<br>isoquinoline-1,6-diol | white solid (mp decomposed). Yield = 87%; MS (ESI) m/z 161.9 [M + H]$^+$, 184.0 [M + Na]$^+$; $^1$H NMR (DMSO-d$_6$, 300 MHz): δ 10.90 (bs, 1H), 10.21 (s, 1H), 8.01 (d, J = 8.7 Hz, 1H), 7.05 (dd, J = 6.9, 5.7 Hz, 1H), 6.89 (m, 2H), 6.35 (d, J = 7.2 Hz, 1H). |
| 14w<br>6-hydroxy-2-(4-methoxyphenyl)isoquinolin-1(2H)-one | brown solid (mp decomposed). Yield = 32%; MS (ESI) m/z 268.0 [M + H]$^+$, 290.0 [M + Na]$^+$; $^1$H NMR (DMSO-d$_6$, 300 MHz): δ 10.35 (s, 1H), 8.07 (d, J = 8.7 Hz, 1H), 7.33 (m, 3H), 7.06-6.92 (m, 4H), 6.52 (d, J = 7.5 Hz, 1H), 3.81 (s, 3H). |
| 14xME<br>4-bromo-6-hydroxy-2-(4-methoxyphenyl)isoquinolin-1(2H)-one | white solid (mp decomposed)Yield = 42%; MS (ESI) m/z 345.8 [M − H]$^−$; $^1$H NMR (CDCl$_3$, 500 MHz): δ 10.72 (s, 1H), 8.14 (d, J = 5.4 Hz, 1H), 7.53 (s, 1H), 7.38 (d, J = 5.4 Hz, 2H), 7.10 (d, J = 1.2 Hz, 1H), 7.06 (m, 1H), 7.04 (d, J = 5.4 Hz, 2H), 3.81 (s, 3H). |
| 14xAC<br>4-(6-acetoxy-4-bromo-1-oxoisoquinolin-2(1H)-yl)phenyl acetate | white solid (mp: 200-201° C.)Yield = 86%; MS (ESI) m/z 440.1 [M + Na]$^+$; $^1$H NMR (CDCl$_3$, 300 MHz): δ 8.52 (d, J = 8.7 Hz, 1H), 7.61 (d, J = 2.1 Hz, 1H), 7.52 (s, 1H), 7.45 (d, J = 8.7 Hz, 2H), 7.33 (dd, J = 8.7, 2.1 Hz, 1H), 7.25 (d, J = 8.7 Hz, 2H), 2.40 (s, 3H), 2.25 (s, 3H). Mass (ESI, positive) m/z 440.1 [M + Na]$^+$ |
| 14xME_AC<br>4-(4-bromo-6-methoxy-1-oxoisoquinolin-2(1H)-yl)phenyl acetate | white solid (mp; 189-190° C.). Yield = 87%; MS (ESI) m/z 389.0 [M + H]$^+$, 412.1 [M + Na]$^+$; $^1$H NMR CDCl$_3$, 300 MHz): δ 8.42 (d, J = 9.0 Hz, 1H), 7.50 (s, 1H), 7.46 (d, J = 8.7 Hz, 2H), 7.25 (d, J = 8.7 Hz, 2H), 7.24 (d, J = 2.4 Hz, 1H), 7.15 (dd, J = 9.0, 2.4 Hz, 1H), 4.00 (s, 3H), 2.36 (s, 3H). |
| 14yAM<br>4-bromo-6-hydroxy-2-(4-hydroxyphenyl)-1-oxo-1,2-dihydroisoquinoline-8-carbimidic acid | off-white solid. mp >300° C. Mass (ESI, positive) m/z 397.0 [M + Na]$^+$; $^1$H NMR (300 MHz, DMSO-d$_3$) δ 10.84 (s, 1H, OH), 9.74 (s, 1H, OH), 7.77 (s, 1H, ArH), 7.41 (s, 1H, OH or NH), 7.20-7.17 (m, 2H, ArH), 7.13 (s, 1H, OH or NH), 7.11 (d, J = 2.4 Hz, 1H, ArH), 6.86-6.83 (m, 2H, ArH), 6.80 (d, J = 2.4 Hz, 1H, ArH)., 2H, ArH), 6.80 (d, J = 2.4 Hz, 1H, ArH). |
| 14yME<br>methyl 4-bromo-6-hydroxy-2-(4-hydroxyphenyl)-1-oxo-1,2-dihydroisoquinoline-8-carboxylate | white solid. mp 296° C. (decomposition); Mass (ESI, positive) m/z 390.2 [M + H]$^+$; Mass (ESI, negative) m/z 387.8 [M − H]$^−$; $^1$H NMR (300 MHz, DMSO-d$_3$) δ 11.10 (s, 1H, OH), 9.76 (s, 1H, OH), 7.81 (s, 1H, ArH), 7.27-7.19 (m, 2H, ArH), 7.20 (d, J = 2.4 Hz, 1H, ArH), 6.93 (d, J = 2.4 Hz, 1H, ArH), 6.87-6.83 (m, 2H, ArH), 3.72 (s, 3H, OCH$_3$). |
| 14z<br>4-bromo-6-hydroxy-2-(4-hydroxyphenyl)-1-oxo-1,2-dihydroisoquinoline-8-carboxylic acid | |
| 15a<br>6-hydroxy-2-(4-hydroxyphenyl)-4-phenylisoquinolin-1(2H)-one | white solid. 87.9% yield. M.p. 296.9-297.5° C. MS: 330.2 [M + H]$^+$. $^1$H NMR (DMSO-d$_6$, 300 MHz): δ 10.31 (s, 1H), 9.69 (s, 1H), 8.19 (d, 1H, J = 8.7 Hz), 7.52-7.39 (m, 5H), 7.28 (d, 2H, J = 8.7 Hz), 7.18 (s. 1H), 7.00 (dd, 1H, J$_1$ = 8.7 Hz, J$_2$ = 2.4 Hz), 6.87-6.82 (m, 3H). |
| 15b<br>6-hydroxy-2-(4-hydroxyphenyl)-4-(4-methoxyphenyl)isoquinolin-1(2H)-one: | white solid. 72.5% yield. M.p. 295.1-296.0° C. MS: 360.1 [M + H]$^+$. $^1$H NMR (DMSO-d$_6$, 300 MHz): δ 10.28 (s, 1H), 9.68 (s, 1H), 8.18 (d, 1H, J = 8.7 Hz), 7.38 (d, 2H, J = 9.0 Hz), 7.27 (d, 2H, J = 8.7 Hz), 7.13 (s, 1H), 7.04 (d, 2H, J = 8.7 Hz), 6.99 (dd, 1H, J$_1$ = 8.7 Hz, J$_2$ = 2.4 Hz), 6.87-6.82 (m, 3H), 3.81 (s, 3H). |
| 15c<br>2-(3-fluoro-4-hydroxyphenyl)-6,8-dihydroxy-4-vinylisoquinolin-1(2H)-one | white solid. 67.6% yield. M.p. 221.9-223.0° C. MS: 311.9 [M − H]$^−$. $^1$H NMR (DMSO-d$_6$, 300 MHz) δ 13.12 (s, 1H), 10.51 (s, 1H), 10.24 (s, 1H), 7.44-7.40 (m, 2H), 7.17-7.03 (m, 2H), 6.80 (dd, 1H, J$_1$ = 17.1 Hz, J$_2$ = 10.8 Hz), 6.57 (d, 1H, J = 2.1 Hz), 6.34 (d, 1H, J = 2.1 Hz), 5.67 (dd, 1H, J$_1$ = 17.1 Hz, J$_2$ = 1.2 Hz), 5.30 (dd, 1H, J$_1$ = 10.8 Hz, J$_2$ = 1.2 Hz). |
| 15d<br>2-(3-fluoro-4-hydroxyphenyl)-6,8-dihydroxy-1-oxo-1,2-dihydroisoquinoline-4-carbonitrile | white solid. 63.4% yield. M.p. 280.8-282.0° C. MS: 310.9 [M − H]$^−$. $^1$H NMR (DMSO-d$_6$, 300 MHz) δ 12.35 (s, 1H), 10.94 (s, 1H), 10.33 (s, 1H), 8.39 (s, 1H), 7.44 (dd, 1H, J$_1$ = 11.7 Hz, J$_2$ = 2.4 Hz), 7.18-7.03 (m, 2H), 6.57 (d, 1H, J = 2.1 Hz), 6.41 (d, 1H, J = 2.1 Hz). |
| 15e<br>6-hydroxy-2-(4-hydroxyphenyl)-8-vinylisoquinolin-1(2H)-one | white solid. 36.5% yield. M.p. >240.0° C. (decomposed). MS: 277.9 [M − H]$^−$. $^1$H NMR (DMSO-d$_6$, 300 MHz) δ 10.33 (s, 1H), 9.66 (s, 1H), 7.79 (dd, 1H, J$_1$ = 17.4 Hz, J$_2$ = 10.8 Hz), 7.25 (d, 1H, J = 7.5 Hz), 7.15 (d, 2H, J = 8.7 Hz), 6.97 (d, 1H, J = 2.1 Hz), 6.88 (d, 1H, J = 2.1 Hz), 6.83 (d, 2H, J = 8.7 Hz), 6.46 (d, 1H, J = 7.5 Hz), 5.44 (dd, 1H, J$_1$ = 17.4 Hz, J$_2$ = 1.8 Hz), 5.19 (dd, 1H, J$_1$ = 10.8 Hz, J$_2$ = 1.8 Hz). |
| 15f<br>4-bromo-6-hydroxy-2-(4-hydroxyphenyl)-8-vinylisoquinolin-1(2H)-one | white solid. 54.5% yield. M.p. >188.0° C. (decomposed). MS: 355.9 [M − H]$^−$. $^1$H NMR (DMSO-d$_6$, 300 MHz) δ 10.71 (s, 1H), 9.71 (s, 1H), 7.89 (dd, 1H, J$_1$ = 17.4 Hz, J$_2$ = 10.5 Hz), 7.72 (s, 1H), 7.19 (d, 2H, J = 8.7 Hz), 7.12 (d, 1H, J = 2.4 Hz), 7.03 (d, 1H, J = 2.4 Hz), 6.83 (d, 2H, J = 8.7 Hz), 5.47 (dd, 1H, J$_1$ = 10.5 Hz, J$_2$ = 1.5 Hz). |
| 15g<br>6,8-dihydroxy-2-(4-hydroxyphenyl)-4-(4- | white solid. 83.3% yield. M.p. 141.3-142.0° C. MS: 373.9 [M − H]$^−$. $^1$H NMR (DMSO-d$_6$, 300 MHz): δ 10.32 (s, 1H), 10.33 (s, 1H), 9.76 (s, 1H), 7.36 (d, 2H, J = 8.7 Hz), 7.30 (d, 2H, J = 8.7 Hz), 7.11 (s, 1H), 7.04 (d, |

TABLE 1-continued

| COMPOUND # and IUPAC NAME | PHYSICAL CHARACTERIZATION |
|---|---|
| methoxyphenyl)isoquinolin-1(2H)-one | 2H, J = 8.7 Hz), 6.86 (d, 2H, J = 8.7 Hz), 6.32 (d, 1H, J = 2.1 Hz), 6.30 (d, 1H, J = 2.1 Hz), 3.80 (s, 3H). |
| 15h<br>6,8-dihydroxy-2-(4-hydroxyphenyl)-4-phenylisoquinolin-1(2H)-one | white solid. 89.9% yield. M.p. 133.2-134.0° C. MS: 343.9 [M − H]$^-$. $^1$H NMR (DMSO-d$_6$, 300 MHz): δ 10.30 (s, 1H), 10.35 (s, 1H), 9.76 (s, 1H), 7.52-7.39 (m, 5H), 7.31 (d, 2H, J = 8.7 Hz), 7.16 (s, 1H), 6.86 (d, 2H, J = 8.7 Hz), 6.32 (d, 1H, J = 2.1 Hz), 6.31 (d, 1H, J = 2.1 Hz). |
| 15i<br>(E)-6,8-dihydroxy-2-(4-hydroxyphenyl)-4-(prop-1-enyl)isoquinolin-1(2H)-one | white solid. 78.7% yield. M.p. 206.9-207.0° C. MS: 310.0 [M + H]$^+$. $^1$H NMR (DMSO-d$_6$, 300 MHz) δ 13.26 (s, 1H), 10.42 (s, 1H), 9.77 (s, 1H), 7.26 (d, 2H, J = 8.5 Hz), 7.24 (s, 1H), 6.86 (d, 2H, J = 8.5 Hz), 6.55 (d, 1H, J = 2.0 Hz), 6.45 (d, 1H, J = 15.0 Hz), 6.31 (d, 1H, J = 2.0 Hz), 6.10-6.03 (m, 1H), 1.83 (d, 3H, J = 6.5 Hz). |
| 15j<br>(E)-ethyl 3-(8-hydroxy-6-methoxy-2-(4-methoxyphenyl)-1-oxo-1,2-dihydroisoquinolin-4-yl)acrylate | white solid. 76.4% yield. M.p. 160.2-160.7° C. MS: 396.1 [M + H]$^+$. $^1$H NMR (DMSO-d$_6$, 300 MHz) δ 13.09 (s, 1H), 7.97 (s, 1H), 7.85 (d, 1H, J = 15.9 Hz), 7.46 (d, 2H, J = 8.7 Hz), 7.07 (d, 2H, J = 8.7 Hz), 6.74 (d, 1H, J = 2.4 Hz), 6.60 (d, 1H, J = 11.4 Hz), 6.56 (d, 1H, J = 2.1 Hz), 4.18 (q, 2H, J 7.2 Hz), 3.91 (s, 3H), 3.83 (s, 3H), 1.25 (t, 3H, J = 7.2 Hz). |
| 15k<br>(E)-3-(6-hydroxy-2-(4-hydroxyphenyl)-1-oxo-1,2-dihydroisoquinolin-4-yl)acrylic acid | yellow solid. 74.9% yield. M.p. >350.0° C. MS: 321.9 [M − H]$^-$. $^1$H NMR (DMSO-d$_6$, 300 MHz) δ 8.11 (d, 1H, J = 9.0 Hz), 7.66 (d, 1H, J = 15.5 Hz), 7.65 (s, 1H), 7.31 (s, 1H), 7.24 (d, 2H, J = 9.0 Hz), 6.98 (d, 1H, J = 8.5 Hz), 6.85 (d, 2H, J = 8.5 Hz), 6.36 (d, 1H, J = 16.0 Hz). |
| 15l<br>(E)-3-(6,8-dihydroxy-2-(4-hydroxyphenyl)-1-oxo-1,2-dihydroisoquinolin-4-yl)acrylic acid | yellow solid. 33.3% yield.. M.p. >350.0° C. MS: 337.9 [M − H]$^-$. $^1$H NMR (DMSO-d$_6$, 300 MHz) δ 13.09 (s, 1H), 9.86 (s, 1H), 8.59 (s, 1H), 7.73 (s, 1H), 7.60 (d, 1H, J = 15.9 Hz), 7.29 (d, 2H, J = 9.0 Hz), 6.87 (d, 2H, J = 8.7 Hz), 6.70 (d, 1H, J = 2.1 Hz), 6.40 (d, 1H, J = 15.6 Hz), 6.34 (d, 1H, J = 2.1 Hz). |
| 15m<br>4-chloro-6-methoxy-2-(4-methoxyphenyl)-1-oxo-1,2-dihydroisoquinolin-8-yl 4-(trifluoromethyl)benzoate | white solid. 94.9% yield.. M.p. 195.4-196.0° C. MS: 526.2 [M + Na]$^+$. $^1$H NMR (DMSO-d$_6$, 300 MHz) δ 8.26 (d, 2H, J = 8.1 Hz), 7.94 (d, 2H, J = 8.4 Hz), 7.85 (d, 2H, J = 9.0 Hz), 7.23 (d, 1H, J = 2.4 Hz), 7.21 (d, 1H, J = 2.4 Hz), 6.97 (d, 2H, J = 9.0 Hz), 3.99 (s, 3H), 3.76 (s, 3H). |

Table 2 presents competitive inhibition of the respective estrogen receptors by some embodiments of NRBAs of the invention. Recombinant ERα or ERβ ligand binding domain was incubated with [$^3$H]-estradiol and increasing concentration of some embodiments of the NRBAs of this invention, ranging in concentration from $10^{-11}$ to $10^{-4}$ M. Following incubation, plates were harvested onto GF/B filters and radioactivity was measured with a TopCount NXT (PerkinElmer). Nonspecific binding was subtracted from total binding to yield specific binding. The percent inhibition of [$^3$H]-estradiol at 100 nM of compound is as follows:

TABLE 2

Percent Inhibition of [$^3$H]-Estradiol Binding to ERα and ERβ by NRBAs

| Compound | ER-α | ER-β |
|---|---|---|
| 12b | 0 | 53.6 |
| 12d | 0 | 38.7 |
| 12f | 0 | 47.5 |
| 12g | 0 | 29.4 |
| 12h | 7.7 | 40.5 |
| 12l | 2.5 | 34.4 |
| 12m | 5.2 | 0 |
| 12n | 6.2 | 8.7 |
| 12p | 25.8 | 80.7 |
| 12r | 35.7 | 75.5 |
| 12s | 4.5 | 52.8 |
| 12u | 61.3 | 96.7 |
| 12y | 51.9 | 97.5 |
| 12z | 52.8 | 95.3 |

| Compound | ER-α binding constant (nM) | ER-β binding constant (nM) |
|---|---|---|
| 12b | 998 | 49 |
| 12u | 32 | 3 |
| 12z | 40 | 3 |
| 14l | 76 | 6 |
| 14m | 94 | 7 |
| 14k | >394 | 46 |

The NRBAs of Table 3 inhibited Cyp 3A and/or Cyp 2C9 at very low concentrations, with the exception of 12b [data not shown].

Example 2

Effects of NRBA on ER-α and ER-β Transactivation

COS or 293 cells were plated in DME without phenol red+10% cs FBS at 90,000 cells per well in 24 well plates, and were transfected with 0.25 μg of the vector "ERE-LUC", where a firefly luciferase gene was driven by two estrogen responsive elements and 0.02 μg of the control CMV-LUC, Renilla where a luciferase gene was driven by a CMV promoter. Also 25 ng of ER-α), 50 ng of ER-β or 12.5 ng of AR were introduced by lipofectamine. All the receptors were cloned from rat tissue into the PCR3.1 vector backbone. Twenty four hours post transfection, cells were treated with compounds of this invention, estrogen, DHT, and other NRBAs or combinations thereof. Cells were harvested 48 hrs after transfection, and assayed for firefly and Renilla luciferase activity.

Representative examples of the NRBAs of this invention and their activity under the indicated conditions were as follows ER-α agonists: 12y (ER-α: $K_i$=36 nM; 12u (ER-α: $K_i$=32 nM;
% activity of 100 nM 12u compared to 1 nM estradiol=62%).
ER-β agonists: 12b (ER-β: $K_i$=49 nM; % activity of 100 nM 12b compared to 1 nM estradiol=79%), 12p (ER-β: $K_i$=17 nM; % activity of 100 nM 12p compared to 1 nM estradiol=85%).

Representative Table 4 below has the % estradiol activity at 100 nM of NRBA for representative examples of the NRBAs of this invention and their % estradiol activity at 100 nM.

| Compound | ER-α | ER-β |
|---|---|---|
| 12b | 31.2 | 78.8 |
| 12p | 45 | 85 |
| 12q | 25 | 10 |
| 12s | 29 | 76.9 |
| 12u | 62 | 85 |
| 12v | 17 | 10 |
| 14l | 50 | 52.7 |
| 14m | 49 | 74.5 |

The compounds 12b, 12f, 12h, 12p, 12s, 12u, 12y and 12z were found to possess ER-β agonist activity. The binding affinity of the compounds is presented in FIG. 5.

Table 5 below shows the ratio between the binding constants of ER-α and ER-β for representative examples of these agonists.

| Compound | $K_i$ Ratio (ER-α/ER-β) |
|---|---|
| Estradiol | 0.13 |
| 12b | 20 |
| 12f | 61 |
| 12h | 22 |
| 12p | 8 |
| 12s | 25 |
| 12u | 17 |
| 12y | 11 |
| 12z | 12 |

Figure 6:
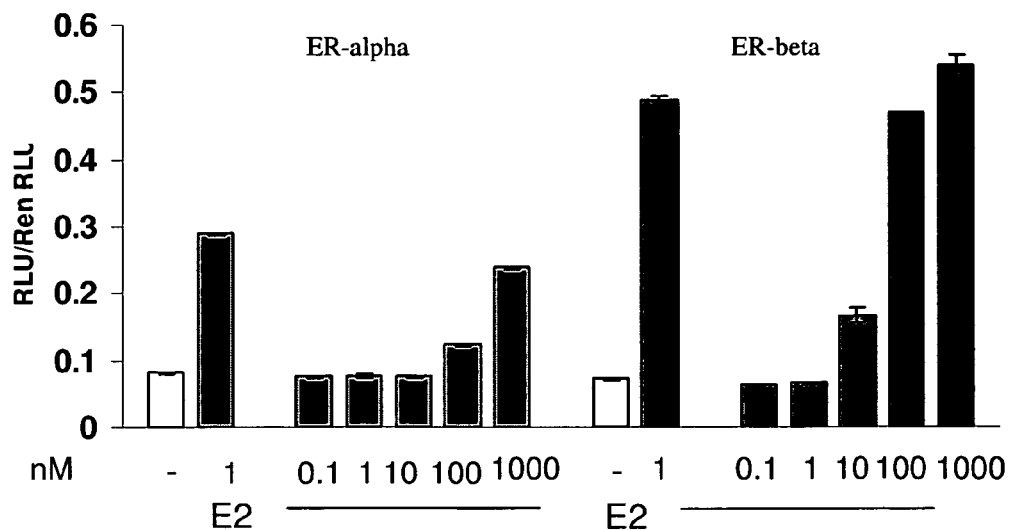
FIG. 6 depicts ER-α and ER-β activation by 12l, with 0.1, 1, 10, 100, 1000 nM doses.

As an example, the in vitro activation of ER-α and ER-β of 12l compound compared to estradiol using 0.1, 1, 10, 100 and 1000 nM doses was evaluated (FIG. 6) and the data is presented in Table 6 below.

| | ER-α RLU/RenRLU | ER-β RLU/RenRLU |
|---|---|---|
| Doses (nM) of 12l | | |
| 0.1 | 0.07 | 0.06 |
| 1 | 0.07 | 0.07 |
| 10 | 0.07 | 0.16 |
| 100 | 0.12 | 0.46 |
| 1000 | 0.24 | 0.55 |
| Doses of estradiol (nM) | | |
| 1 | 0.29 | 0.48 |

Example 3

Anti-Proliferative Effect of NRBAs on Prostate and Colon Cancer Cell Lines

Figure 2:
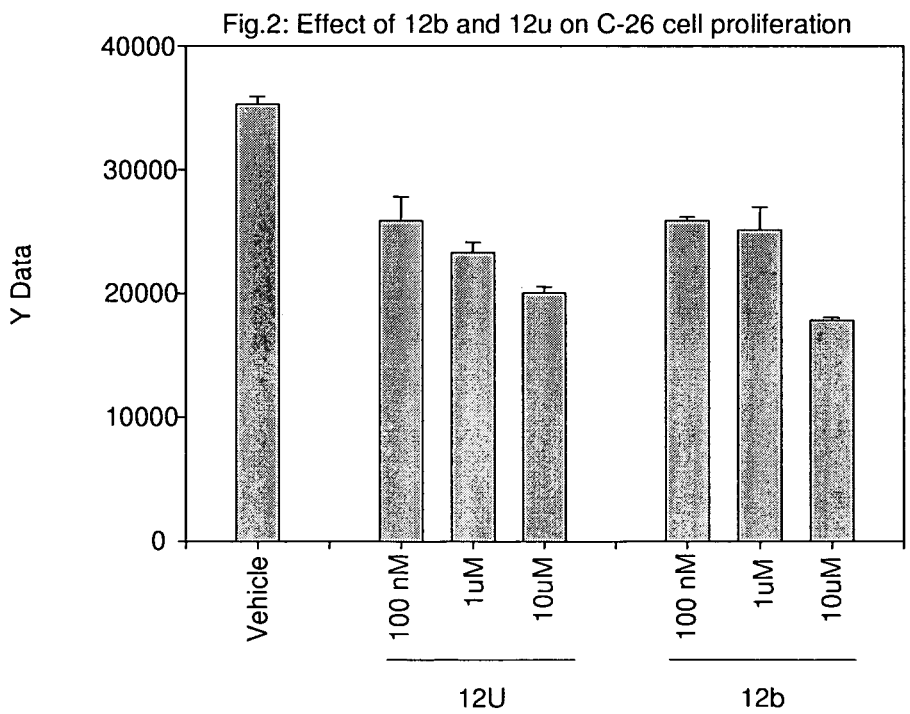
FIG. 2 depicts the effect of 12b and 12u on C-26 (colon cancer) cell proliferation.

The effects of treatment of an ER-β selective NRBA of this invention on cancer cell proliferation was examined using LNCaP prostate cancer cells and C-26 colon cancer cells. LNCaP or C-26 cells were plated in growth medium in 24 well and 6 well plates, respectively. LNCaP cells were treated for 6 days and C-26 cells were treated for 3 days at the indicated concentration. $^3$H thymidine incorporation was measured at the end of treatment as an indicator of cell proliferation. FIGS. 1 and 2 show that 12b and 12u significantly inhibited the growth of LNCaP prostate cancer and C-26 colon cancer cells, respectively, indicative of their potent anti-proliferative effects.

Example 4

Figure 3:
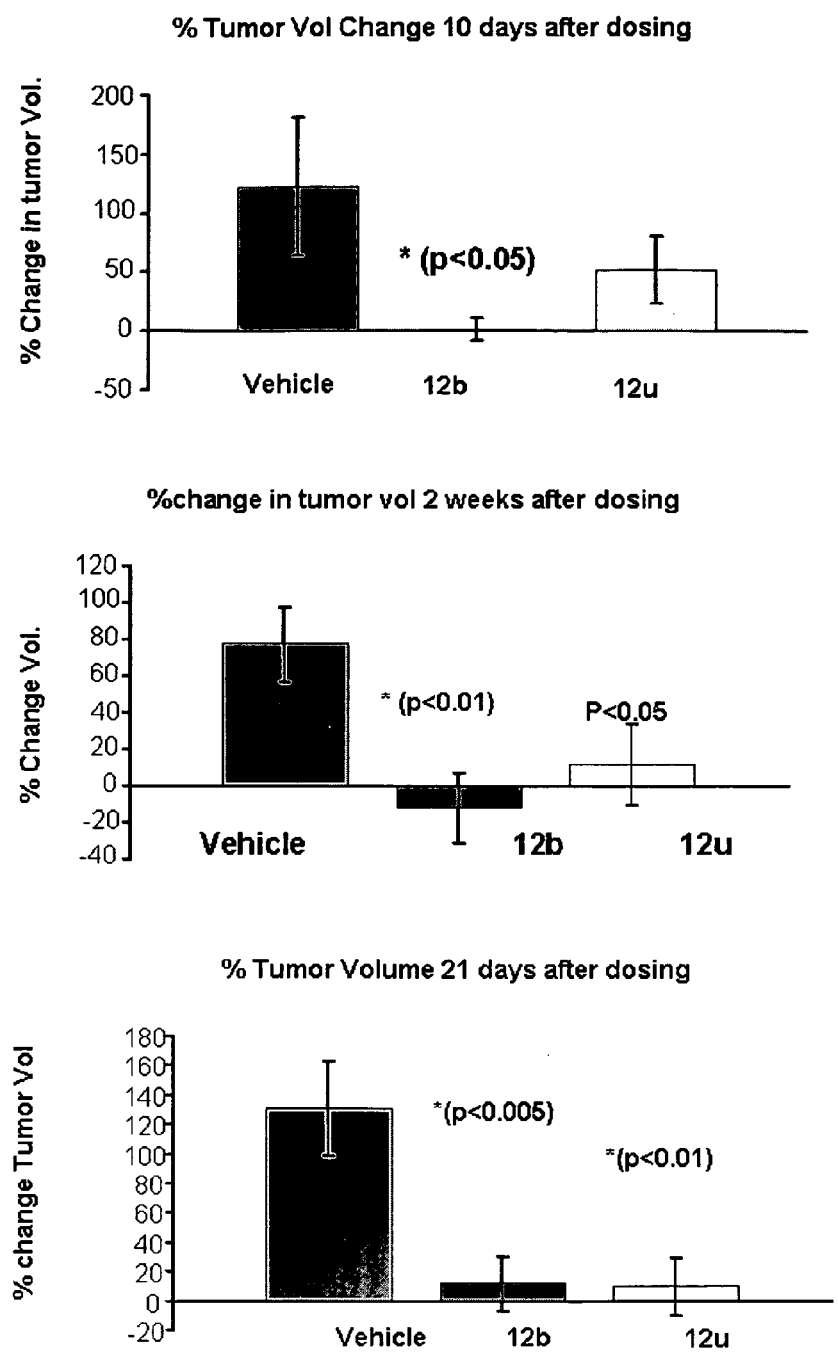
FIG. 3 depicts the effect of 12b and 12u on LNCaP-stromal cell xenograft tumor growth, after 10, 14 and 21 days.

In Vivo Anti-Proliferative Effect of NRBAs on Prostate Cancer Xenograft Tumor Growth Prostate tumor xenografts were established with LNCaP cells and human prostate stromal cells in nude mice to establish the in vivo anti-proliferative effects of these ER-β NRBAs. A 4:1 ratio (based on cell number) of LNCaP:stroma cells was injected subcutaneously in nude mice and allowed to grow until they attained 100 mm$^3$ in volume, as measured by calipers. The animals were treated with 12b and 12u at 30 mg/kg/day for 21 days. Tumor volumes were measured twice a week and percent tumor volume calculated, after 10, 14 and 21 days. FIG. 3 shows that both 12b and 12u inhibited the growth of tumor significantly by day 21, indicating that these NRBAs are anti-proliferative both in vitro and in vivo.

Example 5

Anti-Inflammatory Effect of NRBAs on Macrophage-Endothelial Cell Adhesion

Figure 4A:
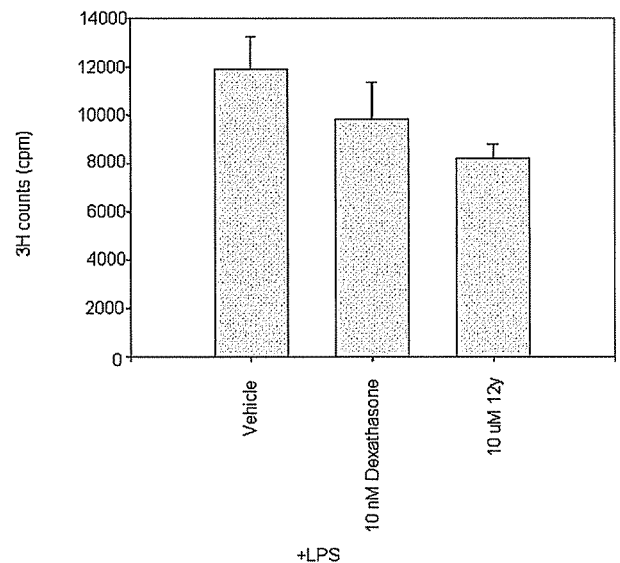
FIG. 4 depicts the effect of 12y (FIG. 4A) and 12u (FIG. 4B) on macrophage adhesion to endothelial cells.
Figure 4B:
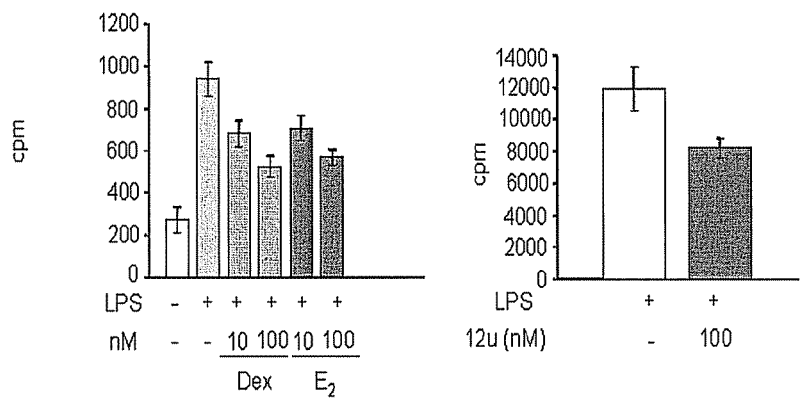

To determine the anti-inflammatory effects of ER-β NRBAs in vitro, a macrophage adhesion assay was performed. Macrophages adhere to endothelial cells due to elevated levels of pro-inflammatory cytokines. This principle was used in this assay to determine the effect of one of the ER-β NRBAs on bacterial lipopolysaccharide (LPS) induced THP-1 macrophage cell adhesion to bEND-3 endothelial cells. As shown in the FIG. 4, 12y (panel A) and 12u (panel B) significantly inhibited the adhesion of $^3$H labeled THP-1 cells to bEND-3 cells indicative of reduced inflammatory cytokine levels and a subsequent anti-inflammatory effect.

Example 6

Effect of the Compounds on TRAP Positive Multinucleated Osteoclasts

Bone marrow cells isolated from rat femur are cultured in Alpha MEM without phenol red+10% sterile FBS without phenol red in the presence or absence of 30 ng/mL RANKL and 10 ng/ml GMCSF, and the compounds. The cells treated for 12 days are stained for tartarate resistant acid phosphatase activity (TRAP) positive multinucleated osteoclasts and are counted. Suppression of osteoclast activity is evaluated.

Example 7

The Compounds Inhibit Androgen Independent Prostate Cancer Cell Growth

The prostate cancer cell line PC-3 is plated in RPMI+10% csFBS at 6000 cells per well of a 96 well plate. Medium is changed to RPMI+1% csFBS without phenol red and cells are treated for 72 hrs with increasing concentrations of NRBAs. Growth inhibition is evaluated.

Example 8

In Vivo Estrogenic Activity of Some Embodiments of the Compounds

Female rats are administered increasing doses of toremifene, estrogen and the respective NRBAs, and uterine weights are determined. Rats administered the vehicle alone serve as controls.

Example 9

Metabolic Stability of Some Embodiments of the Compounds in Human Liver Microsomes Human liver microsomes are utilized as a representative system in order to assess the potential of the compounds to form pharmacologically inactive or undesired potentially toxic metabolites due to phase I metabolism.

Each substrate or reference control is dissolved at a concentration of 10 mM in DMSO, from which a 5 μM spiking solution prepared by dilution in water. Substrates (1 μM) are incubated in the presence of human liver microsomes (Xenotech LLC, Kansas City Mo.) at 0.5 mg/mL fortified with an NADPH regenerating system at 37° C. and pH 7.4. The NADPH regenerating system consists of glucose-6-phosphate dehydrogenase (1 units/mL) in 0.05M $K_2HPO_4$. Duplicate incubations are performed in 96-well polypropylene cluster tubes in a final volume of 250 μL per reaction. At 0, 2, 4, 6, 10, 30, and 60 minutes a stop solution (300 μL acetonitrile) is added to aliquots of the reaction mixture. Precipitated protein is removed by centrifugation (3000 rpm for 15 minutes) and the supernatants are transferred to clean 96-well plates for analysis.

LC-MS/MS Analysis:

The samples are injected onto a Phenomenex Luna hexylphenyl 50×2 mm i.d. 5 uM, column fitted with a guard column. An isocratic mobile phase consisting of 50% acetonitrile and 0.1% formic acid in water is used at a flow rate of 0.3 mL/min. The protonated molecular ion $(M+H)^+$ of the analyte is monitored by MDS/Sciex API 4000QTrap triple quadrupole mass spectrometer using electrospray positive mode ionization with a temperature of 500° C. and a spray voltage of 4000V.

Data Evaluation:

Metabolic stability is defined as the amount of substrate metabolized by the incubation with hepatic microsomes and expressed as a percentage of the initial amount of substrate (% remaining) based on peak area. The initial peak area of each substrate is determined at time zero and metabolic stability is assessed based on the change in analyte peak area from time 0 min to a single fixed timepoint for each sample.

Example 10

Compound Lowering of LDL Cholesterol Levels

The compounds may be evaluated in clinical trial settings. Following administration of the compounds, their effect in altering lipid profiles in subjects with prostate cancer, undergoing or having undergone ADT may be similarly evaluated.

Example 11

In Vivo Anti-Inflammation Activity

Figure 7:
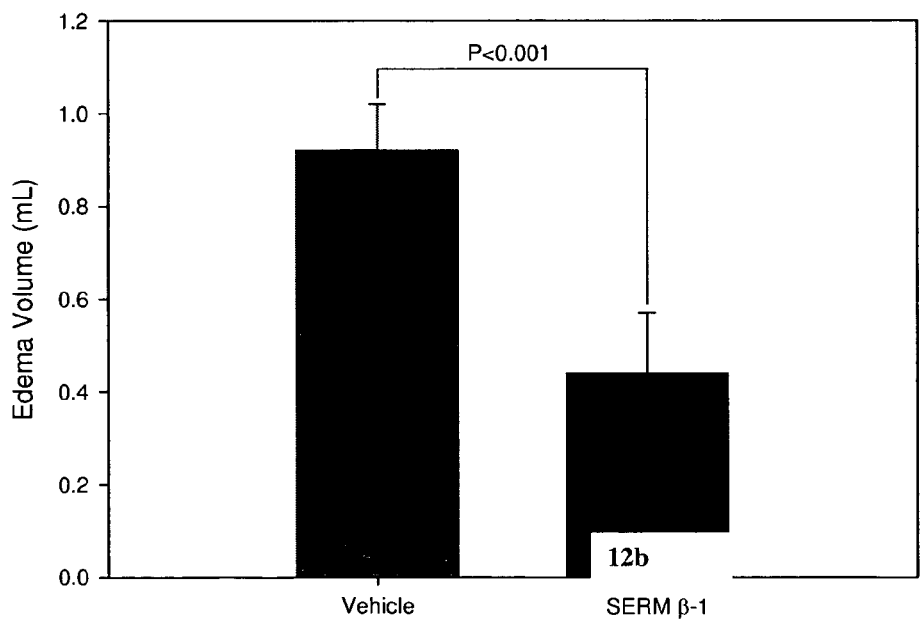
FIG. 7 depicts the effect of 12b compound on the rat paw edema volume which was induced by Carrageenan. (i.e. Carrageenan-induce raw paw edema as an acute inflammation model).

To determine the anti-inflammatory effects of ER-β NRBAs in vivo, animal paws were injected with carrageenan, which elicits an acute local inflammatory response. Per-oral treatment of 12b, 1 hr prior to Carrageenan challenge resulted in a 53% reduction in paw edema, measured 4 hours post-Carrageenan injection, as shown in FIG. 7, indicating the compound's anti-inflammatory affect.

Example 12

The Effect of NRBAs on the Rat Aorta

Experimental Protocol.

Equipment used in these studies included a 4-tissue bath system with reservoirs and circulators (RadnotiGlass Technology, Monrovia, Calif.), DSI/Ponemah tissue force analyzer 7700 (Valley View, Ohio), and iWorx/CB Sciencesforce transducers FT-302. The 250 g rats were anesthetized with isoflurane to produce deep anesthesia. The chest of the rat was opened, and about 3 cm length of aorta was removed and placed in a Petri dish containing room temperature Krebs salt solution (KSS, in mM: 120 NaCl, 5 KCl, 1.2 $MgSO_4.7H_2O$, 2.5 $CaCl_2.2H_2O$, 1 $KH_2PO_4$, 25 $NaHCO_3$, and 11 glucose). Fat and connective tissue were removed from the aorta taking care not to stretch the vessel. The aorta was then divided into 3-mm-wide rings. Triangular wire holders were inserted through the lumen of the vessel and connected to the force transducer and tissue holder rod in the vessel bath.

Data and Statistical Analyses.

Analog-to-digital conversions of force waveforms were accomplished with a DSI/Ponemah tissue force analyzer 7700. The converted data were automatically analyzed with Ponemah Physiology-Smooth Muscle software. All data are summarized as means±standard error. Differences between means were assessed by a conventional ANOVA. This was followed by Student's test. $P<0.05$ was considered to be statistically significant.

Preload and Equilibration.

The tension on the rings was adjusted to 1.0 g passive force using the tension adjustment dial for each transducer and allowed to equilibrate for 60 min in the bath with a 95% $O_2$-5% $CO_2$ gas mixture. The rings were washed with fresh buffer every 20 min. Passive force was readjusted to 1.0 g as needed during this period. When rings were stable at 1.0 g of passive force, the baseline was calculated.

Preconditioning of Aortic Rings.

Phenylephrine (PE) at a final concentration of $10^{-7}$ M was added to the bath to contract the ring, and force was allowed to stabilize for 10 min. Then acetylcholine (ACH) at a final concentration of $10^{-5}$ M was added to the precontracted rings to test for endothelial integrity (10 min). After the initial test for vessel viability and endothelial integrity, the rings were washed three times for 10 min with buffer, allowing it to equilibrate to active force stabilized at 1 g.

Relaxation Protocol.

Figure 8:
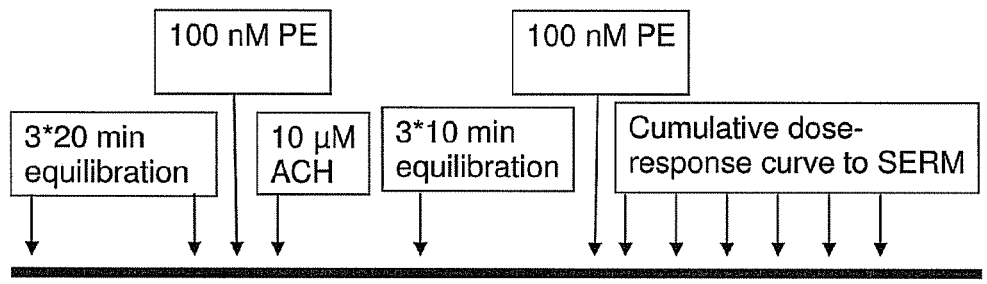
FIG. 8 depicts treatment protocol for measuring rapid (non-genomic) aortic ring relaxation by NRBA's of this invention.
Figure 9:
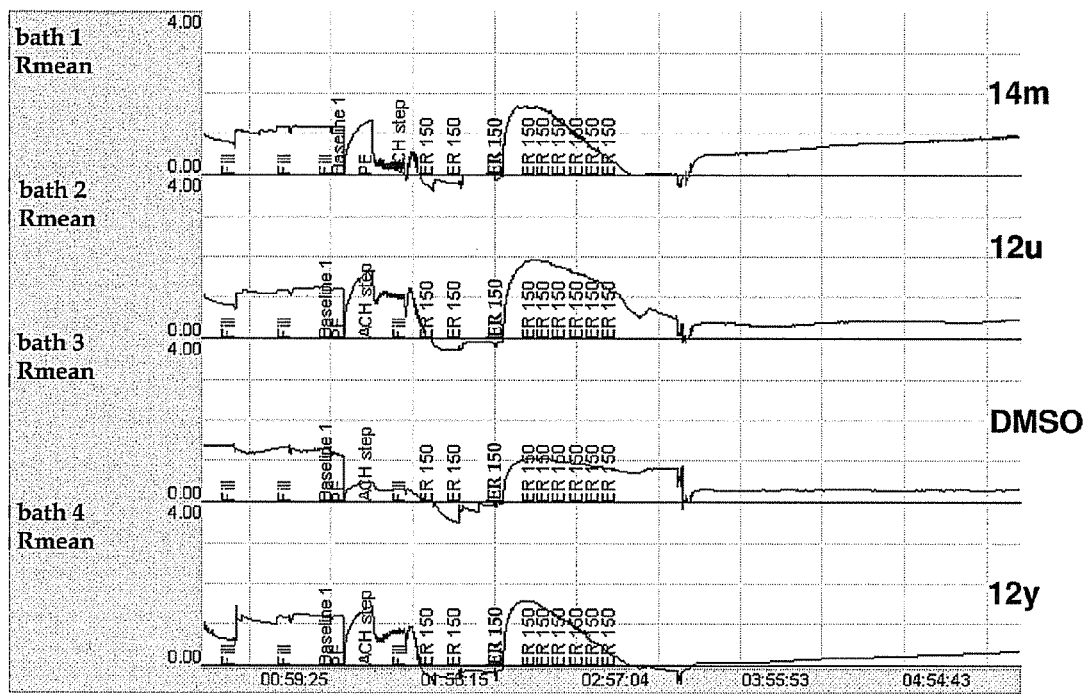
FIG. 9 depicts a concentration-response curves generated as in FIG. 8 for 14m, 12u and 12y

FIG. 8 shows a typical concentration-response protocol for NRBAs. Cumulative concentration-response curves to NRBAs were created by increasing the NRBAs concentration in the tissue bath by successive addition of appropriate dilutions of stock solutions to achieve final bath concentrations of 300 nM to 0.15 mM NRBAs. FIG. 9 shows a typical concentration-response curve generated for NRBAs.

Figure 10:
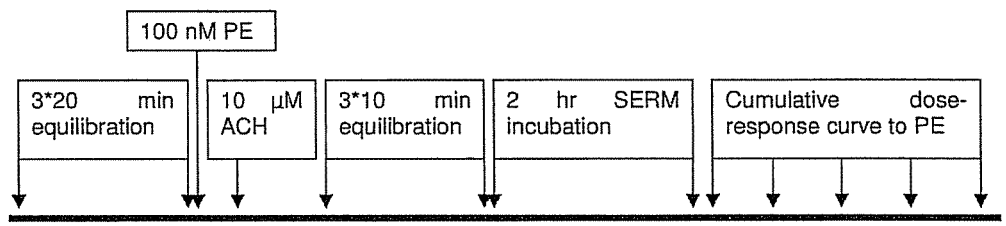
FIG. 10 depicts response treatment protocol for measuring attenuation of aortic ring constriction induced by phenylephrine (PE).
Figure 11:
FIG. 11 depicts a concentration-response curve generated as in FIG. 10 for 12y, 12z, and 14l.

Contraction protocol. FIG. 10 shows a typical concentration-response protocol for PE. After the preconditioning step, the rings were incubated in the baths with a NRBAs for 2 hrs. Then cumulative concentration-response curves to PE were created by increasing the PE concentration in the tissue bath by successive addition of appropriate dilutions of stock solutions to achieve final bath concentrations of 1 nM to 300 µM PE. FIG. 11 shows a typical concentration-response curve generated for PE.

Figure 12:
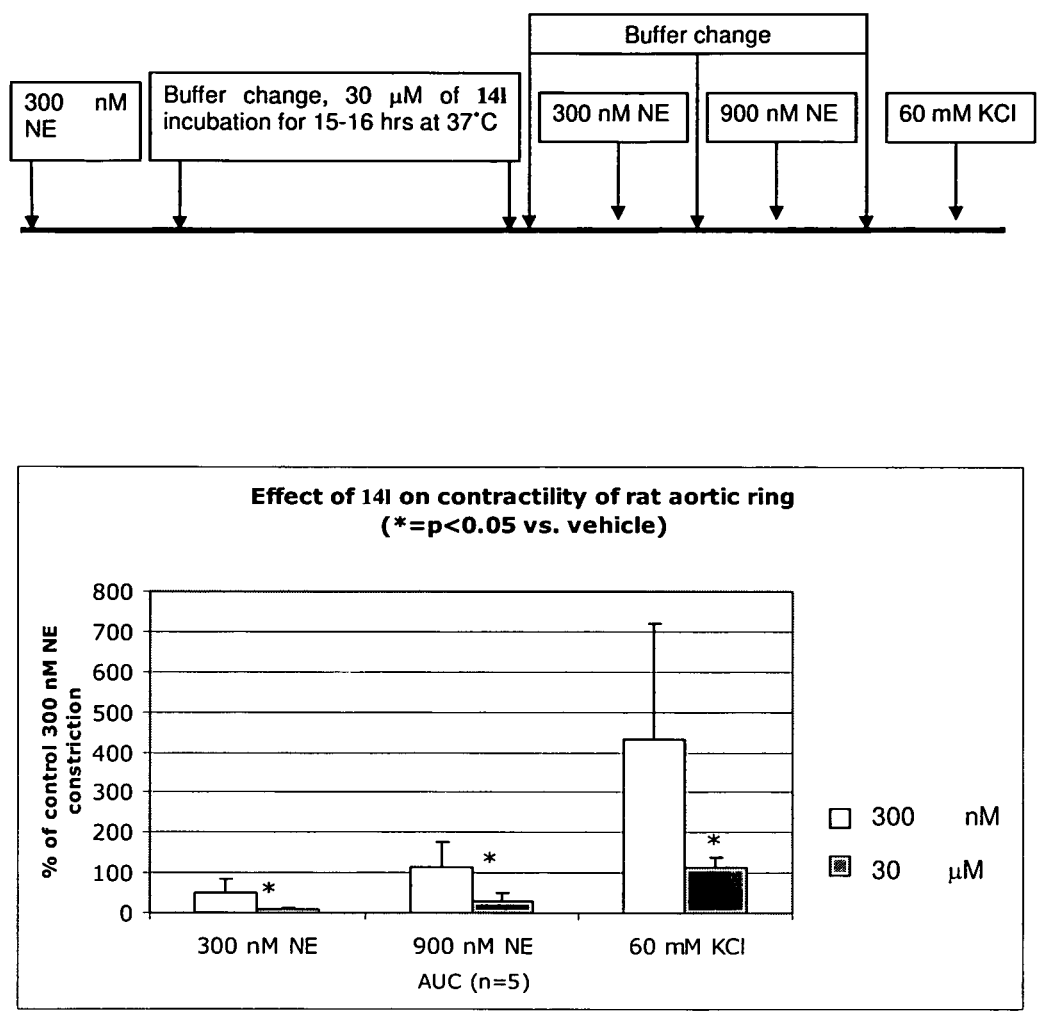
FIG. 12 depicts a protocol to measure the effect of long-term incubation of aortic rings with NRBAs of this invention, and an example graph for 14l.
Figure 13:
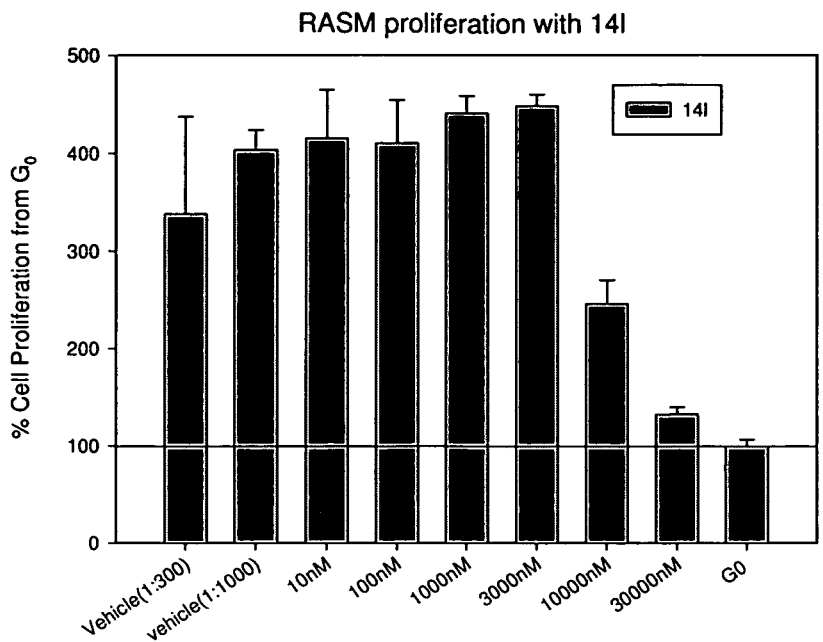
FIG. 13: Inhibition of RASMC proliferation by ER-β ligand 14l. Cell proliferation was estimated using the WST-1 calorimetric assay. Absorbance at 450 nm was measured and expressed as a percentage of the absorbance in control wells containing cells only on day 0 (G0).
Figure 14:
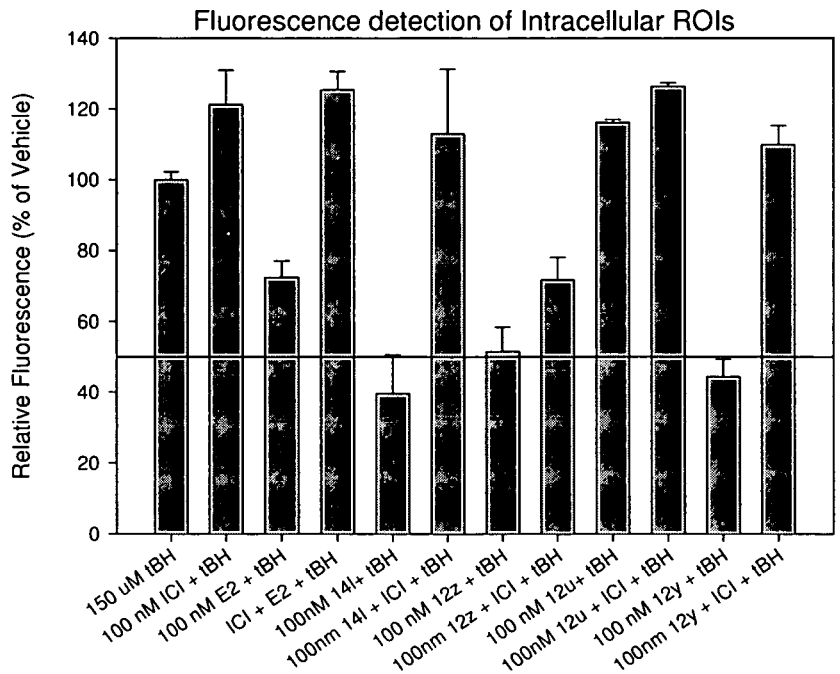
FIG. 14: Fluorescent detection of intracellular ROS. Subconfluent monolayer of ARPE-19 cells were pretreated with the respective drugs with or without ICI, before exposure to oxidative stress with tBH as described in the methods section. Values for cells treated with dye only were subtracted from the raw fluorescence data. Fluorescence is reported relative to cells containing dye in the presence of oxidant alone. Each drug treatment was done in triplicate and is plotted +/−s.e.m.

The effect of long-term incubation of aortic rings with NRBAs on aortic ring contractility was studied after 15-16 hr incubation of the aortic rings with NRBAs in oxygenated KSS under 0 g tension. Then two subsequent concentrations of norepinephrine (NE) were added each for 10 min and the tension was recorded. At the end of the experiment 60 mM KCl was used to further constrict the aortic rings. The results expressed as the percentage of the maximal constriction prior to the NRBAs incubation are summarized on FIG. 12.

|  | Mean $EC_{50}$ (µM) | SD | Mean of Maximal % Decrease | SD |
| --- | --- | --- | --- | --- |
| 14l (n − 1) | 19.8 |  | 45.01 |  |
| 14m (n = 3) | 7.64 | 3.34 | 94.49 | 3.09 |
| 12u (n = 2) | 30 | 14.28 | 50.97 | 12.23 |
| 12y (n = 2) | 13.24 | 11.12 | 80.63 | 13.94 |
| 12z (n = 1) | 15.1 |  | 83.58 |  |
| DMSO (n = 3) | 8.05 | 5.64 | 40.01 | 20.74 |

Conclusions.

The experiments show effects of the some embodiments of the NRBAs of this invention, on rat aorta relaxation. The effects occur at low micromolar concentrations and have rapid time-course effects suggesting non-genomic action as well as longtime-course action possibly involving genomic effects. These effects were similar in aortas from male or female rats indicating there is no gender difference in vascular response under studied conditions.

These effects might confer protective outcome in cardiovascular system and be clinically useful as a substitute for estrogens in preventing cardiovascular diseases in postmenopausal women as well as men.

Example 13

The Effect of GTx-ER-Beta Agonists on Proliferation of Rat Aortic Smooth Muscle Cells Rationale: Cardiovascular diseases such as hypertension, coronary heart disease and atherosclerosis have a higher incidence in post-menopausal women than in premenopausal women. This loss of cardiovascular protection is often attributed to the deficiency in circulating estrogen levels in post-menopausal women. Hormone replacement therapy (HRT) can markedly reduce the risk of cardiovascular disease in post-menopausal women (Kalin M F et al., 1990 and Wenger N K et al., 1993). However, the use of HRT for cardioprotection is limited due to the increased incidence of endometrial cancer in women and gynecomastia in men. This has led to a search for compound that can provide the beneficial effects of estrogen on the heart but do not have the undesirable side effects on uterus or breast.

Estrogen action in target tissues is mediated by its interaction with its cognate receptors ER-α and ER-β. Both ER-α as well as ER-β specific ligands have been shown to modulate cardioprotection in rats (Arias-Loza et al., 2007). Using isotype selective knockout models, Wada-Hirake et al., 2006 showed that the proliferative effects of estrogen on uterus and breast are mediated predominantly through ER-α and not through ER-β. These data indicate that an ideal compound for cardioprotection would be an ER-β specific ligand that would provide cardioprotection alone and have a better safety profile for breast and uterine tissues.

The pathogenesis of vasculoproliferative disorders like congestive heart disease, arteriosclerosis and restenosis involves structural changes in the vessel wall characterized by migration of smooth muscle cells (SMC) from the media into the intima and proliferation and deposition of extracellular matrix proteins (ECM) such as collagen (Dubey et al., 1999). In this study we examined the role of ER-β ligands in preventing a early stage in this process; namely, the proliferation of Rat Aortic Smooth Muscle Cells (RASMC) in culture.

Materials and Methods

Cells and Reagents:

HyQ-DMEM/F12 1:1 modified medium and fetal bovine serum was obtained from HyClone Laboratories Inc. DMEM/F12 50:50 was obtained from Cellgro Technologies. 17β Estradiol, Biochanin A, and tamoxifen were obtained from Sigma Chemical Co. WST-1 reagent was obtained from Roche. Rat Aortic Smooth Muscle cells (RASMC) were obtained from Lonza, Switzerland.

Cell Proliferation Assay:

All cells used in the assay were between passage 3 to 5. RASMCs were plated at a density of $1 \times 10^4$ cells/well in a 24 well plate, allowed to attach and grown to subconfluence in HyQ-DMEM/F12+10% FBS overnight. Cells were then growth arrested by replacing the medium with DMEM (phenol-red free) containing 0.4% BSA for 48 hrs. After 48 hrs, growth was initiated by replacing the medium with DMEM (phenol-red free)+2.5% FCS containing vehicle or appropriate drug concentration for 4 days. Fresh drug-containing medium was added to the cells every 2 days. On the $5^{th}$ day 50 µl of WST-1 reagent (Roche) was then added to the cells and incubated for 1 hr at 37° C. Absorbance was then determined in the samples at 450 nm wavelength in a Victor plate reader (Perkin-Elmer Inc, USA). The WST-1 assay is based on the estimation of the cleavage of tetrazolium salts to formazan by cellular enzymes. An expansion in the number of viable cells results in an increase in activity of the mitochondrial dehydrogenases in the sample. This increased activity results in increased formazan dye formation which gives an absorbance between 420-480 nm. Absorbance measured is directly correlated to the number of metabolically active cells in culture. Absorbance of the cells in control wells on day 0 (G0) of drug treatment was obtained and the cell proliferation following drug treatment was expressed as a percentage of the day 0 growth.

Results

We tested a range of compounds in this assay, including an ER-α antagonist (tamoxifen), ER-β agonist (Biochanin A, 14l, 12u 14m, 12z) and mixed agonist (estradiol). Cell proliferation was calculated as a percentage of cell number on Day 0 of drug treatment. The ER-β ligands Biochanin A, 14l, 12u, and 14m inhibited the proliferation of RASMC in a dose-dependent manner at concentration between 10-30 µM. An increase in absorbance (increase in cell number) from Day 0 was seen in all drug treatments except for the two highest concentrations of tamoxifen (10 µM and 30 µM) indicating that all the ER-β ligands were well tolerated by cells even at the highest concentration. The reduced cell numbers in the tamoxifen (10 µM and 30 µM) compared to day 0 treated wells indicates toxicity of the drug. The $EC_{50}$ values for the reduction in cell proliferation were calculated for all the drugs and is shown in Table 8.

TABLE 8

$EC_{50}$ values for inhibition of RASMC proliferation by ER-β ligands. $EC_{50}$ values were calculated using WinNonLin 5.0.1 using the inhibitory effect sigmoid $E_{max}$ model.

| Compound | $EC_{50}$ (µM) |
|---|---|
| Estradiol | 36.41 |
| Biochanin A | 9.79 |
| 12z | 25.05 |
| 12u | 9.56 |
| 14l | 9.63 |
| 14m | 7.89 |
| Tamoxifen | 4.03 |

Conclusions:

ER-β specific ligands in general inhibited the proliferation of RASMC better than a mixed agonist like estradiol. The ER-α antagonist tamoxifen at lower concentration did not have any effect on cell proliferation while at the higher concentration it was shown to be toxic to cells leading to significant reduction in cell numbers. Interestingly the ER-β ligands did not seem to have any toxic effects on cells even at the highest concentration tested, indicating that the observed effect on cell numbers is more a function on cell cycle arrest/progression than apoptosis and cell death. These data indicate that ER-β ligands can significantly inhibit an early step in vascular remodeling and could be of benefit for treatment of vasculoocclusive disorders like arteriosclerosis and restenosis.

Example 14

Effect of GTx ER-Beta SERMs on Preventing Oxidative Stress in ARPE Cells

Rationale: Cardiovascular diseases such as hypertension, coronary heart disease, atherosclerosis have a higher incidence in post-menopausal women than in premenopausal women. This loss of cardiovascular protection is attributed to the deficiency in circulating estrogen levels in the post-menopausal women. Hormone replacement therapy (HRT) can markedly reduce the risk of cardiovascular disease in post-menopausal women (Kalin M F et al, 1990 and Wenger N K et al, 1993). However, the use of HRT for cardioprotection is limited due to the increased incidence of endometrial cancer in women and gynecomastia in men. This has led to a search for compounds that can provide the beneficial effects of estrogen on the heart but do not have the undesirable side effects on uterus or breast.

Estrogen action in target tissues is mediated by its interaction with its cognate receptors ER-α and ER-β. Both ER-α as well as ER-β specific ligands have been shown to modulate cardioprotection in rats (Arias-Loza et. al, 2007). The proliferative effects of estrogen on uterus and breast is mediated predominantly through the ER-α while the ER-β does not have any stimulatory effect on these tissues (Wada-Hirake et. al, 2006). These studies make a case for using ER-β specific ligands for cardiovascular protection without the systemic effects that could be expected from ER-α ligands. Oxidative stress is one of the main etiological factors of cardiovascular diseases like hypertension, CHD and atherosclerosis. Estrogens through various molecular mechanisms (genomic and nongenomic) have been shown to activate intracellular signaling cascades that are involved in the transcriptional activation of eNOS and other antioxidant defense genes (Reviewed by Siow R C M et. al, 2007).

In this study we measured the ability of GTx ER-β compounds to prevent the oxidative damage caused by tert-butyl hydroperoxide (t-BH) on retinal pigmented epithelial cells (RPE). The retinal pigment epithelium (RPE) due to their location between the photoreceptors and choroid are continuously exposed to high oxygen fluxes. A high level of oxidative stress occurs in the RPE as a result of the formation of abnormal levels of reactive oxygen species (ROS). These features apart from ready availability of the transformed cell line from ATCC makes RPE an ideal system to study the effects of oxidative stress.

Materials and Methods

Cells and Reagents: Human ARPE-19 cells were obtained from ATCC (Manassas, Va.). All cells used in the experiments were between passage 9 to 12. HyQ-DMEM/F12 1:1 modified medium and fetal bovine serum was obtained from HyClone Laboratories Inc. DMEM/F12 50:50 was obtained from Celigro technologies. 17β Estradiol, Biochanin A were obtained from Sigma Chemical Co. WST-1 reagent was obtained from Roche. HBSS media was from Gibco. Dichorodihydrofluorescein diacetate was obtained from (H2DCFDA; Molecular Probes, Eugene Oreg.). ICI was from Tocris.

Fluorescent Detection of Intracellular ROS: ARPE-19 cells were plated at 100,000 cells/well in a 24 well plate in complete medium (HyQ-DMEM/F12 1:1 modified medium). Cells were allowed to adhere overnight. The next day, media was removed and cells were washed 1× with HBSS. 10 µM H2DCFDA diluted in HBSS was then added to the cells and cells were incubated at 37° C. for 30 mins. After the incubation period the excess dye was removed and cells washed 1× with HBSS. The cells were then preincubated with the respective concentrations of drugs for 1 hour. Following the incubation period oxidative stress was induced with 150 µM tBH for 1 hr at 37° C. Remove and wash cells once with HBSS. The ability of intracellular ROS to oxidize the dye to its fluorescent product was measured and quantified using a Victor plate reader (Perkin Elmer Corporation, Norwalk, Conn.; excitation at 485 nm; emission at 535 nm). Each drug concentration was done in triplicates. The relative fluorescence was calculated as a percentage of tBH only control.

Results

The ability of ER-β SERMs to prevent oxidative damage induced by 150 µM tBH was measured in ARPE-19 cells using a fluorescence based assay. Estradiol was used as a control for the experiment. The experiment was done in the presence and absence of estrogen receptor antagonist ICI. As seen in FIG. 1, 150 µM tBH was sufficient to cause the accumulation of reactive oxidative species (ROS) in the ARPE cells following 1 hour of incubation at 37° C. Estradiol at a concentration of 100 nM was able to prevent ROS formation with a reduction in ROS formation of approximately 30%. This inhibitory effect of estradiol was reversed with treatment with 100 nM ICI. The ER-β ligands 14l and 12y were also able to prevent the ROS formation with inhibition of more than 50%. 12z was able to prevent ROS formation as well as estradiol while 12u did not seem to have any effect on prevention of oxidative stress in the ARPE cells. As seen with estradiol the inhibitory effect of the ER-β was reversed with ICI indicating a receptor dependent mechanism of action. Cells treated with oxidant in absence of dye did not result in background fluorescence (data not shown).

Conclusions

ER-β compounds 14l, 12z and 12y protected ARPE-19 cells from oxidative damage. This protective effect was reversed with a non-selective ER antagonist ICI indicating that the protective effect is mediated through an estrogen receptor mediated mechanism.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A nuclear receptor binding agent (NRBA) represented by the structure of Formula VI:

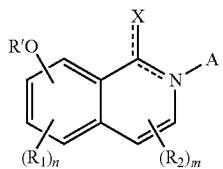

I wherein $R_1$, $R_2$ and $R_{11}$ are independently selected from hydrogen, COOH, —C(=NH)—OH, CHNOH, CH=CHCO$_2$H, CH=CHCO$_2$R, —CH=CH$_2$, halogen, hydroxyl, alkoxy, cyano, nitro, CF$_3$, NH$_2$, 4-methoxyphenyl, 4-hydroxyphenyl, SH, COR, COOR, OCOR, alkenyl, OSO$_2$CF$_3$, OSO$_2$CH$_3$, NHR, NHCOR, N(R)$_2$, sulfonamide, SO$_2$R, alkyl, haloalkyl, or protected hydroxyl;

$R_9$ is hydrogen, halogen, hydroxyl, alkoxy, cyano, nitro, or CF$_3$;

$R_{10}$ is hydrogen, C(=NH)—OH, CHNOH, CH=CHCO$_2$H, CH=CHCO$_2$R, —CH=CH$_2$, halogen, hydroxyl, alkoxy, cyano, nitro, CF$_3$, NH$_2$, 4-methoxyphenyl, 4-hydroxyphenyl, SH, COR, COOR, OCOR, alkenyl, OSO$_2$CF$_3$, OSO$_2$CH$_3$, NHR, NHCOR, N(R)$_2$, sulfonamide, SO$_2$R, alkyl, haloalkyl, aryl, phenyl, or protected hydroxyl;

$R_3$, $R_6$, $R_7$ and $R_8$ are independently selected from hydrogen, aldehyde, C(=NH)—OH, CHNOH, CH=CHCO$_2$H, CH=CHCO$_2$R, —CH=CH$_2$, halogen, hydroxyl, alkoxy, cyano, nitro, CF$_3$, NH$_2$, 4-methoxyphenyl, 4-hydroxyphenyl, SH, COR, COOR, OCOR, alkenyl, OSO$_2$CF$_3$, OSO$_2$CH$_3$, NHR, NHCOR, N(R)$_2$, sulfonamide, SO$_2$R, alkyl, haloalkyl, or protected hydroxyl;

R' is hydrogen, Alk or COR;

R" is hydrogen, Alk or COR;

R is alkyl, haloalkyl, dihaloalkyl, trihaloalkyl, CH$_2$F, CHF$_2$, CF$_3$, CF$_2$CF$_3$, aryl, phenyl, benzyl, -Ph-CF$_3$, -Ph-CH$_2$F, -Ph-CHF$_2$, -Ph-CF$_2$CF$_3$, halogen, alkenyl, CN or NO$_2$; and Alk is a linear alkyl of 1-7 carbons, branched alkyl of 1-7 carbons, or cyclic alkyl of 3-8 carbons.

2. A composition comprising the NRBA of claim 1 and a suitable carrier or diluent.

3. A nuclear receptor binding agent (NRBA), wherein said nuclear receptor binding agent is 4-bromo-6,8-dihydroxy-2-(4-hydroxyphenyl)isoquinolin-1(2H)-one.

4. A composition comprising the NRBA of claim 3 and a suitable carrier or diluent.

5. A nuclear receptor binding agent (NRBA), or its pharmaceutically acceptable salt, pharmaceutical product or any combination thereof, wherein said nuclear receptor binding agent is 4-chloro-6,8-dihydroxy-2-(4-hydroxyphenyl)isoquinolin-1(2H)-one.

6. A composition comprising the NRBA of claim 5 and a suitable carrier or diluent.

7. A nuclear receptor binding agent (NRBA), or its pharmaceutically acceptable salt, pharmaceutical product or any combination thereof, wherein said nuclear receptor binding agent is 4-bromo-6,8-dihydroxy-2-(3-fluoro-4-hydroxyphenyl)isoquinolin-1(2H)-one.

8. A composition comprising the NRBA of claim 7 and a suitable carrier or diluent.

9. The nuclear receptor binding agent (NRBA) of claim 1, wherein said NRBA is a pharmaceutically acceptable salt.

10. The nuclear receptor binding agent (NRBA) of claim 1, wherein said NRBA is an isomer.

11. The nuclear receptor binding agent (NRBA) of claim 3, wherein said NRBA is a pharmaceutically acceptable salt.

12. A nuclear receptor binding agent (NRBA), wherein said nuclear receptor binding agent is 6,8-dihydroxy-2-(4-hydroxyphenyl)-1-oxo-1,2-dihydroisoquinolin-4-carbonitrile.

13. The nuclear receptor binding agent (NRBA) of claim 12, wherein said NRBA is a pharmaceutically acceptable salt.

* * * * *

UNITED STATES PATENT AND TRADEMARK OFFICE
CERTIFICATE OF CORRECTION

PATENT NO. : 9,078,888 B2
APPLICATION NO. : 12/010225
DATED : July 14, 2015
INVENTOR(S) : James T. Dalton et al.

Page 1 of 2

It is certified that error appears in the above-identified patent and that said Letters Patent is hereby corrected as shown below:

In the claims,
- Claim 1, col. 145, after line 15 – to correct Formula VI:

Replace

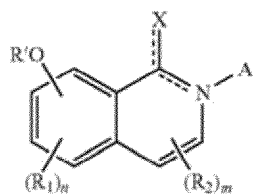

With

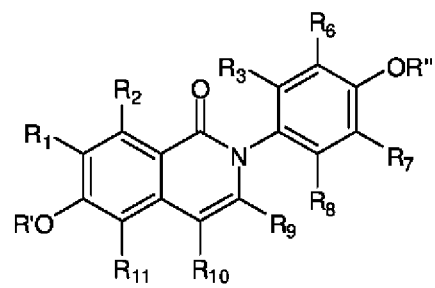

- Claim 1, col. 145, lines 43-46 and col. 146 lines 1-4:

Replace $R_3$, $R_6$, $R_7$ and $R_8$ are independently selected from hydrogen, aldehyde, C(=NH)-OH, CHNOH, CH=CHCO$_2$H, CH=CHCO$_2$R, -CH=CH$_2$, halogen, hydroxyl, alkoxy, cyano, nitro, CF$_3$, NH$_2$, 4-methoxyphenyl, 4-hydroxyphenyl, SH, COR, COOR, OCOR, alkenyl, OSO$_2$CF$_3$, OSO$_2$CH$_3$, NHR, NHCOR, N(R)$_2$, sulfonamide, SO$_2$R, alkyl, haloalkyl, or protected hydroxyl;

Signed and Sealed this
Twelfth Day of January, 2016

Michelle K. Lee
*Director of the United States Patent and Trademark Office*

With $R_3$, $R_6$, $R_7$ and $R_8$ are independently selected from hydrogen, C(=NH)-OH, CHNOH, CH=CHCO$_2$H, CH=CHCO$_2$R, -CH=CH$_2$, halogen, hydroxyl, alkoxy, cyano, nitro, CF$_3$, NH$_2$, 4-methoxyphenyl, 4-hydroxyphenyl, SH, COR, COOR, OCOR, alkenyl, OSO$_2$CF$_3$, OSO$_2$CH$_3$, NHR, NHCOR, N(R)$_2$, sulfonamide, SO$_2$R, alkyl, haloalkyl, or protected hydroxyl;